(12) United States Patent
Zhang et al.

(10) Patent No.: US 7,465,718 B2
(45) Date of Patent: Dec. 16, 2008

(54) ANSAMYCINS HAVING IMPROVED PHARMACOLOGICAL AND BIOLOGICAL PROPERTIES

(75) Inventors: Lin Zhang, San Diego, CA (US); Jean-Yves Le Brazidec, San Diego, CA (US); Lawrence C. Fritz, Rancho Santa Fe, CA (US); Francis J. Burrows, Solana Beach, CA (US); Marcus F. Boehm, San Diego, CA (US); Junhua Fan, San Diego, CA (US); Sean Konrad McHugh, Ingleside, IL (US)

(73) Assignee: Conforma Therapeutics Corporation, San Diego, CA (US)

( * ) Notice: Subject to any disclaimer, the term of this patent is extended or adjusted under 35 U.S.C. 154(b) by 211 days.

(21) Appl. No.: 10/503,880

(22) PCT Filed: Feb. 10, 2003

(86) PCT No.: PCT/US03/04283

§ 371 (c)(1),
(2), (4) Date: Feb. 22, 2005

(87) PCT Pub. No.: WO03/066005

PCT Pub. Date: Aug. 14, 2003

(65) Prior Publication Data

US 2005/0267122 A1    Dec. 1, 2005

Related U.S. Application Data

(60) Provisional application No. 60/367,055, filed on Mar. 22, 2002, provisional application No. 60/355,275, filed on Feb. 8, 2002.

(51) Int. Cl.
C07D 233/14    (2006.01)
A61K 31/33    (2006.01)

(52) U.S. Cl. ............... 514/183; 514/231.5; 514/252.13; 514/308; 514/339; 514/359; 514/361; 514/378; 514/403; 514/422; 514/444; 514/471; 540/456

(58) Field of Classification Search ............... 540/456; 514/183, 231.5, 252.13, 308, 339, 361, 378, 514/403, 359, 422, 444, 471
See application file for complete search history.

(56) References Cited

U.S. PATENT DOCUMENTS

| 3,595,955 | A | 7/1971 | De Boer et al. |
| 4,261,989 | A | 4/1981 | Sasaki et al. |
| 4,699,877 | A | 10/1987 | Cline et al. |
| 4,918,162 | A | 4/1990 | Slamon et al. |
| 4,968,603 | A | 11/1990 | Slamon et al. |
| 4,975,278 | A | 12/1990 | Senter et al. |
| 5,387,584 | A | 2/1995 | Schnur |
| 5,627,165 | A | 5/1997 | Glazier |
| 5,846,749 | A | 12/1998 | Slamon et al. |
| 5,932,566 | A | 8/1999 | Schnur et al. |
| 6,174,875 | B1 | 1/2001 | DeFranco et al. |
| 6,210,974 | B1 | 4/2001 | Gold |
| 6,348,209 | B2 | 2/2002 | Placke et al. |

FOREIGN PATENT DOCUMENTS

| WO | WO-93-14215 A1 | 7/1993 |
| WO | WO-95-01342 A1 | 1/1995 |
| WO | WO-98-51702 A1 | 11/1998 |
| WO | WO-99-51223 A1 | 10/1999 |
| WO | WO-01-72779 A1 | 10/2001 |
| WO | WO-02-02123 A1 | 1/2002 |
| WO | WO-02-09696 A1 | 2/2002 |
| WO | WO-02-36075 A2 | 5/2002 |
| WO | WO-02-36171 A1 | 5/2002 |
| WO | WO-02-069900 A2 | 9/2002 |
| WO | WO-02-094196 A2 | 11/2002 |
| WO | WO-03-026571 A2 | 4/2003 |
| WO | WO-03-037860 A2 | 5/2003 |
| WO | WO-03-041643 A2 | 5/2003 |
| WO | WO-03-050295 A2 | 6/2003 |
| WO | WO-03-066005 A2 | 8/2003 |
| WO | WO-03-072794 A1 | 9/2003 |

OTHER PUBLICATIONS

Ausubel et al., Current Protocols in Molecular Biology, John Wiley & Sons, NY 1994.
Bagatell, R. et al., "Induction of a Heat Shock Factor 1-dependent Stress Response Alters the Cytotoxic Activity of Hsp-90-binding Agents," Clinical Cancer Res., Aug. 2000, vol. 6, pp. 3312-3318.
Berge et al., "Pharmaceutical Salts," J. Pharm. Sci. 66:1-19 (1977).
Boehm et al., J. Org. Chem. 51:5447-5450 (1986).
Buchner, Trends Biochem, Sci. 24:136-141 (1999).
Buchwald et al., Surgery 88:507 (1980).
Cailleau, R. et al., "Long-term human breast carcinoma cell lines of metastatic origin: preliminary characterization," In Vitro 14:911-915, 1978, PubMed 730202.
Caplan, Trends Cell. Biol. 9:262-258 (1999).

(Continued)

Primary Examiner—Bruck Kifle
(74) Attorney, Agent, or Firm—Finnegan, Henderson, Farabow, Garrett, & Dunner LLP

(57) ABSTRACT

Ansamycins and methods of preparing and using the same are described. At least some of these ansamycins exhibit one or more of improved aqueous formulation ability, chemical stability, and bioavailability. Some of the derivatives described are dimers. These and others described can include one or more solubilizing groups that have expected merit in rendering the overall compounds useful as drugs and prodrugs.

23 Claims, 6 Drawing Sheets

OTHER PUBLICATIONS

Chiosis, G. et al., "A small molecule designed to bind to the adenine nucleotide pocket of Hsp90 causes Her2 degradation and the growth arrest and differentiation of breast cancer cells," Chem. & Biol. 8 (2001) 289-299.
Corey et al., J. Am Chem. Soc., 96: 5581-5583 (1974).
Chumpradit, S. et al., "Fluorinated and iodinated dopamine agents: D2 imaging agents for Pet and Spect," J. of Med. Chem. 36 (2):221-8 (1993).
Dai, K. et al., J. Biol. Chem. 271:22030-4 (1996).
De La Torre-Bueno, J. et al., Modern Pathology 13:221A (2000).
Erlichman et al., Proc. AACR (2001) 42, Abstract 4474.
Eng et al., Bull. Chim. Soc. Belges 95:895-914 (1986).
Federal Register 66 (129): 35443-35444.
Goodman and Gilman, *The Pharmacological Basis of Therapeutics*, current ed., Pergamon Press.
Goodson, *Medical Applications of Controlled Release*, vol. 2, pp. 115-138 (1984).
Grenert, J.P. et al., J. Biol. Chem. 272:23843-50 (1997).
Hanson et al., Int. J. Appli. Radiat. Isot. 35:810-812 (1984).
Harlow et al., *Antibodies: A Laboratory Manual*, 2nd ed., Cold Spring Harbor Laboratory Press, Cold Spring Harbor, NY 1988.
Hartmann, F. et al., Int. J. Cancer 70:221-9 (1997).
Howard, G., "Labeling Proteins with Fluorochromes," *Methods in Nonradioactive Detection*, T. Hward, Ed. Appleton and Lange, Norwalk Conn USA 1993, pp. 39-68.
Jalilian et al., J. Pharm. Pharmaceut. Sci. 3:114-124 (2000).
Kelland, L.R. et al., "DT-Diaphorase Expression and Tumor Cell Sensitivity to 17-Allylamino, 17-Demethoxygeldanamycin, An Inhibitor of Heat Shock Protein," J. Natl. Cancer Inst., Nov. 17, 1999, vol. 91, No. 22, pp. 1940-1949.
Kurokawa, H. et al., Cancer Res. 60:5887-5894 (2000).
Langer, Science 249:1527-1533 (1990).
Mandelkern et al., "Positron emission tomography in cancer research and treatment," Technologies in Cancer Research and Treatment 1(6):423-39 (2002).
Marcu, M.G. et al., "The Heat Shock Protein 90 Antagonist Novobiocin Interacts with a Previously Unrecognized ATP-Binding Domain in the Carboxyl Terminus of the Chaperone," J. Biol. Chem., Nov. 24, 2000, vol. 274, No. 47, pp. 37181-37186.
Miller, P. et al., Cancer Research 54:2724-2730 (1994).
Mimnaugh, E.G. et al., J. Biol. Chem. 271:22796-801 (1996).
Mitchell, M.S. and Press, M.F., Semin. Oncol. Suppl.12:108-116 (1999).
Muise-Heimericks et al., J. Biol. Chem. 273:29864-72 (1998).
Panaretou et al., Embo J. 17:4829-4836 (1998).
Press, M. et al., Modern Pathology 13:225A (2000).
Prestwich et al., Tetrahedron 40:529-537 (1984).
Prodromou, C. et al., Cell 90:65-75 (1997).
Qualls, et al., "Synergistic Photoxicity of Chloroaluminum Phthalocyanine Tetrasulfonate Delivered via Acid-Labile Diplanmenylcholine-Folate Lipsomes," Int. J. of Cancer 93:384-392 (2001).
Remington, *Pharmaceutical Sciences*, current ed., Mack Publishing Co., Easton PA USA.
Sambrook et al., *Molecular Cloning: A Laboratory Manual*, 2nd ed., Cold Spring Harbor Laboratory Press, Cold Spring Harbor, NY 1989.
Saudek et al., N. Eng. J. Med. 321:574 (1989).
Scheibel et al., PNAS USA 96A:1297-1302 (1999).
Schneider et al.,, PNAS USA 93:14536-41 (1996).
Schulte et al., Biochem. Biophys. Res. Commun. 239-655-9 (1997).
Schulte et al., J. Biol. Chem. 270:24585-8 (1995).
Sefton, CRC Grit. Ref. Biomed. Eng. 14:201 (1987).
Segnitz, B. and Gehring, U., J. Biol. Chem. 272:18694-18701 (1997).
Sepp-Lorenzino et al., J. Biol. Chem. 270:16580-16587 (1995).
Smith, D.F. et al., Mol. Cell. Biol. 15:6804-12 (1995).
Stebbins et al., Cell 89:239-250 (1997).
Stepanova et al., Genes Dev. 10:1491-1502 (1997).
Treat et al., *Liposomes in the Therapy of Infectious Disease and Cancer*, Lopez-Bernstein and Fidler (eds.), Liss, NY USA pp. 353-365.
Vasilevskaya et al., Cancer Res. 59:3935-40 (1999).
Voges, Rolf and Pleiss, Ulrich, eds., *Synthesis and Applications of Isotopically Labelled Compounds*, vol. 7., John Wiley & Sons, Ltd. (2001).
Whitesell et al., PNAS USA 91:8324-8328 (1994).
Zimny et al., "Positron emission tomography scanning in gynecologic and breast cancer," Curr. Op. in Obstetrics and Gynecology 15(1):69-75 (2003).
Ojwang et al., Antimicrobial Agents and Chemotherapy 39:2426-2435 (1995).
Buckheit et al, AIDS Research and Human Retroviruses 7:295-302 (1991).
Rinehart, Jr., K.L. and Shield, L.S., "Chemistry of the Ansamycin Antibiotics," *Progress in the Chemistry of Organic Natural Products*, pp. 231-307.
Melton, R.G. and Sherwood, R.E., J. National Cancer Inst. 88:153-165 (1996).
Neel et al., Bioorg. Med. Chem. Lett. 8:47-50 (1998).

ANSAMYCINS HAVING IMPROVED PHARMACOLOGICAL AND BIOLOGICAL PROPERTIES

RELATED APPLICATIONS

This application claims priority to U.S. Provisional Patent Application Ser. No. 60/367,055, filed Mar. 22, 2002 entitled ANSAMYCINS HAVING IMPROVED PHARMACOLOGICAL AND BIOLOGICAL PROPERTIES, U.S. Provisional Patent Application Ser. No. 60/355,275, filed Feb. 8, 2002, entitled NOVEL ANSAMYCINS HAVING IMPROVED PHARMACOLOGICAL AND BIOLOGICAL PROPERTIES, and PCT/US02/39993, filed Dec. 12, 2002, entitled Assay for Determining HSP90 Binding Activity. Each is herein incorporated by reference in its entirety including all drawings and figures.

FIELD OF INVENTION

The invention relates to ansamycin compounds that are useful, e.g. as antibiotics and in the treatment of various cancers, inflammatory diseases and infectious diseases.

BACKGROUND

The following description includes information that may be useful in understanding the present invention. It is not an admission that any of the information provided herein is prior art or relevant to the presently claimed inventions, or that any publication specifically or implicitly referenced is prior art.

Ansamycins are a class of naturally occurring, synthetic, and semi-synthetic formulas characterized by aliphatic rings of various length and constitution bridging opposite ends of aromatic ring formulas and their reduced equivalents. Subsumed within this class is the sub-class, benzoquinone ansamycins, which possess a benzoquinone as the aromatic ring formula U.S. Pat. Nos. 3,595,955, 4,261,989, 5,387,584, and 5,932,566, and International Applications PCT/US92/10189 (WO 93/14215) and PCT/IB94/00160 (WO 95/01342) describe the isolation, characterization, preparation and/or use of many ansamycins, including the well-known benzoquinone ansamycin, geldanamycin, and its hydrogenated equivalents. See also Progress in the Chemistry of Organic Natural Products, *Chemistry of the Ansamycin Antibiotics*, 33 1976, p. 278.

Geldanamycin, as first isolated from the microorganism *Streptomyces hygroscopicus*, was originally identified as a potent inhibitor of certain kinases, and was later shown to act by stimulating kinase degradation, specifically by targeting "molecular chaperones", e.g., heat shock protein 90s (HSP90s). Subsequently, various other ansamyins have demonstrated more or less such activity, with 17 allyl amino geldanamycin (17-AAG) being among the most promising and the subject of intensive clinical studies currently being conducted by the National Cancer Institute (NCI) for their use as potential anti-cancer agents. See, e.g., Federal Register, 66(129): 35443-35444; Erlichman et al., Proc. AACR (2001), 42, abstract 4474.

HSP90s are ubiquitous chaperone proteins that are highly conserved in nature and that are thought to be involved in folding, activation and assembly of a wide range of proteins, including key proteins involved in signal transduction, cell cycle control and transcriptional regulation. NCBI accession #'s P07900 and XM 004515 (human α and β HSP90, respectively), P11499 (mouse), AAB2369 (rat), P46633 (chinese hamster), JC1468 (chicken), AAF69019 (flesh fly), AAC21566 (zebrafish), AAD30275 (salmon), O02075 (pig), NP 015084 (yeast), and CAC29071 (frog) are illustrative of HSP90s. Grp94 and Trap-1 are related molecules that may exhibit a similar effect when contacted with HSP90 inhibitors. Researchers have reported that HSP90s are associated with important signaling proteins, such as steroid hormone receptors and protein kinases, including, e.g., Raf-1, EGFR, v-Src family kinases, Cdk4, and ErbB-2 (Buchner J., 1999, *TIBS*, 24: 136-141; Stepanova, L. et al., 1996, *Genes Dev.* 10: 1491-502; Dai, K. et al., 1996, *J. Biol. Chem.* 271: 22030-4). Studies further indicate that certain co-chaperones, e.g., Hsp70, p60/Hop/Stil, Hip, Bag1, HSP40/Hdj2/Hsj1, immunophilins, p23, and p50, may assist HSP90 function (see, e.g., Caplan, A., 1999, *Trends in Cell Biol.*, 9: 262-68).

Ansamycins are thought to exert their anti-cancerous effects by tight binding of the N-terminus pocket of HSP90s (Stebbins, C. et al., 1997, *Cell*, 89: 239-250). This pocket is highly conserved and has weak homology to the ATP-binding site of DNA gyrase (Stebbins, C. et al., supra; Grenert, J. P. et al., 1997, *J. Biol. Chem.*, 272: 23843-50). Further, ATP and ADP have both been shown to bind this pocket with low affinity and to have weak ATPase activity (Proromou, C. et al., 1997, *Cell*, 90: 65-75; Panaretou, B. et al., 1998, *EMBO J.*, 17: 4829-36). In vitro and in vivo studies have demonstrated that occupancy of this N-terminal pocket by ansamycins and other HSP90 inhibitors alters HSP90 function and inhibits protein folding. At high concentrations, ansamycins and other HSP90 inhibitors have been shown to prevent binding of protein substrates to HSP90 (Scheibel, T., H. et al., 1999, *Proc. Natl. Acad. Sci. USA* 96: 1297-302; Schulte, T. W. et al., 1995, *J. Biol. Chem.* 270: 24585-8; Whitesell, L., et al., 1994, *Proc. Natl. Acad. Sci. USA* 91: 8324-8328). Ansamycins have also been demonstrated to inhibit the ATP-dependent release of chaperone-associated protein substrates (Schneider, C., L. et al., 1996, *Proc. Natl. Acad. Sci. USA*, 93: 14536-41; Sepp-Lorenzino et al., 1995, *J. Biol. Chem.* 270: 16580-16587). In either event, the substrates are degraded by a ubiquitin-dependent process in the proteasome (Schneider, C., L., supra; Sepp-Lorenzino, L., et al., 1995, *J. Biol. Chem.*, 270: 16580-16587; Whitesell, L. et al., 1994, *Proc. Natl. Acad. Sci. USA*, 91: 8324-8328).

This substrate destabilization occurs in tumor and non-transformed cells alike and has been shown to be especially effective on a subset of signaling regulators, e.g., Raf (Schulte, T. W. et al., 1997, *Biochem. Biophys. Res. Commun.* 239: 655-9; Schulte, T. W., et al., 1995, *J. Biol. Chem.* 270: 24585-8), nuclear steroid receptors (Segnitz, B., and U. Gehring. 1997, *J. Biol. Chem.* 272: 18694-18701; Smith, D. F. et al., 1995, *Mol. Cell. Biol.* 15: 6804-12), v-src (Whitesell, L., et al., 1994, *Proc. Natl. Acad. Sci. USA* 91: 8324-8328) and certain transmembrane tyrosine kinases (Sepp-Lorenzino, L. et al., 1995, *J. Biol. Chem.* 270: 16580-16587) such as EGF receptor (EGFR) and Her2/Neu (Hartmann, F., et al., 1997, *Int. J. Cancer* 70: 221-9; Miller, P. et al., 1994, *Cancer Res.* 54: 2724-2730; Minmaugh, E. G., et al., 1996, *J. Biol. Chem.* 271: 22796-801; Schnur, R. et al., 1995, *J. Med. Chem.* 38: 3806-3812), CDK4, and mutant p53. Erlichman et al., Proc. AACR (2001), 42, abstract 4474. The ansamycin-induced loss of these proteins leads to the selective disruption of certain regulatory pathways and results in growth arrest at specific phases of the cell cycle (Muise-Heimericks, R. C. et al., 1998, *J. Biol. Chem.* 273: 29864-72), and apoptsosis, and/or differentiation of cells so treated (Vasilevskaya, A. et al., 1999, *Cancer Res.*, 59: 3935-40).

Recently, Nicchitta et al., WO 01/72779 (PCT/US01/09512), demonstrated that HSP90 can assume a different conformation upon heat shock and/or binding by the fluorophore bis-ANS. Specifically, Nicchitta et al. demonstrated that this induced conformation exhibits a higher affinity for certain HSP90 ligands than for a different form of HSP90 that predominates in normal cells. Commonly-owned application PCT/US02/39993carries this discovery even further by demonstrating the utility and uses of cancer cell lystates as excellent sources of high affinity HSP90.

In addition to anti-cancer and antitumorgenic activity, HSP90 inhibitors have also been implicated in a wide variety of other utilities, including use as anti-inflammation agents, anti-infectious disease agents, agents for treating autoimmunity, agents for treating stroke, ischemia, cardiac disorders and agents useful in promoting nerve regeneration (See, e.g., Rosen et al., WO 02/09696 (PCT/US01/23640); Degranco et al., WO 99/51223 (PCT/US99/07242); Gold, U.S. Pat. No. 6,210,974 B1; DeFranco et al., U.S. Pat. No. 6,174,875). Overlapping somewhat with the above, there are reports in the literature that fibrogenetic disorders including but not limited to scleroderma, polymyositis, systemic lupus, rheumatoid arthritis, liver cirrhosis, keloid formation, interstitial nephritis, and pulmonary fibrosis also may be treatable. (Strehlow, WO 02/02123; PCT/US01/20578). Still further HSP90 modulation, modulators, and uses thereof are reported in PCT/US02/35938, PCT/US02/16287, PCT/US02/06518, PCT/US98/09805, PCT/US00/09512, PCT/US01/09512, PCT/US01/23640, PCT/US01/46303, PCT/US01/46304, PCT/US02/06518, PCT/US02/29715, PCT/US02/35069, PCT/US02/35938, PCT/US02/39993, 60/293,246, 60/371,668, 60/331,893, 60/335,391, 06/128,593, 60/337,919, 60/340,762, 60/355,275, 60/367,055 and 60/359,484.

However, at present the various known methods of producing ansamycins exhibit one or more of low yield, low purity, low solubility, chemical instability (in vivo and/or in vitro), poor pharmaceutical properties (short t1/2, metabolic instability), environmental toxicity associated with the use of halogenated organic solvents, and additional attendant costs in terms of time, expense, waste disposal, and health risks to those taking the drugs so made. Commonly-owned applications, Ser. Nos. 60/272,251, filed Mar. 1, 2001, and entitled Methods for Treating Genetically Defined Proliferative Disorders with HSP90; Ser. Nos. 60/326,639 and 60/331,893, filed respectively Sep. 24, 2001 and Nov. 21, 2001, and both entitled Chemical Process for Preparing 17-Allyl Amino Geldanamycin (17-AAG) and other Ansamycins and Ansamycin Derivatives; and a provisional application filed Dec. 2, 2001, and entitled Assay for Determining HSP90 Binding Activity, describe some of these problems and how they may be addressed.

It is an object of the present invention to ameliorate one or more of the problems associated with traditional ansamycin preparations and use, e.g. low metabolic stability, low bioavailability, low water solubility and/or formulation difficulty. Another object is to provide new ansamycin compounds, preferably of improved potency and pharmacokinetic properties.

SUMMARY OF THE INVENTION

A deficiency of the previous generation of ansamycins such as geldanamycin (GM) and 17-allyl amino geldanamycin (17-AAG) is that they exhibit one or more poor pharmacological properties, e.g., metabolic instability, poor bioavailability, and/or difficult formulation ability, particularly for in vivo intravenous administration. In order to develop an effective ansamycin drug, it is desirable to address these deficiencies, as well as to provide new GM analogs and derivatives.

Applicants herein describe new ansamycin derivatives and methods of preparation thereof. At least some exhibit improved pharmacological properties, e.g., one or more of high biological exposure, improved biological half-life, increased water solubility, and increased metabolic and chemical stability. Some of these ansamycin derivatives are especially well suited for use as pro-drugs, e.g., 17-alkyl amino geldanamycin and 17-alkyl amino dihydrogeldanamycin. Some others take the form of dimers, e.g., of geldanamycin and/or dihydrogeldanamycin.

In a first aspect, the invention features compounds of formula (I)

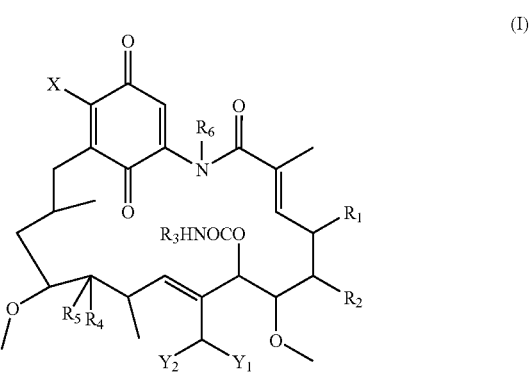

or pharmaceutically acceptable salts thereof, wherein

X is selected from the group consisting of optionally substituted (C1-C20)alkyl, optionally substituted (C1-C20)heteroalkyl, optionally substituted (C2-C20)alkenyl, optionally substituted (C2-C20)heteroalkenyl, optionally substituted (C2-C20)alkynyl, optionally substituted aryl, optionally substituted heteroaryl, optionally substituted arylalkyl, optionally substituted heteroarylalkyl, optionally substituted cycloalkyl optionally substituted cycloheteroalkyl, —N($R_9$)—C(O)$R_7$, —N($R_9$)—C(O)—O $R_7$, —N($R_9$)—C(O)—N $R_7R_8$, —N($R_9$)-C(S)$R_7$, —N($R_9$)-C(S)—O $R_7$, —N($R_9$)-C(S)—N $R_7$ $R_8$, —O$R_6$ and —N($R_{14}$)($R_{15}$);

$R_1$ and $R_2$ are both H or together form a bond;

$R_3$ is selected from the group consisting of H and optionally substituted C1-C3 alkyl;

$R_4$ and $R_5$ are independently selected from the group consisting of H, —OH, O-alkyl, O-acetyl, —O-aryl, OC(O)$R_{10}$, —S $O_2$—$R_{10}$, and —NH $R_{10}$, or together form oxo (=O), or hydroxylamino alkoxyimine or aryloxyimine, thioketo, wherein $R_{10}$ is selected from the group consisting of H, optionally substituted (C1-C20)alkyl, optionally substituted (C1-C20)heteroalkyl, optionally substituted aryl; and optionally substituted heteroaryl;

$R_6$ is selected from the group consisting of H, optionally substituted C1-C8 alkyl, optionally substituted C5-C8 aryl, and optionally substituted C1-C6 acyl;

$R_7$ and $R_8$ each independently is selected from the group consisting of H, optionally substituted (C1-C20)alkyl, optionally substituted (C1-C20)heteroalkyl, optionally substituted (C2-C20)alkenyl, optionally substituted (C2-C20) heteroalkenyl, optionally substituted (C2-C20)alkynyl, optionally substituted aryl, optionally substituted heteroaryl, optionally substituted arylalkyl, optionally substituted heteroarylalkyl, optionally substituted cycloalkyl, and optionally substituted cycloheteroalkyl; or together form a 4-7 membered optionally substituted ring;

$R_9$ is selected from the group consisting of H, optionally substituted C1-C6 alkyl, optionally substituted C5-C8 aryl, and optionally substituted C5-C8 heteroaryl, or together with $R_7$ or $R_8$ forms a 4-7 membered optionally substituted ring;

$R_{14}$ and $R_{15}$ are independently selected from the group consisting of H, optionally substituted (C1-C20)alkyl, optionally substituted (C2-C20)heteroalkyl optionally substituted (C2-C20)alkenyl, optionally substituted (C2-C20) heteroalkenyl, optionally substituted (C2-C20)alkynyl, optionally substituted aryl, optionally substituted heteroaryl, optionally substituted arylalkyl, optionally substituted heteroarylalkyl, optionally substituted cycloalkyl, and optionally substituted cycloheteroalkyl; or $R_{14}$ and $R_{15}$ together form an optionally substituted 4-7 membered heterocyclic or carbocyclic ring;

wherein $Y_1$ and $Y_2$ are independently selected from the group consisting H, —OH, O-alkyl, O-acetyl, —O-aryl, $OC(O)R_{10}$, —S $O_2$—$R_{10}$, and —NH $R_{10}$, or together form oxo (=O), or hydroxylamino alkoxyimine or aryloxyimine, thioketo, wherein $R_{10}$ is selected from H, optionally substituted (C1-C20)alkyl, optionally substituted (C1-C20)heteroalkyl, optionally substituted aryl and optionally substituted heteroaryl;

or $Y_1$ or $Y_2$ taken with $R_4$ or $R_5$ form an optionally substituted 5-7 membered heterocyclic or carbocyclic ring;

provided that, if $Y_1$ and $Y_2$ are both H and X is $N(R_{14})(R_{15})$ or —$OR_6$, then at least one of $R_4$, $R_5$, $R_6$, $R_{14}$, and $R_{15}$ comprises a phosphorous moiety selected from the group consisting of —OP(O)(OR$_{16}$)$_2$ (phosphate), —CH$_2$P(O)(O R$_{16}$ (phosphonate), and —NP(O)(O R$_{16}$)$_2$ (phosphoramide), wherein $R_{16}$ is selected from the group consisting of H, alkyl, heteroalkyl, alkenyl, heteroalkenyl alkynyl, heteroalkynyl, aryl and heteroaryl.

In some embodiments, X is further selected from —N(R$_9$)—C(O)R$_7$, —N(R$_9$)—C(O)—O R$_7$, —N(R$_9$)—C(O)—N R$_7$, —N(R$_9$)—C(S)R$_7$, —N(R$_9$)—C(S)—O R$_7$, —N(R$_9$)—C(S)—N R$_7$, and N(R$_{14}$)(R$_{15}$).

In some embodiments, X is further selected from from the group consisting of optionally substituted (C1-C20)alkyl, optionally substituted (C1-C20)heteroalkyl, optionally substituted (C2-C20)alkenyl, optionally substituted (C2-C20) heteroalkenyl, optionally substituted (C2-C20)alkynyl, optionally substituted aryl, optionally substituted heteroaryl, optionally substituted arylalkyl, optionally substituted heteroarylalkyl, optionally substituted cycloalkyl, and optionally substituted cycloheteroalkyl.

In some embodiments, X is —N(R$_{14}$)(R$_{15}$),

In some embodiments, X is —N(R$_9$)—C(O)R$_7$.

In some embodiments, the compound has a formula selected from the following group of formulas:

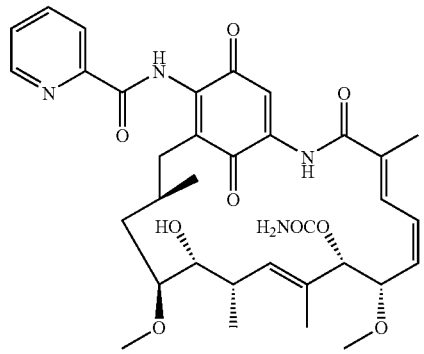 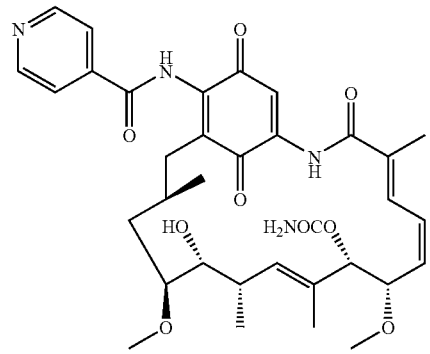

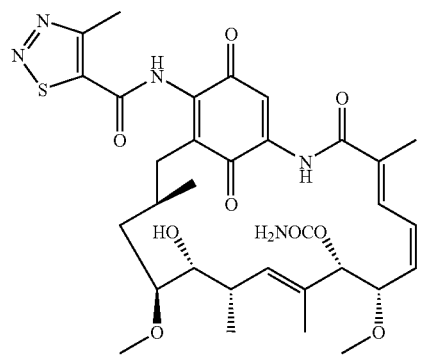 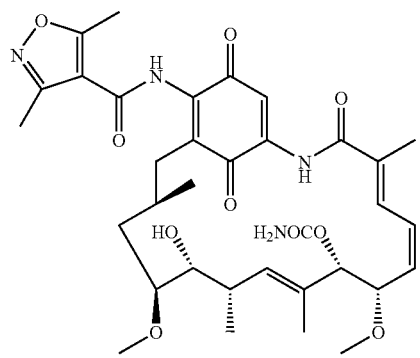

-continued
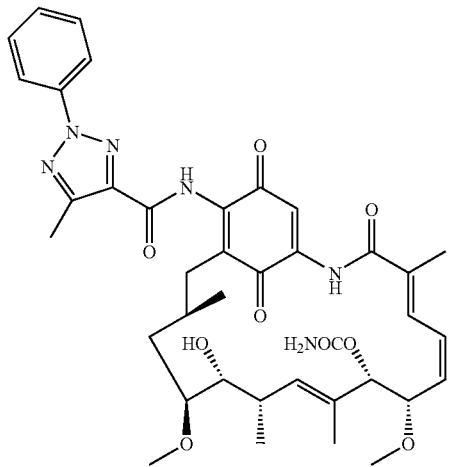
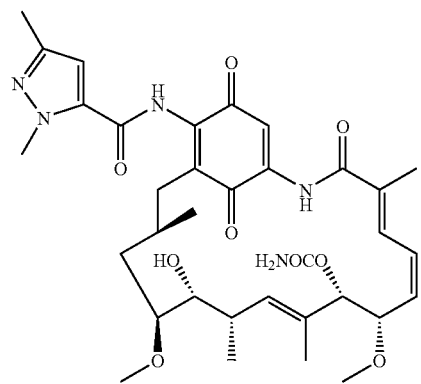
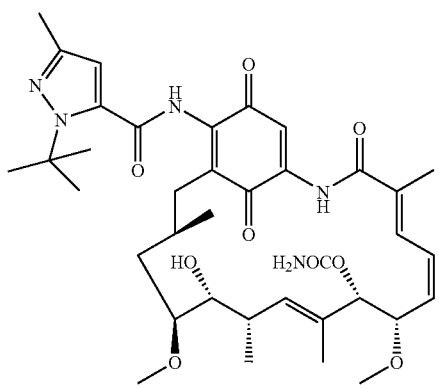
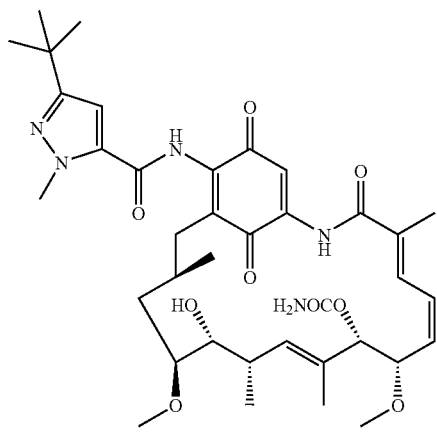
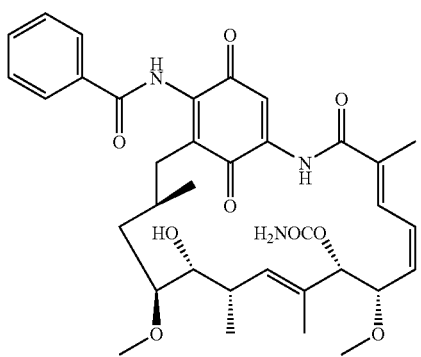
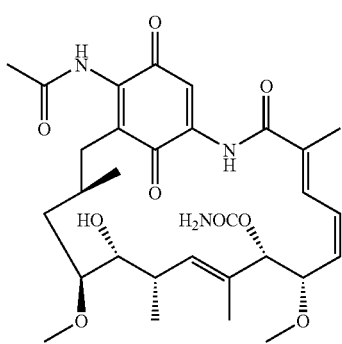
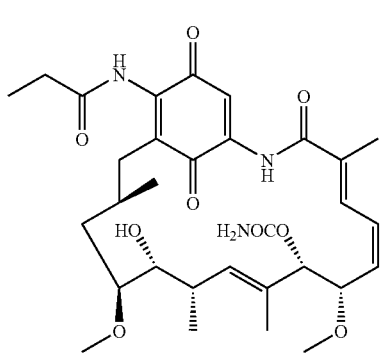
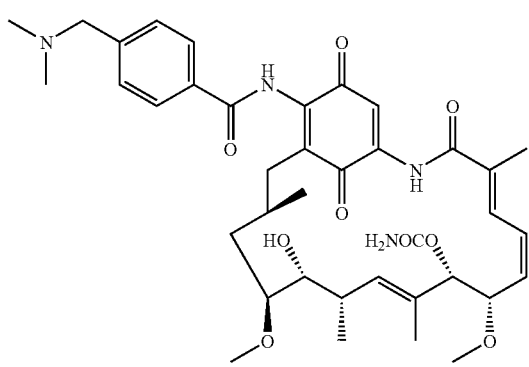

-continued
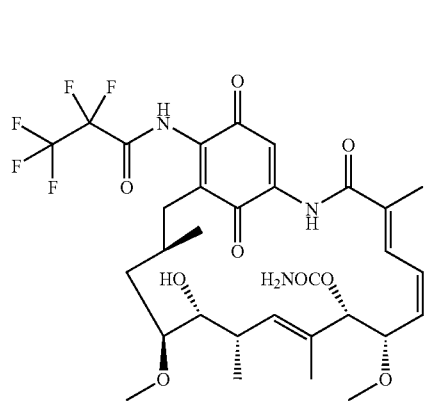
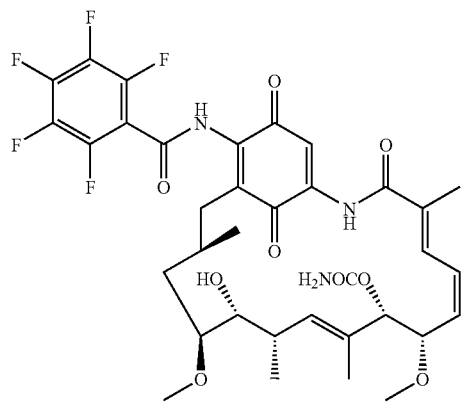
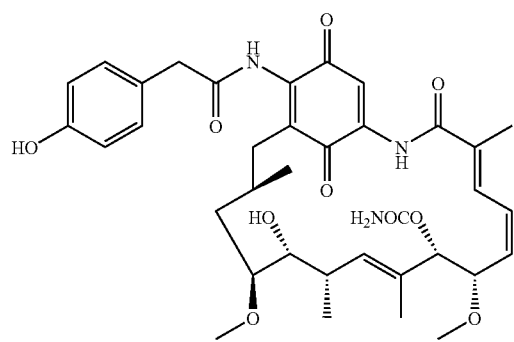
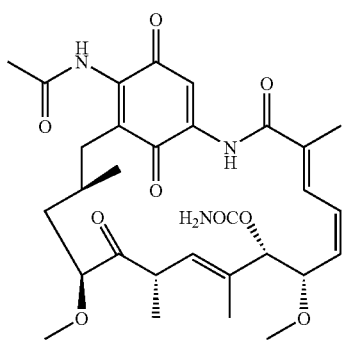
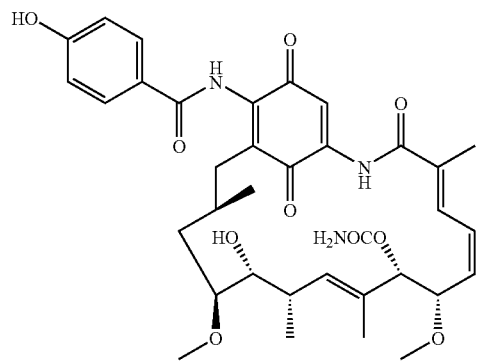
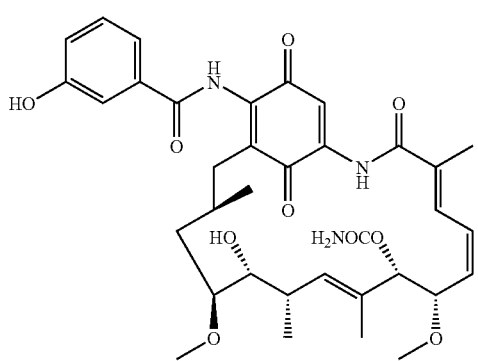
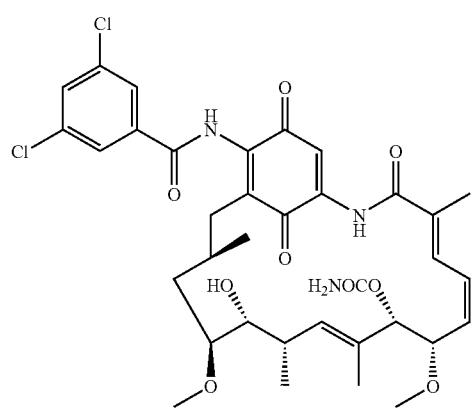
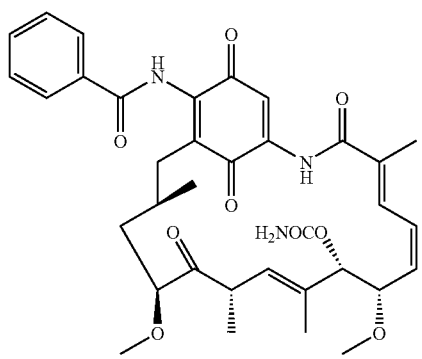

11
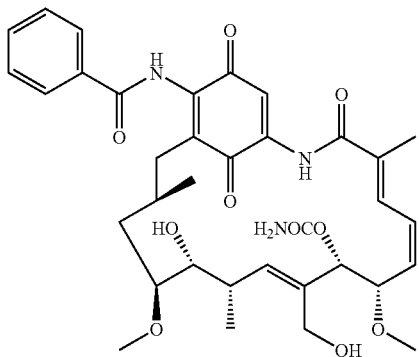
12
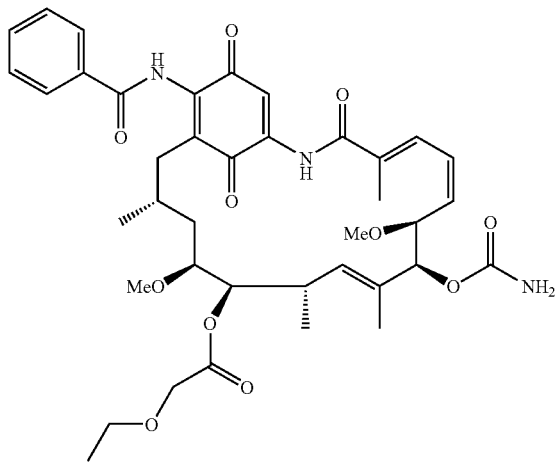
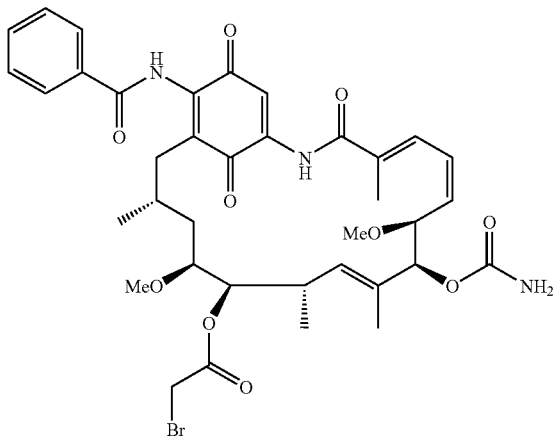
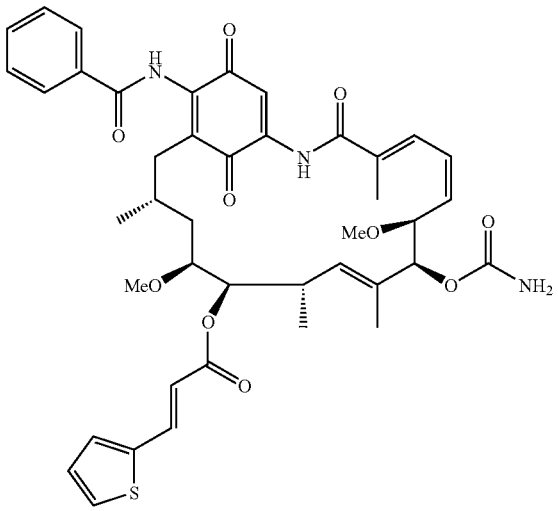
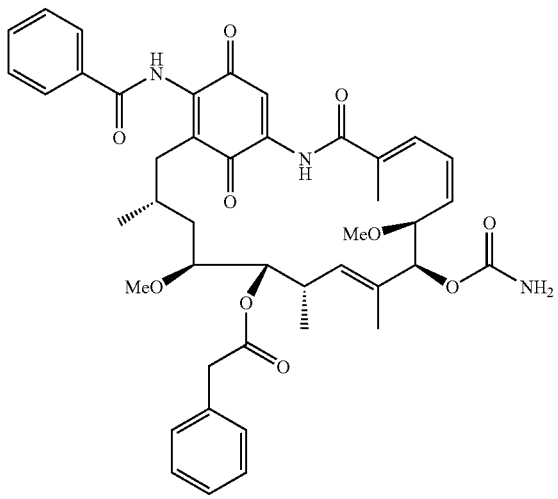
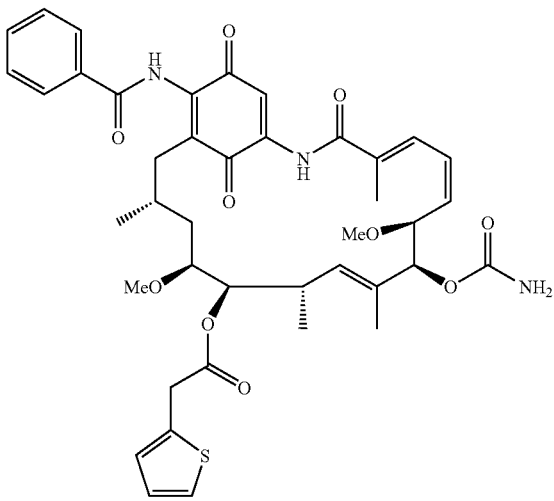

-continued
13
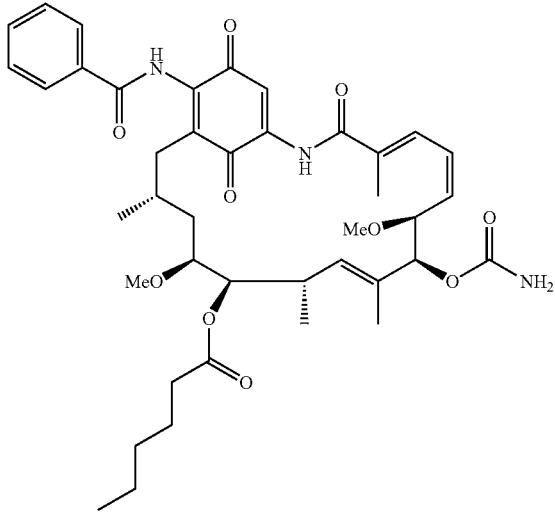
14
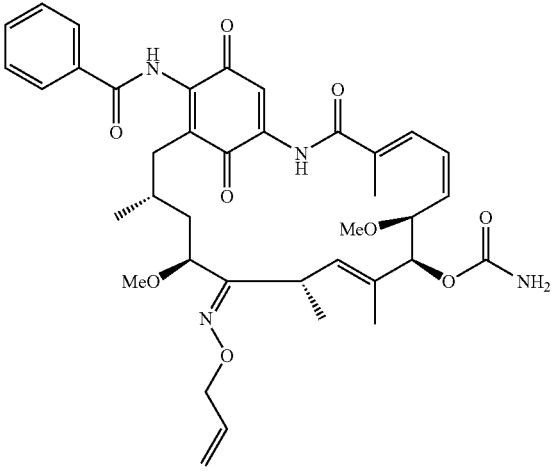
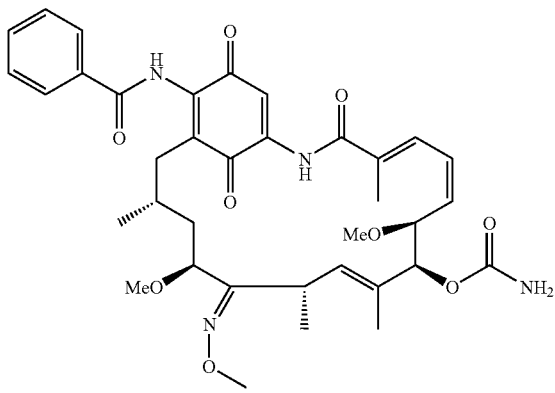
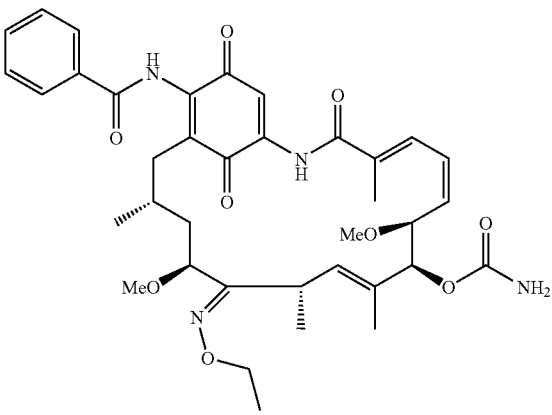
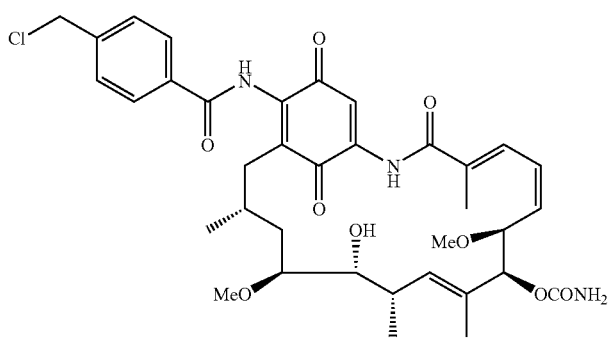
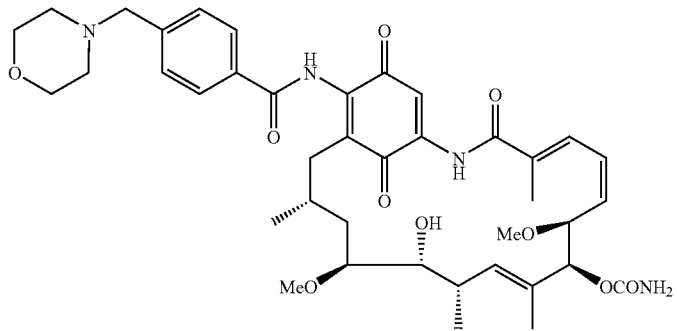

-continued
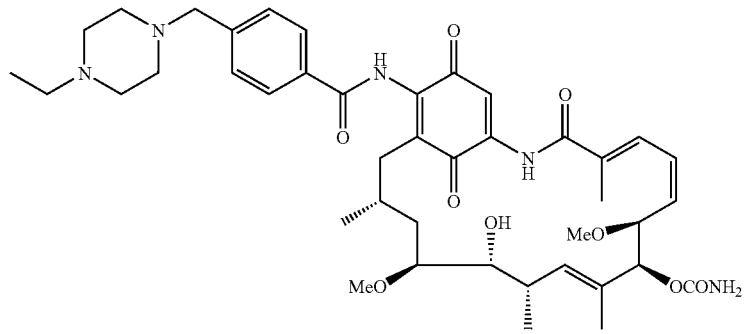
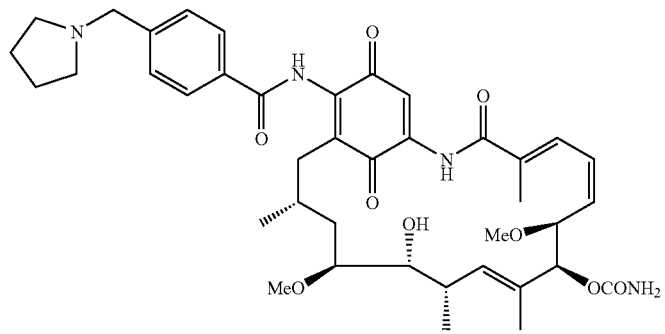
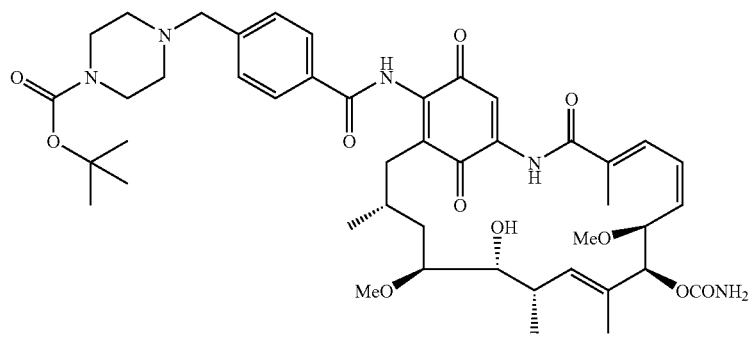
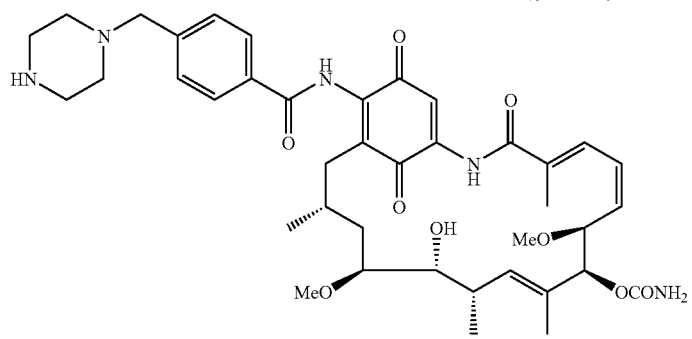
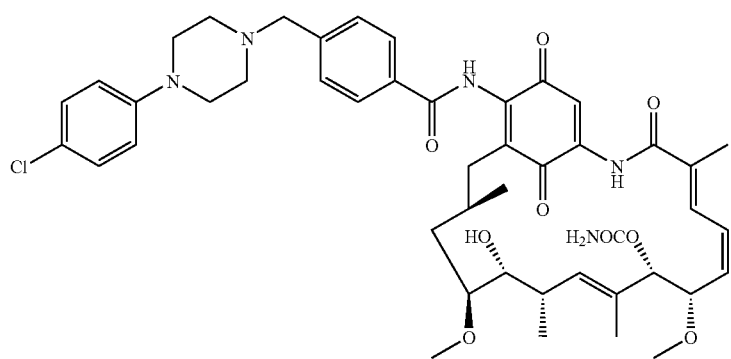

-continued
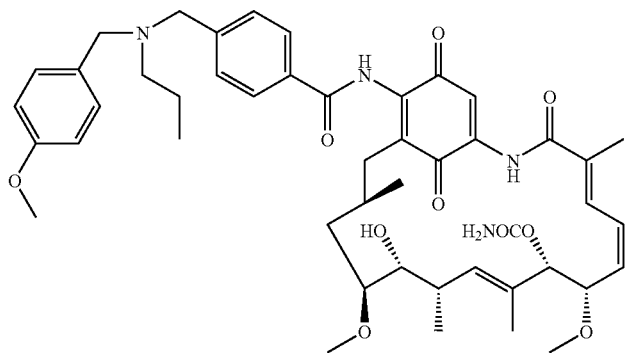
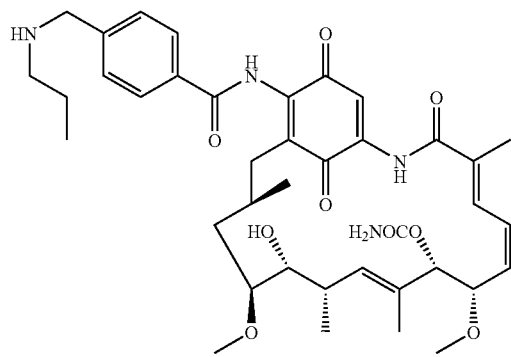
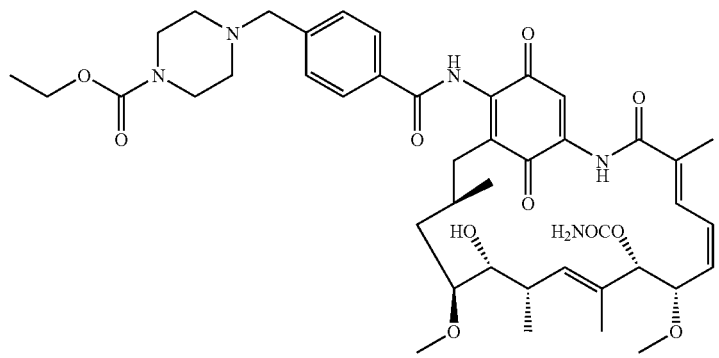
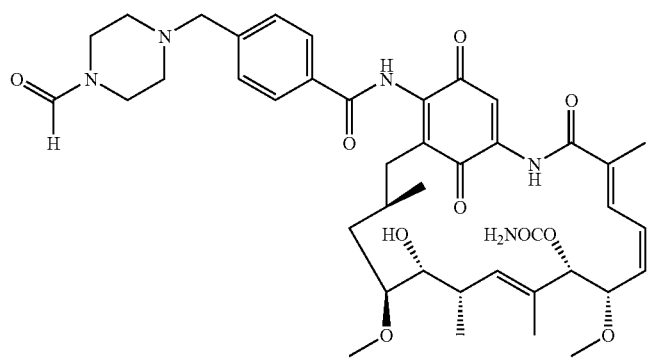

-continued
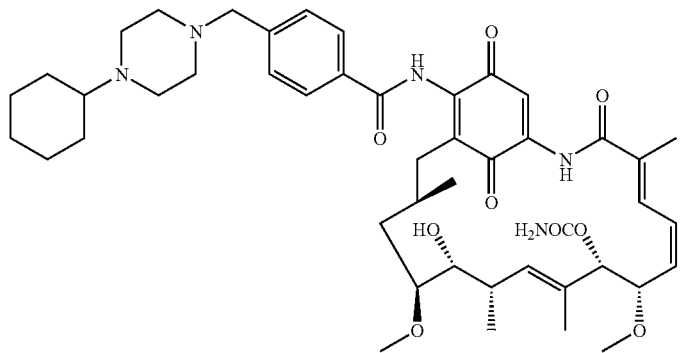
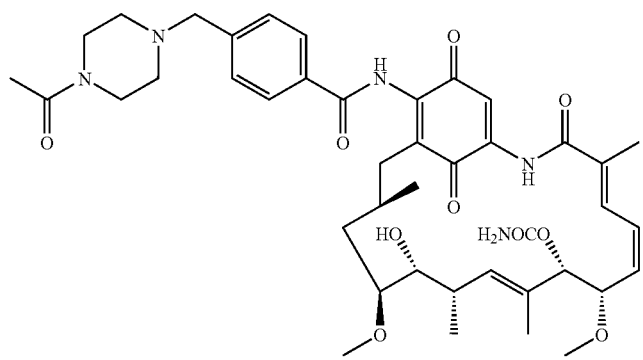
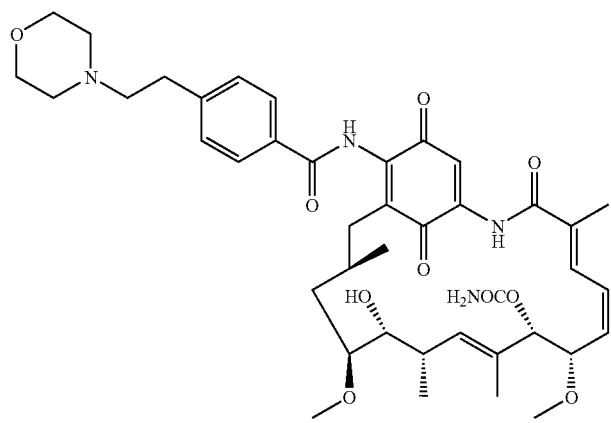
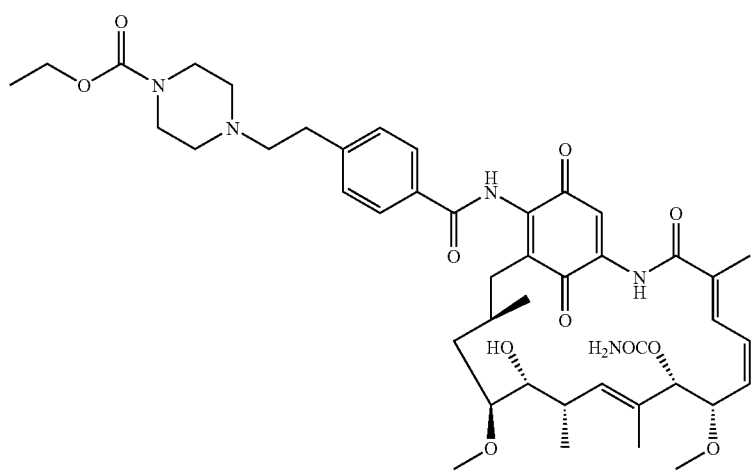

-continued
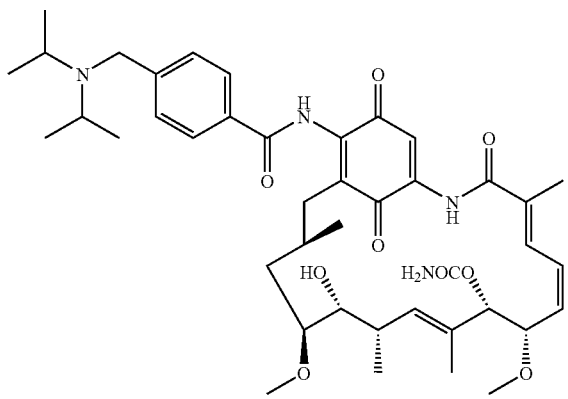
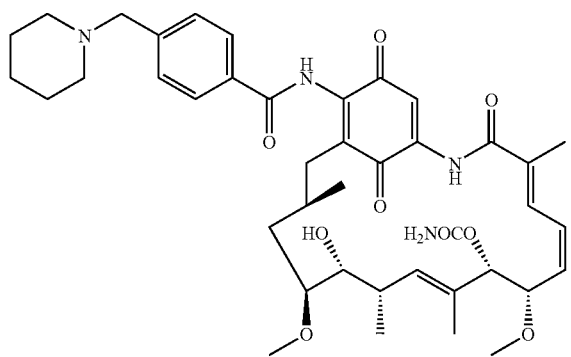
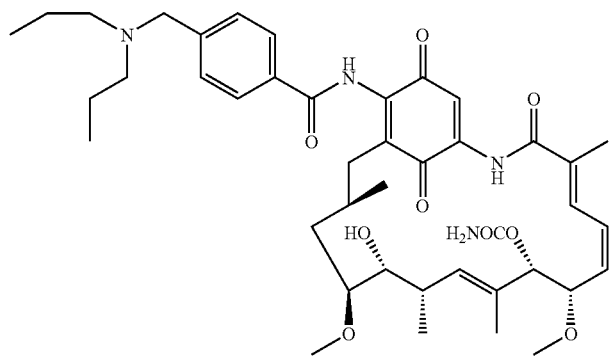
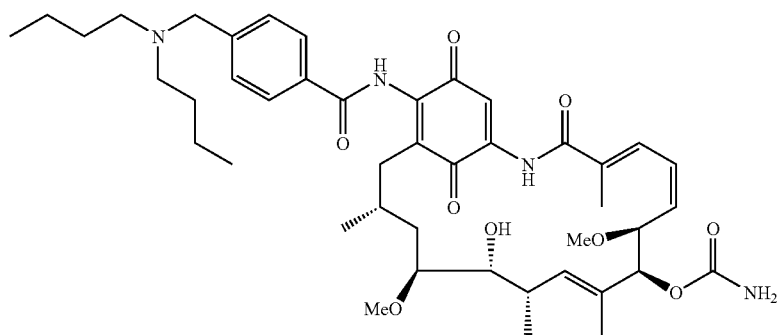

-continued
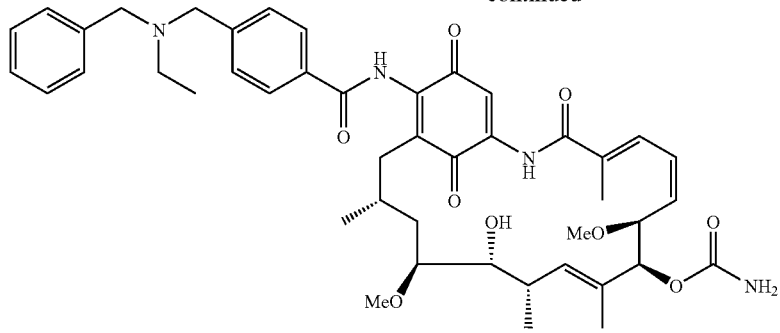
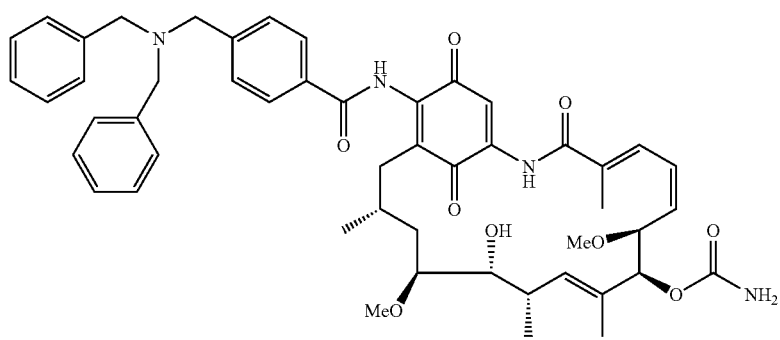
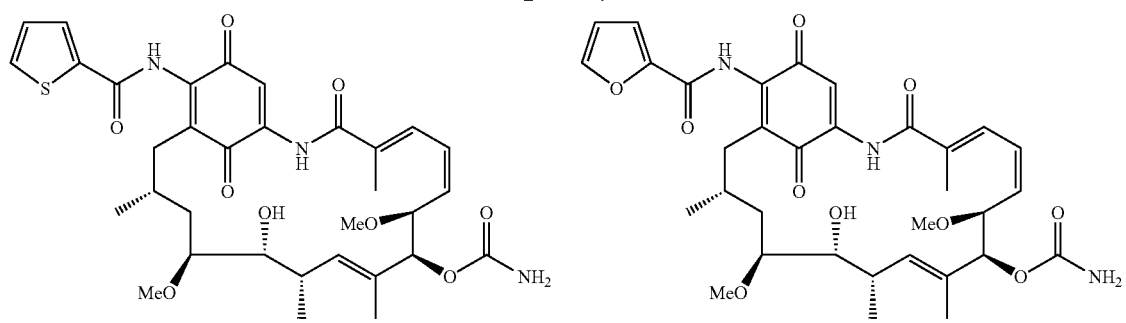
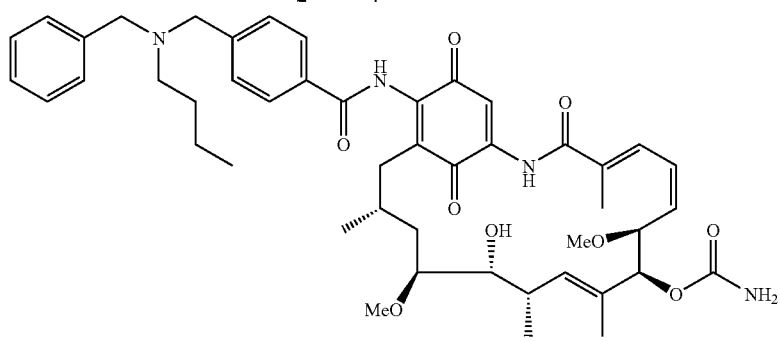
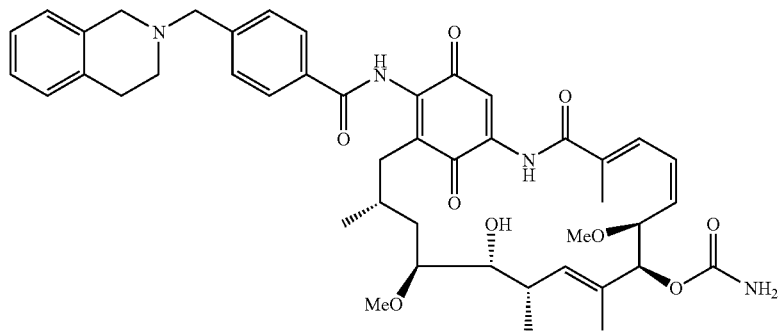

In some embodiments, the compound has a formula selected from the following group of formulas:
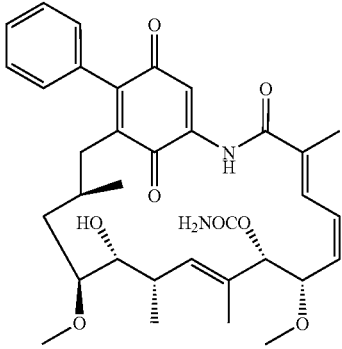
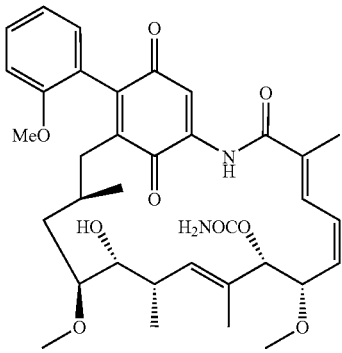
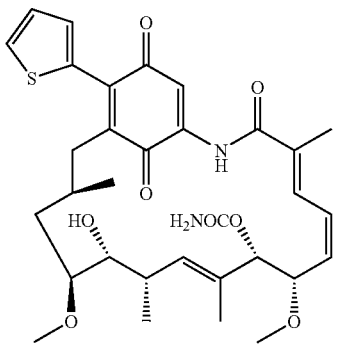
In some embodiments, the compound has a formula selected from the following group of formulas:
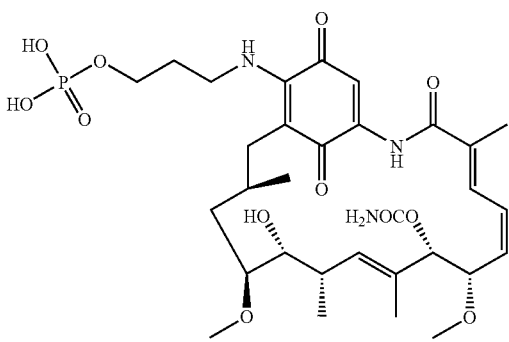
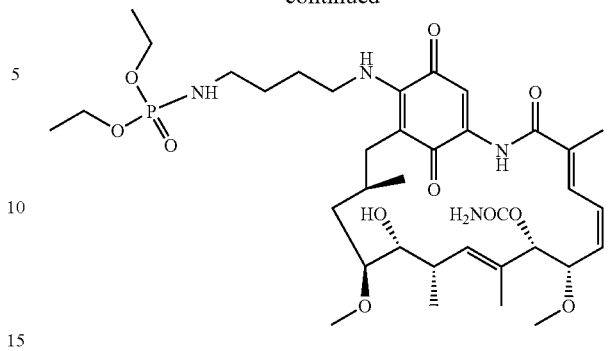
In some embodiments, X is —N(R$_9$)—C(O)—OR$_7$.
In some embodiments, the compound is selected from the group consisting of:
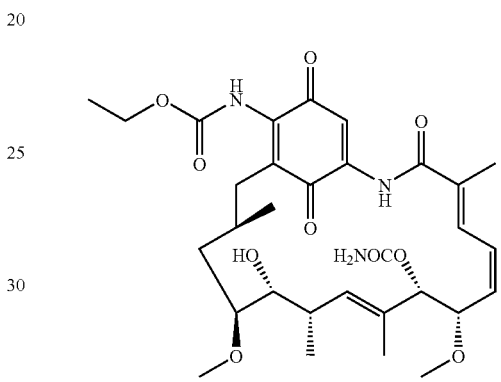
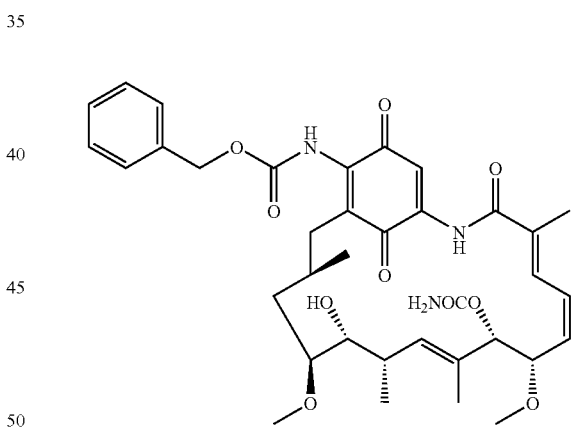
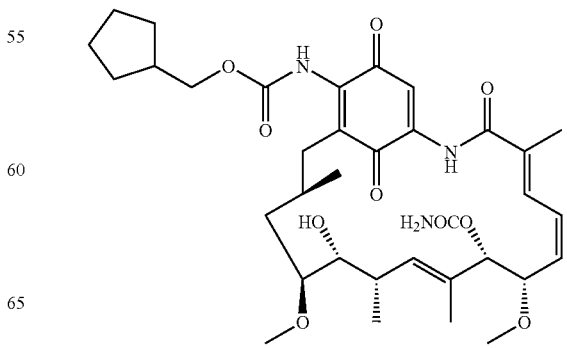

27
-continued
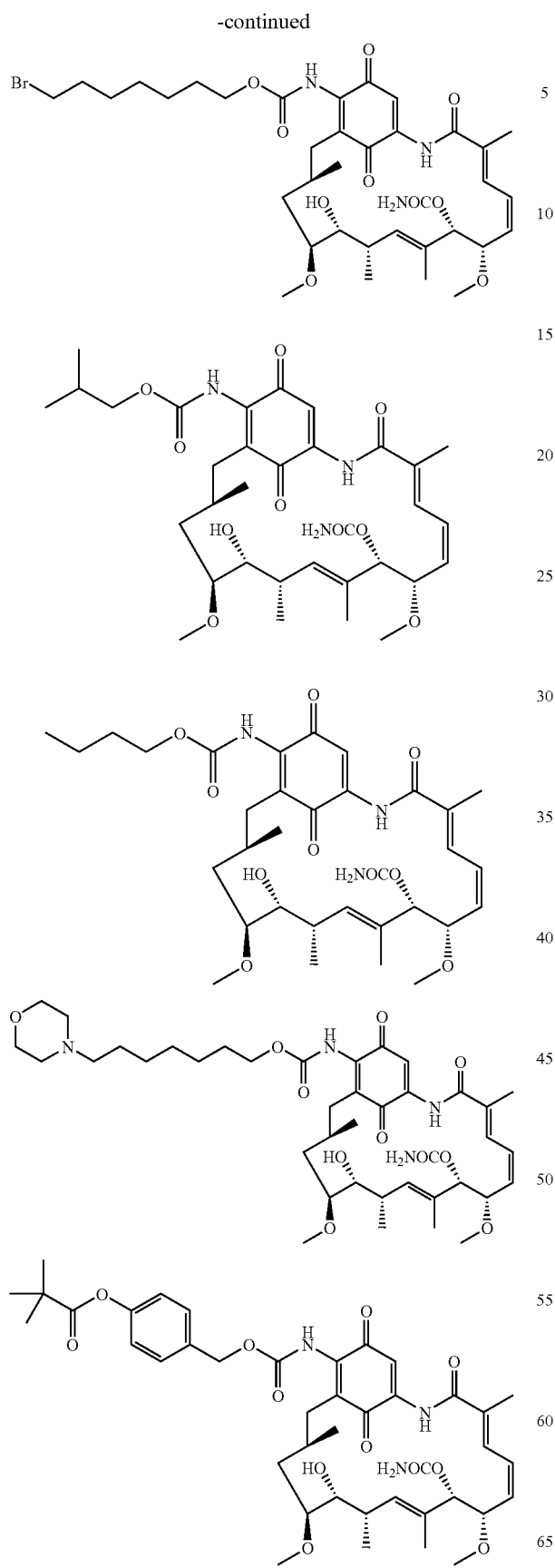
28
-continued
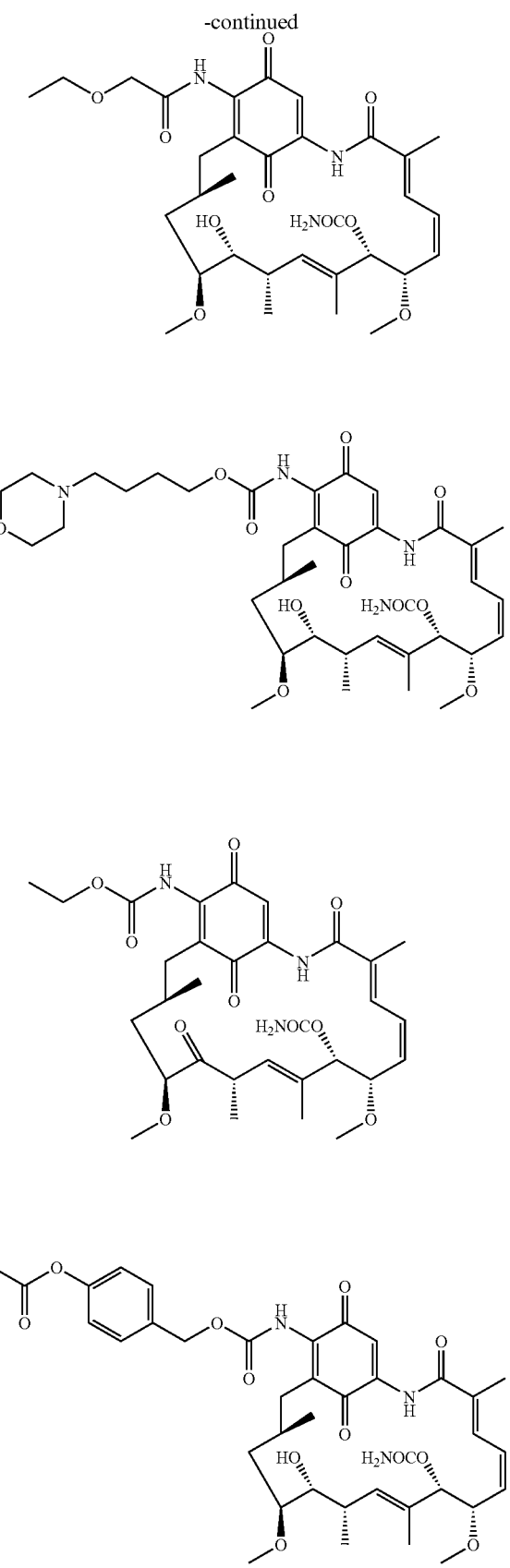

In some embodiments, the compound is selected from the group consisting of:
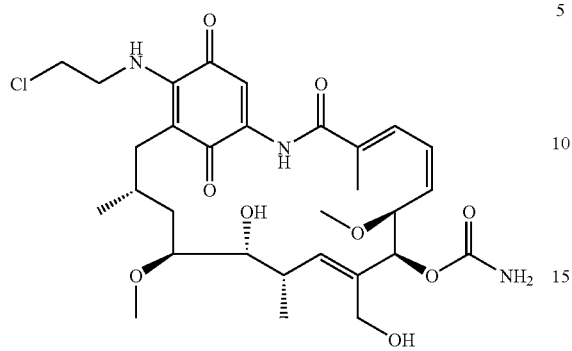
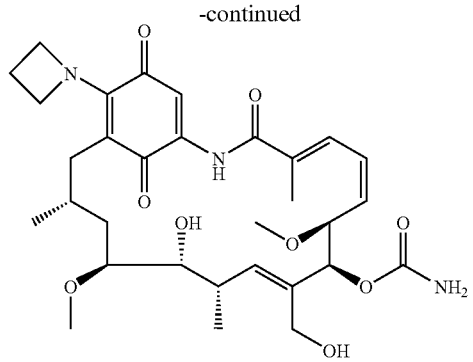
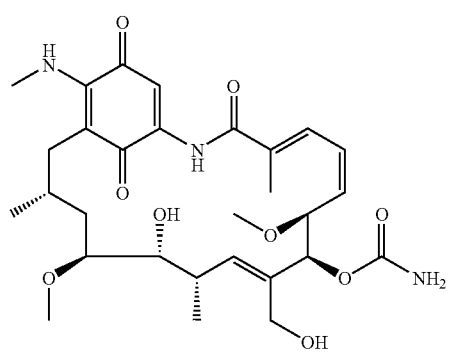
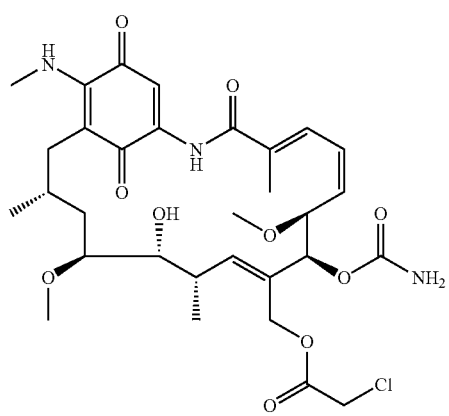
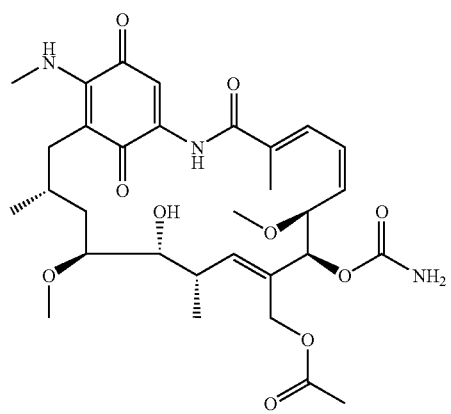
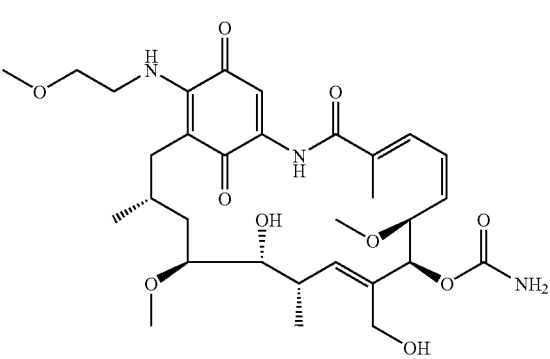
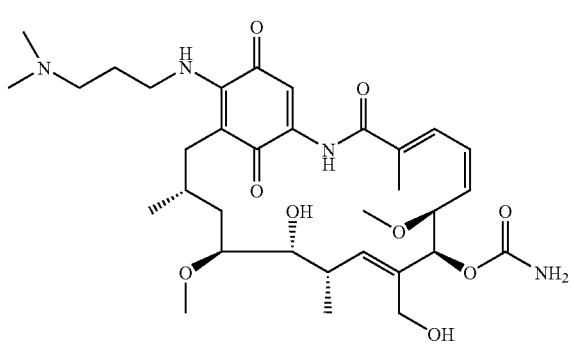
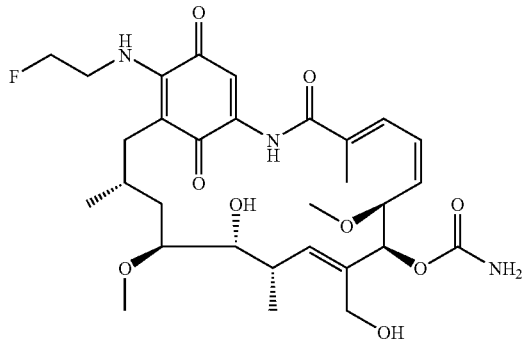

-continued
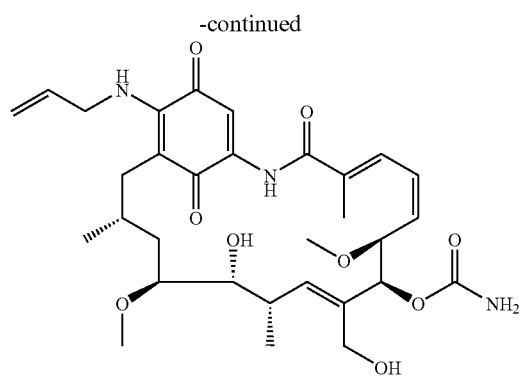
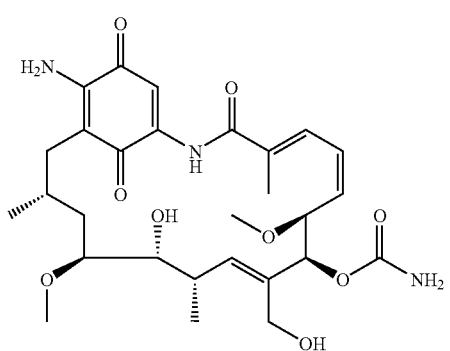
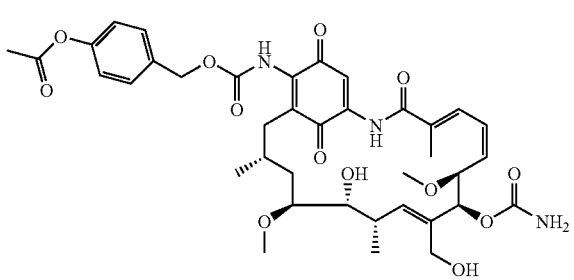
In some embodiments, the compound is selected from the group consisting of:
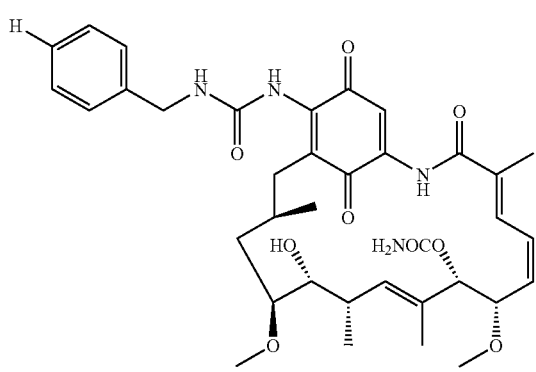
-continued
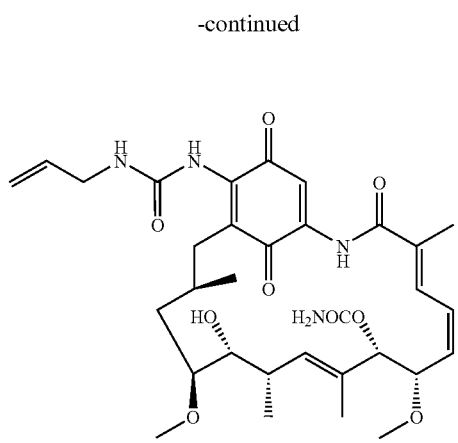
In some embodiments, the compound is selected from the group consisting of:
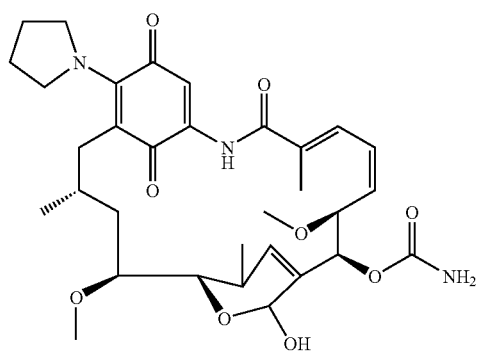
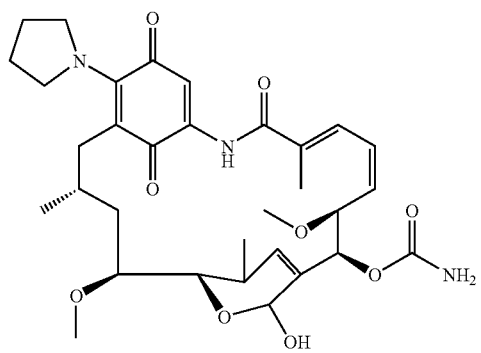

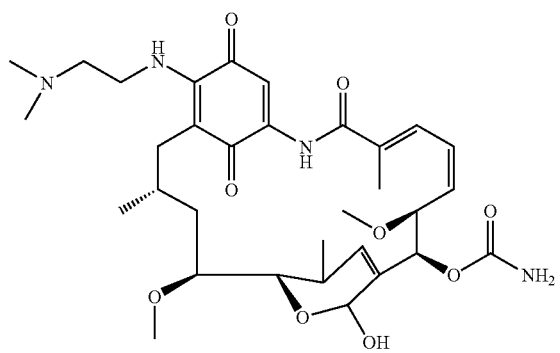
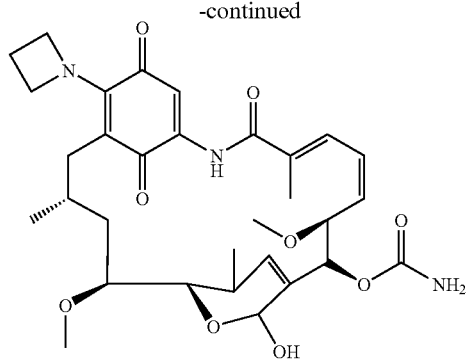
In some embodiments, the compound is selected from the group consisting of:
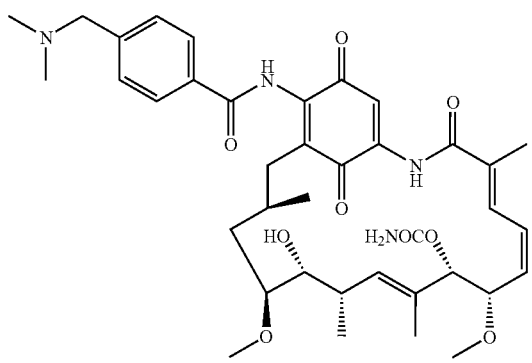
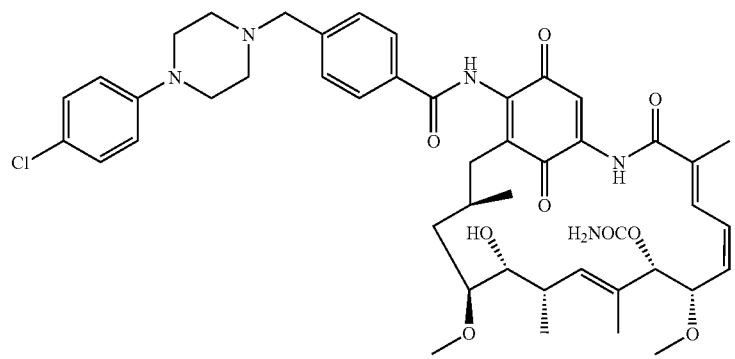
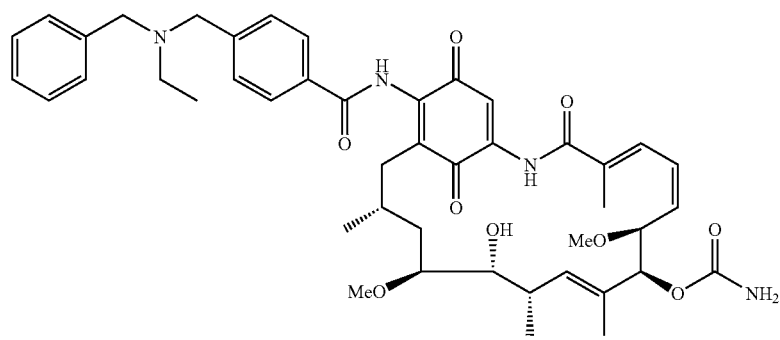

In some embodiments, X is —O R$_6$.
In some embodiments, the compound has formula:

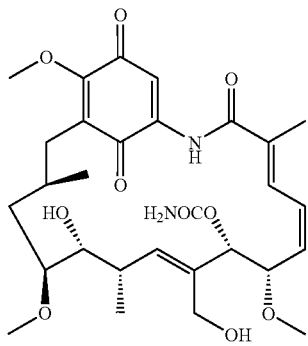

In some embodiments, the compound has formula:

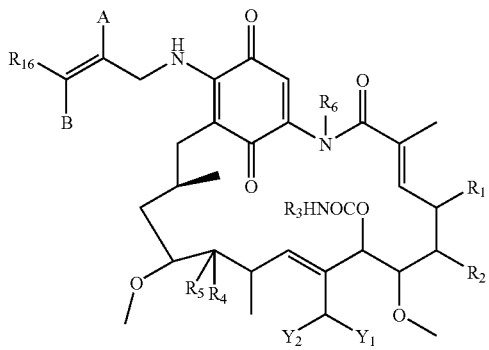

In another aspect the compound features compounds of formula (II):

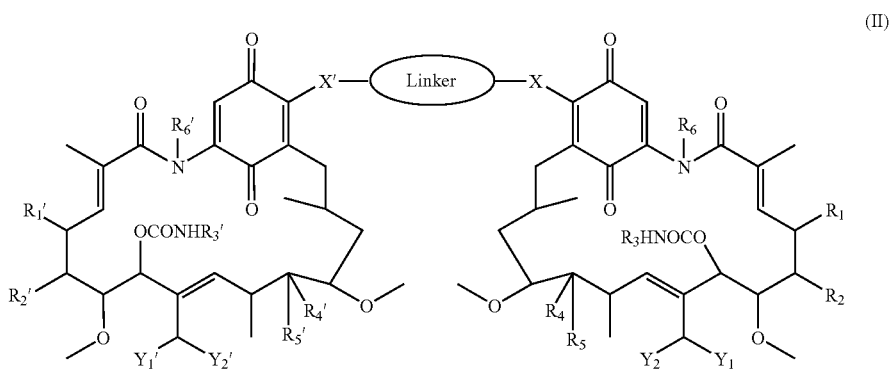

(II)

or pharmaceutically acceptable salts thereof, wherein

R$_1$ and R$_2$ are independently both H or together form a bond;

R$_1$' and R$_2$' are independently both H or together form a bond;

R$_3$ and R$_3$' are independently selected from the group consisting of H and optionally substituted C1-C6 alkyl;

R$_4$ and R$_5$ are independently selected from the group consisting of H, —OH, O-alkyl, O-acetyl, —O-aryl, OC(O)R$_{10}$, —S O$_2$—R$_{10}$, and —NH R$_{10}$, or together form oxo (=O), or hydroxylamino, alkoxyimine, or aryloxyimine, thioketo, wherein R$_{10}$ is selected from H, optionally substituted (C1-C20)alkyl, optionally substituted (C1-C20)heteroalkyl, optionally substituted aryl; and optionally substituted heteroaryl;

R$_4$' and R$_5$' are independently selected from the group consisting of H, —OH, O-alkyl, O-acetyl, -O-aryl, OC(O)R$_{10}$, —S O$_2$—R$_{10}$, and —NH R$_{10}$, or together form oxo (=O), or hydroxylamino, alkoxyimine, or aryloxyimine, thioketo, wherein R$_{10}$ is selected from H, optionally substituted (C1-C20)alkyl, optionally substituted (C1-C20)heteroalkyl, optionally substituted aryl; and optionally substituted heteroaryl;

R$_6$ and R$_6$' are independently selected from the group consisting of H, optionally substituted (C1-C6)alkyl, optionally substituted (C5-C10)aryl, and optionally substituted (C1-C6) acyl;

X and X' are independently selected from NR$_{11}$R$_{12}$, —N(CO)—, —N(R$_{13}$)—, —NC(O)—O—, —NC(S)—, —NC(O)N—, —NC(CH$_2$)—, —NC(NH)—, optionally substituted alkyl, optionally substituted alkenyl, optionally substituted alkynyl, optionally substituted aryl, optionally substituted heteroaryl, —O R$_{11}$—, and —S R$_{11}$—; wherein R$_{11}$ and R$_{12}$ are independently selected from optionally substituted (C1-C20)alkyl, optionally substituted (C2-C20)alkenyl, optionally substituted (C2-C20)alkynyl, optionally substituted aryl, optionally substituted heteroaryl, optionally substituted arylalkyl and optionally substituted cycloalkyl; and wherein R$_{13}$ is selected from the group consisting of H, optionally substituted (C1-C6)alkyl, optionally substituted (C5-C10)aryl, and optionally substituted (C1-C6)acyl; and wherein Y$_1$ and Y$_2$ are independently selected from the group consisting H, —OH, O-alkyl, O-acetyl, —O-aryl, OC(O)R$_{10}$, —S O$_2$—R$_{10}$, and —NH R$_{10}$, or together form oxo (=O), or hydroxylamino alkoxyimine or aryloxyimine, thioketo, wherein R$_{10}$ is selected from H, optionally substituted (C1-C20)alkyl, optionally substituted (C1-C20)heteroalkyl, optionally substituted aryl and optionally substituted heteroaryl;

or Y$_1$ or Y$_2$ taken with R$_4$ or R$_5$ form an optionally substituted 5-7 membered heterocyclic or carbocyclic ring; and the Linker is an optionally substituted 3-20 carbon atom chain having at least 1 heteroatom moiety in the chain, wherein said heteroatom moiety is optionally selected from the group consisting of —N R$_6$, —O—, —S—, —P—, sulfone, sulfonate, phosphonate, phosphate, and —Y—C(O)-Q-

C(O)—Y—, wherein Y is selected from O, S, and N, and wherein Q is selected from optionally substituted alkyl, optionally substituted aryl, and optionally substituted heteroaryl;

In some embodiments, the compound is a homodimer.
In some embodiments, the compound is a heterodimer.
In some embodiments, the compound has a formula selected from the group of formulas consisting of:

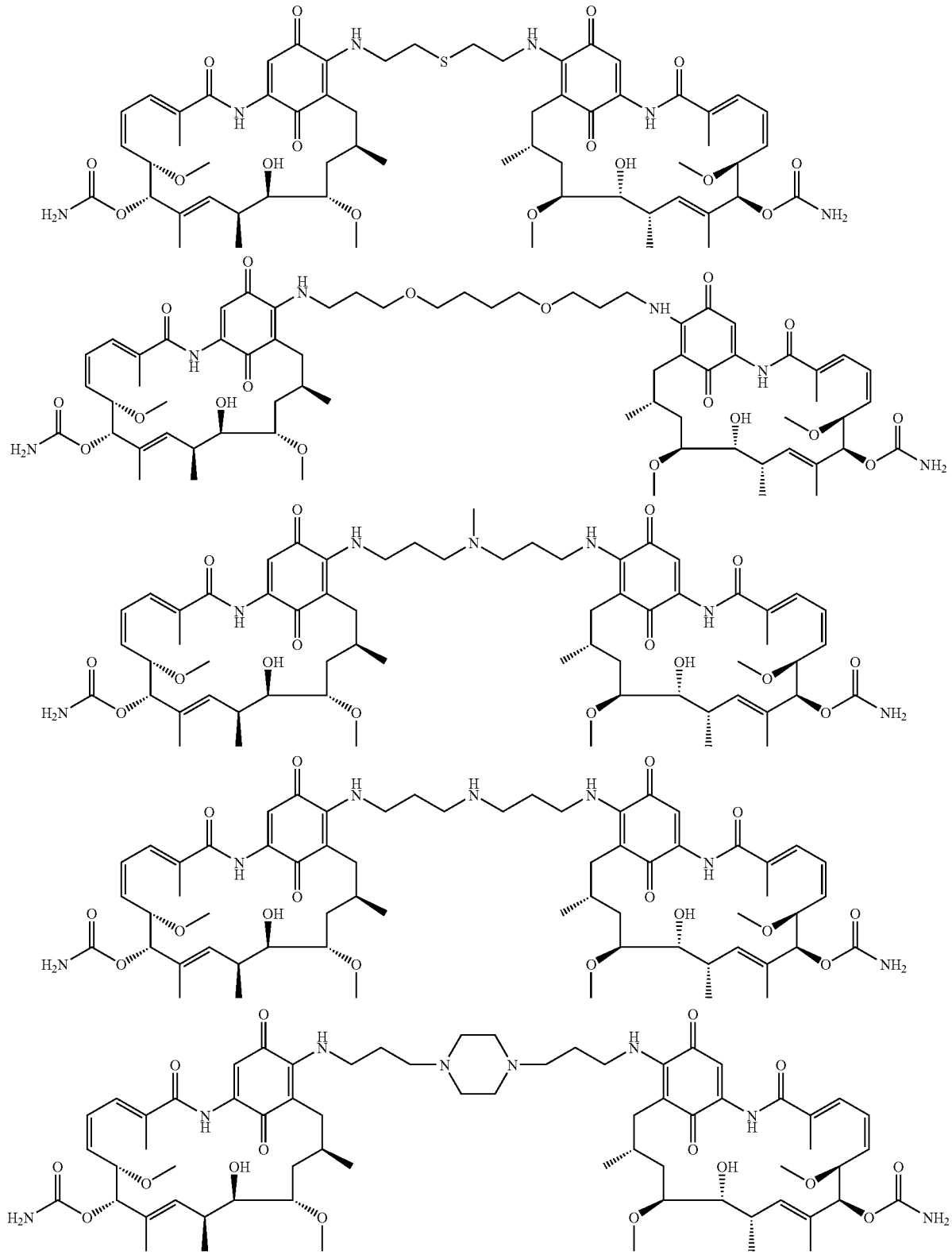

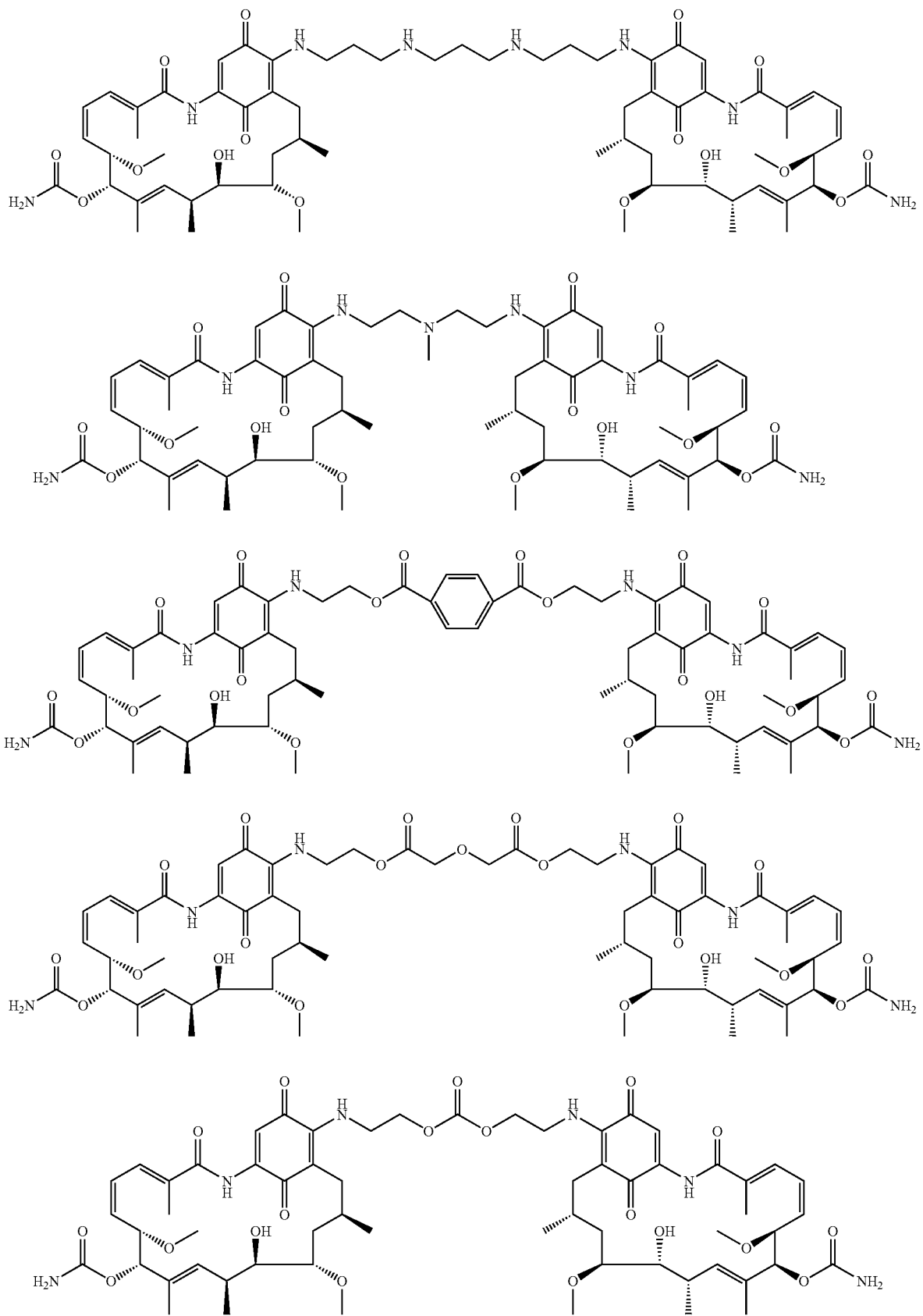

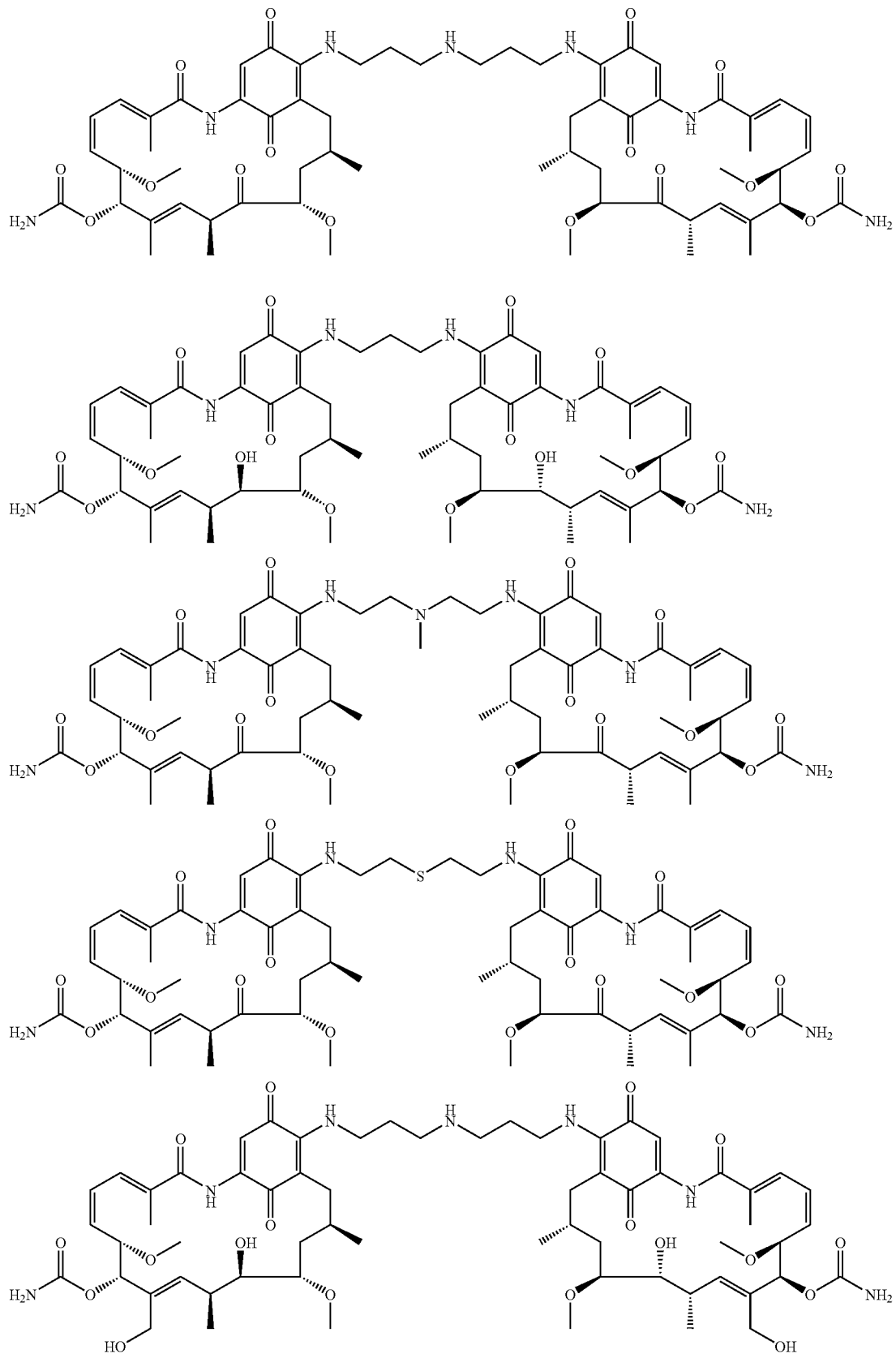

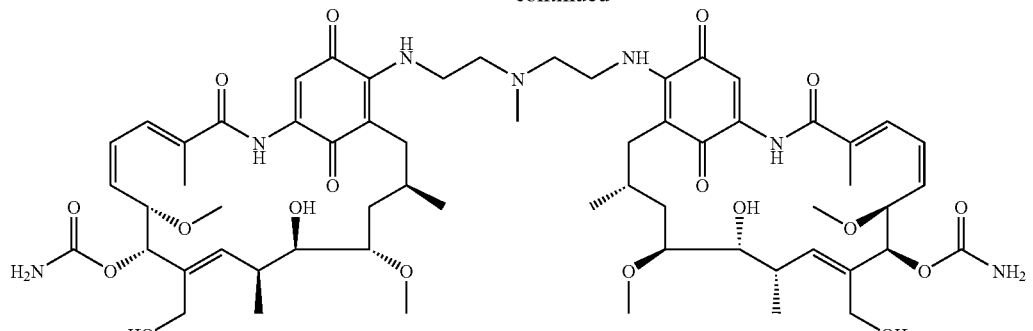
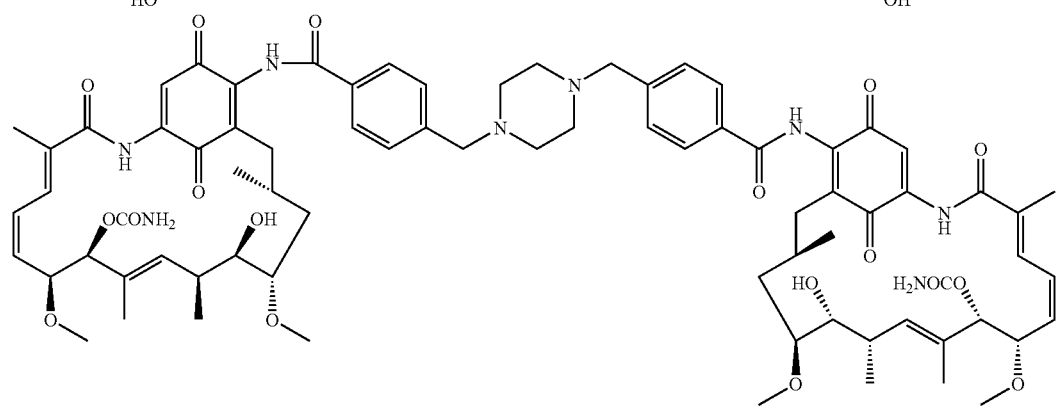
In some embodiments, the compound has a formula selected from the group of formulas consisting of:
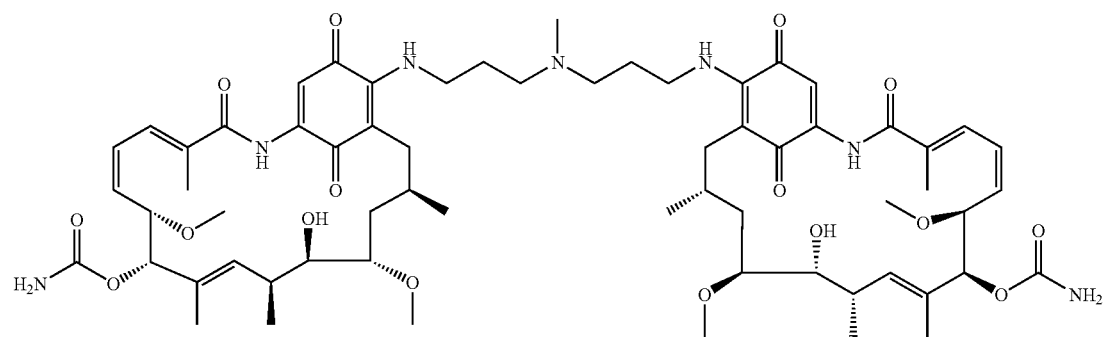
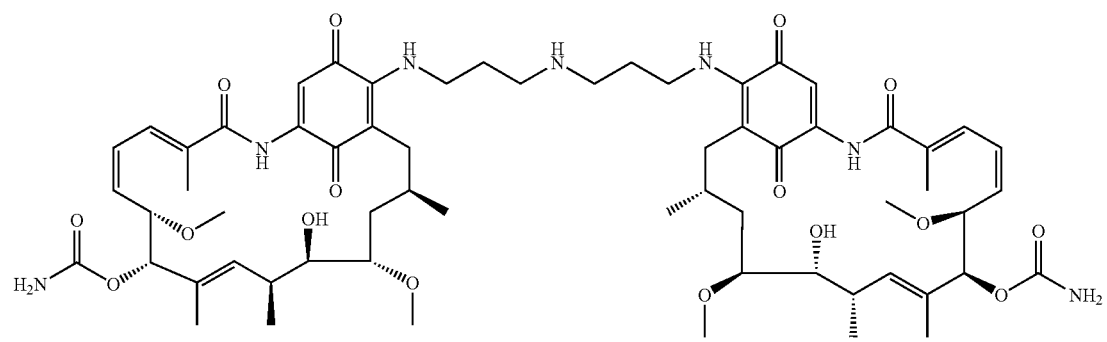

In some embodiments, the compound has a formula represented by formula:

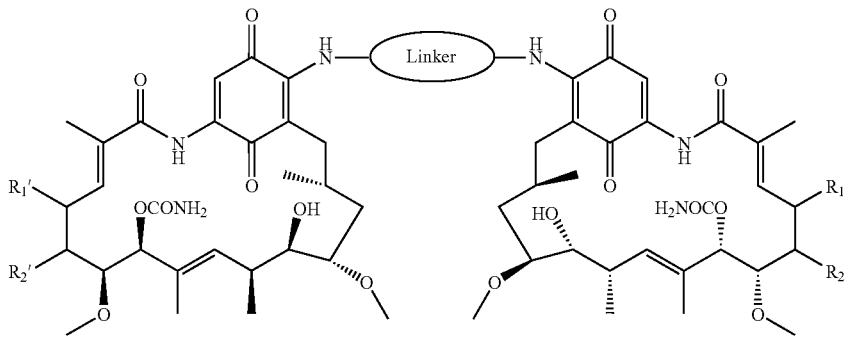

In another aspect, the invention features pharmaceutical compositions comprising a compound according to any one of the preceding aspects or embodiments, and further comprising one or more members selected from the group consisting of pharmaceutically acceptable excipients, carriers, bulking agents, salts, water, and alcohol.

In some embodiments, the composition is formulated for intravenous administration, and optionally disposed in a container member selected from the group consisting of vials and syringes.

In some embodiments, the pharmaceutical composition is formulated for oral administration, and optionally disposed in a container member selected from the group consisting of gel capsules, tablets, bottles, vials, and inhalers.

In another aspect, the invention features a method of treating or preventing a proliferative disorder that is sensitive to HSP90 inhibition, comprising contacting a cell characterized by or sought to be protected from a proliferative disorder sensitive to HSP90 inhibition with a pharmaceutically effective amount of a compound according to any one of the preceding aspects or embodiments.

In some embodiments, the cell is human and said proliferative disorder is selected from the group consisting of cancers and inflammatory disorders.

In some embodiments, the cancer is a breast cancer characterized by high levels of HER-2 and wherein said method further comprises monitoring the amount of HER-2 as a measure of the treatment or prevention of said breast cancer.

In some embodiments, the proliferative disorder is a genetically defined proliferative disorder characterized by a chromosomal aberration.

In some embodiments, the proliferative disorder is viral, fungal or bacterial-induced.

In some embodiments, the proliferative disorder is rheumatoid arthritis.

In another aspect, the invention features a synthetic scheme comprising the following steps:

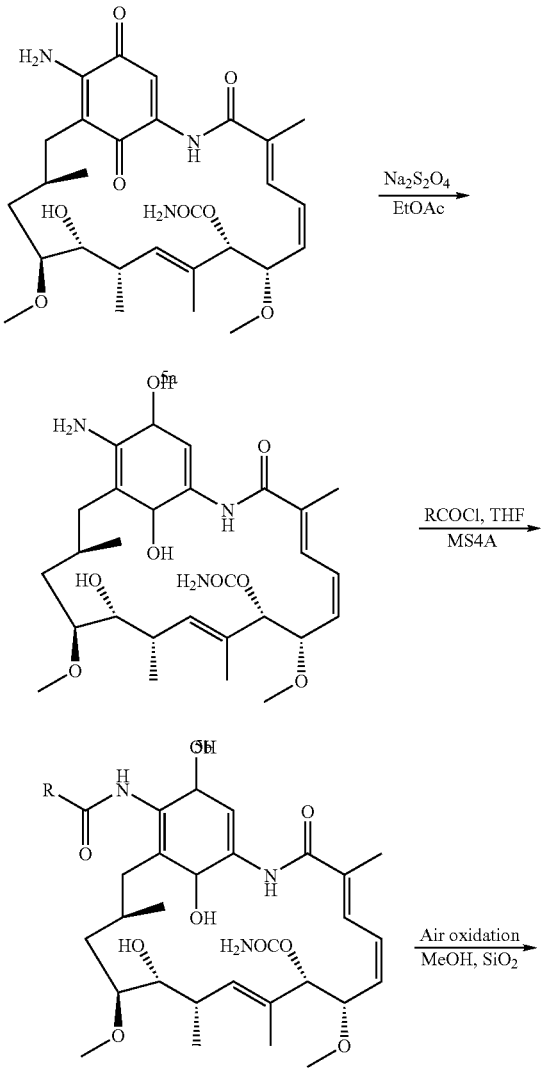

-continued

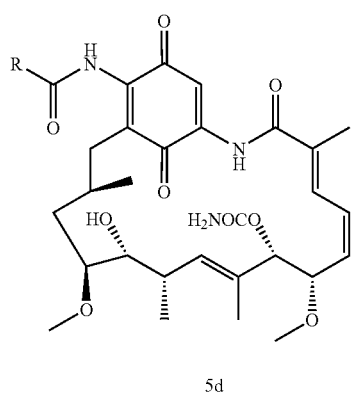

5d

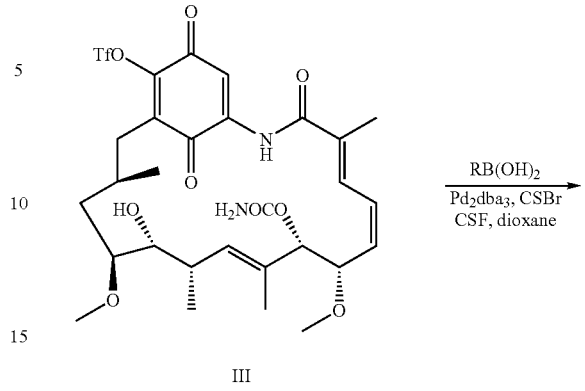

III (a) reducing a compound of formula 5a to form a compound of formula 5b;

(b) reacting the compound of formula 5b with an alkyl or aryl carboxyl halide or anhydride to form an amide compound of formula 5c; and (c) oxidizing the amide compound of formula 5c to produce the compound of formula 5d;

wherein R is $R_7$, $OR_7$, and $NR_7R_8$ from preceding aspects or embodiments.

In another aspect, the invention features a synthetic scheme comprising the following steps:

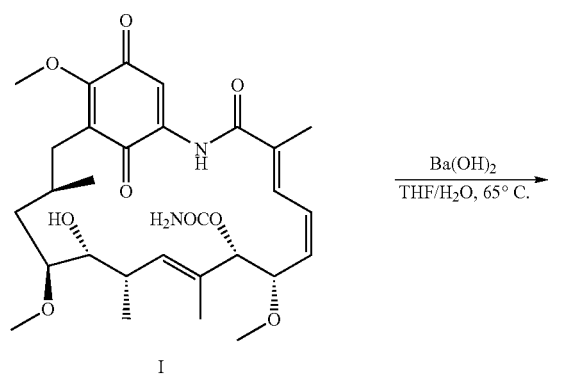

I

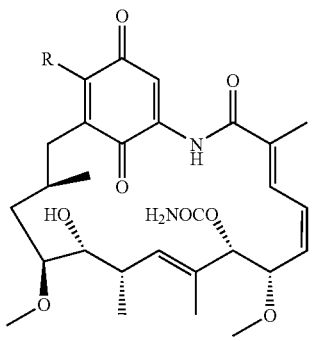

IV wherein R is optionally substituted (C1-C20)alkyl, optionally substituted (C1-C20)heteroalkyl, optionally substituted (C2-C20)alkenyl, optionally substituted (C2-C20)heteroalkenyl, optionally substituted (C2-C20)alkynyl, optionally substituted aryl, optionally substituted heteroaryl, optionally substituted arylalkyl, optionally substituted heteroarylalkyl, optionally substituted cycloalkyl, and optionally substituted cycloheteroalkyl.

In another aspect, the inventions feature ansamycins bound by ("derivatized with") TfO blocking groups. In some embodiments, the compound ansamycin is a benzoquinone ansamycin. In some embodiments, the ansamycin is derivatized with TfO at the 17 position. In some embodiments, the ansamycin has formula:

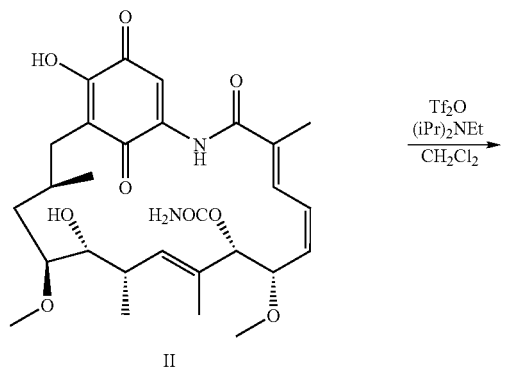

II

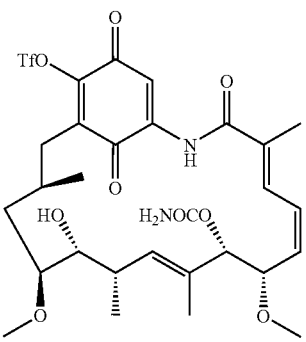

In another aspect, the invention features a method of treating or preventing a fibrogenetic disorder, comprising contacting a cell characterized by or sought to be protected from a fibrogenetic disorder a pharmaceutically effective amount of a compound according to preceding aspects or embodiments.

In another aspect, the invention features a method of treating or preventing oxidative-stress-induced cell death, comprising contacting a cell characterized by or sought to be protected from oxidative-stress-induced cell death a pharmaceutically effective amount of a compound according to preceding aspects or embodiments.

In another aspect, the invention features a method of treating or preventing a neurological injury, comprising contacting a cell characterized by or sought to be protected from a neurological injury a pharmaceutically effective amount of a compound according to preceding aspects or embodiments.

In another aspect, the invention features a method of reducing neurological injury resulting from cardiac arrest or stroke comprising administering to a patient suffering from cardiac arrest or stroke a composition comprising an effective amount of a compound according to preceding aspects or embodiments.

In some embodiments of the preceding method aspects, the composition is administered within two hours of cardiac arrest or stroke. In some embodiments of the preceding method aspects, the composition is administered by intravenous infusion. In some embodiments of the preceding method aspects, the composition is orally administered.

In another aspect, the invention features an article of manufacture comprising a container; said container having a pharmaceutical composition comprising a compound according to preceding aspects or embodiments and further comprising a label with instructions for use of said compound.

In some aspects, the invention features a method of treating or preventing infection, comprising contacting a cell that is infected or sought to be protected from infection with a pharmaceutically effective amount of a benzoquinoid ansamycin.

In some aspects, the invention features a method of treating or preventing infection, comprising contacting a cell that is infected or sought to be protected from infection with a pharmaceutically effective amount of a compound according to preceding aspects or embodiments. In some embodiments, the infection is caused by a virus selected from the group consisting of HIV, HTLV, HSV, HBV, HCV, ebola, retroviruses, rhinoviruses, hepatitis, VZV, HAV, CMV, adenovirus, influenza, flaviviruses, echovirus, coxsackle virus, comovirus, respiratory syncytial virus, mumps virus, rotavirus, measles virus, rubella virus, parvovirus, vaccinia virus, dengue virus, papillomavirus, molluscum virus, poliovirus, rabies virus, JC virus, arboviral encephalitis virus, arenaviruses, bunyaviruses, coronaviruses, hepadnaviruses, Epstein-Barr virus, cytomegalovirus, flaviviruses, orthomyxoviruses, paramyxoviruses, picomoviruses, polyomaviruses, poxviruses, reovirus, rhabdoviruses, rotaviruses, togaviruses, rabies, vesicular stomatitis, reovirus, vaccinia, measles virus, cytomegalovirus, sindbis virus, leukemia, polyoma virus, Rous sarcoma Virus (RSV), BK virus, JC virus, mouse mammary tumor virus (MMTV), alphavirus junction region, Varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackle virus, mumps virus, measles virus, rubella virus and polio virus.

In some embodiments, the virus is selected from HIV, HSV, rhinoviruses or ebola.

In another aspect, the invention features treatment of HIV using compounds selected from the group:

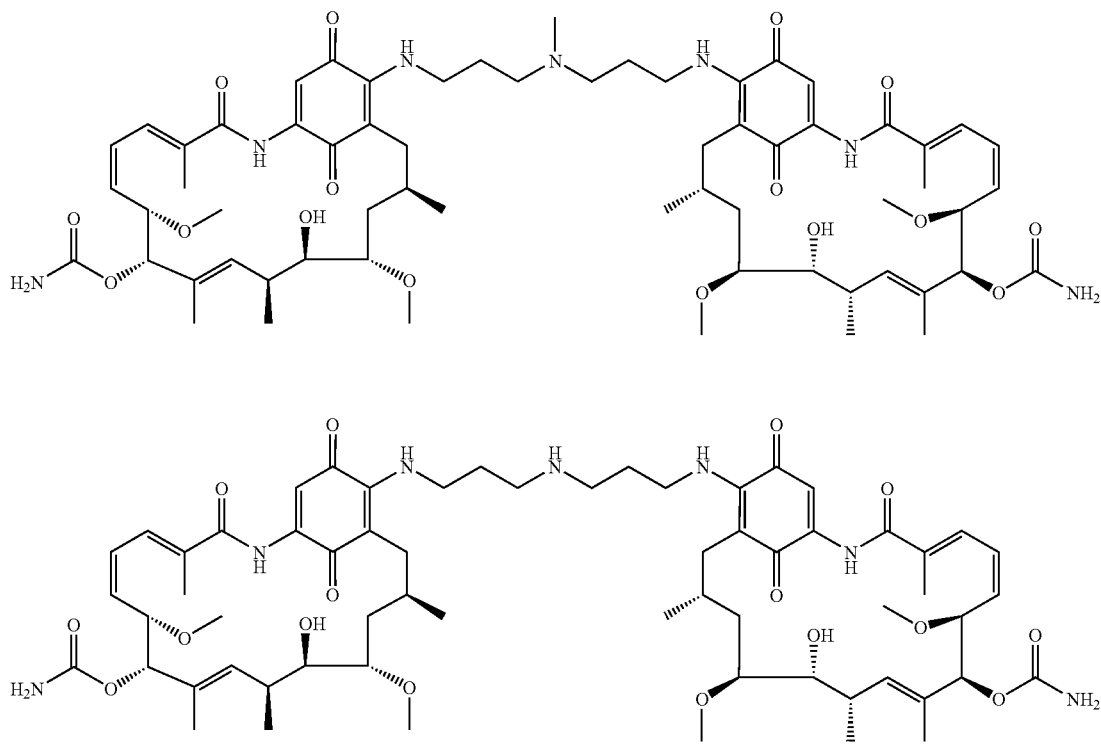

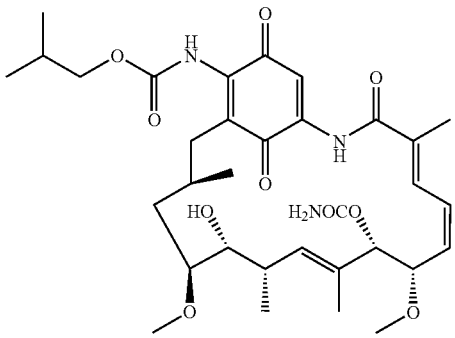

In some aspects, the invention features a method of treatment of HIV comprising administering a pharmaceutically effective amount of a compound selected from the group of:

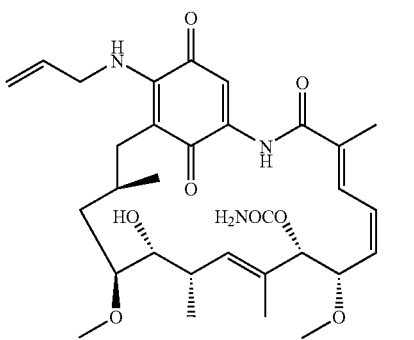
17-AAG

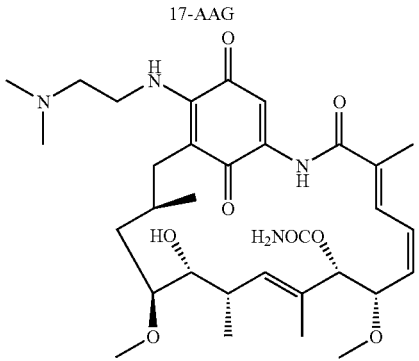
DMAG

Other aspects include pharmaceutical compositions comprising a compound according to any one of the preceding aspects or embodiments and further comprising one or more members selected from the group consisting of pharmaceutically acceptable salts, excipients, carriers, bulking agents, water, and alcohol. The pharmaceutical composition can be formulated for any type of administration, e.g., intravenous, oral, etc. and may be disposed in a container member such as a vial or syringe.

In another aspect, the invention features methods of using the above compounds, e.g., to treat and/or prevent proliferative disorders that are reliant on HSP90 or otherwise sensitive to HSP90 inhibition. The methods include contacting a cell with an effective amount of a compound according to any of the preceding structures and genuses. The cell can be any organism having an HSP90 of HSP90 analog that can be inhibited. The organism can be plant or animal, but is preferably animal, and more preferably still human. The proliferative disorder is selected from the group consisting of cancers, inflammatory disorders such as rheumatoid arthritus, and bacterial, yeast, fungal, and viral infections (e.g., HIV, HSV, HBV, HCV, retroviruses, etc.). Bacterial, yeast, fungal and viral infections are collectively "pathogens". In some preferred embodiments, the proliferative disorder is a breast cancer characterized by high levels of HER-2. In other embodiments, the proliferative disorder is a genetically defined proliferative disorder characterized by a chromosomal aberration.

In other aspects, the invention features methods of treating and/or preventing fibrogenetic disorders including but not limited to scleroderma, polymyositis, systemic lupus, rheumatoid arthritis, liver cirrhosis, keloid formation, interstitial nephritis, and pulmonary fibrosis.

In still other aspects, the invention features methods of treating and/or preventing oxidative-stress-induced cell death and neurological injury such as might occur from cardiac arrest, stroke, and ischemia 1. The compositions may be administered at any time preceding or following oxidative-stress-induced cell death and neurological injury, preferably within 2 hours of such. The route of administration may be any type. The methods can be "in vitro", e.g., contacting a cell line in culture, or else can be "in vivo", e.g., contacting a cell or cells that are contained within or on a live multicellular organism. One type of in vivo administration is made "in situ", or directly to a specific cell or group of cells within an organism, e.g., intratumorally. "Ex vivo" procedures are also envisioned wherein the cells are first removed from a patient, treated by contacting them with the compounds or compositions of the invention, and then administered back to a patient. The compounds and compositions can be administered in a variety of ways, e.g. intravenously, parenterally, orally, bucally, intramuscularly, sublingually, topically, by aerosol, subcutaneously, intramuscularly, intraperitoneally, rectally, vaginally, intratumorally, or peritumorally.

In still other aspects, the invention features articles of manufacture that include any of the compounds above that are packaged and optionally supplied with labels and instructions for use.

In another aspect, the invention features various synthetic schemes for producing compounds of the invention, as described in the examples. Although the schemes are illustrated using geldanamycin as starting ansamycin, it will be clear that other ansamycins can also be used as starting reagent. The ansamycin starting reagents are preferably, although not necessarily, benzoquinone ansamycins.

Each aspect of the invention may assume any embodiment consistent with any other aspect of the invention.

Some specific species embodiments of the invention include compounds having the formulas depicted in the following table, some of which exhibit improved water solubility, some of which bode utility as prodrugs, and some of which bode both utilities:

TABLE 1

| Compound # | Formula |
|---|---|
| 133 | |
| 207 | |
| 208 | |
| 212 | |

TABLE 1-continued

| Compound # | Formula |
|---|---|
| 232 | |
| 237 | |
| 481 | |
| 482 | |

TABLE 1-continued
| Compound # | Formula |
|---|---|
| 483 | 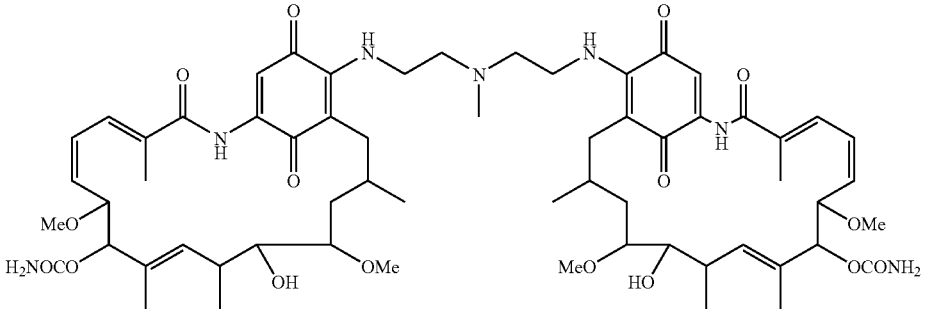 |
| 484 | 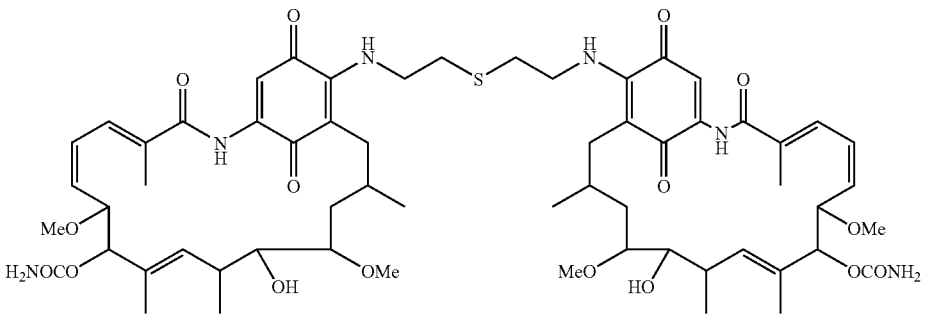 |
| 486 | 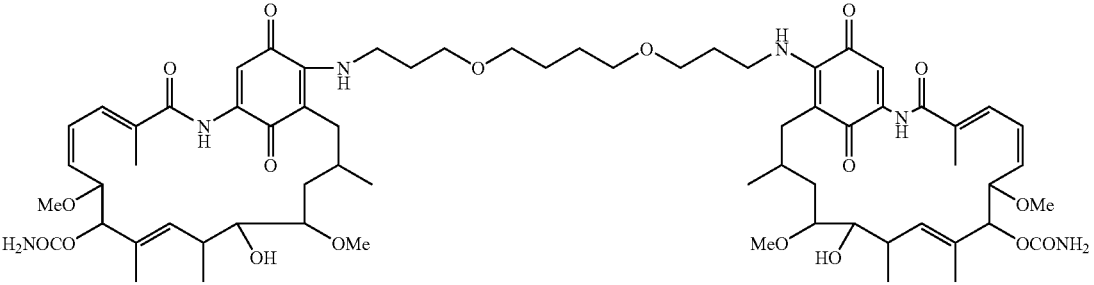 |
| 487 | 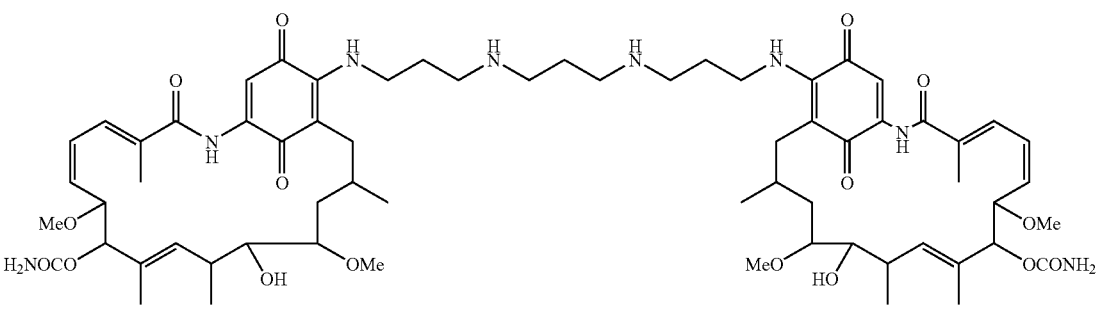 |

TABLE 1-continued
| Compound # | Formula |
|---|---|
| 495 | 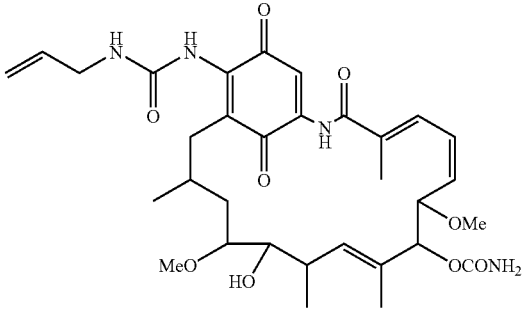 |
| 513 | 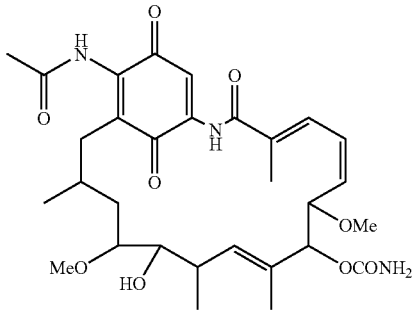 |
| 514 | 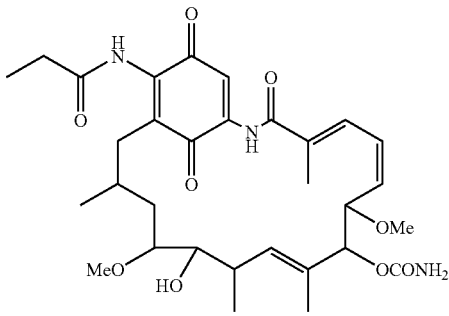 |
| 515 | 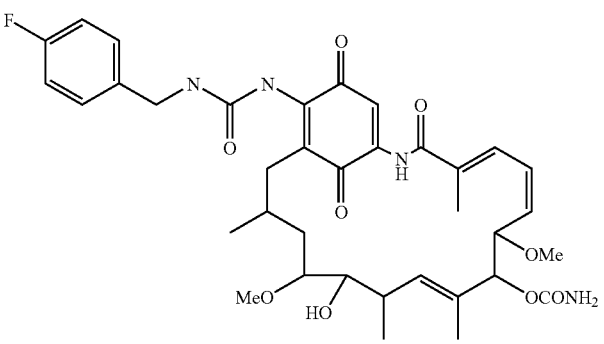 |

TABLE 1-continued
| Compound # | Formula |
|---|---|
| 529 | 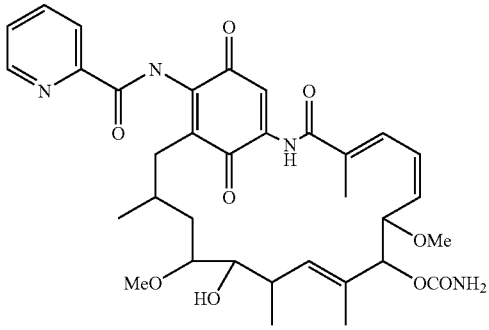 |
| 530 | 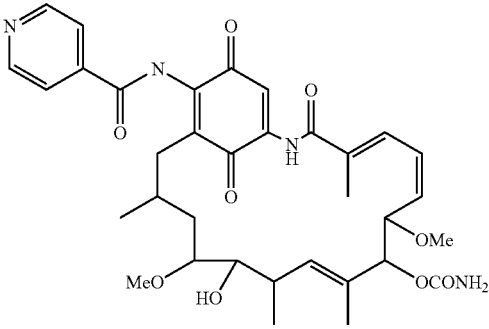 |
| 556 | 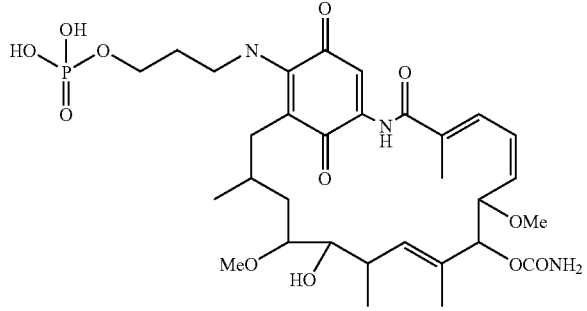 |
| 557 | 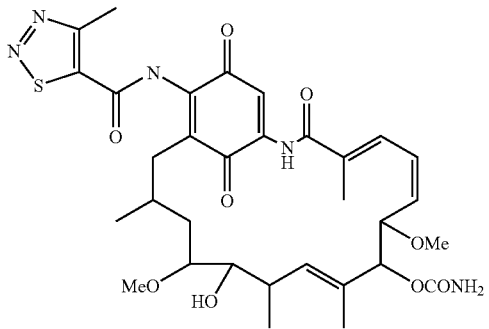 |

TABLE 1-continued

| Compound # | Formula |
|---|---|
| 558 | |
| 559 | |
| 560 | |
| 561 | |

TABLE 1-continued
| Compound # | Formula |
|---|---|
| 562 | 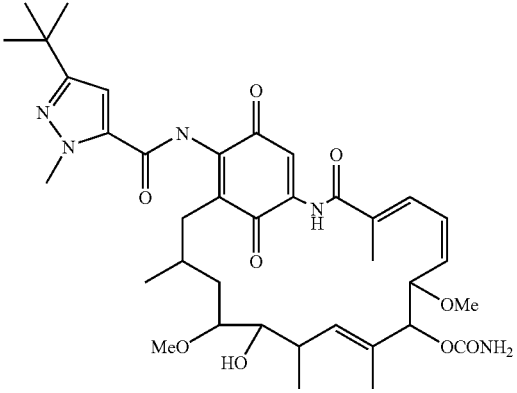 |
| 563 | 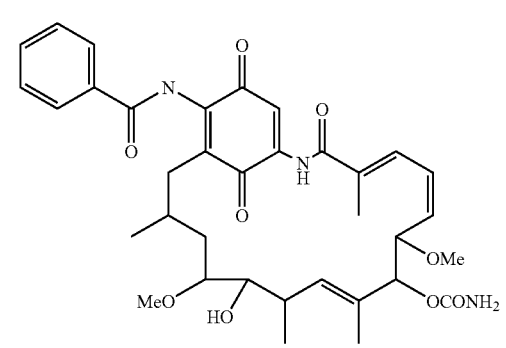 |
| 594 | 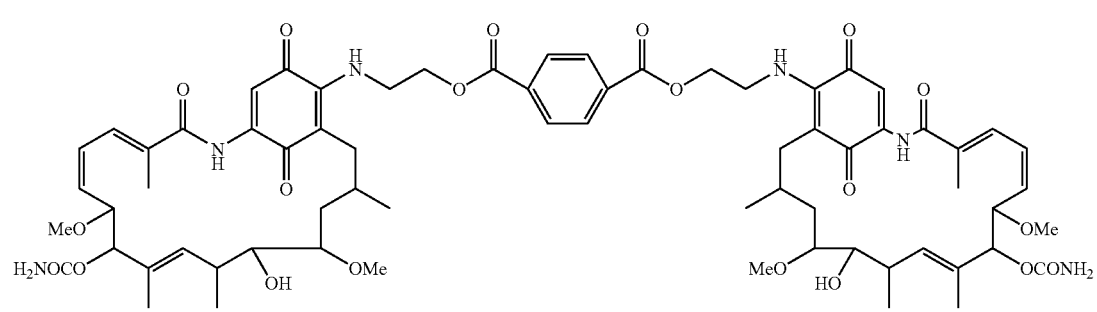 |
| 635 | 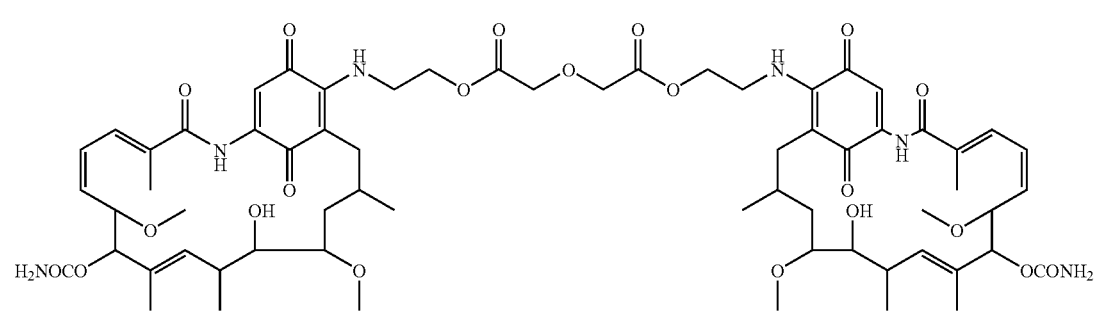 |

TABLE 1-continued

| Compound # | Formula |
|---|---|
| 656 | |
| 687 | |
| 696 | |
| 697 | |

TABLE 1-continued

| Compound # | Formula |
|---|---|
| 709 | |
| 713 | |
| 723 | |
| 736 | |

TABLE 1-continued

| Compound # | Formula |
|---|---|
| 737 | |
| 748 | |
| 749 | |
| 750 | |

TABLE 1-continued

| Compound # | Formula |
|---|---|
| 760 | |
| 765 | |
| 766 | |
| 777 | |

TABLE 1-continued

| Compound # | Formula |
|---|---|
| 822 | |
| 840 | |
| 841 | |
| 842 | |

TABLE 1-continued

| Compound # | Formula |
|---|---|
| 846 | |
| 847 | |
| 850 | |
| 861 | |

TABLE 1-continued

| Compound # | Formula |
|---|---|
| 863 | |
| 864 | |
| 865 | |
| 867 | |

TABLE 1-continued

| Compound # | Formula |
|---|---|
| 868 | |
| 914 | |
| 915 | |
| 950 | |

TABLE 1-continued

| Compound # | Formula |
|---|---|
| 951 | |
| 952 | |
| 956 | |
| 959 | |

| Compound # | Formula |
|---|---|
| 960 | |
| 964 | |
| 965 | |
| 967 | |

TABLE 1-continued
| Compound # | Formula |
|---|---|
| 970 | 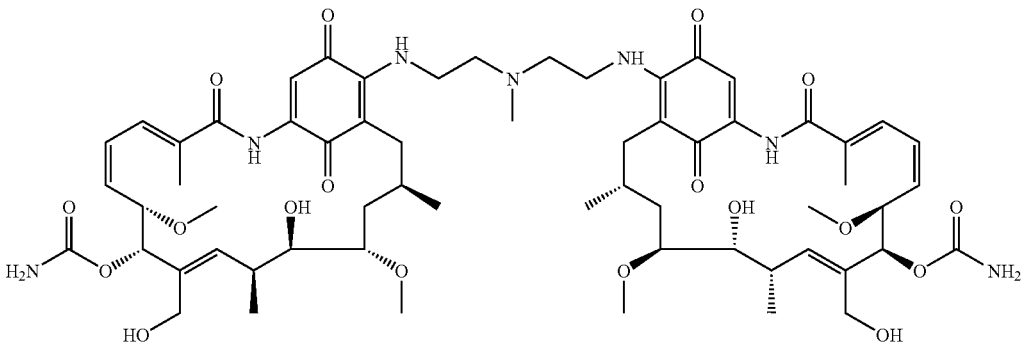 |
| 979 | 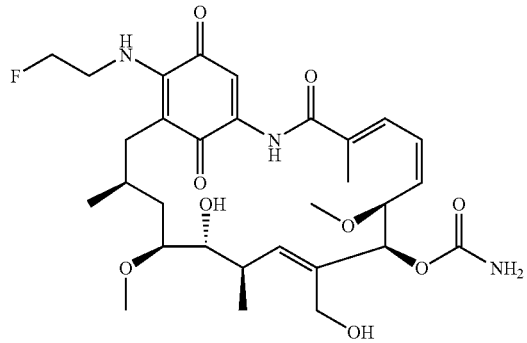 |
| 981 | 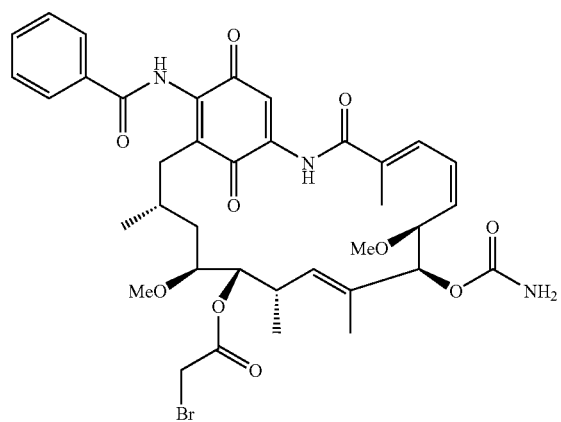 |

TABLE 1-continued

| Compound # | Formula |
|---|---|
| 982 | |
| 983 | |
| 984 | |

TABLE 1-continued

| Compound # | Formula |
|---|---|
| 985 | |
| 996 | |
| 1011 | |

TABLE 1-continued

| Compound # | Formula |
|---|---|
| 1012 | |
| 1013 | |
| 1026 | |
| 1046 | |

TABLE 1-continued

| Compound # | Formula |
| --- | --- |
| 1048 | |
| 1059 | |
| 1060 | |
| 1066 | |

TABLE 1-continued

| Compound # | Formula |
|---|---|
| 1078 | |
| 1102 | |
| 1126 | |
| 1140 | |

TABLE 1-continued
| Compound # | Formula |
|---|---|
| 1143 | 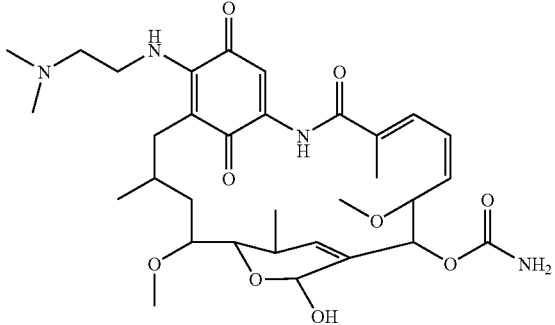 |
| 1148 | 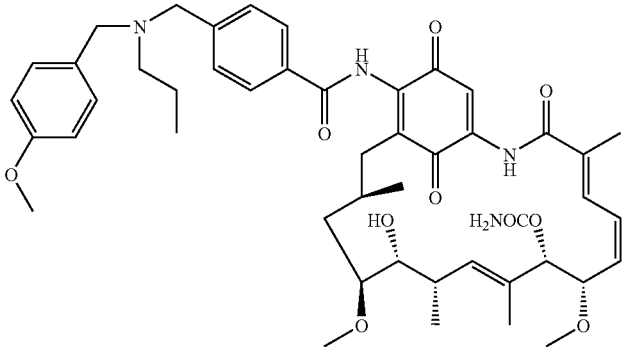 |
| 1149 | 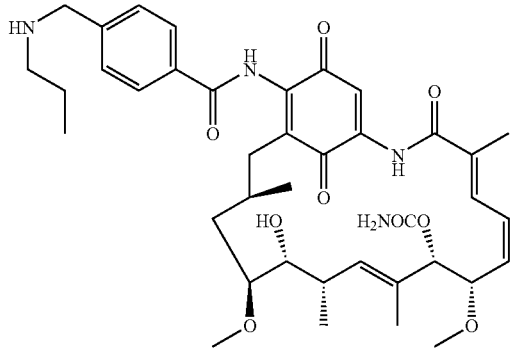 |
| 1058 | 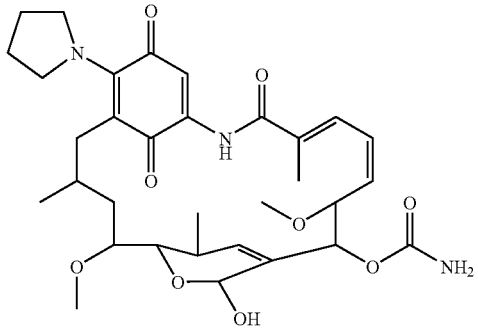 |

TABLE 1-continued

| Compound # | Formula |
|---|---|
| 1168 | |
| 1169 | |
| 1170 | |
| 1171 | |

TABLE 1-continued

| Compound # | Formula |
|---|---|
| 1172 | |
| 1188 | |
| 1189 | |

TABLE 1-continued

| Compound # | Formula |
|---|---|
| 1203 | |
| 1205 | |
| 1219 | |
| 1235 | |

TABLE 1-continued

| Compound # | Formula |
|---|---|
| 1236 | |
| 1237 | |
| 1238 | |
| 1239 | |

TABLE 1-continued

| Compound # | Formula |
|---|---|
| 1252 | |
| 1253 | |

Depending on the specific aspect and/or embodiment, advantages realized by the invention include one or more of better aqueous solubility (which increases biological exposure in vivo and ease of formulation), prodrug utility (insofar as at least some of compounds and compositions described herein have the ability to release active drug substance in vivo), distinct biological profiles, and improved chemical stability. With regard to the latter, many of the compounds and compositions described herein exhibit longer half-lives in vivo as compared to previously described ansamycins, thus allowing for higher and/or more consistent drug concentrations in the blood and less frequent administration.

Other aspects, embodiments and advantages of the invention will be clear to one of ordinary skill in the art from the drawings, description and claims to follow.

DETAILED DESCRIPTION OF THE INVENTION

Figure 1:
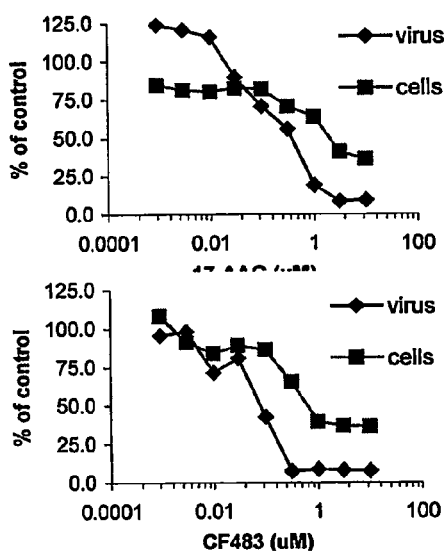
FIG. 1 shows HIV replication inhibition using nanomolar quantities of ansamycins.
Figure 1:
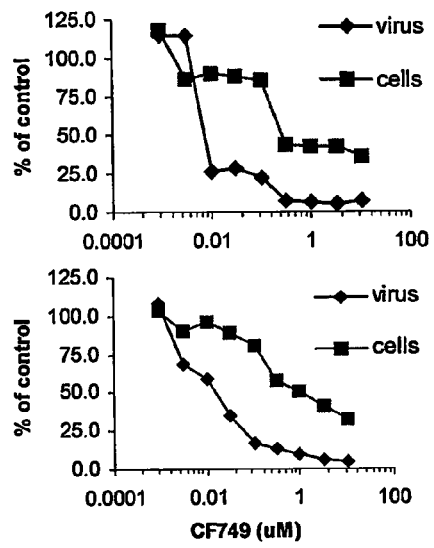
Figure 1:
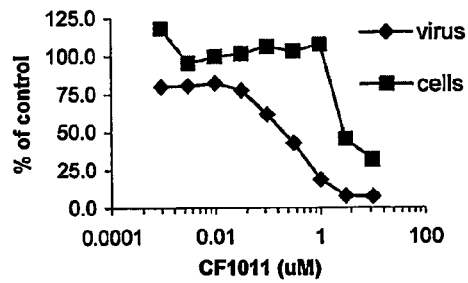
Figure 1:
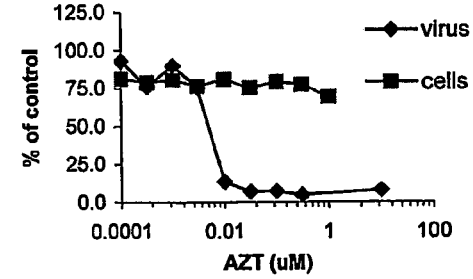
Figure 2:
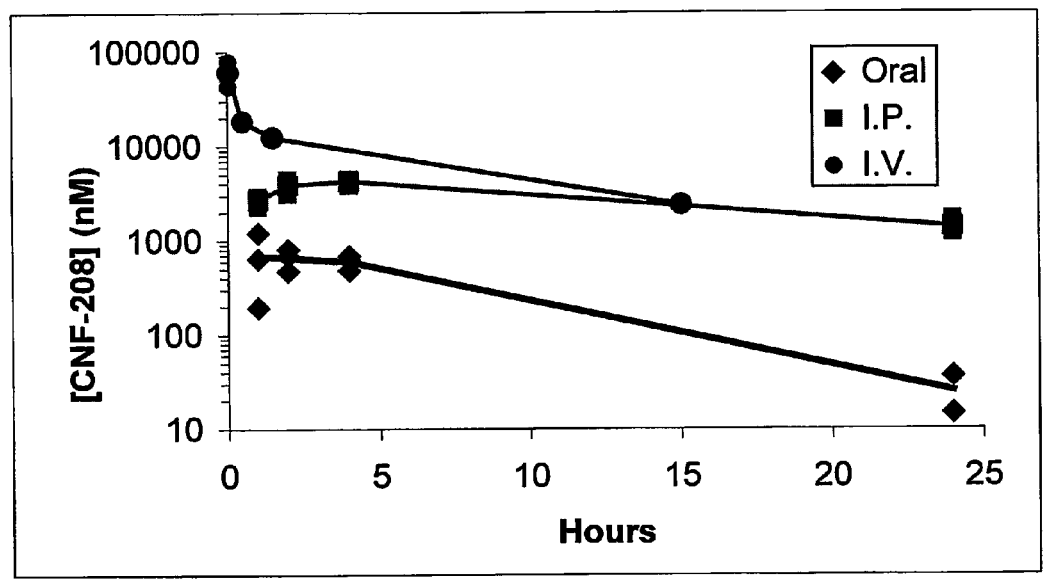
FIG. 2 shows a stability profile in mice for the water soluble dimer, Compound #208, administered orally, intravenously, and intraperitoneally.

Definitions:

The term "carbon chain" means a plurality of carbon atoms covalently bonded to one another. The chain may be alkyl, alkenyl, alkynyl, aromatic, conjugated, branched, unbranched, substituted, cyclic, or combinations thereof, etc. The carbon chain may also contain one or more heteroatoms, i.e., atoms other than carbon.

A "pharmaceutically effective amount" means an amount which provides a therapeutic and/or prophylactic effect, which may be through inhibition of an HSP90. The specific dose of compound administered will, of course, be determined by the particular circumstances surrounding the case, including, for example, the specific compound administered, the route of administration, the condition being treated, and the individual being treated. A typical daily dose (administered in single or divided doses) will contain a dosage level of from about 0.01 mg/kg to about 50-100 mg/kg of body weight of an active compound of the invention. Preferred daily doses generally will be from about 0.05 mg/kg to about 20 mg/kg and ideally from about 0.1 mg/kg to about 10 mg/kg. Factors such as clearance rate, half-life, drug form (e.g., drugs versus prodrugs), and maximum tolerated dose (MTD) have yet to be determined but one of ordinary skill in the art can determine these using standard procedures.

In some embodiments, the preferred therapeutic effect is the inhibition, to some extent, of the growth of cells characteristic of a proliferative disorder, e.g., breast cancer. A therapeutic effect will also normally, but need not, relieve to some extent one or more of the symptoms other than cell growth or size of cell mass. A therapeutic effect may include, for example, one or more of 1) a reduction in the number of cells; 2) a reduction in cell size; 3) inhibition (i.e., slowing to some extent, preferably stopping) of cell infiltration into peripheral organs, e.g., in the instance of cancer metastasis; 3) inhibition (i.e., slowing to some extent, preferably stopping) of tumor metastasis; 4) inhibition, to some extent, of cell growth; and/or 5) relieving to some extent one or more of the symptoms associated with the disorder.

In the proliferative disorders targeted by the compounds of the invention, the HSP90 "$IC_{50}$" is preferably greater for normal cells than for cells exhibiting a proliferative disorder, e.g., breast cancer cells, and the amount administered is preferably sufficient to prevent or treat an afflicted cell more so than a nonafflicted cell.

By a "standard" is meant a positive or negative control. A negative control in the context of HER-2 expression levels is, e.g., a sample possessing an amount of HER-2 protein that correlates with a normal cell. A negative control may also include a sample that contains no HER-2 protein. By contrast, a positive control does contain HER-2 protein, preferably of an amount that correlates with overexpression as found in proliferative disorders, e.g., breast cancers. The controls may be from cell or tissue samples, or else contain purified ligand (or absent ligand), immobilized or otherwise. In some embodiments, one or more of the controls may be in the form of a diagnostic "dipstick".

By "selectively targeting" is meant affecting one type of cell to a greater extent than another, e.g., in the case of cells with high as opposed to relatively low or normal Her-2 levels, as in certain breast cancers.

A "pharmacological composition" refers to a mixture of one or more of the compounds described herein, or physiologically acceptable salts thereof, with other chemical components, such as physiologically acceptable carriers and/or excipients. The purpose of a pharmacological composition is to facilitate administration of a compound to an organism.

"Pharmaceutically acceptable salts" of the compounds of the invention include those derived from pharmaceutically acceptable inorganic and organic acids and bases. Examples of suitable acids include hydrochloric, hydrobrornic, sulfuric, nitric, perchloric, fumaric, maleic, phosphoric, glycolic, gluconic, lactic, salicylic, succinic, toluene-p-sulfonic, tartaric, acetic, citric, methanesulfonic, formic, benzoic, malonic, naphthalene-2-sulfonic, benzenesulfonic, 1,2 ethanesulfonic acid (edisylate), galactosyl-d-gluconic acid, and the like. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N-(C.sub.1-C.sub.4 alkyl).sub.4.sup.+ salts, and the like. Illustrative examples of some of these include sodium hydroxide, potassium hydroxide, choline hydroxide, sodium carbonate, and the like. Where the claims recite "a compound (e.g., compound 'x') or pharmaceutically acceptable salt thereof," and only the compound is displayed, those claims are to be interpreted as embracing, in the alternative or conjunctive, a pharmaceutically acceptable salt or salts of such compound.

A "physiologically acceptable carrier" refers to a carrier or diluent that does not cause significant irritation to an organism and does not abrogate the biological activity and properties of the administered compound.

An "excipient" refers to an inert substance added to a pharmacological composition to further facilitate administration of a compound. Examples of excipients include but are not limited to calcium carbonate, calcium phosphate, various sugars and types of starch, cellulose derivatives, gelatin, vegetable oils and polyethylene glycols.

The term "alkyl", alone or in combination, refers to an optionally substituted straight-chain, optionally substituted branched-chain, or optionally substituted cyclic alkyl radical having from 1 to about 30 carbons, more preferably 1 to 12 carbons. Examples of alkyl radicals include methyl, ethyl, n-propyl, isopropyl, n-butyl, isobutyl, sec-butyl, tert-butyl, tert-amyl, pentyl, hexyl, heptyl, octyl and the like. The term "cycloalkyl" embraces cyclic configurations, is subsumed within the definition of alkyl and specifically refers to a monocyclic, bicyclic, tricyclic, and higher multicyclic alkyl radicals wherein each cyclic moiety has from 3 to about 8 carbon atoms. Examples of cycloalkyl radicals include cyclopropyl, cyclobutyl, cyclopentyl, cyclohexyl and the like. A "lower alkyl" is a shorter alkyl, e.g., one containing from 1 to about 6 carbon atoms.

The term "alkenyl", alone or in combination, refers to an optionally substituted straight-chain, optionally substituted branched-chain, or optionally substituted cyclic alkenyl hydrocarbon radical having one or more carbon-carbon double-bonds and having from 2 to about 30 carbon atoms, more preferably 2 to about 18 carbons. Examples of alkenyl radicals include ethenyl, propenyl, butenyl, 1,4-butadienyl and the like. The term can also embrace cyclic alkenyl structures. A "lower akenyl" refers to an alkenyl having from 2 to about 6 carbons.

The term "alkynyl", alone or in combination, refers to an optionally substituted straight-chain, optionally substituted branched-chain, or cyclic alkynyl hydrocarbon radical having one or more carbon-carbon triple-bonds and having from 2 to about 30 carbon atoms, more preferably 2 to about 12 carbon atoms. The term also includes optionally substituted straight-chain or optionally substituted branched-chain hydrocarbon radicals having one or more carbon-carbon triple bonds and having from 2 to about 6 carbon atoms as well as those having from 2 to about 4 carbon atoms. Examples of alkynyl radicals include ethynyl, propynyl, butynyl and the like.

The terms heteroalkyl, heteroalkenyl and heteroalkynyl include optionally substituted alkyl, alkenyl and alkynyl structures, as described above, and which have one or more skeletal chain atoms selected from an atom other that carbon, e.g., oxygen, nitrogen, sulfur, phosphorous or combinations thereof.

The term "carbon chain" may embrace any alkyl, alkenyl, alkynyl, or heteroalkyl, heteroalkenyl, or heteroalkynyl group, and may be linear, cyclic, or any combination thereof. If part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining chain length. If the chain contains heteroatoms as part of the backbone, those atoms are not calculated as part of the carbon chain length.

The term "alkoxy", alone or in combination, refers to an alkyl ether radical, alkyl-O—, wherein the term alkyl is defined as above. Examples of alkoxy radicals include methoxy, ethoxy, n-propoxy, isopropoxy, n-butoxy, iso-butoxy, sec-butoxy, tert-butoxy and the like.

The term "aryloxy", alone or in combination, refers to an aryl ether radical wherein the term aryl is defined as below. Examples of aryloxy radicals include phenoxy, benzyloxy and the like.

The term "alkylthio", alone or in combination, refers to an alkyl thio radical, alkyl-S—, wherein the term alkyl is defined as above.

The term "arylthio", alone or in combination, refers to an aryl thio radical, aryl-S—, wherein the term aryl is defined as below.

The term "oxo" refers to =O.

The term "aryl", alone or in combination, refers to an optionally substituted aromatic ring system. The term aryl includes monocyclic aromatic rings, polyaromatic rings and polycyclic aromatic ring systems containing from six to about twenty carbon atoms. The term aryl also includes monocyclic aromatic rings, polyaromatic rings and polycyclic ring systems containing from 6 to about 12 carbon atoms, as well as those containing from 6 to about 10 carbon atoms. The polyaromatic and polycyclic aromatic rings systems may contain from two to four rings. Examples of aryl groups include, without limitation, phenyl, biphenyl, naphthyl and anthryl ring systems.

The term "heteroaryl" refers to optionally substituted aromatic ring systems containing from about five to about 20 skeletal ring atoms and having one or more heteroatoms such as, for example, oxygen, nitrogen, sulfur, and phosphorus. The term heteroaryl also includes optionally substituted aromatic ring systems having from 5 to about 12 skeletal ring atoms, as well as those having from 5 to about 10 skeletal ring atoms. The term heteroaryl may include five- or six-membered heterocyclic rings, polycyclic heteroaromatic ring systems and polyheteroaromatic ring systems where the ring system has two, three or four rings. The terms heterocyclic, polycyclic heteroaromatic and polyheteroaromatic include ring systems containing optionally substituted heteroaromatic rings having more than one heteroatom as described above (e.g., a six membered ring with two nitrogens), including polyheterocyclic ring systems of from two to four rings. The term heteroaryl includes ring systems such as, for example, furanyl, benzofuranyl, chromenyl, pyridyl, pyrrolyl, indolyl, quinolinyl, N-alkyl pyrrolyl, pyridyl-N-oxide, pyrimidoyl, pyrazinyl, imidazolyl, pyrazolyl, oxazolyl, benzothiophenyl, purinyl, indolizinyl, thienyl and the like.

The term "heteroarylalkyl" refers to a C1-C4 alkyl group containing a heteroaryl group, each of which may be optionally substituted.

The term "heteroarylthio" refers to the group —S-heteroaryl.

The term "acyloxy" refers to the ester group —OC(O)—R, where R is H, alkyl, alkenyl, alkynyl, aryl, or arylalkyl, wherein the alkyl, alkenyl, alkynyl and arylalkyl groups may be optionally substituted.

The term "carboxy esters" refers to —C(O)OR where R is alkyl, aryl or arylalkyl, wherein the alkyl, aryl and arylalkyl groups may be optionally substituted.

The term "carboxamido" refers to

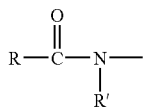

where each of R and R' are independently selected from the group consisting of H, alkyl, aryl and arylalkyl, wherein the alkyl, aryl and arylalkyl groups may be optionally substituted.

The term "arylalkyl", alone or in combination, refers to an alkyl radical as defined above in which one H atom is replaced by an aryl radical as defined above, such as, for example, benzyl, 2-phenylethyl and the like.

The terms haloalkyl, haloalkenyl, haloalkynyl and haloalkoxy include alkyl, alkenyl, alkynyl and alkoxy structures, as described above, that are substituted with one or more fluorines, chlorines, bromines or iodines, or with combinations thereof.

The terms cycloalkyl, aryl, arylalkyl, heteroaryl, alkyl, alkynyl, alkenyl, haloalkyl and heteroalkyl include optionally substituted cycloalkyl, aryl, arylalkyl, heteroaryl, alkyl, alkynyl, alkenyl, haloalkyl and heteroalkyl groups.

The term "carbocycle" includes optionally substituted, saturated or unsaturated, three- to eight-membered cyclic structures in which all of the skeletal atoms are carbon.

The term "heterocycle" includes optionally substituted, saturated or unsaturated, three- to eight-membered cyclic structures in which one or more skeletal atoms is oxygen, nitrogen, sulfur, phosphorus or combinations thereof. Illustrative examples include pyridine, pyran, thiophan, pyrrole, furan, thiophen, pentatomic and hexatomic lactam rings, and the like.

The term "membered ring" can embrace any cyclic structure, including carbocycles and heterocycles as described above. The term "membered" is meant to denote the number of skeletal atoms that constitute the ring. Thus, for example, pyridine, pyran, and thiophan are 6 membered rings and pyrrole, furan, and thiophen are 5 membered rings.

The term "acyl" includes alkyl, aryl, heteroaryl, arylalkyl or heteroarylalkyl substituents attached to a compound via a carbonyl functionality (e.g., —CO-alkyl, —CO-aryl, —CO-arylalkyl or —CO-heteroarylalkyl, etc.).

"Optionally substituted" groups may be substituted or unsubstituted. The substituents of an "optionally substituted" group may include, without limitation, one or more substituents independently selected from the following groups or designated subsets thereof: alkyl, alkenyl, allynyl, heteroalkyl, haloalkyl, haloalkenyl, haloalkynyl, cycloalkyl, aryl, heteroaryl, arylalkyl, heteroarylalkyl, alkoxy, aryloxy, haloalkoxy, amino, alkylamino, dialkylamino, alkylthio, arylthio, heteroarylthio, oxo, carboxyesters, carboxamido, acyloxy, H, F, Cl, Br, I, CN, $NO_2$, NH2, N3, $NHCH_3$, N$(CH_3)_2$, SH, S$CH_3$, OH, O$CH_3$, OC$F_3$, $CH_3$, $CF_3$, C(O)$CH_3$, C$O_2$ $CH_3$, C $O_2$H, C(O)NH2, pyridinyl, thiophene, furanyl, indole, indazol, esters, amides, phosphonates, phosphates, phosphoramides, sulfonates, sulfates, sulphonamides, carbamates, ureas, thioureas, thioamides, thioalkyls. An optionally substituted group may be unsubstituted (e.g., —$CH_2$ $CH_3$), fully substituted (e.g., —$CF_2$C $F_3$), monosubstituted (e.g., —$CH_2$ $CH_2$F) or substituted at a level anywhere in-between fully substituted and monosubstututed (e.g. —$CH_2$C $F_3$).

The term "halogen" includes F, Cl, Br and I.

The term "DMAG" is an abbreviation for 17-dimethylaminoethylamino-17-demethoxygeldanamycin.

Ansamycins, Their Preparation and Use

Ansamycins include a broad class of structures characterized by aliphatic rings of various length and constitution bridging opposite ends of aromatic ring structures and their reduced equivalents. Some more common ansamycins include, e.g., geldanamycin, the geldanamycin derivative 17-AAG, herbimycin A, and macbecin, many of which are described in U.S. Pat. Nos. 3,595,955, 4,261,989, 5,387,584, and 5,932,566. Subsumed within the class of ansamycins is the sub-class, benzoquinone ansamycins. Benzoquinone ansamycins possess a benzoquinone as the aromatic ring structure. Ansamycins and benzoquinone ansainycins can be synthetic, naturally-occurring, or a combination of the two, i.e., semi-synthetic. Geldanamycin is commercially available, e.g., from CN Biosciences, an Affiliate of Merck KGaA, Darmstadt, Germany, and headquartered in San Diego, Calif., USA (cat. no. 345805) and many other ansamycins can be fashioned using geldanamycin as a starting reagent. The biochemical purification of another ansamycin, 4,5-dihydrogeldanamycin and its hydroquinone, from cultures of *Streptomyces hygroscopicus* (ATCC 55256) is described in International Application Number PCT/US92/10189, assigned to Pfizer Inc., published as WO 93/14215 on Jul. 22, 1993, and listing Cullen et al. as inventors; an alternative method of synthesis for 4,5-Dihydrogeldanamycin by catalytic hydrogenation of geldanamycin is also known. See e.g., Progress in the Chemistry of Organic Natural Products, *Chemistry of the Ansamycin Antibiotics*, 33 1976, p. 278.

Commonly-owned provisional applications, Ser. Nos. 60/326,639 and 60/331,893, filed respectively Sep. 24, 2001 and Nov. 21, 2001, both entitled Chemical Process for Preparing 17-Allyl Amino Geldanamycin (17-AAG) and other Ansamycins and Ansamycin Derivatives relate to improved processes for preparing ansamycins, e.g., benzoquinone ansamycins and derivatives thereof, e.g., 17-AGG and its 4,5 dihydro analog. The processes avoid time-consuming and expensive work-ups associated with extractions and preparative chromatographic separations, while affording good purity and yield. Techniques of preparation include nucleophilic attack of geldanamycin or its dihydro equivalent in one or more volatile aprotic solvents, e.g., an ether or acetate, preferably nonhalogenated, and under conditions suitable for dissolving both reactants and product(s). The resulting product(s) is/are then concentrated by evaporation, and to the concentrated product added a volatile protic solvent, e.g., a volatile alcohol and/or water, under conditions in which the volatile protic solvent either serves the purpose of a wash or a (re)crystalization media. Filtration, centrifugation, decanting, and/or evaporation may be used to aid either procedure. The resulting product(s) can be used directly or indirectly for a utility associated with ansamycins, e.g., as antibiotics or anti-cancer agents. In terms of indirect utility, the product(s) is/are useful, e.g., as an intermediate(s) in the synthesis of yet further ansamycin derivatives, e.g., those described in U.S. Pat. No. 5,932,566 and PCT/IB94/00160 (WO 95/01342), issued to Schnur et al, and assigned to Pfizer Inc.

Commonly-owned application Ser. No. 60/272,251, filed Mar. 1, 2001, and entitled Methods for Treating Genetically Defined Proliferative Disorders with HSP90 describes how ansamycin-induced loss of certain HSP90-dependent proteins leads to the selective disruption of certain regulatory pathways and results in growth arrest at specific phases of the cell cycle (Muise-Heimericks, R. C. et al., 1998, J. Biol. Chem. 273: 29864-72), and apoptosis of cells so treated (Vasilevskaya, A. et al., 1999, Cancer Res., 59: 3935-40). This application further instructs how growth arrest can be made selective against cancers and other proliferative disorders that are caused by two different groups of aberrantly expressed proteins that have a dependence on HSP90. Within the first group are fusion proteins generated as a result of chromosomal aberrations (such as translocations, deletions and inversions) that juxtapose parts of the coding sequences of two normal cellular proteins (Rabbitts, T., 1994, Nature 372: 143-149). Within the second group are mutants and isoforms of cellular proteins that override, dominate, or otherwise obscure the natural gene products and their function. For example, mutants and isoforms of p53 family proteins and other tumor suppressor gene products can act as dominant-negative inhibitors of the corresponding normal protein in heterozygous tumor cells (Blagosklonny, M., et al, 1995, Oncogene, 11: 933-939). Other examples include virally-encoded species of certain kinases, such as v-src and other dominantly-acting mutant oncogene products (Uehara, Y. et al., 1985, supra).

Commonly-owned PCT application PCT/US02/39993, filed Dec. 12, 2002, entitled Assay for Determining HSP90 Binding Activity, describes an assay for identifying and/or evaluating binding affinity of HSP90 ligands, and demonstrates the existence and utility of high-affinity forms of HSP90, e.g., such as exist in cancer cell lysates. In the assay, an HSP90 is contacted with a known HSP90 ligand, e.g., an ansamycin such as geldanamycin. The ansamycin ligand is "labeled" at the 17 position (the same position is derivatized in various aspects and embodiments of the instant invention) with biotin/streptavidin to permit detection of its binding with HSP90. During the assay, the labeled ansamycin's ability to bind to, or remain bound to, HSP90, is potentially competed with by the co-presence of a compound of interest suspected of having, or being screened for, HSP90 binding ability. Binding ability and affinity of the compound of interest is based on the amount of signal present by way of the competing ligand. Label is preferably detected on a solid support, e.g., a multi-well dish or plate, which detection may be aided by the use of various commercially available detection devices well known in the art. Another, different assay is described by Chiosis et al., Chemistry and Biology 8: 289-299 (2001), but is cumbersome and time-consuming from the standpoint of requiring gels to be run, blotted, and probed with antibody. The Chiosis assay is further limited in its ability to conveniently support high-throughput screening. Either of the foregoing assays can be used to evaluate HSP90 binding (and by inference, HSP90 inhibition ability) of the compounds of the present invention.

International patent application PCT/US01/232640 (WO 0209696), filed Jul. 27, 2001, and entitled Methods for Treating Cell-Proliferative Diseases and Viral Infections, is also of background value to the present invention. Viruses targeted in various aspects of the present invention include all viruses, e.g., HIV, HTLV, HSV, HBV, HCV, ebola, retroviruses, rhinoviruses, hepatitis, VZV, HAV, CMV, adenovirus, influenza, flaviviruses, echovirus, coxsackie virus, comovirus, respiratory syncytial virus, mumps virus, rotavirus, measles virus, rubella virus, parvovirus, vaccinia virus, dengue virus, papillomavirus, molluscum virus, poliovirus, rabies virus, JC virus, arboviral encephalitis virus, arenaviruses, bunyaviruses, coronaviruses, hepadnaviruses, Epstein-Barr virus, cytomegalovirus, flaviviruses, orthomyxoviruses, paramyxoviruses, picomoviruses, polyomaviruses, poxviruses, reovirus, rhabdoviruses, rotaviruses, togaviruses, rabies, vesicular stomatitis, reovirus, vaccinia, measles virus, cytomegalovirus, sindbis virus, leukemia, polyoma virus, Rous sarcoma Virus (RSV), BK virus, JC virus, mouse mammary tumor virus (MMTV), alphavirus junction region, Varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus and polio virus. The foregoing may also have different strains and serotypes, all of which are contemplated in use with the invention.

WO 02/02123 (PCT/US01/20578) filed Jul. 28, 2001 reports the use of geldanamycin and related compounds for prophylaxis and treatment of fibrogenetic disorders including but not limited to connective tissues diseases, such as scleroderma, polymyositis, systemic lupus, rheumatoid arthritis, liver cirrhosis, keloid formation, interstitial nephritis, and pulmonary fibrosis.

WO 99-US7242, published Jan. 1, 1999, reports the use of benzoquinoid anasamycins, e.g., GD, herbimycin A and macbecin for inhibiting oxidative-stress-induced cell death and treating injury from cardiac arrest and stroke.

U.S. Pat. No. 6,210,974; issued Apr. 3, 2001; filed Apr. 7, 1999 reports compositions and methods for promoting nerve regeneration.

U.S. Patent Publication 2001/0038827 A1, published Nov. 8, 2001 and filed Dec. 30, 1997 reports formulations and methods of use in treating neoplasms by inhalation.

Within the scope of invention are ansamycin derivatives based both on naturally occurring ansamycin structures, e.g., as isolated from *Streptomyces hygoscopicus*, and unnatural ansamycin structures. An example of a naturally occurring geldanamycin ansamycin isolated from *Streptomyces hygoscopicus* is shown below.

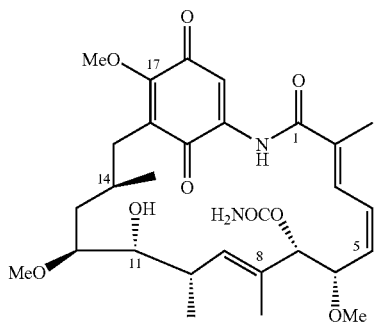

Unnatural isomers of geldanamycin can also be synthesized in order to optimize biological, pharmacological and drug-like properties. For example, the inverse configuration of the carbon-11 (C-11) can be achieved by first oxidizing the hydroxyl group to a ketone group followed by stereoselective reduction to the hydroxyl. Alternatively, Mitsunobu conditions can be utilized to prepare the opposite C-11 hydroxyl configuration via the corresponding ester. Similarly, synthetic chemistry known to those in the art can be performed at C-6, C-7, and C-12 to obtain the inverse configurations at those centers.

Mixtures of stereoisomers when present may also be separated into their individual stereoisomer components using well-known methods such as HPLC. Thus, while generic structures are indicated in the claims and description herein, it will be understood that such structures can embrace all stereoisomers, and various purities or combinations thereof. Some embodiments may feature a substantially pure (>about 95% purity) stereoisomer.

Prodrugs

Prodrugs contain a chemical moiety, e.g., an amide or phosphorus group whose function is to endow enhanced solubility and/or stability to the attached drug so that it can be effectively preserved/delivered to a host. Once in the body, the prodrug is typically acted upon by an enzyme in vivo, e.g., an esterase, amidase, or phosphatase, to liberate/generate the more pharmacologically active drug. This activation may occur through the action of an endogenous host enzyme or a non-endogenous enzyme that is administered to the host preceding, following, or during administration of the prodrug. An example of targeted cell delivery of enzymes by antibody ("ADEPT") is described in U.S. Pat. No. 4,975,278. Another example, "GDEPT", or gene dependent enzyme-prodrug therapy is described by Melton, R. G. and Sherwood, R. E., J. Natl. Cancer Inst. 88: 153-65 (1996). Prodrug use in general is further discussed, e.g., in U.S. Pat. No. 5,627,165, as well as in Pathak et al., *Enzymic protecting group techniques in organic synthesis*, Stereosel. Biocatal. 775-797 (2000), and is otherwise well-known in the art, although not to Applicants' knowledge using the specific compounds and compositions claimed herein.

Pharmaceutical Compositions/Formulations, Dosaging, and Modes of Administration

Those of ordinary skill in the art are familiar with formulation and administration techniques, e.g., as discussed in Goodman and Gilman's The Pharmacological Basis of Therapeutics, current edition; Pergamon Press; and Remington's Pharmaceutical Sciences (current edition.) Mack Publishing Co., Easton, Pa. These techniques can be employed in appropriate aspects and embodiments of the invention.

The compounds utilized in the methods of the instant invention may be administered either alone or in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

For example, the therapeutic or pharmaceutical compositions of the invention can be administered locally to the area in need of treatment. This may be achieved by, for example, but not limited to, local infusion during surgery, topical application, e.g., cream, ointment, injection, catheter, or implant, said implant made, e.g, out of a porous, non-porous, or gelatinous material, including membranes, such as sialastic membranes, or fibers. The administration can also be by direct injection at the site (or former site) of a tumor or neoplastic or pre-neoplastic tissue.

Still further, the therapeutic or pharmaceutical composition can be delivered in a vesicle, e.g., a liposome (see, for example, Langer, 1990, Science, 249: 1527-1533; Treat et al., 1989, Liposomes in the Therapy of Infectious Disease and Cancer, Lopez-Bernstein and Fidler (eds.), Liss, N.Y., pp. 353-365).

The pharmaceutical compositions used in the methods of the present invention can be delivered in a controlled release system. In one embodiment, a pump may be used (see, Sefton, 1987, CRC Crit. Ref. Biomed. Eng. 14: 201; Buchwald et al., 1980, Surgery, 88: 507; Saudek et al., 1989, N. Engl. J. Med., 321: 574). Additionally, a controlled release system can be placed in proximity of the therapeutic target. (see, Goodson, 1984, Medical Applications of Controlled Release, Vol. 2, pp. 115-138).

The pharmaceutical compositions used in the methods of the instant invention can contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropyl-cellulose, or a time delay material such as ethyl cellulose, or cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions can contain the active material in admixture with excipients suitable for the manufacture of aqueous suspensions. Such excipients can act as suspending agents and include, e.g., sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant, e.g. butylated hydroxyanisol, alpha-tocopherol, or ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of anti-oxidant(s).

The pharmaceutical compositions used in the methods of the instant invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The HSP90 inhibitors used in the methods of the present invention may also be administered in the form of suppositories for rectal administration of the drug. These compositions can be prepared by mixing the inhibitors with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing an HSP90 inhibitor can be used. As used herein, topical application can include mouth washes and gargles.

The compounds used in the methods of the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The methods and compounds of the instant invention may also be used in conjunction with other well known therapeutic agents that are selected for their particular usefulness against the condition that is being treated. For example, the instant compounds may be useful in combination with known anti-cancer and cytotoxic agents. Further, the instant methods and compounds may also be useful in combination with other inhibitors of parts of the signaling pathway that links cell surface growth factor receptors to nuclear signals initiating cellular proliferation.

The methods of the present invention may also be useful with other agents that inhibit angiogenesis and thereby inhibit the growth and invasiveness of tumor cells, including, but not limited to VEGF receptor inhibitors, including ribozymes and antisense targeted to VEGF receptors, angiostatin and endostatin.

Examples of antineoplastic agents which can be used in combination with the methods of the present invention include, in general, alkylating agents, anti-metabolites; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents and haematopoietic growth factors.

Exemplary classes of antineoplastic agents include, for example, the anthracycline family of drugs, the vinca drugs, the mitomycins, the bleomycins, the cytotoxic nucleosides, the epothilones, discodermolide, the pteridine family of drugs, diynenes and the podophyllotoxins. Particularly useful members of those classes include, for example, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

When an HSP90 inhibitor used in the methods of the present invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer, for example, breast cancer. Administration typically occurs in an amount of between about 0.01 mg/kg of body weight to about 100 mg/kg of body weight per day (administered in single or divided doses), more preferably at least about 0.1 mg/kg of body weight per day. A particular therapeutic dosage can include, e.g., from about 0.01 mg to about 1000 mg of compound, and preferably includes, e.g., from about 1 mg to about 1000 mg. The quantity of active compound in a unit dose of preparation may be varied or adjusted from about 0.1 mg to 1000 mg, preferably from about 1 mg to 300 mg, more preferably 10 mg to 200 mg, according to the particular application. The amount administered will vary depending on the particular IC50 value of the compound used and the judgment of the attending clinician taking into consideration factors such as health, weight, and age.

Preferably the pharmaceutical preparation is in unit dosage form. In such form, the preparation is subdivided into unit doses containing appropriate quantities of the active component, e.g., an amount that is effective to achieve the desired purpose.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The amount and frequency of administration of the compounds used in the methods of the present invention and, if applicable, other chemotherapeutic agents will be regulated according to the judgment of the attending clinician (physician) considering such factors as age, condition and size of the patient as well as severity of the disease being treated.

In general, compounds of the invention and, in embodiments where combinational therapy is employed, other chemotherapeutic agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician. The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the proliferative disease, the condition of the patient, and the actual choice of compounds used.

The determination of the order of administration, and the number of repetitions of administration of each therapeutic agent during a treatment protocol, is well within the knowledge of the skilled physician after evaluation of the disease being treated and the condition of the patient.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor (in embodiments where a tumor is targeted) can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

Assays to Determine HSP90 Binding and Downstream Effect

A variety of in vitro and in vivo assays are available to test the effect of the compounds of the invention on HSP90. HSP90 competitive binding assays and functional assays can be performed as known in the art substituting in the compounds of the invention. Chiosis et al., Chemistry & Biology 8: 289-299 (2001), describe some of the known ways in which this can be done. For example, competition binding assays using, e.g., geldanamycin or 17-AAG as a competitive binding inhibitor of HSP90 can be used to determine relative HSP90 affinity of the compounds of the invention by immobilizing the compound of interest or other competitive inhibitor on a gel or solid matrix, preincubating HSP90 with the other inhibitor, passing the preincubated mix over the gel or matrix, and then measuring the amount of HSP90 that sticks or does not stick to the gel or matrix.

Downstream effects can also be evaluated based on the known effect of HSP90 inhibition on function and stability of various steroid receptors and signaling proteins including, e.g., Raf1 and Her2. HSP90 inhibitors induce dose-dependent degradation of these molecules, which can be measured using standard techniques. Inhibition of HSP90 also results in up-regulation of HSP90 and related chaperone proteins that can similarly be measured. Antiproliferative activity on various cancer cell lines can also be measured, as can morphological and functional differentiation related to HSP90 inhibition. For example, the Many different types of methods are known in the art for determining protein concentrations and measuring or predicting the level of proteins within cells and in fluid samples. Indirect techniques include nucleic acid hybridization and amplification using, e.g., polymerase chain reaction (PCR). These techniques are known to the person of skill and are discussed, e.g., in Sambrook, Fritsch & Maniatis, Molecular Cloning: A Laboratory Manual, Second Edition (1989) Cold Spring Harbor Laboratory Press, Cold Spring Harbor, N.Y., Ausubel, et al., Current Protocols in Molecular Biology, John Wiley & Sons, NY, 1994, and, as specifically applied to the quantification, detection, and relative activity of Her-2/neu in patient samples, e.g., in U.S. Pat. Nos. 4,699,877, 4,918,162, 4,968,603, and 5,846,749. A brief discussion of two generic techniques that can be used follows.

The determination of whether cells overexpress or contain elevated levels of HER-2 can be determined using well known antibody techniques such as immunoblotting, radioimmunoassays, western blotting, immunoprecipitation, enzyme-linked immunosorbant assays (ELISA), and derivative techniques that make use of antibodies directed against HER-2. As an example, HER-2 expression in breast cancer cells can be determined with the use of an immunohistochemical assay, such as the Dako Hercep™ test (Dako Corp., Carpinteria, Calif.). The Hercep™ test is an antibody staining assay designed to detect HER-2 overexpression in tumor tissue specimens. This particular assay grades HER-2 expression into four levels: 0, 1, 2, and 3, with level 3 representing the highest level of HER-2 expression. Accurate quantitation can be enhanced by employing an Automated Cellular Imaging System (ACIS) as described, e.g., by Press, M, et al, 2000, Modern Pathology 13:225A.

Antibodies, polyclonal or monoclonal, can be purchased from a variety of commercial suppliers, or may be manufactured using well-known methods, e.g., as described in Harlow et al., Antibodies: A Laboratory Manual, 2nd Ed; Cold Spring Harbor Laboratory Press, Cold Spring Harbor, N.Y. (1988).

HER-2 overexpression can also be determined at the nucleic acid level since there is a reported high correlation between overexpression of the HER-2 protein and amplification of the gene that codes for it. One way to test this is by using RT-PCR. The genomic and cDNA sequences for HER-2 are known. Specific DNA primers can be generated using standard, well-known techniques, and can then be used to amplify template already present in the cell. An example of this is described in Kurokawa, H et al, Cancer Res. 60: 5887-5894 (2000), (which describes illustrative forward and reverse primer DNA sequences that can be used in the PCR 5'. PCR can be standardized such that quantitative differences are observed as between normal and abnormal cells, e.g., cancerous and noncancerous cells. Well-known methods employing, e.g., densitometry, can be used to quantitate and/or compare nucleic acid levels amplified using PCR.

Similarly, fluorescent in situ hybridization (FISH) assays and other assays can be used, e.g., Northern and/or Southern blotting. These rely on nucleic acid hybridization between the HER-2 gene or mRNA and a corresponding nucleic acid probe that can be designed in the same or a similar way as for PCR primers, above. See, e.g., Mitchell M S, and Press M F., 1999, Semin. Oncol., Suppl. 12: 108-16. For FISH, this nucleic acid probe can be conjugated to a fluorescent molecule, e.g., fluorescein and/or rhodamine, that preferably does not interfere with hybridization, and which fluorescence can later be measured following hybridization. See, e.g., Kurokawa, H et al, Cancer Res. 60: 5887-5894 (2000) (describing a nucleic acid probe having sequence a specific DNA sequence flanked on the 5' end by FAM and on the 3' end by TAMRA-p. ACIS-based approaches as described above can be employed to make the assay more quantitative (de la Torre-Bueno, J, et al, 2000, Modern Pathology 13: 221A).

Immuno and nucleic acid detection can also be directed against proteins other than HSP90 and Her-2, which proteins are nevertheless affected in response to HSP90 inhibition.

Hardware Useful in Performing Various Aspects of the Invention

Compounds of the invention can be encapsulated in containers, e.g., vials, syringes, etc. for storage and/or administration to a patient. Such containers are well-known in the art and may be light-resistant to prevent light-induced oxidation/decay of the compounds of the invention.

Various hardware may also be useful to evaluate the synthesis, purity, and/or biological or in vitro effect of the compounds of the invention, e.g., spectrophotometers, mass spectroscopy machines, densitometers, NMR devices, scintillation counters, HPLC apparati and other chromatographic equipment, etc. These items are all well-known in the art and can be routinely employed without undue experimentation in furtherance of appropriate aspects and embodiments of the invention.

The following examples are offered by way of illustration only and are not intended to be limiting of the full scope and spirit of the invention.

EXAMPLES

The following compounds were all produced from ansamycin substrates isolated from *Streptomyces hygoscopicus*.

Dimers

The following general synthetic scheme is applicable to Examples 1-5 and describes the synthesis of water-soluble dimers of geldanamycin and geldanamycin analogs. Dimers created according to the scheme have potencies similar to 17-amino geldanamycin but exhibit a relatively longer half-life in vivo and have salts that afford greater water-solubility for aqueous formulation. Thus, these compounds can be expected to require relatively less frequent administration and to afford more consistent relative blood level concentrations when administered to patients.

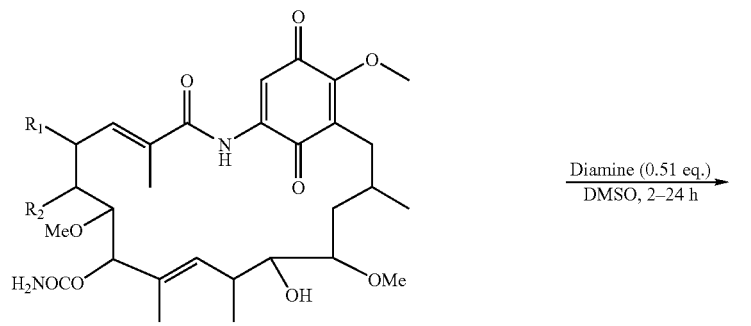

1a

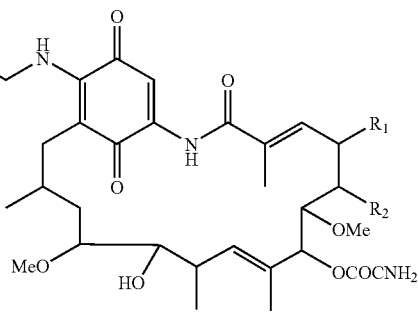

1b                1c

Example 1

Preparation of Compound #208

3,3'-diamino-N-methyldipropylamine (1.32 g, 9.1 mmol) was added dropwise to a solution of Geldanamycin (10 g, 17.83 mmol) in DMSO (200 ml) in a flame-dried flask under $N_2$ and stirred at room temperature. The reaction mixture was diluted with water after 12 hours. A precipitate was formed and filtered to give the crude product. The crude product was chromatographed by silica chromatography (5% $CH_3OH/CH_2Cl_2$) to afford the desired dimer as a purple solid (8.92 g, 7.2 mmol). Yield: 81%; mp 153° C. (dec.); $^1H$ NMR ($CDCl_3$) δ 0.95 (d, J=7 Hz, 6H, $2CH_3$), 1.00 (d, J=7 Hz, 6H, $2CH_3$), 1.69 (m, 4H, 2 $CH_2$), 1.74 (m, 4H, $2CH_2$), 1.76 (s, 6H, 2 $CH_3$), 1.83 (m, 2H, 2CH), 2.00 (s, 6H, $2CH_3$), 2.30 (s, 3H, N—$CH_3$), 2.36 (dd, J=14 Hz, 2H, 2CH), 2.50 (m, 4H, $2CH_2$), 2.63 (d, 2H, 2CH), 2.75 (m, 2H, 2CH), 3.25 (s, 6H, $2OCH_3$), 3.35 (s, 6H, $2OCH_3$), 3.40 (m, 2H, 2CH), 3.50 (m, 4H, $2CH_2$), 3.68 (m, 2H, 2CH), 4.20 (Bs, 2H, OH), 4.30 (d, J=10 Hz, 2H, 2CH), 4.80 (s, 4H, 2NH2), 5.19 (s, 2H, 2CH), 5.82 (t, J=15 Hz, 2H, 2CH═), 5.89 (d, J=10 Hz, 2H, 2CH═), 6.59 (t, J=15 Hz, 2H, 2CH═), 6.92 (d, J=10 Hz, 2H, 2CH═), 7.13 (t, 2H, 2NH), 7.24 (s, 2H, 2CH═), 9.21 (s, 2H, 2NH); MS (m/z) 1203 (M+H).

The corresponding HCl salt was prepared by the following method: an HCl solution in EtOH (5 ml, 0.123N) was added to a solution of compound #208 (1 gm as prepared above) in THF (15 ml) and EtOH (50 ml) at room temperature. The reaction mixture was stirred for 10 min. The salt was precipitated, filtered and washed with large amount of EtOH and dried in vacuo.

Example 2

Preparation of Compound #237

Compound #237 was prepared by the same method described in example 1 except that 3,3'-diamino-dipropylamine was used instead of 3,3'-diamino-N-methyldipropylamine. The pure purple product was obtained after flash chromatography (silica gel); yield: 93%; mp 165° C.; $^1H$ NMR ($CDCl_3$) δ 0.97 (d, J=6.6 Hz, 6H, $2CH_3$), 1.0 (d, J=6.6 Hz, 6H, $2CH_3$), 1.72 (m, 4H, 2 $CH_2$), 1.78 (m, 4H, $2CH_2$), 1.80 (s, 6H, 2 $CH_3$), 1.85 (m, 2H, 2CH), 2.0 (s, 6H, $2CH_3$), 2.4 (dd, J=11 Hz, 2H, 2CH), 2.67 (d, J=15 Hz, 2H, 2CH), 2.63 (t, J=10 HZ, 2H, 2CH), 2.78 (t, J=6.5 Hz, 4H, $2CH_2$), 3.26 (s, 6H, $2OCH_3$), 3.38 (s, 6H, $2OCH_3$), 3.40 (m, 2H, 2CH), 3.60 (m, 4H, $2CH_2$), 3.75 (m, 2H, 2CH), 4.60 (d, J=10 Hz, 2H, 2CH), 4.65 (Bs, 2H, 2OH), 4.80 (Bs, 4H, 2NH2), 5.19 (s, 2H, 2CH), 5.83 (t, J=15 Hz, 2H, 2CH═), 5.89 (d, J=10 Hz, 2H, 2CH═), 6.58 (t, J=15 Hz, 2H, 2CH═), 6.94 (d, J=10 Hz, 2H, 2CH═), 7.17 (m, 2H, 2NH), 7.24 (s, 2H, 2CH═), 9.20 (s, 2H, 2NH); MS (m/z)1189 (M+H); The corresponding HCl salt was prepared by the same procedure as described in example 1.

Example 3

Preparation of Compound #207

Compound #207 was prepared by the same method described in example 1 except that 1,4-bis (3-aminopropyl) piperazine was used instead of 3,3'-diamino-N-methyldipropylamine. The pure purple product was obtained after column chromatography (silica gel); yield: 90%; mp 162° C.; $^1$H NMR (CDCl$_3$) δ 0.97 (d, J=6.6 Hz, 6H, 2CH$_3$), 1.00 (d, J=6.6 Hz, 6H, 2CH$_3$), 1.73 (m, 4H, 2 CH$_2$), 1.78 (m, 4H, 2CH$_2$), 1.80 (s, 6H, 2 CH$_3$), 1.85 (m, 2H, 2CH), 2.00 (s, 6H, 2CH$_3$), 2.40 (dd, J=11 Hz, 2H, 2CH), 2.55 (m, 8H, 4CH$_2$), 2.67 (d, J=15 Hz, 2H, 2CH), 2.63 (t, J=10 HZ, 2H, 2CH), 2.78 (t, J=6.5 Hz, 4H, 2CH$_2$), 3.26 (s, 6H, 2OCH$_3$), 3.38 (s, 6H, 2OCH$_3$), 3.40 (m, 2H, 2CH), 3.60 (m, 4H, 2CH$_2$), 3.75 (m, 2H, 2CH), 4.60 (d, J=10 Hz, 2H, 2CH), 4.65 (Bs, 2H, 2OH), 4.80 (Bs, 4H, 2NH$_2$), 5.19 (s, 2H, CH), 5.83 (t, J=15 Hz, 2H, 2CH=), 5.89 (d, J=10 Hz, 2H, 2CH=), 6.58 (t, J=15 Hz, 2H, 2CH=), 6.94 (d, J=10 Hz, 2H, 2CH=), 7.24 (s, 2H, 2CH=), 7.60 (m, 2H, 2NH), 9.20 (s, 2H, 2NH); MS (m/z) 1258 (M+H); The corresponding HCl salt was prepared by the same procedure as described in example 1.

Example 4

Preparation of Compound #487

Compound #487 was prepared by the same method described in example 1 except that N,N-bis (3-aminopropyl)-1,3-propane diamine was used instead of 3,3'-diamino-N-methyldipropylamine. The pure purple product was obtained after silica gel flash chromatography; yield: 90%; mp155° C. (dec.); $^1$H NMR (CDCl$_3$) δ 0.97 (d, J=6.6 Hz, 6H, 2CH$_3$), 1.00 (d, J=6.6 Hz, 6H, 2CH$_3$), 1.72 (m, 4H, 2 CH$_2$), 1.78 (m, 4H, 2CH$_2$), 1.80 (s, 6H, 2 CH$_3$), 1.82 (m, 2H, CH$_2$), 1.85 (m, 2H, 2CH), 2.00 (s, 6H, 2CH$_3$), 2.02 (m, 4H, 2CH$_2$), 2.40 (dd, J=11 Hz, 2H, 2CH), 2.67 (d, J=15 Hz, 2H, 2CH), 2.63 (t, J=10 HZ, 2H, 2CH), 2.78 (t, J=6.5 Hz, 4H, 2CH$_2$), 3.26 (s, 6H, 2OCH$_3$), 3.38 (s, 6H, 2OCH$_3$), 3.40 (m, 2H, 2CH), 3.60 (m, 4H, 2CH$_2$), 3.75 (m, 2H, 2CH), 4.60 (d, J=10 Hz, 2H, 2CH), 4.65 (s, 2H, 2OH), 4.80 (Bs, 4H, 2NH$_2$), 5.19 (s, 2H, CH), 5.83 (t, J=15 Hz, 2H, 2CH=), 5.89 (d, J=10 Hz, 2H, 2CH=), 6.58 (t, J=15 Hz, 2H, 2CH=), 6.94 (d, J=10 Hz, 2H, 2CH=), 7.29 (s, 2H, 2CH=), 7.62 (bs, 2H, 2NH), 9.20 (s, 2H, 2NH); MS (m/z)1246 (M+H). The corresponding HCl salt was prepared by the same procedure as described in example 1.

Example 5

Preparation of Compound #483

Compound #483 was prepared by the same method described in example 1 except that 2,2'-diamino-N-methyldiethyllamine was used instead of 3,3'-diamino-N-methyl-dipropylamine. The pure purple product was obtained after flash chromatography; yield: 90%; mp 161-163° C.; $^1$HNMR (CDCl$_3$) δ 0.95 (d, J=7 Hz, 6H, 2CH$_3$), 1.00 (d, J=7 Hz, 6H, 2CH$_3$), 1.85 (m, 4H, 2CH$_2$), 1.75 (s, 6H, 2 CH$_3$), 1.80 (m, 2H, 2CH), 2.00 (s, 6H, 2CH$_3$), 2.30 (s, 3H, N—CH$_3$), 2.30 (dd, J=14 Hz, 2H, 2CH), 2.50 (m, 4H, 2CH$_2$), 2.63 (d, 2H, 2CH), 2.75 (m, 2H, 2CH), 3.25 (s, 6H, 2OCH$_3$), 3.35 (s, 6H, 2OCH$_3$), 3.40 (m, 2H, 2CH), 3.50 (m, 4H, 2CH$_2$), 3.68 (m, 2H, 2CH), 4.20 (Bs, 2H, OH), 4.30 (d, J=10 Hz, 2H, 2CH), 4.80 (Bs, 4H, 2NH$_2$), 5.19 (s, 2H, 2CH), 5.82 (t, J=15 Hz, 2H, 2CH=), 5.90 (d, J=10 Hz, 2H, 2CH=), 6.59 (t, J=15 Hz, 2H, 2CH=), 6.92 (d, J=10 Hz, 2H, 2CH=), 7.13 (t, 2H, 2NH), 7.24 (s, 2H, 2CH=), 9.20 (s, 2H, 2NH); MS (m/z)1175 (M+H);); The corresponding HCl salt was prepared by the same procedure as described in example 1.

Prodrugs of 17-AG

The following compounds can be metabolically degraded to 17-amino geldanamycin (17-AG), which is one of the most potent geldanamycin derivatives known. Although 17-AG exhibits poor solubility, these water-soluble prodrugs are much more soluble and increase the bioavailability of the highly biologically active 17-AG. These compounds can be administered by oral or intravenous routes. One synthesis embodiment for such a prodrug may be depicted as follows:

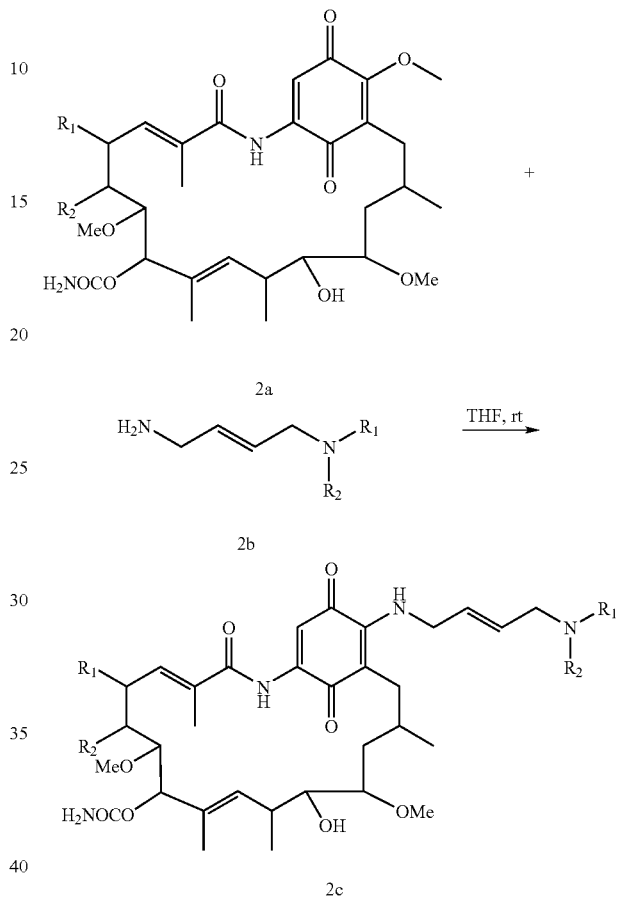

Example 6

Preparation of Compound #481

To 200 mg (0.357 mmol) of geldanamycin in 8 ml of dry THF in a flame-dried flask was added 91.6 mg (0.714 mmol) of N-propyl-1,4-diamino-2-butene drop-wise under nitrogen. The reaction mixture was stirred at room temperature for 4 h at which time TLC analysis indicated the reaction was complete. The solvent was removed by rotary evaporation and the crude material was chromatographed (5% CH$_3$OH/CH$_2$Cl$_2$ to 15% CH$_3$OH/CH$_2$Cl$_2$) to afford the desired compound as a purple solid (150 mg, 0.228 mmol); yield: 64%; mp131° C.; $^1$H NMR (CDCl$_3$) δ 0.97 (m, 9H, 3CH$_3$), 1.52 (m, 2H, CH$_2$), 1.72 (m, 3H, CH+CH$_2$), 1.80 (s, 3H, CH$_3$), 2.0 (s, 3H, CH$_3$), 2.38 (dd, J=11 Hz, 1H, CH), 2.72 (m, 4H, 2CH, CH$_2$), 3.26(s, 3H, OCH$_3$), 3.38(s, 3H, OCH$_3$), 3.46 (m, H, CH), 3.6 (m, H, CH), 4.18(m, 4H, 2CH$_2$), 4.34(d, J=10 Hz, 1H, CH), 4.8(1s, 2H, NH$_2$), 5.19(s, 1H, CH), 5.88(m, 4H, 4CH=), 6.38 (m, 1H, NH), 6.61(t, J=15 Hz, 1H, CH=), 6.94 (d, J=10 Hz, 1H, CH=), 7.30(s, H, CH=), 9.16(s, H, NH); MS (m/z)658 (M+H). The corresponding HCl salt was prepared by the same procedure as described in example 1.

Water Soluble Geldanamycin Derivatives

The following synthetic scheme may be used to generate water-soluble analogs of geldanamycin. The creation of two such analogs is illustrated in more detail in Examples 7 and 8. Salts of these compounds afford improved aqueous formulation and hence intravenous administration, lessening the need for other formulation ingredients. Such compounds can also be administered orally in tablet or capsule form.

Example 7

Preparation of Compound #480

To 500 mg (0.0.89 mmol) of geldanamycin in 300 ml of dry THF in a flame-dried flask was added 66 mg (0.75 mmol) of 1,4-diamino-butane drop-wise under nitrogen. The reaction mixture was stirred at room temperature for 48 h at which

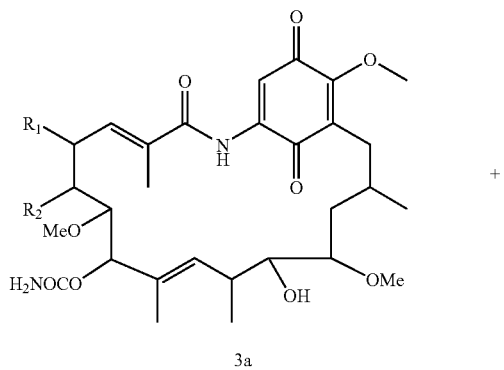

3a

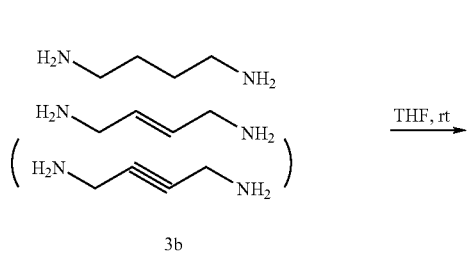

3b

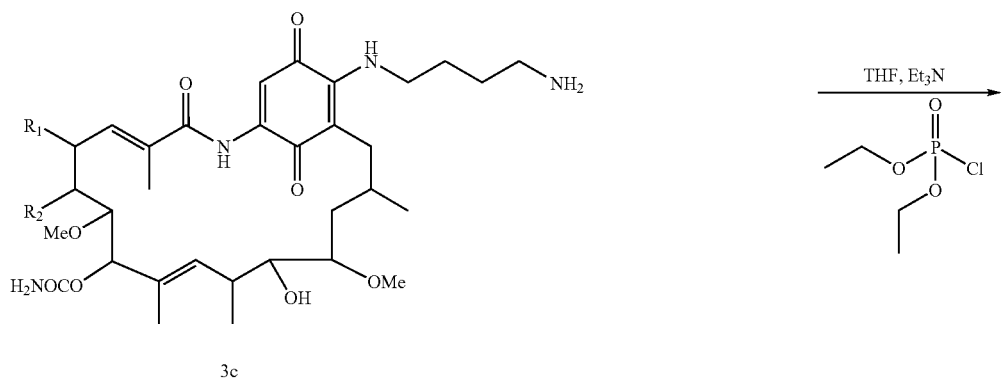

3c

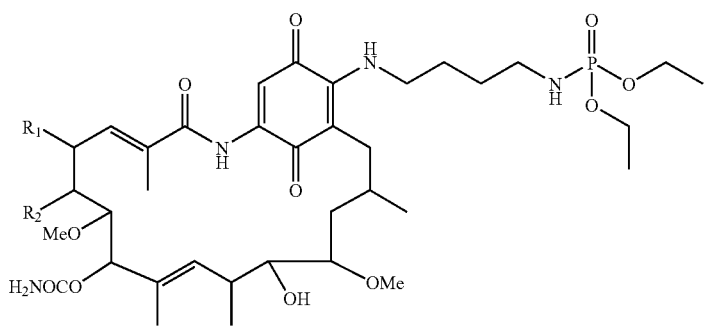

3d time TLC analysis indicated the reaction was complete. The solvent was removed by rotary evaporation and the crude material was chromatographed (5% CH$_3$OH/CH$_2$Cl$_2$ to 15% CH$_3$OH/CH$_2$Cl$_2$) to afford the desired compound as a purple solid (450 mg, 0.73 mmol); yield: 97%; mp 171° C.; $^1$H NMR (CDCl$_3$) δ 0.97 (d, J=6.6 Hz, 3H, CH$_3$), 1.00 (d, J=6.6 Hz, 3H, CH$_3$), 1.72 (m, 6H, 3 CH$_2$), 1.80 (s, 3H, CH$_3$), 1.85 (m, 1H, CH), 2.0 (s, 3H, CH$_3$), 2.40 (dd, J=11 Hz, 1H, CH), 2.67 (d, J=15 Hz, 1H, CH), 2.63 (t, J=10 HZ, 1H, CH), 2.78 (t, J=6.5 Hz, 2H, CH$_2$), 3.26 (s, 3H, OCH$_3$), 3.38 (s, 3H, OCH$_3$), 3.40 (m, 1H, CH), 3.60 (m, 2H, CH$_2$), 3.75 (m, 1H, CH), 4.60 (d, J=10 Hz, 1H, CH), 4.65 (Bs, 1H, OH), 4.80 (13s, 2H, NH$_2$), 5.19 (s, 1H, CH), 5.83 (t, J=15 Hz, 1H, CH=), 5.89 (d, J=10 Hz, 1H, CH=), 6.45 (m, 1H, NH), 6.58 (t, J=15 Hz, 1H, CH=), 6.94 (d, J=10 Hz, 1H, CH=), 7.24 (s, 1H, CH=), 9.20 (s, 1H, NH), MS (m/z) 618 (M+H).

Example 8

Preparation of Compound #482

To 35 mg (0.057 mmol) of Compound #480 in 8 ml of dry THF in a flame-dried flask was added 21.5 mg (0.12 mmol) of diethylchlorophosphate and 12.6 mg (0.12 mmol) of triethylamine. The reaction mixture was stirred at room temperature for 0.5 h at which time TLC analysis indicated the reaction was complete. The solvent was removed by rotary evaporation and the crude material was chromatographed (5% CH$_3$OH/CH$_2$Cl$_2$) to afford the desired compound as a purple solid (38 mg, 0.05 mmol); yield: 89%; mp 94.8-96.2° C.; $^1$H NMR (CDCl$_3$) δ 0.97 (d, J=6.6 Hz, 3H, CH$_3$), 1.00 (d, J=6.6 Hz, 3H, CH$_3$), 1.35 (t, J=8 Hz, 6H, 2CH$_3$), 1.72 (m, 6H, 3 CH$_2$), 1.80 (s, 3H, CH$_3$), 1.85 (m, 1H, CH), 2.00 (s, 3H, CH$_3$), 2.40 (dd, J=11 Hz, 1H, CH), 2.67 (d, J=15 Hz, 1H, CH), 2.63 (t, J=10 HZ, 1H, CH), 2.78 (t, J=6.5 Hz, 2H, CH$_2$), 3.26 (s, 3H, OCH$_3$), 3.38 (s, 3H, OCH$_3$), 3.40 (m, 1H, CH), 3.60 (m, 2H, CH$_2$), 3.75 (m, 1H, CH), 4.06 (m, 4H, 2CH$_2$), 4.60 (d, J=10 Hz, 1H, CH), 4.65 (Bs, 1H, OH), 4.80 (Bs, 2H, NH$_2$), 5.19 (s, 1H, CH), 5.83 (t, J=15 Hz, 1H, CH=), 5.89 (d, J=10 Hz, 1H, CH=), 6.45 (m, 1H, NH), 6.58 (t, J=15 Hz, 1H, CH=), 6.94 (d, J=10 Hz, 1H, CH=), 7.24 (s, 1H, CH=), 9.20 (s, 1H, NHH, CH=); MS (m/z) 776 (M+Na);

Examples 9-13

There are None

The following general synthetic schemes are applicable to Examples 14-16

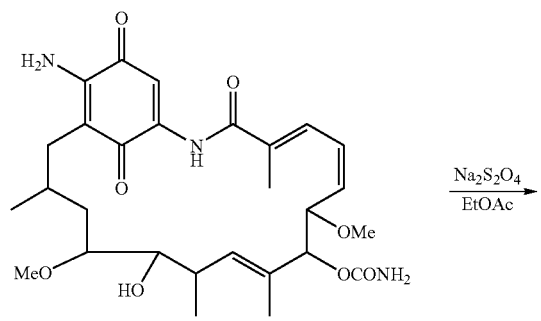

5a

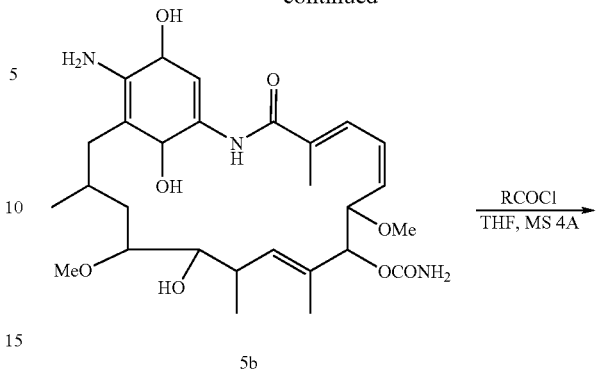

5b

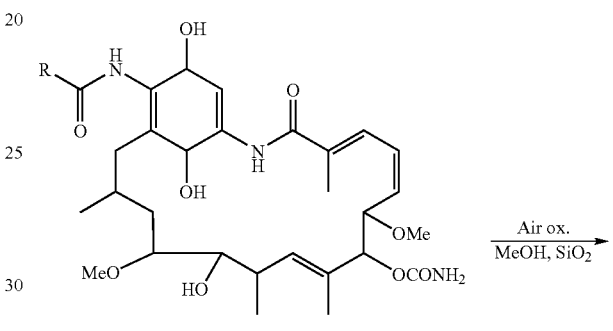

5c

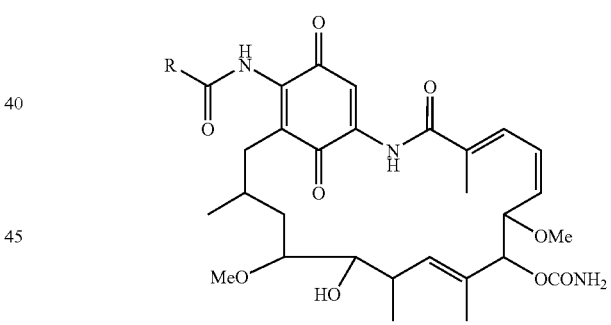

5d or

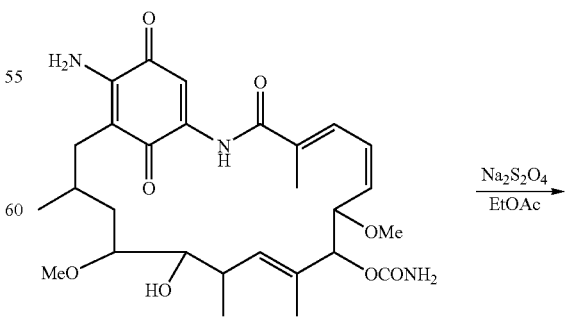

5a

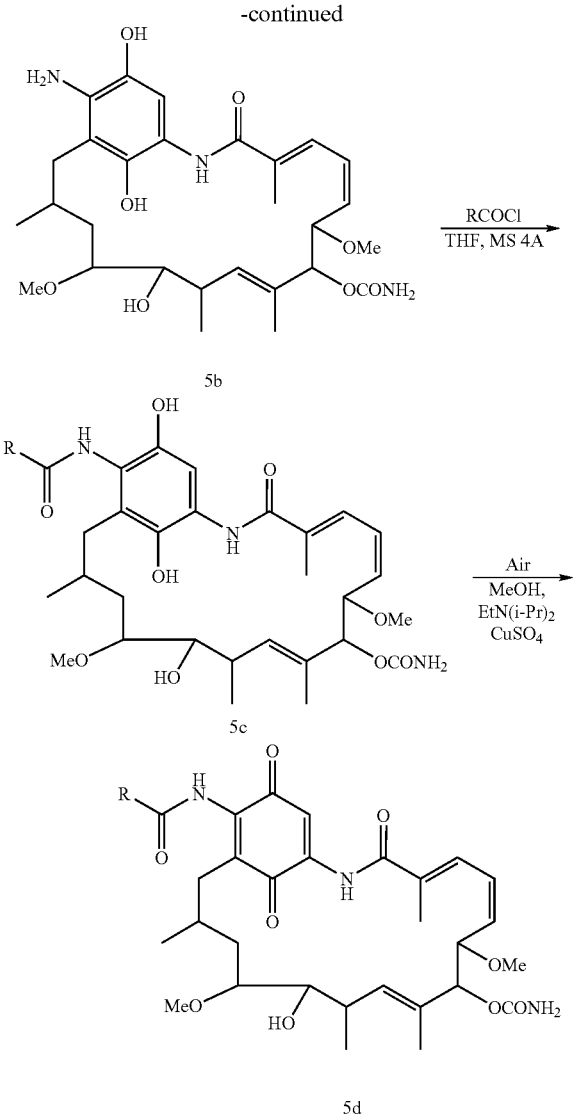

Synthesis of compound 5d of the present invention typically includes some or all of the following steps. 17-aminogeldanamycin 5a is first reduced into the corresponding dihydroquinone of formula 5b, which then reacts cleanly with alkyl or aryl carboxyl chlorides to give the amides of formula 5c. Compound 5c is allowed to air oxidize in methanol to afford the final compound 5d.

Example 14

Preparation of Compound #513

A solution of 17-aminogeldanamycin (1 mmol) in EtOAc was treated with $Na_2S_2O_4$ (0.1 M, 300 ml) at RT. After 2 h, the aqueous layer was extracted twice with EtOAc and the combined organic layers were dried over $Na_2SO_4$, concentrated under reduced pressure to give 18,21-dihydro-17-aminogeldanamycin as a brown solid. This latter was dissolved in anhydrous $CH_2Cl_2$ under nitrogen atmosphere and to the resulting solution were added EtN(i-Pr)$_2$ (1.5 mmol) and $Ac_2O$ (1.2 nmol) at 0° C. After 2 h at RT, the reaction mixture was diluted with EtOAc, washed with sat. NaHCO$_3$, and dried over $Na_2SO_4$ overnight under air atmosphere. After filtration and removal of the solvent under reduced pressure, the crude product was purified by flash chromatography to give 17-acetylaminogeldanamycin as a yellow solid. Rf=0.46 in 80:15:5 $CH_2Cl_2$: EtOAc: MeOH.

$^1$H NMR (CDCl$_3$) δ 0.91 (d, 3H), 0.95 (d, 3H), 1.68-1.73 (m, 3H), 1.78 (d, 3H), 2.03 (s, 3H), 2.24 (s, 3H), 2.46 (dd, 1H), 2.56 (dd, 1H), 2.74-2.79 (m, 1H), 3.32 (s, 3H), 3.34 (s, 3H), 3.31-3.34 (m, 1H), 3.43-3.47 (m, 1H), 4.31 (d, 1H), 5.16 (s, 1H), 5.75 (d, 1H), 5.91 (t, 1H), 6.59 (t, 1H), 6.92 (d, 1H), 7.44 (s, 1H), 7.73 (s, 1H), 8.72 (s, 1H).

Example 15

Preparation of Compound #514

A solution of 17-aminogeldanamycin (1 mmol) in EtOAc was treated with $Na_2S_2O_4$ (0.1 M, 300 ml) at RT. After 2 h, the aqueous layer was extracted twice with EtOAc and the combined organic layers were dried over $Na_2SO_4$, concentrated under reduce pressure to give 18,21-dihydro-17-aminogeldanamycin as a brown solid. This latter compound was dissolved in anhydrous $CH_2Cl_2$ under nitrogen atmosphere and to the resulting solution were added EtN(i-Pr)$_2$ (1.5 mmol) and $(CH_3CH_2CO)_2O$ (1.2 mmol) at 0° C. After 2 h at RT, the reaction mixture was diluted with EtOAc, washed with sat. NaHCO$_3$, dried over $Na_2SO_4$ overnight under air atmosphere. After filtration and removal of the solvent under reduce pressure, the crude was purified by flash chromatography to give 17-propanoylaminogeldanamycin as a yellow solid. Rf=0.47 in 80:15:5 $CH_2Cl_2$: EtOAc: MeOH. $^1$H NMR (CDCl$_3$) δ 0.90 (d, 3H), 0.96 (d, 3), 1.25 (t, 3H), 1.65-1.75 (m, 3H), 1.78 (d, 3H), 2.03 (s, 3H), 2.45-2.51 (m, 3H), 2.55-2.59 (m, 1H), 2.74-2.78 (m, 1H), 3.32 (s, 3H), 3.34 (s, 3H), 3.31-3.34 (m, 1H), 3.43-3.46 (m, 1H), 4.31 (d, 1H), 5.16 (s, 1H), 5.76 (d, 1H), 5.91 (t, 1H), 6.57 (t, 1H), 6.92 (d, 1H), 7.45 (s, 1H), 7.73 (s, 1H), 8.72 (s, 1H).

Example 16

Preparation of Compound #495

A solution of 17-aminogeldanamycin (1 mmol) in EtOAc was treated with $Na_2S_2O_4$ (0.1 M, 300 ml) at RT. After 2 h, the aqueous layer was extracted twice with EtOAc and the combined organic layers were dried over 18,21-dihydro-17-aminogeldanamycin as a brown solid. This latter compound was dissolved in anhydrous THF under nitrogen atmosphere and to the resulting solution was added allylisocyanate (1.2 mmol) at RT. After 1 h, the solvent was removed under reduce pressure whereby the residue was dissolved in MeOH and stirred over night in presence of silica. After filtration, the solvent was removed under reduce pressure and the residue was purified by flash chromatography to give 1-allyl-3-(17-geldanamycinyl)-urea as a brick red solid. Rf=0.38 in 80:15:5 $CH_2Cl_2$: EtOAc: MeOH. $^1$H NMR (CDCl$_3$) δ 0.92 (d, 3H), 0.95 (d, 3H), 1.61-1.72 (m, 3H), 1.78 (d, 3H), 2.03 (s, 3H), 2.55 (br d, 2H), 2.74-2.78 (m, 1H), 3.31 (s, 3H), 3.34 (s, 3H), 3.31-3.34 (m, 1H), 3.90 (br s, 2H), 4.31 (d, 1H), 5.16 (s, 1H), 5.20-5.29 (m, 3H), 5.79 (d, 1H), 5.84-5.94 (m, 2H), 6.57 (t, 1H), 6.92 (d, 1H), 7.28 (s, 1H), 7.41 (s, 1H), 8.79 (s, 1H).

Example 17

Preparation of Compound #529

A solution of 17-aminogeldanamycin (1 mmol) in EtOAc was treated with $Na_2S_2O_4$ (0.1 M, 300 ml) at RT. After 2 h, the aqueous layer was extracted twice with EtOAc and the combined organic layers were dried over $Na_2SO_4$, concentrated under reduce pressure to give 18,21-dihydro-17-aminogeldanamycin as a yellow solid. This latter was dissolved in anhydrous THF and transferred via cannula to a mixture of picolinoyl chloride (1.1 mmol) and MS4 Å (1.2 g). Two hours later, $EtN(i-Pr)_2$ (2.5 mmol) was further added to the reaction mixture. After overnight stirring, the reaction mixture was filtered and concentrated under reduce pressure. Water was then added to the residue which was extracted with EtOAc three times, the combined organic layers were dried over $Na_2SO_4$ and concentrated under reduce pressure to give the crude product which was purified by flash chromatography to give 17-picolinoyl-aminogeldanamycin as a yellow solid. Rf=0.52 in 80:15:5 $CH_2Cl_2$: EtOAc: MeOH. Mp=195-197° C. $^1H$ NM ($CDCl_3$) δ 0.91 (d, 3H), 0.96 (d, 3H), 1.71-1.73 (m, 2H), 1.75-1.79 (m, 4H), 2.04 (s, 3H), 2.70-2.72 (m, 2H), 2.74-2.80 (m, 1H), 3.33-3.35 (m, 7H), 3.46-3.49 (m, 1H), 4.33 (d, 1H), 5.18 (s, 1H), 5.77 (d, 1H), 5.91 (t, 1H), 6.57 (t, 1H), 6.94 (d, 1H), 7.51-7.56 (m, 2H); 7.91 (dt, 1H), 8.23 (d, 1H), 8.69-8.70 (m, 1H), 8.75(s, 1H), 10.51 (s, 1H).

Example 18

Preparation of Compound #530

Synthesis of 17-isonicotinoyl-aminogeldanamycin. This product was prepared according to the procedure described for Compound #529 (Example 17) except that isonicotinoyl chloride was used instead of picolinoyl chloride. Rf=0.44 in 80:15:5 $CH_2Cl_2$: EtOAc: MeOH. Mp=167-169° C. $^1H$ NMR ($CDCl_3$) δ 0.94-0.96 (m, 6H), 1.69 (br s, 2H), 1.83 (br s, 3H), 2.04 (s, 3H), 2.34 (br s, 1H), 2.54 (dd, 1H), 2.63 (dd, 1H), 2.77-2.81 (m, 1H), 3.31-3.34 (m, 7H), 3.44 (br s, 1H), 4.33 (d, 1H), 5.16 (s, 1H), 5.73 (d, 1H), 5.93 (t, 1H), 6.57 (t, 1H), 6.94 (d, 1H), 7.51 (s, 1H), 7.76 (d, 2H), 8.53 (s, 1H), 8.76 (s, 1H), 8.86 (dd, 2H).

Example 19

Preparation of Compound #557

Synthesis of 17-(4-methyl-1,2,3-thiadiazole-5-carbonyl-amino)-geldanamycin. This product was prepared according to the procedure described for Compound #529 (Example 17) except that 4-methyl-1,2,3-thiadiazole-5-carboxoyl chloride was used instead of picolinoyl chloride. Rf=0.35 in 80:15:5 $CH_2Cl_2$: EtOAc: MeOH. Mp=157-159° C. $^1H$ NMR ($CDCl_3$) δ 0.94 (d, 3H), 0.96 (d, 3H), 1.66-1.69 (m, 2H), 1.78 (br s, 3H), 1.83-1.85 (m, 1H), 2.04 (s, 3H), 2.49 (dd, 1H), 2.58 (dd, 1H), 2.76-2.81 (m, 1H), 3.00 (s, 3H), 3.29-3.34 (m, 7H), 3.39-3.44 (m, 1H), 4.32 (d, 1H), 5.12 (s, 1H), 5.70 (d, 1H), 5.93 (t, 1H), 6.56 (t, 1H), 6.93 (d, 1H), 7.50 (s, 1H), 8.29 (s, 1H), 8.76 (s, 1H).

Example 20

Preparation of Compound #558

Synthesis of 17-(3,5-dimethyl-isoxazol-4-carbonyl-amino)-geldanamycin. This product was prepared according to the procedure described for Compound #529 (Example 17) except that 3,5-dimethyl-isoxazol-4-carboxoyl chloride was used instead of A picolinoyl chloride. Rf=0.35 in 80:15:5 $CH_2Cl_2$: EtOAc: MeOH. Mp=190-192° C. $^1H$ NMR ($CDCl_3$) δ 0.94 (t, 6H), 1.70 (br s, 2H), 1.74-1.79 (m, 4H), 2.04 (s, 3H), 2.46 (dd, 1H), 2.51 (s, 3H), 2.61 (dd, 1H), 2.70 (s, 3H), 2.75-2.80 (m, 1), 3.28-3.39 (m, 7H), 3.45 (br d, 1H), 4.32 (d, 1H), 5.15 (s, 1H), 5.74 (d, 1H), 5.92 (t, 1H), 6.57 (t, 1H), 6.93 (d, 1H), 7.49 (s, 1H), 8.04 (s, 1H), 8.77 (s, 1H).

Example 21

Preparation of Compound #559

Synthesis of 17-(5-methyl-2-phenyl-2H-1,2,3-triazole-4-carbonyl-amino)-geldanamycin. This product was prepared according to the procedure described for Compound #529 (Example 17) except that 5-methyl-2-phenyl-2H-1,2,3-triazole-4-carboxoyl chloride was used instead of picolinoyl chloride. Rf=0.44 in 80:15:5 $CH_2Cl_2$: EtOAc: MeOH. Mp=230-232° C. $^1H$ NMR ($CDCl_3$) δ 0.95 (d, 3H), 0.96 (d, 3H), 1.73 (br s, 2H), 1.79 (br s, 4H), 2.04 (s, 3H), 2.62-2.72 (m, 5H), 2.76-2.80 (m, 1H), 3.28-3.35 (m, 7H), 3.45-3.49 (m, 1H), 4.33 (d, 1H), 5.17 (s, 1H), 5.76 (d, 1H), 5.93 (t, 1H), 6.57 (t, 1H), 6.94 (d, 1H), 7.40-7.44 (m, 1H), 7.50-7.54 (m, 3H), 8.10-8.12 (m, 2H), 8.75 (s, 1H), 9.23(s, 1H).

Example 22

Preparation of Compound #560

Synthesis of 17-(1,3-dimethyl-1H-pyrazole-5-carbonyl-amino)-geldanamycin. This product was prepared according to the procedure described for Compound #529 (Example 17) except that 1,3-dimethyl-1H-pyrazole-5-carboxoyl chloride was used instead of picolinoyl chloride. Rf=0.30 in 80:15:5 $CH_2Cl_2$: EtOAc: MeOH. Mp=193-195° C. $^1H$ NMR ($CDCl_3$) δ 0.93 (d, 3H), 0.95 (d, 3H), 1.69 (br s, 2H), 1.79 (br s, 4H), 2.04 (s, 3H), 2.31 (s, 3H), 2.51 (dd, 1H), 2.62 (dd, 1H), 2.75-2.80 (m, 1H), 3.28-3.39 (m, 7H), 3.43-3.45 (m, 1H), 4.12 (s, 3H), 4.32 (d, 1H), 5.16 (s, 1H), 5.74 (d, 1H), 5.92 (t, 1H), 6.56 (s, 1H), 6.57 (t, 1H), 6.93 (d, 1H), 7.49 (s, 1H), 8.29 (s, 1H), 8.75 (s, 1H).

Example 23

Preparation of Compound #561

Synthesis of 17-(1-t-butyl-3-methyl-1H-pyrazole-5-carbonyl-amino)-geldanamycin. This product was prepared according to the procedure described for Compound #529 (Example 17) except that 1-t-butyl-3-methyl-1H-pyrazole-5-carboxoyl chloride was used instead of picolinoyl chloride. Rf=0.37 in 80:15:5 $CH_2Cl_2$: EtOAc: MeOH. Mp=216-218° C. $^1H$ NMR ($CDCl_3$) δ 0.95 (t, 6H), 1.68 (s, 9H), 1.71 (br s, 2H), 1.79 (br s, 4H), 2.04 (s, 3H), 2.29 (s, 3H), 2.50 (dd, 1H), 2.66 (dd, 1H), 2.75-2.80 (m, 1H), 3.27-3.39 (m, 7H), 3.45-3.47 (m, 1H), 4.32 (d, 1H), 5.16 (s, 1H), 5.75 (d, 1H), 5.91 (t, 1H), 6.47 (s, 1H), 6.57 (t, 1H), 6.93 (d, 1H), 7.48 (s, 1H), 8.17 (s, 1H), 8.74 (s, 1H).

Example 24

Preparation of Compound #562

Synthesis of 17-(3-t-butyl-1-methyl-1H-pyrazole-5-carbonyl-amino)-geldanamycin. This product was prepared according to the procedure described for Compound #529 (Example 17) except that 3-t-butyl-1-methyl-1H-pyrazole-5-carboxoyl chloride was used instead of picolinoyl chloride. Rf=0.30 in 80:15:5 $CH_2Cl_2$: EtOAc: MeOH. $^1H$ NMR ($CDCl_3$) δ 0.95 (t, 6H), 1.33 (s, 9H), 1.69 (br s, 2H), 1.79 (br s, 4H), 2.04 (s, 3H), 2.52 (dd, 1H), 2.63 (dd, 1H), 2.75-2.80

(m, 1H), 3.28-3.39 (m, 7H), 3.44-3.46 (m, 1H), 4.13 (s, 3H), 4.33 (d, 1H), 5.16 (s, 1H), 5.745 (d, 1H), 5.92 (t, 1H), 6.57 (t, 1H), 6.59 (s, 1H), 6.94 (d, 1H), 7.50 (s, 1H), 8.31 (s, 1H), 8.76 (s, 1H).

Example 25

Preparation of Compound #563

Synthesis of 17-(benzoyl)-aminogeldanamycin. This product was prepared according to the procedure described for Compound #529 (Example 17) except, that benzoyl chloride was used instead of picolinoyl chloride. Rf=0.50 in 80:15:5 $CH_2Cl_2$: EtOAc: MeOH. Mp=218-220° C. $^1$H NMR ($CDCl_3$) δ 0.94 (t, 6H), 1.70 (br s, 2H), 1.79 (br s, 4H), 2.03 (s, 3H), 2.56 (dd, 1H), 2.64 (dd, 1H), 2.76-2.79 (m, 1H), 3.33 (br s, 7H), 3.44-3.46 (m, 1H), 4.325 (d, 1H), 5.16 (s, 1H), 5.77 (d, 1H), 5.91 (t, 1H), 6.57 (t, 1H), 6.94 (d, 1H), 7.48 (s, 1H), 7.52 (t, 2H), 7.62 (t, 1H), 7.91 (d, 2H), 8.47 (s, 1H), 8.77 (s, 1H).

Example 26

Preparation of Compound #515

Synthesis of 17-(4-fluoro-benzyl)-3-(17-geldanamycinyl)-urea This product was prepared according to the procedure described for Compound #495 (Example 16), except that 4-fluoro-bezylisocyanate was used instead of allylisocyanate. Rf=0.42 in 80:15:5 $CH_2Cl_2$: EtOAc: MeOH. Mp=175-177° C. $^1$H NMR ($CDCl_3$) δ 0.93 (m, 6H), 1.68 (br s, 2H), 1.77 (br s, 4H), 2.02 (s, 3H), 2.50-2.55 (m, 2H), 2.74-2.78 (m, 1H), 3.31 (s, 3H), 3.33 (s, 3H), 3.29-3.32 (m, 1H), 3.40-3.43 (m, 1H), 4.30 (d, 1H), 4.41 (d, 2H), 5.14 (s, 1H), 5.75 (m, 2H), 5.89 (t, 1H), 6.56 (t, 1H), 6.91 (d, 1H), 7.01-7.05 (m, 2H), 7.28-7.31 (m, 2H), 7.37-7.39 (m, 2H), 8.78 (s, 1H).

Example 27

Preparation of Compound #484

Compound 484 was prepared by the same method described in example 1 except that 2,2'thiobis(ethylamine) was used instead of 3,3'-diamino-N-methyldipropylamine. The pure purple product was obtained after column chromatography (silica gel), yield: 89%; mp 151.2-152.9° C.; $^1$H NMR ($CDCl_3$) δ 0.86 (d, J=7 Hz, 6H, 2CH$_3$), 1.00 (d, J=7 Hz, 6H, 2CH3), 1.60 (m, 4H, 2 CH2), 1.64 (m, 4H, 2CH2), 1.72 (m, 2H, 2CH), 1.79 (s, 6H, 2 CH$_3$), 2.00 (s, 6H, 2CH$_3$), 2.36 (dd, J=14 Hz, 2H, 2CH), 2.63 (d, 2H, 2CH), 3.25 (s, 6H, 2OCH3), 3.35 (s, 6H, 2OCH$_3$), 3.40 (m, 2H, 2CH), 3.70 (m, 2H, 2CH), 3.80 (m, 4H, 2CH2), 4.20 (Bs, 2H, OH), 4.30 (d, J=10 Hz, 2H, 2CH), 4.80 (Bs, 4H, 2NH2), 5.19 (s, 2H, 2CH), 5.82 (t, J=15 Hz, 2H, 2CH=), 5.89 (d, J=10 Hz, 2H, 2CH=), 6.49 (t, 2H, 2NH), 6.59 (t, J=15 Hz, 2H, 2CH=), 6.92 (d, J=10 Hz, 2H, 2CH=), 7.24 (s, 2H, 2CH=), 9.21 (s, 2H, 2NH); MS (m/z)1220 (M+Na);

Example 28

Preparation of Compound #486

Compound 486 was prepared by the same method described in example 1 except that 4,9-dioxa-1,12-dodecanediamine was used instead of 3,3'-diamino-N-methyldipropylamine. The pure purple product was obtained after column chromatography (silica gel); yield: 90%; mp 136.6-137.9° C.; $^1$H NMR ($CDCl_3$) δ 0.97 (d, J=6.6 Hz, 6H, 2CH$_3$), 1.00 (d, J=6.6 Hz, 6H, 2CH3), 1.72 (m, 2H, 2 CH), 1.78 (m, 8H, 4CH2), 1.80 (s, 6H, 2 CH$_3$), 1.85 (m, 4H, 2CH$_2$), 2.00 (s, 6H, 2CH$_3$), 2.40 (dd, J=11 Hz, 2H, 2CH), 2.67 (d, J=15 Hz, 2H, 2CH), 2.63 (t, J=10 HZ, 2H, 2CH), 3.26 (s, 6H, 2OCH3), 3.38 (s, 6H, 2OCH3), 3.40 (m, 6H, 2CH+2CH2), 3.60 (m, 6H, 2CH+2CH2), 3.75 (m, 4H, 2CH2), 4.60 (d, J=10 Hz, 2H, 2CH), 4.65 (Bs, 2H, 2OH), 4.80 (Bs, 4H, 2NH2), 5.19 (s, 2H, 2CH), 5.83 (t, J=15 Hz, 2H, 2CH=), 5.89 (d, J=10 Hz, 2H, 2CH=), 6.58 (t, J=15 Hz, 2H, 2CH=), 6.94 (d, J=10 Hz, 2H, 2CH=), 7.24 (s, 2H, 2CH=), 9.20 (s, 2H, 2NH); MS (m/z) 1284 (M+Na).

The following schematic pertains to Example 29:

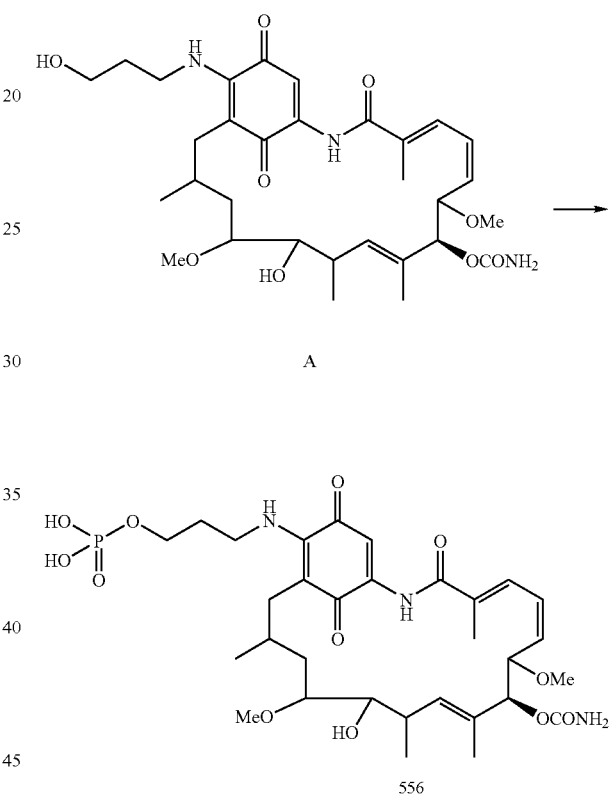

Example 29

Preparation of Compound #556

A 50 ml RBF equipped with a stir bar was charged with 200 mg A in 5 ml anhydrous THF and then the flask flushed with nitrogen. After cooling to 0° C., 15 mg NaH (60% dispersion in mineral oil) was added, and the reaction stirred for 15 minutes. 34 μl of POCl$_3$ was added to the reaction mixture, and the reaction removed from the ice bath. After stirring at room temperature for 16 hours, a small amount of H$_2$O was added. All the solvent and water was removed under high vacuum, and the resulting solid purified by preparative TLC (90/10 Acetone/H$_2$O R$_f$=0.1) to afford 18 mg (8% yield) of 556 as a purple solid.

The following schematic applies to Examples 30-33:

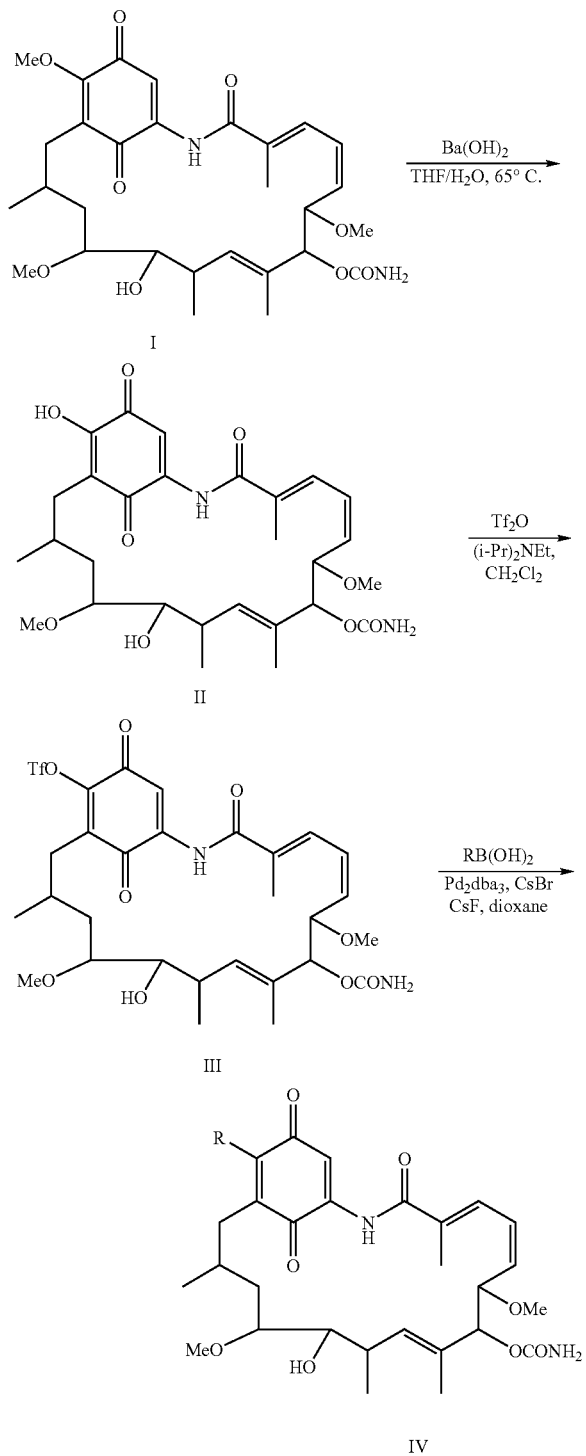

Synthesis of compounds IV of the present invention typically includes some or all of the following steps. In the presence of barium hydroxide, geldanamycin I is first hydrolyzed into 17-hydroxy-geldanamycin of formula II, which reacts quantitatively with triflic anhydride to give the triflate of formula III. Under optimized Suzuki conditions, this latter leads with moderate yield to the 17-aryl-geldanamycins of formula IV. (For synthetic overview, see D. A. Neel et al. Bioorg. Med. Chem. Lett. 8: 47-50, 1998).

Example 30

Preparation of 17-OTf-geldanamycin

To a purple solution of 17-hydroxy-geldanamycin (1 mmol) and (i-Pr)$_2$NEt (2 mmol) in CH2Cl2 at 0° C. was added dropwise the triflic anhydride (1.3 mmol). After 30 min, the reaction mixture was concentrated under reduce pressure. The crude material was then purified by flash chromatography to give 17-OTf-geldanamycin as a yellow solid: Rf=0.28 in 80:15:5 CH$_2$Cl$_2$: EtOAc: MeOH. $^1$H NMR (CDCl$_3$, 500 MHz) δ 0.89 (d, 3H), 1.09 (d, 3H), 1.53-1.62 (m, 2H), 1.68-1.74 (m, 1H), 1.77 (s, 3H), 2.03 (s, 3H), 2.49 (dd, 1H), 2.58 (dd, 1H), 2.78-2.83 (m, 1H), 3.25-3.27 (m, 1H), 3.30-3.32 (m, 1H), 3.35 (s, 3H), 3.38 (s, 3H), 4.32 (d, 1H), 5.10 (s, 1H), 5.59 (d, 1H), 5.96 (dd, 1H), 6.55 (t, 1H), 6.92 (d, 1H), 7.58 (s, 1H), 8.60 (s, 1H).

Example 31

Synthesis of Compound #133

Synthesis of 17-phenyl-geldanamycin. A solution of 17-OTf-geldanamycin (1 mmol), cesium bromide (2 mmol), cesium fluoride (2 mmol), Pd(dba)$_2$ (0.2 mmol) and phenyl boronic acid (2 mmol) in dioxane was heated at 40° C. for 12 hours whereupon it was cooled down to RT and concentrated under reduce pressure to give the crude product. This latter was dissolved in EtOAc and washed with sat. NaHCO3, dried over Na2SO4 and concentrated under reduce pressure. The crude material was purified by flash chromatography to give 17-phenyl-geldanamycin as a yellow solid. Rf=0.49 in 80:15:5 CH$_2$Cl$_2$: EtOAc: MeOH. $^1$H NMR (CDCl$_3$) δ 0.71 (d, 3H), 0.98 (d, 3H), 1.53-1.63 (m, 3H), 1.79 (s, 3H), 2.04 (s, 3H), 2.35 (dd, 1H), 2.54-2.60 (m, 1H), 2.73-2.77 (m, 1H), 3.31 (s, 3H), 3.34 (s, 3H), 3.35-3.37 (m, 1H), 3.47-3.52 (m, 1H), 4.36 (d, 1H), 5.24 (s, 1H), 5.75 (d, 1H), 5.90 (t, 1H), 6.58 (t, 1H), 6.96 (d, 1H), 7.12-7.14 (m, 2H), 7.40-7.43 (m, 3H), 7.56 (s, 1H), 8.68 (s, 1H).

Example 32

Synthesis of Compound #212

Synthesis of 17-(2-methoxy-phenyl)-geldanamycin. Compound 212 was prepared according to the procedure described for 17-phenyl-geldanamycin except that 2-methoxy-phenyl boronic acid was used instead of phenyl boronic acid. Rf=0.36 in 80:15:5 CH$_2$Cl$_2$: EtOAc: MeOH. $^1$H NMR (CDCl$_3$) δ 0.98 (d, 3H), 1.04 (d, 3H), 1.53-1.63 (m, 3H), 1.80 (s, 3H), 2.03 (s, 3H), 2.52-2.62 (m, 2H), 2.78-2.83 (m, 1H), 2.85 (d, 1H), 3.32 (s, 3H), 3.36 (s, 3H), 3.37-3.39 (m, 1H), 3.54-3.56 (m, 1H), 3.76 (s, 3H), 4.34 (d, 1H), 5.19 (s, 1H), 5.83 (d, 1H), 5.90 (t, 1H), 6.58 (t, 1H), 6.89-6.92 (m, 2H), 6.96 (br d, 2H), 7.06 (br t, 1H), 7.29 (s, 1H), 8.74 (s, 1H).

Example 33

Synthesis of Compound #232

Synthesis of 17-(2-thiophen)-geldanamycin was prepared according to the procedure described for 17-phenyl-geldanamycin except that 2-thiophene boronic acid was used instead of phenyl boronic acid. Rf=0.50 in 80:15:5 CH$_2$Cl$_2$: EtOAc: MeOH. $^1$H NMR (CDCl$_3$) δ 0.82 (d, 3H), 0.97 (d, 3H), 1.50-1.603 (m, 3H), 1.78 (s, 3H), 2.05 (s, 3H), 2.42-2.50 (m, 2H), 2.76-2.81 (m, 1H), 3.33 (s, 3H), 3.34 (s, 3H), 3.33-3.36 (m, 1H), 3.48-3.50 (m, 1H), 4.35 (d, 1H), 5.21 (s, 1H), 5.72 (d, 1H), 5.91 (t, 1H), 6.57 (t, 1H), 6.92 (d, 1H), 7.12-7.14 (m, 1H), 7.55 (s, 1H), 7.55-7.58 (m, 2H), 8.68 (s, 1H).

The following schematic applies to Example 34:

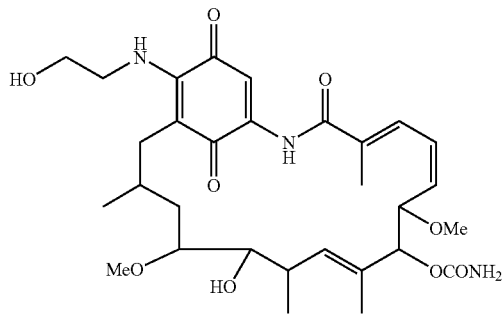

A

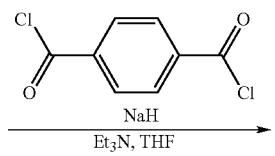

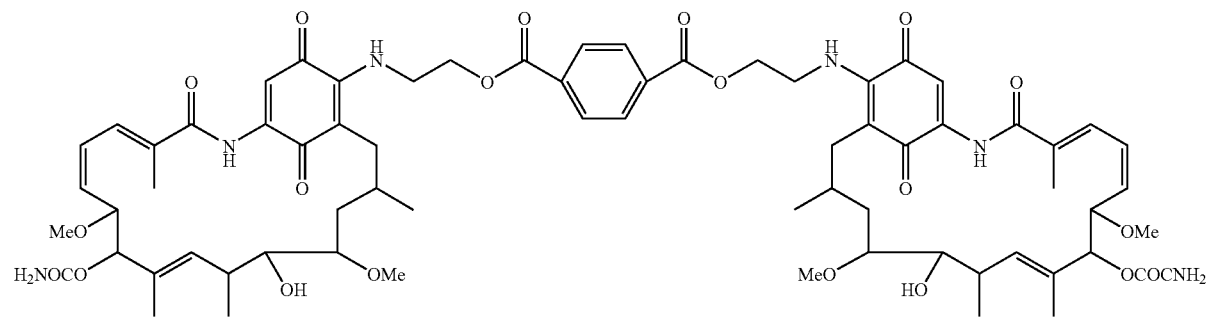

Compound #594

Example 34

Synthesis of Compound #594

Sodium hydride (10.3 mg, 0.257 mmol) was added to a solution of compound A (150 mg, 0.257 mmol) in THF (10 ml) in a flame-dried flask under $N_2$ and stirred at room temperature for 10 minutes. Terephthaloyl chloride (26.1 mg, 0.129 mmol) and triethylamine (36 ul, 0.257 mmol) were added and the reaction mixture was stirred for 2 hours at room temperature. Water was added and the resulting precipitate was filtered to give the crude product Compound#594. Purification by silica gel chromatography (5% $CH_3OH/CH_2Cl_2$) afforded the desired dimer as a purple solid (140 mg, 0.107 mmol). Yield: 83%; $^1H$ NMR ($CDCl_3$) δ 0.95 (d, J=7 Hz, 6H, 2CH$_3$), 1.00 (d, J=7 Hz, 6H, 2CH$_3$), 1.69 (m, 4H, 2 CH$_2$), 1.76 (s, 6H, 2 CH$_3$), 1.83 (m, 2H, 2CH), 2.00 (s, 6H, 2CH$_3$), 2.36 (dd, J=14 Hz, 2H, 2CH), 2.63 (d, 2H, 2CH), 2.75(m, 2H, 2CH), 3.25 (s, 6H, 2OCH$_3$), 3.35 (s, 6H, 2OCH$_3$), 3.40 (m, 2H, 2CH), 3.68(m, 2H, 2CH), 3.90 (m, 4H, 2CH$_2$), 4.0 (m, 4H, 2CH$_2$), 4.20 (Bs, 2H, OH), 4.30 (d, J=10 Hz, 2H, 2CH), 4.80 (Bs, 4H, 2NH$_2$), 5.19 (s, 2H, 2CH), 5.82 (t, J=15 Hz, 2H, 2CH=), 5.89 (d, J=10 Hz, 2H, 2CH=), 6.59 (t, J=15 Hz, 2H, 2CH=), 6.92 (d, J=10 Hz, 2H, 2CH=), 7.13 (t, 2H, 2NH), 7.24 (s, 2H, 2CH=), 8.14 (s, 4H, Ar—H), 9.21 (s, 2H, 2NH); MS (m/z)1308 (M—H).

Example 35

Preparation of Compound #564

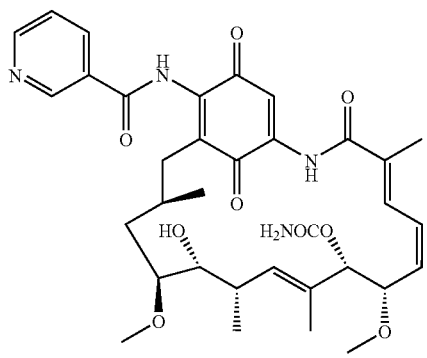

Compound #564 was prepared according to the procedure described for compound #529 using nicotinyl chloride HCl salt instead of picolinoyl chloride. Rf=0.27 in 80:15:5 CH$_2$Cl$_2$: EtOAc: MeOH. $^1H$ NMR CDCl$_3$ δ 0.94 (t, 3H), 0.955 (d, 3H), 1.69-1.74 (m, 2H), 1.79 (s, 3H), 1.83-1.87 (m, 1H), 2.03 (s, 3H), 2.51-2.63 (m, 2H), 2.77-2.81 (m, 1H), 3.30-3.37 (m, 7H), 3.44-3.49 (m, 1H), 4.33 (d, 1H), 5.14 (s, 1H), 5.74 (d, 1H), 5.92 (t, 1H), 6.56 (t, 1H), 6.94 (d, 1H), 7.49-7.52 (m, 2H), 8.25 (d, 1H), 8.56 (br s, 1H), 8.75 (s, 1H), 8.84 (dd, 1H), 9.17 (s, 1H).

Example 36

Preparation of Compound #1046

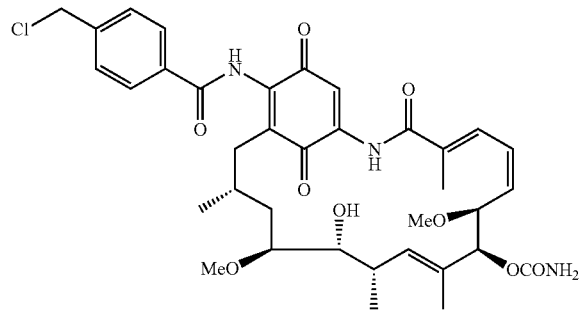

Compound #1046 was prepared according to the procedure described for compound #529 using 4-chloromethyl-benzoyl chloride instead of picolinoyl chloride. (3.1 g, 81%). Rf=0.45 in 80:15:5 $CH_2Cl_2$: EtOAc: MeOH. $^1H$ NMR $CDCl_3$ δ 0.89 (d, 3H), 0.93 (d, 3H), 1.70 (br s, 2H), 1.79 (br s, 4H), 2.04 (s, 3H), 2.52-2.58 (m, 2H), 2.62-2.63 (m, 1H), 2.76-2.79 (m, 1H), 3.33 (br s, 7H), 3.43-3.45 (m, 1H), 4.33 (d, 1H), 4.64 (s, 2H), 5.17 (s, 1H), 5.76 (d, 1H), 5.92 (t, 1H), 6.57 (t, 1H), 6.94 (d, 1H), 7.49 (s, 1H), 7.55 (d, 2H), 7.91 (d, 2H), 8.46 (s, 1H), 8.77 (s, 1H).

Example 37

Preparation of Compound #687

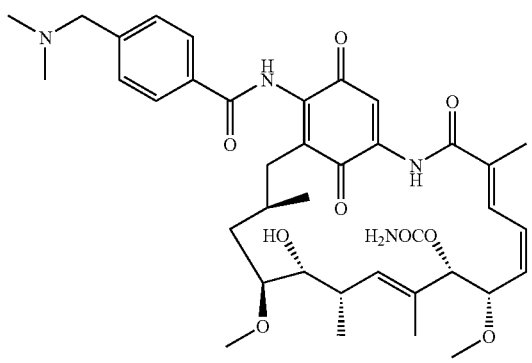

Procedure A:

A solution of 17-aminogeldanamycin (1.12 g, 2.0 mmol) in EtOAc (200 ml) was treated with $Na_2S_2O_4$ (10%, 20 ml) at rt. After 2 h, the aqueous layer was extracted with EtOAc (20 ml), the combined organic layers were dried over $Na_2SO_4$ and concentrated under reduce pressure to give 18,21-dihydro-17-aminogeldanamycin as a yellow solid. This latter was dissolved in anhydrous DMF (10 ml) and transferred via cannula to a mixture 4-N,N-dimethylaminomethyl-benzoic acid (0.48 g, 2.25 mmol), EDCI (0.47 g, 2.46 mmol) and HOBT (0.33 g, 2.46 mmol) in DMF (5 ml) at room temperature. After 12 hours, $CUSO_4$ (0.2 g, 1.26 mmol) and MeOH (2 ml) were further added to the reaction mixture. After 4h, the reaction mixture was poured into water (70 ml) and extracted with EtOAc (2×30 ml). The aqueous layer was then neutralized to pH 7 with sat. $NaHCO_3$ and extracted with EtOAc (3×30 ml). The combined organic layers were dried over $Na_2SO_4$ and concentrated under reduce pressure to give the crude material which was purified by flash chromatography and recrystallization in i-PrOH to give 17-(4-dimethylaminomethyl-benzoyl)-aminogeldanamycin as a yellow solid (0.30 g, 21%). Rf=0.10 in 80:15:5 $CH_2Cl_2$: EtOAc: MeOH. Mp=203-206° C. $^1H$ NMR $CDCl_3$ δ 0.93 (d, 3H), 0.95 (d, 3H), 1.70-1.74 (m, 3H), 1.79 (s, 3H), 2.04 (s, 3H), 2.29 (s, 6H), 2.53-2.59 (m, 1H), 2.63-2.67 (m, 1H), 2.75-2.79 (m, 1H), 3.33 (br s, 7H), 3.46 (br s, 1H), 3.54 (s, 2H), 4.33 (d, 1H), 5.16 (s, 1H), 5.77 (d, 1H), 5.91 (t, 1H), 6.57 (t, 1H), 6.94 (d, 1H), 7.48 (s, 1H), 7.49 (t, 2H), 7.87 (d, 2H), 8.47 (s, 1H), 8.77 (s, 1H).

Procedure B:

To a solution of compound #1046 (3.73 g, 5.3 mmol) in $CH_2Cl_2$ (50 ml) were added $Me_2NH,HCl$ salt (1.51 g, 18.5 mmol), Et(i-Pr)$_2$N (2.8 ml) and NaI (0.79 g, 5.3 mmol). The resulting solution was heated at reflux for 6 hours whereupon it was cooled to rt, diluted with EtOAc (600 ml), washed with water (100 ml), dried with $Na_2SO_4$ and concentrated under reduce pressure to give the crude material which was purified by recrystallization in EtOH to give 17-(4-dimethylaminomethyl-benzoyl)-aminogeldanamycin as a yellow solid (1.74 g, 46%).

Example 38

Preparation of Compound #696

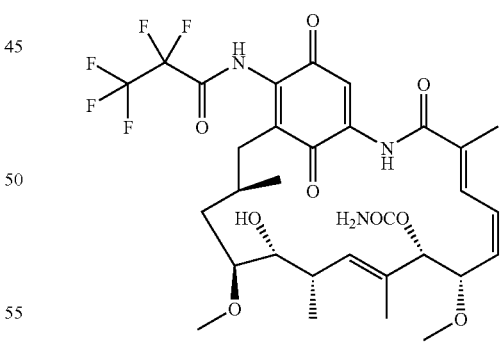

Compound #696 was prepared according to the procedure described for compound #529 using pentafluoropropanoyl chloride instead of picolinoyl chloride.

Rf=0.37 in 80:15:5 $CH_2Cl_2$: EtOAc: MeOH. $^1H$ NMR $CDCl_3$ δ 0.92-0.94 (d, 6H), 1.54 1.69 (m, 2H), 1.77 (s, 3H), 1.80 (br s, 1H), 2.02 (s, 3H), 2.42 (dd, 1H), 2.47-2.51 (m, 1H), 2.76-2.80 (m, 1H), 3.27-3.34 (m, 7H), 3.38-3.41 (m, 1H), 4.32 (d, 1H), 5.14 (s, 1H), 5.68 (d, 1H), 5.93 (t, 1H), 6.55 (t, 1H), 6.92 (d, 1H), 7.53 (s, 1H), 8.59 (s, 1H), 8.68 (s, 1H).

Example 39

Preparation of Compound #697

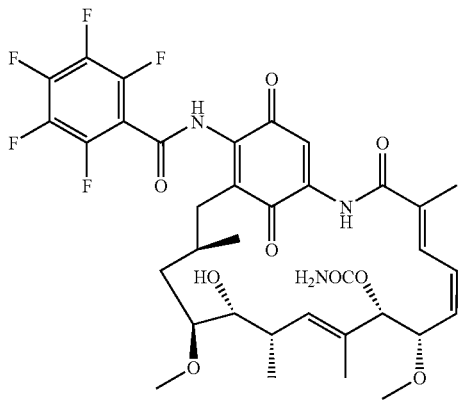

Compound #697 was prepared according to the procedure described for compound #529 using pentafluoro benzoyl chloride instead of picolinoyl chloride. Rf=0.43 in 80:15:5 CH$_2$Cl$_2$: EtOAc: MeOH. $^1$H NMR CDCl$_3$ δ 0.95 (d, 3H), 0.97 (d, 3H), 1.64-1.75 (m, 2H), 1.78 (s, 3H), 1.84 (br s, 1H), 2.04 (s, 3H), 2.54 (dd, 1H), 2.61 (m, 1H), 2.77-2.80 (m, 1H), 3.34-3.35 (m, 7H), 3.42-3.44 (m, 1H), 4.33 (d, 1H), 5.15 (s, 1H), 5.72 (d, 1H), 5.93 (t, 1H), 6.56 (t, 1H), 6.93 (d, 1H), 7.50 (s, 1H), 8.19 (s, 1H), 8.72 (s, 1H).

Example 40

Preparation of Compound #723

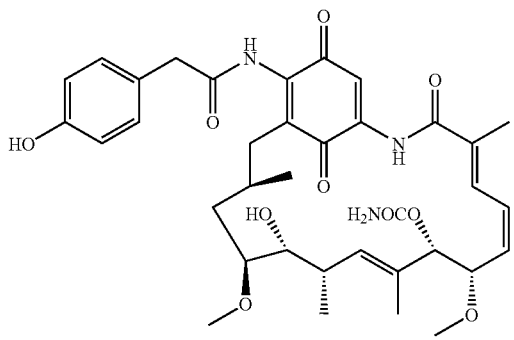

Compound #723 was prepared according to procedure A described for compound #687 using 4-hydroxyphenyl acetic acid instead of 4-(dimethylaminomethyl)benzoic acid. Rf=0.38 in 80:15:5 CH$_2$Cl$_2$: EtOAc: MeOH. $^1$H NMR CDCl$_3$ δ 0.78 (d, 3H), 0.86 (d, 3H), 1.44-1.54 (m, 2H), 1.69 (br s, 4H), 1.97 (s, 3H), 2.29 (dd, 1H), 2.38 (dd, 1H), 2.65-2.70 (m, 1H), 3.22-3.35 (m, 8H), 3.61 (s, 2H), 4.27 (d, 1H), 5.03 (s, 1H), 5.61 (d, 1H), 5.84 (t, 1H), 6.50 (t, 1H), 6.80 (d, 2H), 6.85 (d, 1H), 7.12 (d, 2H), 7.32 (s, 1H).

Example 41

Preparation of Compound #777

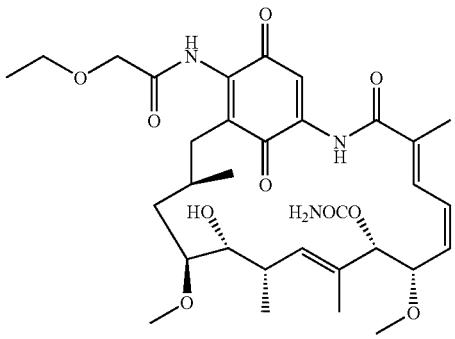

Compound #777 was prepared according to procedure A described for compound #687 using 2Oethoxy acetic acid instead of 4-(dimethylaminomethyl)benzoic acid. Rf=0.43 in 80:15:5 CH$_2$Cl$_2$: EtOAc: MeOH. $^1$H NMR CDCl$_3$ δ 0.96 (t, 6H), 1.33 (t, 3H), 1.68-1.70 (m, 2H), 1.72-1.74 (m, 1H), 1.77 (s, 3H), 2.02 (s, 3H), 2.50-2.60 (m, 2H), 2.72-2.78 (m, 1H), 3.31-3.33 (m, 7H), 3.41-3.44 (m, 1H), 3.66 (q, 2H), 4.08 (d, 2H), 4.31 (d, 1H), 5.14 (s, 1H), 5.74 (d, 1H), 5.90 (t, 1H), 6.55 (t, 1H), 6.915 (d, 1H), 7.45 (s, 1H), 8.70 (s, 1H), 8.86 (s, 1H).

Example 42

Preparation of Compound #846

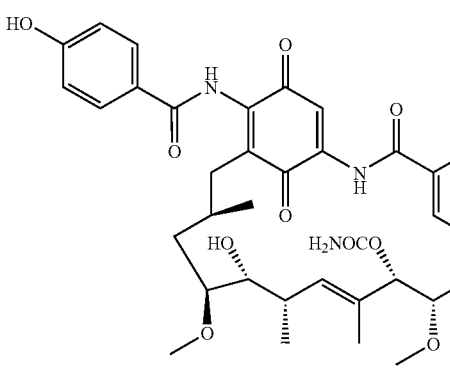

Compound #846 was prepared according to procedure A described for compound #687 using 4-hydroxybenzoic acid instead of 4-(dimethylaminomethyl)benzoic acid. Rf=0.13 in 80:15:5 CH$_2$Cl$_2$: EtOAc: MeOH. $^1$H NMR CDCl$_3$ δ 0.89 (d, 6H), 1.61 (br s, 2H), 1.72 (br s, 4H), 1.99 (s, 3H), 2.46 (dd, 1H), 2.55 (dd, 1H), 2.63-2.72 (m, 1H), 3.27-3.30 (m, 7H), 3.35-3.40 (m, 1H), 4.29 (d, 1H), 5.06 (s, 1H), 5.68 (d, 1H), 5.85 (t, 1H), 6.52 (t, 1H), 6.85-6.90 (m, 3H), 7.24 (s, 1H), 7.40 (s, 1H), 7.75 (d, 2H), 8.70 (s, 1H), 8.86 (s, 1H).

Example 43

Preparation of Compound #847

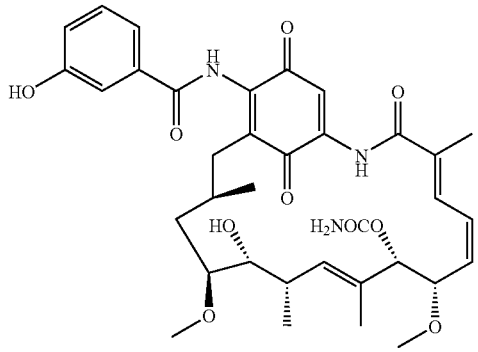

Compound #847 was prepared according to procedure A described for compound #687 using 3,5-dichlorobenzoic acid instead of 4-(dimethylaminomethyl)benzoic acid. Rf=0.13 in 80:15:5 $CH_2Cl_2$: EtOAc: MeOH. $^1H$ NMR $CDCl_3$ δ 0.92 (d, 6H), 1.65 (br s, 2H), 1.75 (br s, 4H), 2.00 (s, 3H), 2.47-2.59 (m, 2H), 2.73-2.76 (m, 1H), 3.30-3.32 (m, 7H), 3.40-3.42 (m, 1H), 4.31 (d, 1H), 5.11 (s, 1H), 5.71 (d, 1H), 5.88 (t, 1H), 6.53 (t, 1H), 6.915 (d, 1H), 7.05 (d, 1H), 7.30-7.34 (m, 3H), 7.44 (s, 1H), 8.49 (s, 1H), 8.80 (s, 1H).

Example 44

Preparation of Compound #850

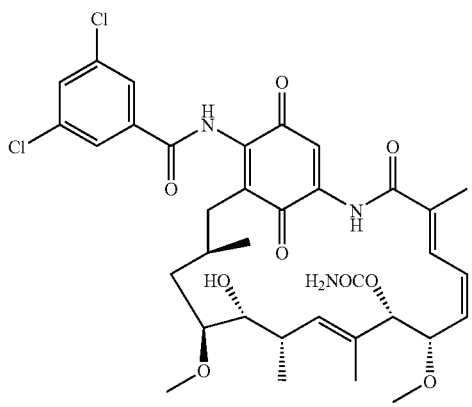

Compound #850 was prepared according to the procedure described for compound #687. Rf=0.45 in 80:15:5 $CH_2C_2$: EtOAc: MeOH. $^1H$ NMR $CDCl_3$ δ 0.93 (d, 3H), 0.95 (d, 3H), 1.59-1.61 (m, 2H), 1.73 (s, 3H), 1.84 (br s, 1H), 2.00 (s, 3H), 2.40-2.47 (m, 2H), 2.71-2.75 (m, 1H), 3.22-3.35 (m, 8H), 4.31 (d, 1H), 5.06 (s, 1H), 5.65 (d, 1H), 5.88 (t, 1H), 6.53 (t, 1H), 6.90 (d, 1H), 7.45 (s, 1H), 7.55 (s, 1H), 7.77 (s, 2H), 8.81 (s, 1H).

Example 45

Preparation of Compound #1059

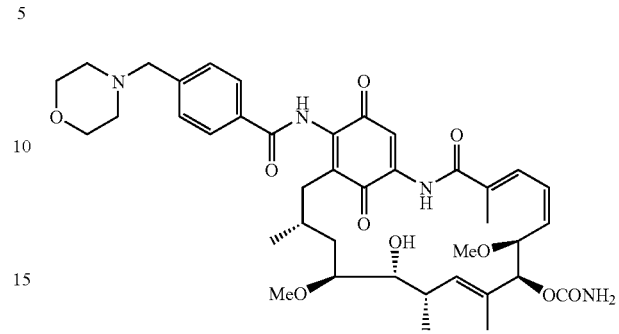

To a solution of compound #1046 (0.14 g, 0.2 mmol) in 1BF (5 ml) were added sodium iodide (30 mg, 0.2 mmol) and morpholine (35 μl, 0.4 mmol). The resulting mixture was heated at reflux for 10 h whereupon it was cooled to room temperature, concentrated under reduce pressure and the residue was redissolved in EtOAc (30 ml), washed with water (10 ml), dried with $Na_2SO_4$ and concentrated again. The residue was then recrystallized in EtOH (10 ml) to give the compound 1059 as a yellow solid (100 mg, 66%). Rf=0.10 in 80:15:5 $CH_2Cl_2$: EtOAc: MeOH. $^1H$ NMR $CDCl_3$ δ 0.93 (s, 3H), 0.95 (d, 3H), 1.70 (br s, 2H), 1.78 (br s, 4H), 2.03 (s, 3H), 2.48 (br s, 4H), 2.55-2.62 (m, 3H), 2.74-2.79 (m, 1H), 3.32 (br s, 71), 3.45 (m, 1H), 3.59 (s, 2H), 3.72-3.74 (m, 4H), 4.32 (d, 1H), 5.15 (s, 1H), 5.76 (d, 1H), 5.91 (t, 1H), 6.56 (t, 1H), 6.94 (d, 1H), 7.48 (s, 1H), 7.50 (d, 2H), 7.87 (d, 2H), 8.47 (s, 1H), 8.77 (s, 1H).

Example 46

Preparation of Compound #1060

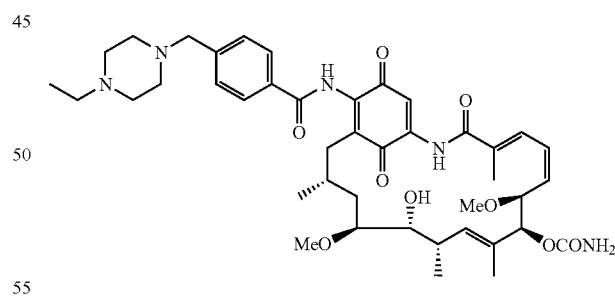

Compound #1060 was prepared according to the procedure described for compound #1059 using N-ethylpiperazine instead of morpholine. Rf=0.04 in 80:15:5 $CH_2Cl_2$: EtOAc: MeOH. $^1H$ NMR $CDCl_3$ δ 0.93 (d, 3H), 0.95 (d, 3H), 1.24 (t, 3H), 1.70 (br s, 2H), 1.79 (br s, 4H), 2.04 (s, 3H), 2.53-2.79 (m, 12H), 3.33 (br s, 71), 3.46 (m, 1H), 3.63 (s, 2H), 4.33 (d, 1H), 5.16 (s, 1H), 5.76 (d, 1H), 5.92 (t, 1H), 6.57 (t, 1H), 6.94 (d, 1H), 7.47 (d, 2H), 7.48 (s, 1H), 7.87 (d, 2H), 8.47 (s, 1H), 8.77 (s, 1H).

Example 47

Preparation of Compound #1066

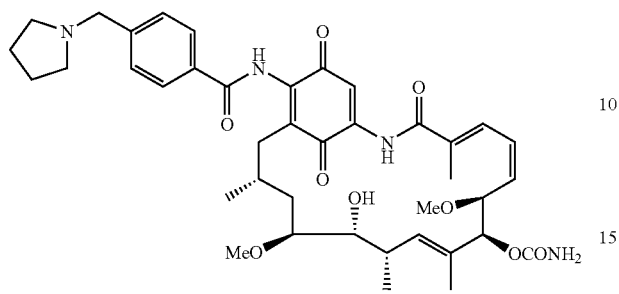

Compound #1066 was prepared according to the procedure described for compound #1059 using pyrrolidine instead of morpholine. Rf=0.28 in 80:10:10 $CH_2Cl_2$: EtOAc: MeOH. $^1$H NMR $CDCl_3$ δ 0.935 (d, 3H), 0.95 (d, 3H), 1.70 (br s, 2H), 1.79 (br s, 4H), 1.92 (br s, 4H), 2.04 (s, 3H), 2.52-2.65 (m, 3H), 2.75-2.79 (m, 5H), 3.33 (br s, 7H), 3.46 (m, 1H), 3.88 (s, 2H), 4.33 (d, 1H), 5.16 (s, 1H), 5.765 (d, 1H), 5.92 (t, 1H), 6.57 (t, 1H), 6.945 (d, 1H), 7.49 (s, 1H), 7.61 (d, 2H), 7.90 (d, 2H), 8.48 (s, 1H), 8.76 (s, 1H).

Example 48

Preparation of Compound #1078

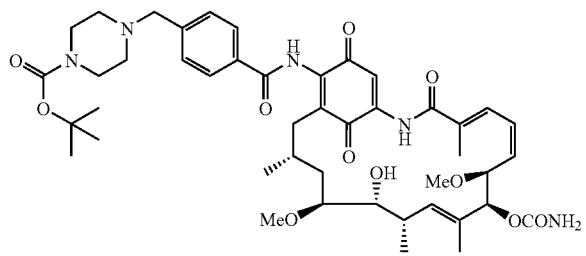

Compound #1078 was prepared according to the procedure described for compound #1059 using tert-butyl-N-piperazine carboxylic acid instead of morpholine. Rf=0.30 in 80:15:5 $CH_2Cl_2$: EtOAc: MeOH. $^1$H NMR $CDCl_3$ δ 0.925 (d, 3H), 0.94 (d, 3H), 1.45 (s, 9H), 1.69 (br s, 2H), 1.79 (br s, 4H), 2.03 (s, 3H), 2.41 (br s, 4H), 2.51-2.60 (m, 2H), 2.75-2.79 (m, 1H), 3.32 (br s, 7H), 3.45 (br s, 5H), 3.59 (s, 2H), 4.32 (d, 1H), 5.15 (s, 1H), 5.76 (d, 1H), 5.91 (t, 1H), 6.56 (t, 1H), 6.935 (d, 1H), 7.47 (s, 1H), 7.48 (d, 2H), 7.86 (d, 2H), 8.46 (s, 1H), 8.77 (s, 1H).

Example 49

Preparation of Compound #1102

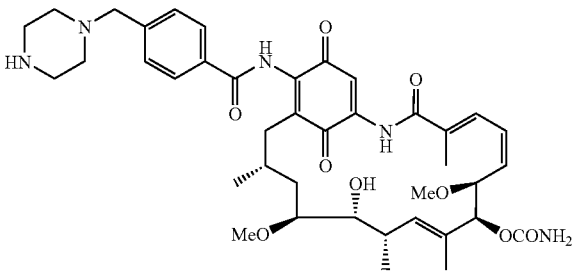

To a solution of compound #1078 (280 mg, 0.33 mmol) in $CH_2Cl_2$ (2 ml) was added dropwise at rt an excess of Compound#$_3$COOH (2 ml) and it was stirred for 15 min whereupon it diluted with $CH_2Cl_2$ (50 ml), washed with saturated $NaHCO_3$ (10 ml), dried over $Na_2SO_4$ and concentrated under reduce pressure. The residue was purified by flash chromatography to give the compound #1102 as a yellow solid (195 mg, 79%). Rf=0.09 in 80:5:15 $CH_2Cl_2$: EtOAc: MeOH. $^1$H NMR $CDCl_3$ δ 0.92 (d, 3H), 0.95 (d, 3H), 1.69 (br s, 2H), 1.78 (br s, 4H), 2.03 (s, 3H), 2.46 (br s, 4H), 2.56-2.62 (m, 2H), 2.75-2.79 (m, 1H), 2.91-2.94 (m, 4H), 3.32 (br s, 7H), 3.45 (m, 1H), 3.57 (s, 2H), 4.32 (d, 1H), 5.16 (s, 1H), 5.76 (d, 1H), 5.91 (t, 1H), 6.56 (t, 1H), 6.93 (d, 1H), 7.47-7.49 (m, 3H), 7.86 (d, 2H), 8.77 (s, 1H).

Example 50

Preparation of Compound #1140

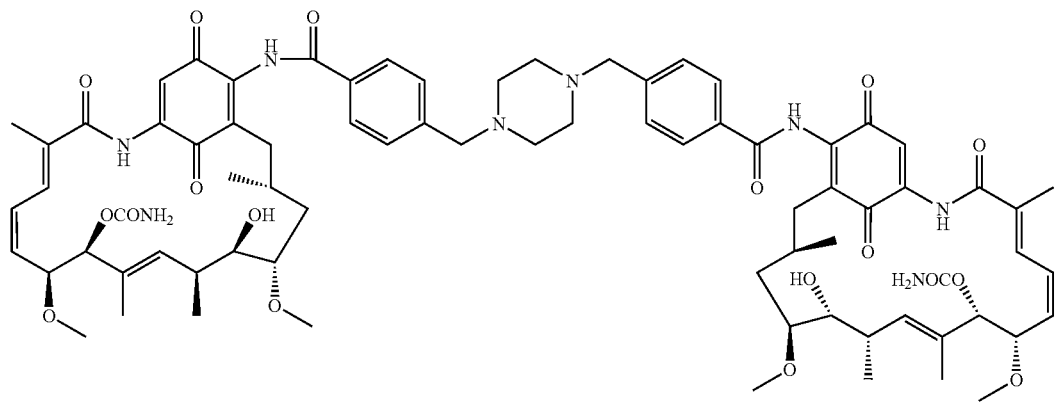

Compound #1140 was prepared according to the procedure described for compound #1059 using compound #1102 instead of morpholine. Rf=0.50 in 80:10:10 CH$_2$Cl$_2$: EtOAc: MeOH. $^1$H NMR CDCl$_3$ δ 1.21 (d, 3H), 1.22 (d, 3H), 1.34 (d, 3H), 1.36 (d, 3H), 1.61 (br s, 4H), 1.72 (br s, 8H), 2.00 (s, 6H), 2.50-2.69 (m, 8H), 2.51-2.60 (m, 2H), 3.07-3.11 (m, 4H), 3.30 (br s, 14H), 3.37 (m, 2H), 3.57 (s, 4H), 4.30 (d, 2H), 5.06 (s, 2H), 5.67 (d, 2H), 5.86 (t, 21), 6.53 (t, 2H), 6.90 (d, 2H), 7.43 (s, 2H), 7.44 (d, 4H), 7.83 (d, 4H), 8.52 (s, 2H), 8.83 (s, 2H).

Example 51

Preparation of Compound #1148

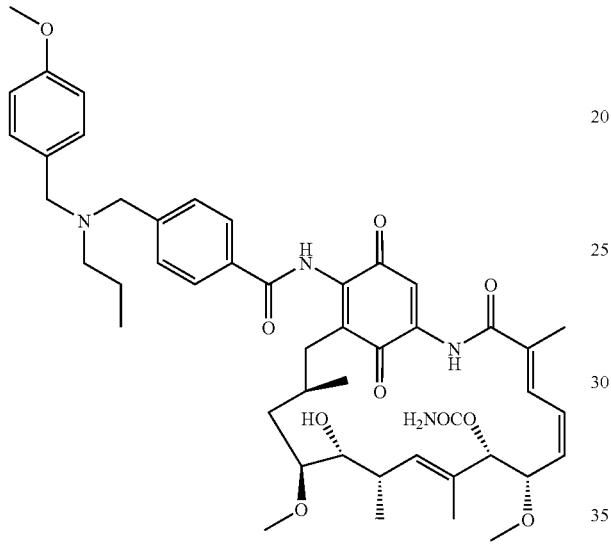

Compound #1148 was prepared according to the procedure described for compound #1059 using N-β-methoxybenzyl)-N-propylamine instead of morpholine. Rf=0.39 in 80:15:5 CH$_2$Cl$_2$: EtOAc: MeOH. $^1$H NMR CDCl$_3$ δ 0.86 (t, 3H), 0.90 (d, 3H), 0.94 (d, 3H), 1.52-1.56 (m, 2H), 1.70 (br s, 2H), 1.79 (br s, 4H), 2.04 (s, 3H), 2.36-2.39 (m, 2H), 2.58-2.64 (m, 3H), 2.74-2.79 (m, 1H), 3.32 (br s, 7H), 3.46 (m, 1H), 3.51 (s, 2H), 3.59 (s, 2H), 3.80 (s, 3H), 4.33 (d, 1H), 5.17 (s, 1H), 5.78 (d, 1H), 5.92 (t, 1H), 6.58 (t, 1H), 6.86 (d, 2H), 6.94 (d, 1H), 7.27 (d, 2H), 7.49 (s, 1H), 7.51 (d, 2H), 7.84 (d, 2H), 8.47 (s, 1H), 8.77 (s, 1H).

Example 52

Preparation of Compound #1149

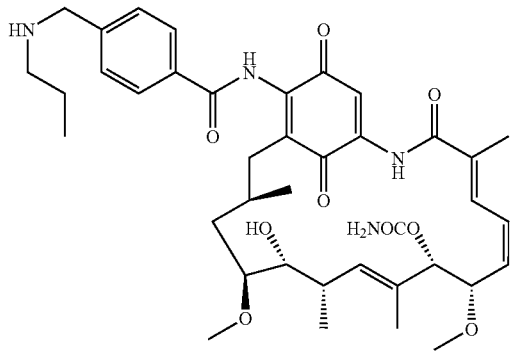

To a solution of compound #1148 (63 mg, 0.075 mmol) in CH$_2$Cl$_2$/H$_2$O (3/0.3 ml) was added DDQ (34 mg, 0.150 mmol) and it was allowed to stir at rt for 5 h whereupon it was diluted with CH$_2$Cl$_2$ (10 ml), washed with NaOH 1N (2 ml), dried over Na2SO4 and concentrated under reduce pressure. The residue was purified by preparative t.l.c. (1000 μM) to give the compound #1149 as a yellow solid (10 mg, 18%). Rf=0.17 in 80:10:10 CH$_2$Cl$_2$: EtOAc: MeOH. $^1$H NMR CDCl$_3$ δ 0.88-0.96 (m, 9H), 1.54-1.60 (m, 2H), 1.70 (br s, 2H), 1.79 (br s, 4H), 2.06 (s, 3H), 2.56-2.64 (m, 5H), 2.75-2.79 (m, 1H), 3.33 (br s, 7H), 3.45 (m, 1H), 3.90 (s, 2H), 4.33 (d, 1H), 5.16 (s, 1H), 5.78 (d, 1H), 5.92 (t, 1H), 6.57 (t, 1H), 6.94 (d, 1H), 7.49 (s, 1H), 7.50 (d, 2H), 7.88 (d, 2H), 8.46 (s, 1H), 8.77 (s, 1H).

Example 53

Preparation of Compound #1167

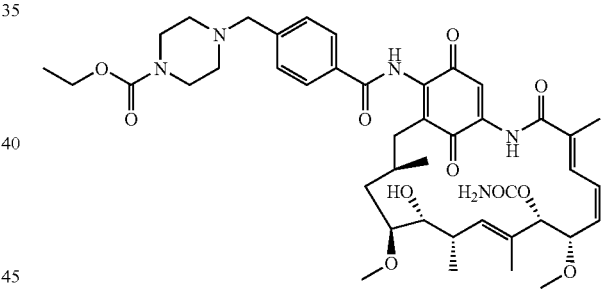

Compound #1167 was prepared according to the procedure described for compound #1059 using ethyl-N-piperazine carboxylate instead of morpholine. Rf=0.30 in 80:15:5 CH$_2$Cl$_2$: EtOAc: MeOH. $^1$H NMR CDCl$_3$ δ 0.925 (s, 3H), 0.95 (d, 3H), 1.25 (t, 3H), 1.70 (br s, 2H), 1.79 (br s, 4H), 2.04 (s, 3H), 2.42 (br s, 4H), 2.52-2.68 (m, 3H), 2.75-2.79 (m, 1H), 3.32 (br s, 71), 3.49 (br s, 5H), 3.59 (s, 21'), 4.13 (q, 21), 4.32 (d, 1H), 5.16 (s, 1H), 5.77 (d, 1H), 5.91 (t, 1H), 6.57 (t, 1H), 6.94 (d, 1H), 7.48 (s, 1H), 7.48 (d, 2H), 7.87 (d, 2H), 8.47 (s, 1H), 8.77 (s, 1H).

Example 54

Preparation of Compound #1168

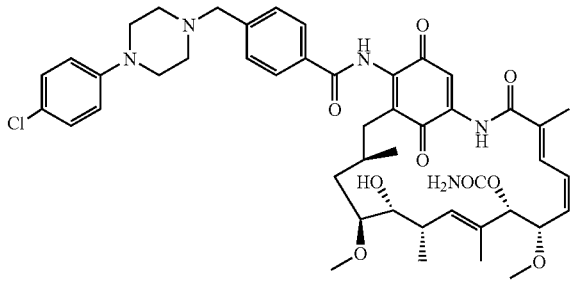

Compound #1168 was prepared according to the procedure described for compound #1059 using N-(4-chlorophenyl)-piperazine instead of morpholine. Rf=0.36 in 80:15:5 CH$_2$Cl$_2$: EtOAc: MeOH. $^1$H NMR CDCl$_3$ δ 0.93 (s, 3H), 0.945 (d, 3H), 1.70 (br s, 2H), 1.79 (br s, 4H), 2.04 (s, 3H), 2.56-2.63 (m, 7H), 2.76-2.79 (m, 1H), 3.18 (br s, 4H), 3.33 (br s, 7H), 3.47 (br s, 1H), 3.64 (s, 2H), 4.33 (d, 1H), 5.17 (s, 1H), 5.77 (d, 1H), 5.92 (t, 1H), 6.60 (t, 1H), 6.83 (d, 2H), 6.94 (d, 1H), 7.20 (d, 2H), 7.49 (s, 1H), 7.52 (d, 2H), 7.88 (d, 2H), 8.48 (s, 1H), 8.78 (s, 1H).

Example 55

Preparation of Compound #1169

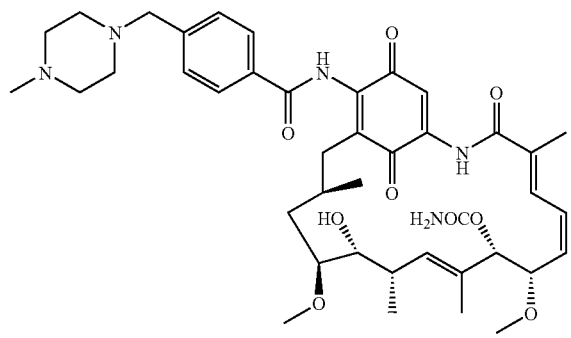

Compound #1169 was prepared according to the procedure described for compound #1059 using N-methyl-piperazine instead of morpholine. Rf=0.09 in 80:10:10 CH$_2$Cl$_2$: EtOAc: MeOH. $^1$H NMR CDCl$_3$ δ 0.93 (s, 3H), 0.96 (d, 3H), 1.70 (br s, 2H), 1.79 (br s, 4H), 2.04 (s, 3H), 2.37 (s, 3H), 2.56-2.64 (m, 10H), 2.76-2.79 (m, 1H), 3.33 (br s, 7H), 3.46 (br s, 1H), 3.60 (s, 2H), 4.33 (d, 1H), 5.17 (s, 1H), 5.77 (d, 1H), 5.92 (t, 1H), 6.58 (t, 1H), 6.95 (d, 1H), 7.48 (d, 2H), 7.49 (s, 1H), 7.86 (d, 2H), 8.47 (s, 1H), 8.77 (s, 1H).

Example 56

Preparation of Compound #1170

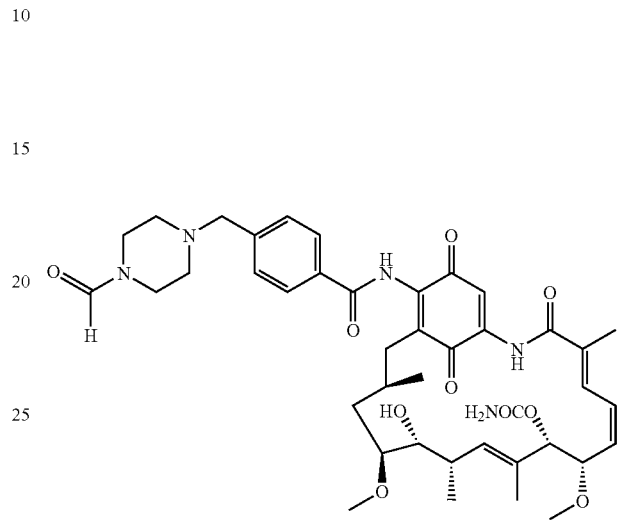

Compound #1170 was prepared according to the procedure described for compound #1059 using N-formyl-piperazine instead of morpholine. Rf=0.52 in 80:10:10 CH$_2$Cl$_2$: EtOAc: MeOH. $^1$H NMR CDCl$_3$ δ 0.93 (s, 3H), 0.96 (d, 3H), 1.70 (br s, 2H), 1.79 (br s, 4H), 2.04 (s, 3H), 2.45-2.48 (m, 4H), 2.50-2.68 (m, 3H), 2.75-2.78 (m, 1H), 3.33 (br s, 7H), 3.39-3.41 (m, 2H), 3.45 (m, 1H), 3.59 (br s, 2H), 3.62 (s, 2H), 4.33 (d, 1H), 5.17 (s, 1H), 5.77 (d, 1H), 5.92 (t, 1H), 6.57 (t, 1H), 6.94 (d, 1H), 7.48 (s, 1H), 7.49 (d, 2H), 7.88 (d, 2H), 8.03 (s, 1H), 8.47 (s, 1H), 8.78 (s, 1H).

Example 57

Preparation of Compound #1171

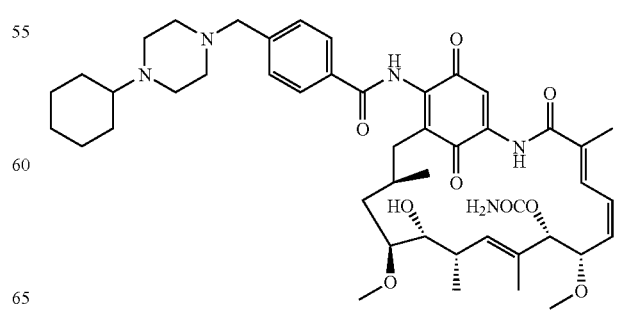

Compound #1171 was prepared according to the procedure described for compound #1059 using N-cyclohexyl-piperazine instead of morpholine. Rf=0.32 in 80:10:10 CH$_2$Cl$_2$: EtOAc: MeOH. $^1$HNMR CDCl$_3$ δ 0.93 (s, 3H, 0.96 (d, 3H), 1.06-1.19 (m, 2H), 1.24-1.35 (m, 4H), 1.63-1.73 (m, 4H), 1.79 (s, 3H), 1.75-1.85 (m, 3H), 2.04 (s, 3H), 2.51-2.83 (m, 13H), 3.33 (br s, 7H), 3.46 (m, 1H), 3.62 (s, 2H), 4.33 (d, 1H), 5.16 (s, 1H), 5.76 (d, 1H), 5.91 (t, 1H), 6.57 (t, 1H), 6.94 (d, 1H), 7.47 (d, 2H), 7.49 (s, 1H), 7.86 (d, 2H), 8.46 (s, 1H), 8.77 (s, 1H).

Example 58

Preparation of Compound #1172

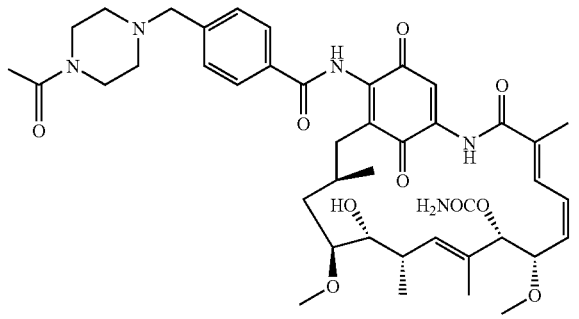

Compound #1171 was prepared according to the procedure described for compound #1059 using N-acetyl-piperazine instead of morpholine. Rf=0.51 in 80:10:10 CH$_2$Cl$_2$: EtOAc: MeOH. $^1$H NMR CDCl$_3$ δ 0.93 (s, 3H), 0.945 (d, 3H), 1.69 (s, 2H), 1.78 (s, 4H), 2.03 (s, 3H), 2.08 (s, 3H), 2.41-2.45 (m, 4H), 2.51-2.63 (m, 3H), 2.76-2.79 (m, 1H), 3.32 (br s, 7H), 3.45-3.48 (m, 3H), 3.59 (s, 2H), 3.62-3.64 (m, 2H), 4.32 (d, 1H), 5.15 (s, 1H), 5.76 (d, 1H), 5.88 (t, 1H), 6.56 (t, 1H), 6.93 (d, 1H), 7.47 (s, 1H), 7.48 (d, 2H), 7.87 (d, 2H), 8.47 (s, 1H), 8.77 (s, 1H).

Example 59

Preparation of Compound #1188

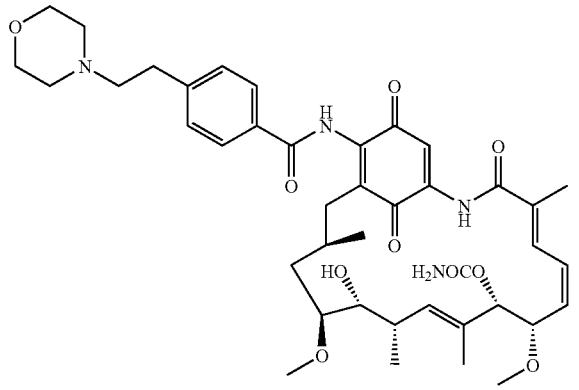

Compound #1188 was prepared according to the procedure described for compound #1059 using 4-(2-bromoethyl)-benzoyl-17-aminogeldanamycin instead of compound 1046. Rf=0.53 in 80:10:10 CH$_2$Cl$_2$: EtOAc: MeOH. $^1$H NMR CDCl$_3$ δ 0.92 (s, 3H), 0.94 (d, 3H), 1.70 (br s, 4H), 1.79 (br s, 4H), 2.03 (s, 3H), 2.54-2.65 (m, 7H), 2.76-2.79 (m, 1H), 2.87 (t, 2H), 3.32 (br s, 7H), 3.47 (m, 1H), 3.74-3.76 (m, 4H), 4.33 (d, 1H), 5.17 (s, 1H), 5.77 (d, 1H), 5.91 (t, 1H), 6.57 (t, 1H), 6.94 (d, 1H), 7.36 (d, 2H), 7.49 (s, 1H), 7.84 (d, 2H), 8.46 (s, 1H), 8.77 (s, 1H).

Example 60

Preparation of Compound #1189

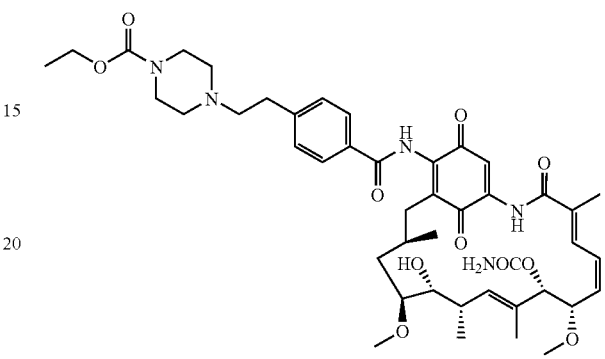

Compound #1189 was prepared according to the procedure described for compound #1188 using Ethyl piperazine carboxylate instead of morpholine. Rf=0.05 in 80:5:15 CH$_2$Cl$_2$: EtOAc: MeOH. $^1$H NMR CDCl$_3$ δ 0.92 (s, 3H), 0.96 (d, 3H), 1.26 (t, 3H), 1.70 (br s, 4H), 1.79 (br s, 4H), 2.04 (s, 3H), 2.49-2.58 (m, 4H), 2.63-2.67 (m, 3H), 2.76-2.79 (m, 1H), 2.89 (t, 2H), 3.32 (br s, 7H), 3.46 (m, 1H), 3.51 (br s, 4H), 4.14 (q, 2H), 4.32 (d, 1H), 5.17 (s, 1H), 5.77 (d, 1H), 5.92 (t, 1H), 6.57 (t, 1H), 6.94 (d, 1H), 7.35 (d, 2H), 7.48 (s, 1H), 7.84 (d, 2H), 8.46 (s, 1H), 8.77 (s, 1H).

Example 61

Preparation of Compound #1203

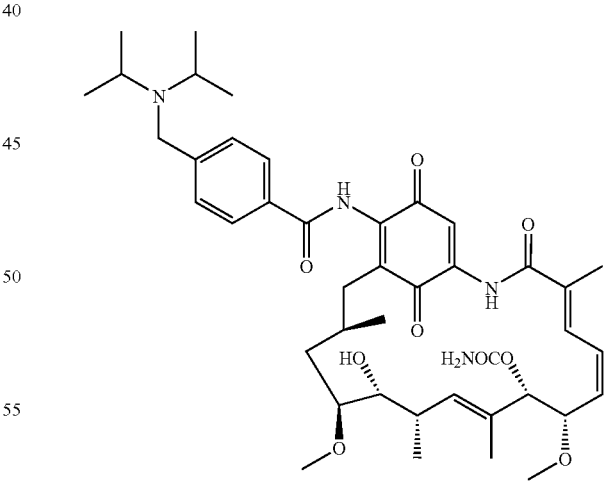

Compound #1203 was prepared according to the procedure described for compound #1059 using diisopropyl amine instead of morpholine. Rf=0.40 in 80:15:5 CH$_2$Cl$_2$: EtOAc: MeOH. $^1$H NMR CDCl$_3$ δ 0.925 (s, 3H), 0.96 (d, 3H), 1.03 (d, 12H), 1.70 (br s, 2H), 1.79 (br s, 4H), 2.04 (s, 3H), 2.57-2.64 (m, 3H), 2.75-2.79 (m, 1H), 2.99-3.04 (m, 2H), 3.33 (br s, 7H), 3.46 (m, 1H), 3.71 (s, 2H), 4.325 (d, 1H), 5.17 (s, 1H), 5.78 (d, 1H), 5.91 (t, 1H), 6.57 (t, 1H), 6.94 (d, 1H), 7.49 (s, 1H), 7.54 (d, 2H), 7.83 (d, 2), 8.47 (s, 1H), 8.78 (s, 1H).

Example 62

Preparation of Compound #1205

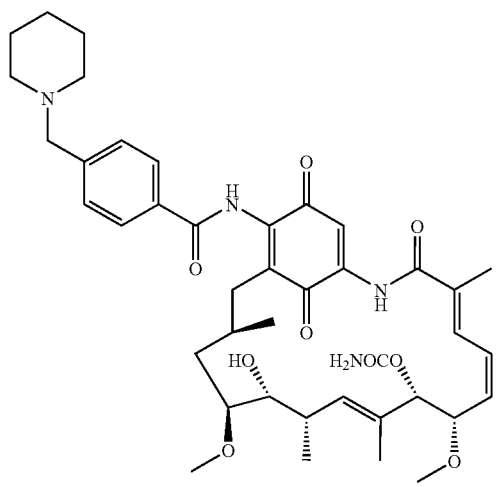

Compound #1205 was prepared according to the procedure described for compound #1059 using piperidine instead of morpholine. Rf=0.41 in 80:10:10 $CH_2Cl_2$: EtOAc: MeOH. $^1$H NMR $CDCl_3$ δ 0.93 (s, 3H), 0.95 (d, 3H), 1.47 (br s, 2H), 1.62 (br s, 4H), 1.70 (br s, 2H), 1.79 (br s, 4H), 2.04 (s, 3H), 2.44 (br s, 4H), 2.53-2.65 (m, 3H), 2.75-2.79 (m, 1H), 3.33 (br s, 7H), 3.46 (m, 1H), 3.59 (s, 2H), 4.325 (d, 1H), 5.16 (s, 1H), 5.77 (d, 1H), 5.91 (t, 1H), 6.57 (t, 1H), 6.94 (d, 1H), 7.48 (s, 1H), 7.50 (d, 2H), 7.86 (d, 2H), 8.47 (s, 1H), 8.77 (s, 1H).

Example 63

Preparation of Compound #1219

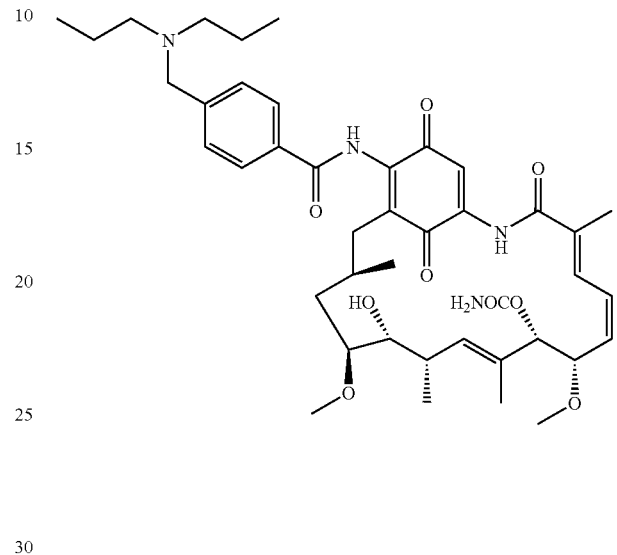

Compound #1219 was prepared according to the procedure described for compound #1059 using dipropyl amine instead of morpholine. Rf=0.38 in 80:15:5 $CH_2Cl_2$: EtOAc: MeOH. $^1$H NMR $CDCl_3$ δ 0.88 (t, 6H), 0.93 (s, 3H), 0.95 (d, 3H), 1.47-1.52 (m, 4H), 1.70 (br s, 2H), 1.79 (br s, 4H), 2.04 (s, 3H), 2.40 (br s, 4H), 2.53-2.65 (m, 3H), 2.75-2.79 (m, 1H), 3.33 (br s, 7H), 3.46 (m, 1H), 3.63 (s, 2H), 4.32 (d, 1H), 5.16 (s, 1H), 5.77 (d, 1H), 5.91 (t, 1H), 6.57 (t, 1H), 6.94 (d, 1H), 7.48 (s, 1H), 7.50 (d, 2H), 7.85 (d, 2H), 8.47 (s, 1H), 8.77 (s, 1H).

Example 64

Preparation of Compound #1235

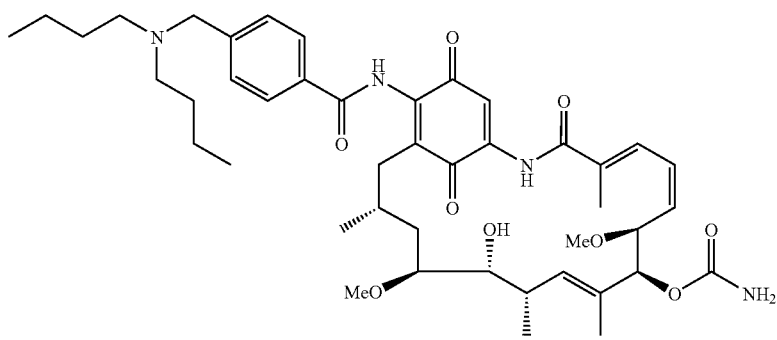

Compound #1235 was prepared according to the procedure described for compound #1059 using dibutyl amine instead of morpholine. Rf=0.38 in 80:15:5 CH$_2$Cl$_2$: EtOAc: MeOH. $^1$H NMR CDCl$_3$ δ 0.88-0.97 (m, 12H), 1.26-1.33 (m, 4H), 1.42-1.48 (m, 4H), 1.71 (br s, 2H), 1.80 (br s, 4H), 2.05 (s, 3H), 2.45 (br s, 4H), 2.54-2.65 (m, 3H), 2.75-2.79 (m, 1H), 3.34 (br s, 7H), 3.47 (m, 1H), 3.66 (s, 2H), 4.33 (d, 1H), 5.17 (s, 1H), 5.78 (d, 1H), 5.92 (t, 1H), 6.59 (t, 1H), 6.94 (d, 1H), 7.49 (s, 1H), 7.52 (d, 2H), 7.86 (d, 2H), 8.48 (s, 1H), 8.78 (s, 1H).

Example 65

Preparation of Compound #1236

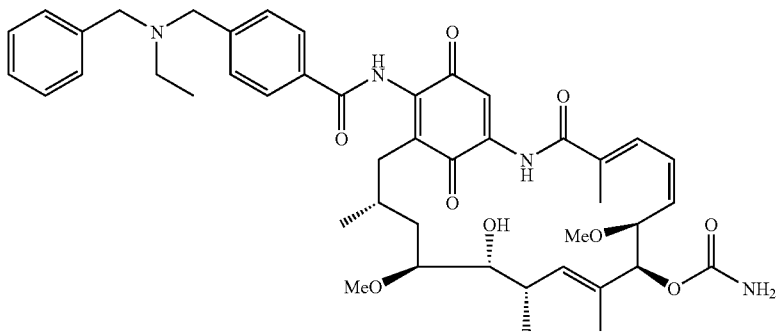

Compound #1236 was prepared according to the procedure described for compound #1059 using benzylethyl amine instead of morpholine. Rf=0.43 in 80:15:5 CH$_2$Cl$_2$: EtOAc: MeOH. $^1$H NMR CDCl$_3$ δ 0.925 (s, 3H), 0.95 (d, 3H), 1.09 (t, 3H), 1.70 (br s, 2H), 1.79 (br s, 4H), 2.04 (s, 3H), 2.50-2.62 (m, 5H), 2.75-2.79 (m, 1H), 3.32 (br s, 7H), 3.46 (m, 1H), 3.59 (s, 2H), 3.63 (s, 2H), 4.33 (d, 1H), 5.16 (s, 1H), 5.78 (d, 1H), 5.91 (t, 1H), 6.57 (t, 1H), 6.94 (d, 1H), 7.25-7.27 (m, 1H), 7.32-7.38 (m, 4H), 7.48 (s, 1H), 7.53 (d, 2H), 7.85 (d, 2H), 8.47 (s, 1H), 8.77 (s, 1H).

Example 66

Preparation of Compound #1237

Compound #1237 was prepared according to the procedure described for compound #1059 using dibenzyl amine instead of morpholine. Rf=0.54 in 80:15:5 CH$_2$Cl$_2$: EtOAc: MeOH. $^1$H NMR CDCl$_3$ δ 0.92 (s, 3H), 0.955 (d, 3H), 1.70 (br s, 2H), 1.79 (br s, 4H), 2.04 (s, 3H), 2.53-2.65 (m, 3H), 2.75-2.79 (m, 1H), 3.32 (br s, 7H), 3.46 (m, 1H), 3.57 (s, 4H), 3.63 (s, 2H), 4.32 (d, 1H), 5.16 (s, 1H), 5.775 (d, 1H), 5.92 (t, 1H), 6.585 (t, 1H), 6.94 (d, 1H), 7.23-7.28 (m, 2H), 7.31-7.35 (m, 4I), 7.39-7.42 (m, 4H), 7.48 (s, 1H), 7.56 (d, 2H), 7.87 (d, 2H), 8.47 (s, 1H), 8.77 (s, 1H).

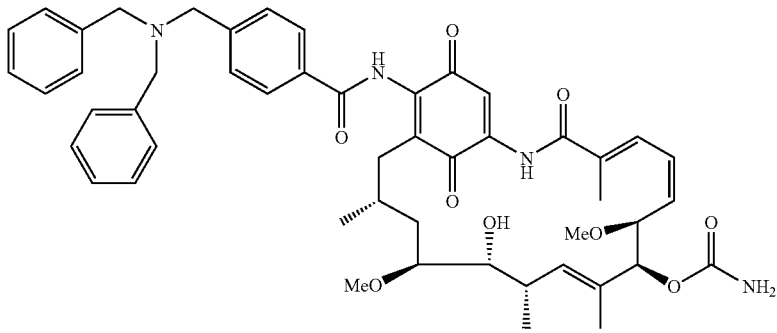

Example 67

Preparation of Compound #1238

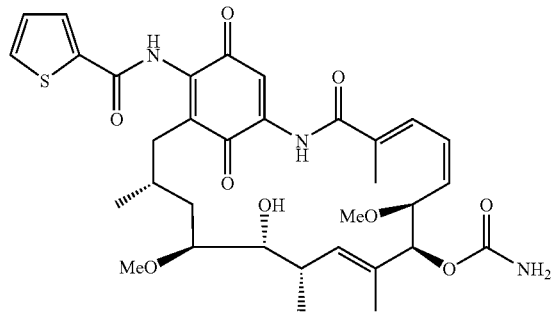

Compound #1238 was prepared according to the procedure described for compound #529 using 2-thiophenylcarbonyl chloride instead of benzoyl chloride. Rf=0.47 in 80:15:5 $CH_2Cl_2$: EtOAc: MeOH. $^1$H NMR $CDCl_3$ δ 0.93 (d, 3H), 0.95 (d, 3H), 1.69 (br s, 2H), 1.79 (br s, 4H), 2.03 (s, 3H), 2.52 (d, 1H), 2.58-2.61 (m, 2H), 2.75-2.79 (m, 1H), 3.33 (br s, 7H), 3.43-3.46 (m, 1H), 4.32 (d, 1H), 5.16 (s, 1H), 5.76 (d, 1H), 5.92 (t, 1H), 6.57 (t, 1H), 6.935 (d, 1H), 7.18 (dd, 1H), 7.49 (s, 1H), 7.564 (d, 1H), 7.725 (1H, d), 8.42 (s, 1H), 8.76 (s, 1H).

Example 68

Preparation of Compound #1239

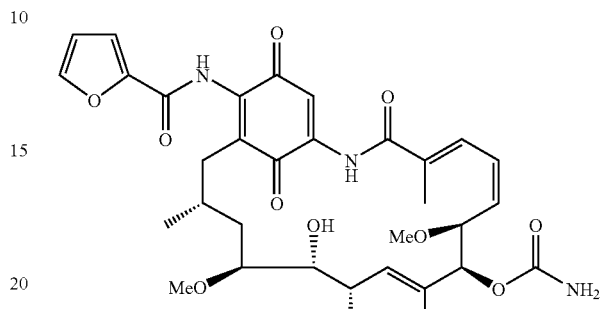

Compound #1239 was prepared according to the procedure described for compound #529 using 2-furoyl chloride instead of benzoyl chloride. Rf=0.47 in 80:15:5 $CH_2Cl_2$: EtOAc: MeOH. $^1$H NMR $CDCl_3$ δ 0.92 (d, 3H), 0.94 (d, 3H), 1.69 (br s, 2H), 1.78 (br s, 4H), 2.03 (s, 3H), 2.51 (d, 1H), 2.62 (d, 2H), 2.75-2.79 (m, 1H), 3.32 (br s, 7H), 3.41-3.45 (m, 1H), 4.32 (d, 1H), 5.15 (s, 1H), 5.75 (d, 1H), 5.91 (t, 1H), 6.56 (t, 1H), 6.60 (br s, 1H), 6.93 (d, 1H), 7.28 (d, 1H), 7.49 (s, 1H), 7.59 (s, 1H), 8.69 (s, 1H), 8.75 (s, 1H).

Example 69

Preparation of Compound #1252

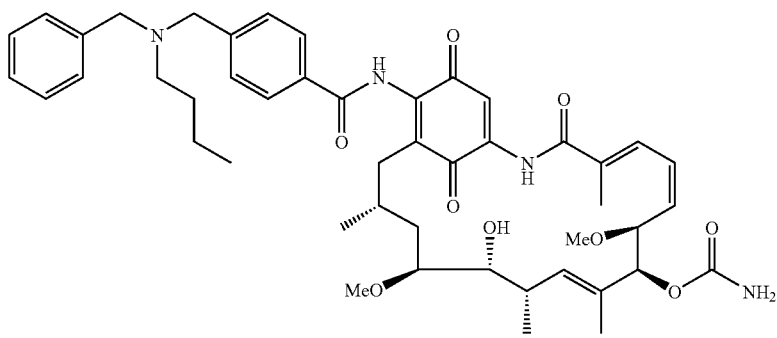

Compound #1252 was prepared according to the procedure described for compound #1059 using benzyl butyl amine instead of morpholine. Rf=0.45 in 80:15:5 CH$_2$Cl$_2$: EtOAc: MeOH. $^1$H NMR CDCl$_3$ δ 0.85 (t, 3H), 0.92 (d, 3H), 0.95 (d, 3H), 1.27-1.31 (m, 2H), 1.49-1.53 (m, 2H), 1.70 (br s, 2H), 1.79 (br s, 4H), 2.04 (s, 3H), 2.43 (t, 2H), 2.52-2.67 (m, 3H), 2.75-2.79 (m, 1H), 3.32 (br s, 7H), 3.46 (m, 1H), 3.57 (s, 2H), 3.61 (s, 2H), 4.325 (d, 1H), 5.16 (s, 1H), 5.77 (d, 1H), 5.91 (t, 1H), 6.60 (t, 1H), 6.93 (d, 1H), 7.24 (m, 1H), 7.30-7.37 (m, 4H), 7.48 (s, 1H), 7.51 (d, 2H), 7.85 (d, 2H), 8.47 (s, 1H), 8.77 (s, 1H).

Example 70

Preparation of Compound #1253

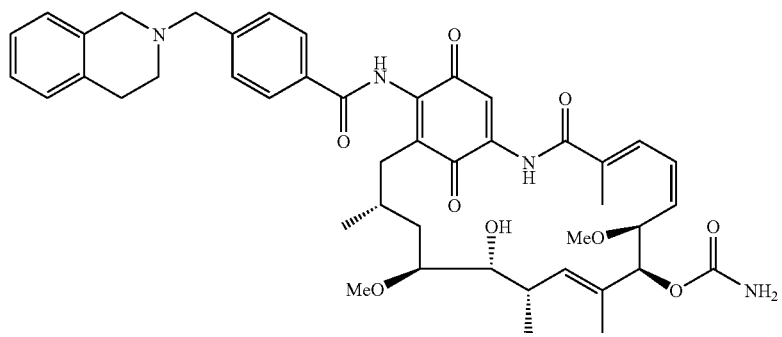

Compound #1253 was prepared according to the procedure described for compound #1059 using 1,2,3,4-tetrahydroisoquinoline instead of morpholine. Rf=0.44 in 80:15:5 CH$_2$Cl$_2$: EtOAc: MeOH. $^1$H NMR CDCl$_3$ δ 0.94 (d, 3H), 0.96 (d, 3H), 1.71 (br s, 2H), 1.80 (br s, 4H), 2.04 (s, 3H), 2.53-2.65 (m, 31), 2.75-2.78 (m, 3H), 2.93 (t, 2H), 3.33 (br s, 7H), 3.45-3.48 (m, 1H), 3.66 (s, 2H), 3.77 (s, 2H), 4.33 (d, 1H), 5.17 (s, 1H), 5.78 (d, 1H), 5.92 (t, 1H), 6.58 (t, 1H), 6.945 (d, 1H), 6.99 (d, 1H), 7.10-7.14 (m, 3H), 7.49 (s, 1H), 7.57 (d, 2H), 7.88 (d, 2H), 8.48 (s, 1H), 8.77 (s, 1H).

17-Carbamate-geldanamycins

Example 71

Preparation of Compound #656

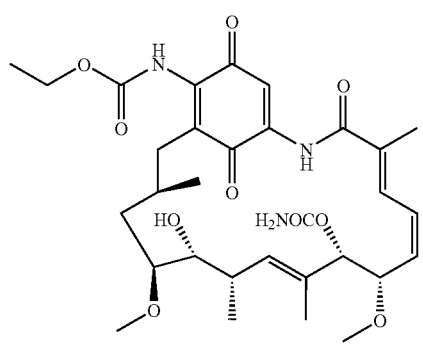

A solution of 17-aminogeldanamycin (0.6 g, 1.10 mmol) in EtOAc (120 ml) was treated with Na$_2$S$_2$O$_4$ (10%, 10 ml) at rt.

After 2 h, the aqueous layer was extracted twice with EtOAc and the combined organic layers were dried over Na$_2$SO$_4$ and concentrated under reduce pressure to give 18,21-dihydro-17-aminogeldanamycin as a yellow solid. This latter was dissolved in anhydrous THF (5 ml) and transferred via cannula to a mixture of ethyl chloroformate (0.11 ml, 1.15 mmol) and MS4 Å (1.2 g) in THF (3 ml) at 0° C. After 12 hours at room temperature, EtN(i-Pr)$_2$ (0.38 ml), CuSO$_4$ (60 mg, 0.37 mmol) and MeOH (2 ml) were further added to the reaction mixture. After 2 h, the reaction mixture was filtered and concentrated under reduce pressure. The crude material was dissolved in EtOAc (100 ml) and washed with 2N HCl (10 ml) and sat. NaHCO$_3$ (10 ml), dried over Na$_2$SO$_4$ and concentrated under reduce pressure to give the crude material which was purified by flash chromatography to give 17-ethoxycarbonyl-aminogeldanamycin as a yellow solid (0.25 g, 40%). Rf=0.31 in 80:15:5 CH$_2$Cl$_2$: EtOAc: MeOH. $^1$H NMR CDCl$_3$ δ 0.94 (t, 6H), 1.32 (t, 3H), 1.62-1.74 (m, 3H), 1.78 (s, 3H), 2.02 (s, 3H), 2.58 (d, 2H), 2.76 (m, 1H), 3.32 (s, 3H), 3.34 (s, 3H), 3.31-3.34 (m, 1H), 3.42-3.44 (m, 1H), 4.23 (q, 2H), 4.32 (d, 1H), 5.16 (s, 1H), 5.74 (d, 1H), 5.90 (t, 1H), 6.56 (t, 1H), 6.91 (d, 1H), 7.44 (s, 1H), 8.73 (s, 1H).

Example 72

Preparation of Compound #709

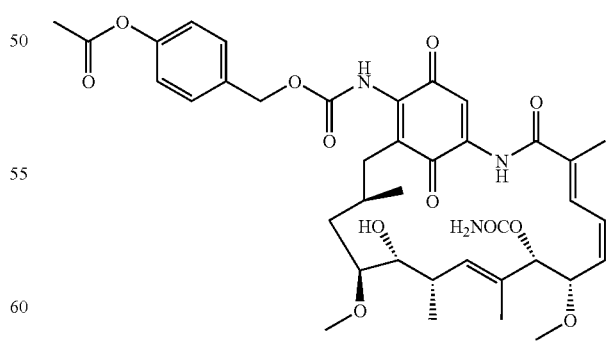

The compound #709 was prepared according to the procedure described for compound #656 using 4'-acetoxy-benzyl chloroformate (freshly prepared from para-acetoxybenzyl alcohol) instead of ethylchloroformate. Rf=0.41 in 80:15:5

CH$_2$Cl$_2$: EtOAc: MeOH. $^1$H NMR CDCl$_3$ 0.92 (d, 3H), 0.93 (d, 3H), 1.61-1.73 (m, 3), 1.77 (s, 3H), 2.01 (s, 3H), 2.30 (s, 3H), 2.55 (d, 2H), 2.74-2.78 (m, 1H), 3.32 (s, 3H), 3.33 (s, 3H); 3.30-3.33 (m, 1), 3.40-3.43 (m, 1H), 4.31 (d, 1H), 5.15 (s, 1H), 5.17 (s, 2H), 5.73 (d, 1H), 5.90 (t, 1H), 6.54 (t, 1H), 6.91 (d, 1H), 7.10 (d, 2H), 7.35 (s, 1H), 7.41 (d, 2H), 7.42 (s, 1H), 8.72 (s, 1H).

Example 73

Preparation of Compound #736

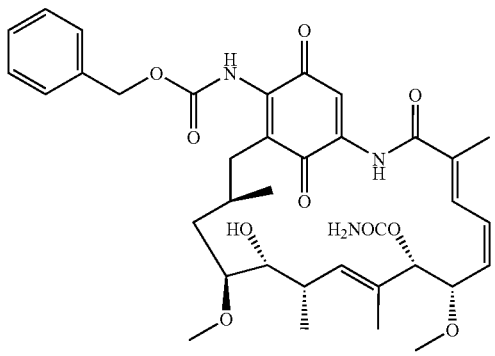

The compound #736 was prepared according to the procedure described for compound #656 using benzyl chloroformate instead of ethylchloroformate. Rf=0.38 in 80:15:5 CH$_2$Cl$_2$: EtOAc: MeOH. $^1$H NMR CDCl$_3$ 0.92 (d, 3H), 0.95 (d, 3H), 1.64-1.74 (m, 3H), 1.78 (s, 3H), 2.03 (s, 3H), 2.59 (d, 2H), 2.74-2.78 (m, 1H), 3.32 (s, 3H), 3.34 (s, 3H), 3.31-3.34 (m, 1H), 3.42-3.45 (m, 1H), 4.32 (d, 1H), 5.16 (s, 1H), 5.20 (s, 2H), 5.74 (d, 1H), 5.91 (t, 1H), 6.57 (t, 1H), 6.92 (d, 1H), 7.34 (s, 1H), 7.36-7.40 (m, 5H), 7.44 (s, 1H), 8.73 (s, 1H).

Example 74

Preparation of Compound #737

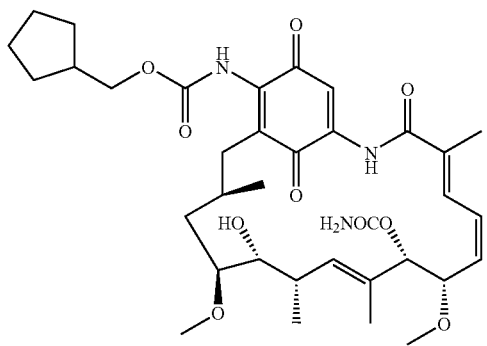

The compound #737 was prepared according to the procedure described for compound #656 using cyclopentyl-methyl chloroformate (freshly prepared from cyclopentane methyl alcohol) instead of ethylchloroformate. Rf=0.30 in 80:15:5 CH$_2$Cl$_2$: EtOAc: MeOH. $^1$H NMR CDCl$_3$ 0.92-0.96 (m, 6H), 1.24-1.30 (m, 2H), 1.54-1.66 (m, 4H), 1.70-1.75 (m, 5H), 1.78 (s, 3H), 2.02 (s, 3H), 2.20-2.27 (m, 1H), 2.58 (d, 2H), 2.74-2.78 (m, 1H), 3.32 (s, 3H), 3.34 (s, 3H), 3.32-3.34 (m, 1H), 3.42-3.45 (m, 1H), 4.01-4.08 (m, 2H), 4.31 (d, 1H), 5.16 (s, 1H), 5.75 (d, 1H), 5.90 (t, 1H), 6.56 (t, 1H), 6.91 (d, 1H), 7.28 (s, 1H), 7.43 (s, 1H), 8.73 (s, 1H).

Example 75

Preparation of Compound #748

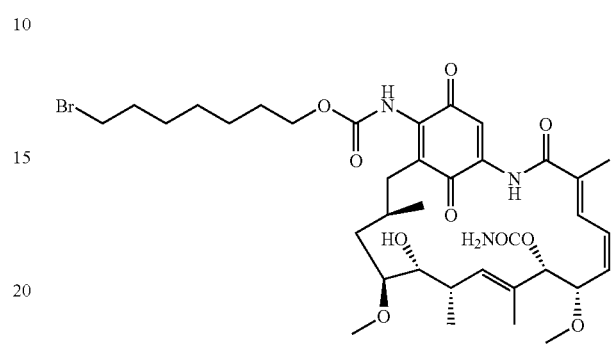

The compound #748 was prepared according to the procedure described for compound #656 using 7-bromoheptyl chloroformate instead of ethylchloroformate. Rf=0.49 in 80:15:5 CH$_2$Cl$_2$: EtOAc: MeOH. $^1$H NMR CDCl$_3$ 0.94 (t, 6H), 1.27-1.48 (m, 6H), 1.65-1.75 (m, 5H), 1.78 (s, 3H), 1.82-1.90 (m, 2H), 2.02 (s, 3H), 2.58 (d, 2H), 2.74-2.78 (m, 1H), 3.32 (s, 3H), 3.34 (s, 3H), 3.31-3.34 (m, 1H), 3.39-3.44 (m, 3H), 4.16 (t, 3H), 4.32 (d, 1H), 5.16 (s, 1H), 5.74 (d, 1H), 5.90 (t, 1H), 6.56 (t, 1H), 6.92 (d, 1H), 7.28 (s, 1H), 7.44(s, 1H) 8.73(s, 1H).

Example 76

Preparation of Compound #749

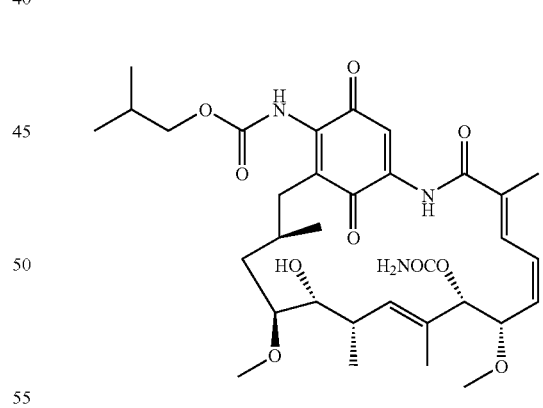

The compound #749 was prepared according to the procedure described for compound #656 using isobutyl chloroformate instead of ethylchloroformate. Rf=0.44 in 80:15:5 CH$_2$Cl$_2$: EtOAc: MeOH. $^1$H NMR CDCl$_3$ 0.94-0.97 (m, 12H), 1.65-1.74 (m, 3H), 1.78 (s, 3H), 1.93-2.01 (m, 1H), 2.02 (s, 3H), 2.58 (d, 2H), 2.74-2.78 (m, 1H), 3.32 (s, 3H), 3.34 (s, 3H), 3.31-3.34 (m, 1H), 3.43-3.45 (m, 1H), 3.91-4.00 (m, 2H), 4.31 (d, 1H), 5.16 (s, 1H), 5.74 (d, 1H), 5.90 (t, 1H), 6.56 (t, 1H), 6.92 (d, 1H), 7.29 (s, 1H), 7.44 (s, 1H), 8.73 (s, 1H).

Example 77

Preparation of Compound #750

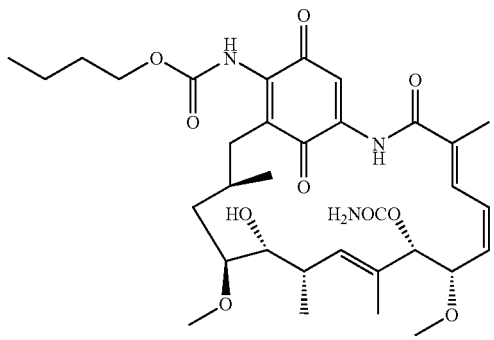

The compound #750 was prepared according to the procedure described for compound #656 using butyl chloroformate instead of ethylchloroformate. Rf=0.44 in 80:15:5 CH$_2$Cl$_2$: EtOAc: MeOH. $^1$H NMR CDCl$_3$ 0.93-0.97 (m, 9H), 1.36-1.45 (m, 2H), 1.62-1.74 (m, 5H), 1.77 (s, 3H), 2.01 (s, 3H), 2.56 (d, 2H), 2.73-2.78 (m, 1H), 3.31 (s, 3H), 3.33 (s, 3H), 3.31-3.33 (m, 1H), 3.41-3.44 (m, 1H), 4.16 (t, 2H), 4.31 (d, 1H), 5.14 (s, 1H), 5.74 (d, 1H), 5.90 (t, 1H), 6.54 (t, 1H), 6.91 (d, 1H), 7.28 (s, 1H), 7.42 (s, 1H), 8.73 (s, 1H).

Example 78

Preparation of Compound #765

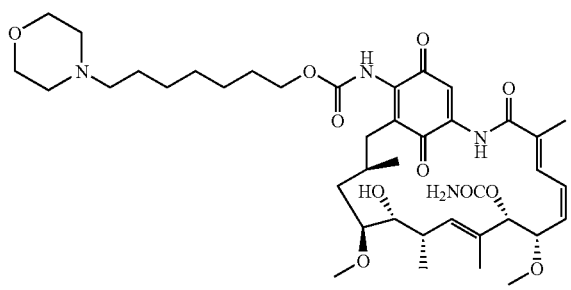

The compound #765 was prepared according to the procedure described for compound #656 using 7-N-morpholino-heptyl chloroformate (freshly prepared from 7-(N-morpholino)-1-heptanol HCl) instead of ethylchloroformate. Rf=0.24 in 80:15:5 CH$_2$Cl$_2$: EtOAc: MeOH. $^1$H NMR CDCl$_3$ 0.94 (d, 3H), 0.95 (s, 3H), 1.38(br s, 5H), 1.57 (br s, 4H), 1.65-1.75 (m, 4H), 1.78 (s, 3H), 1.84-1.87 (m, 4H), 2.03 (s, 3H), 2.53 (d, 2H), 2.57-2.59 (m, 2H), 2.74-2.76 (m, 1H), 3.32 (s, 3H), 3.34 (s, 3H), 3.32-3.34 (m, 1H), 3.41-3.43 (m, 1H), 3.73-3.76 (m, 4H), 4.15-4.17 (m, 2H), 4.32 (d, 1H), 5.16 (s, 1H), 5.74 (d, 1H), 5.91 (t, 1H), 6.56 (t, 1H), 6.93 (d, 1H), 7.28 (s, 1H), 7.43 (s, 1H), 8.73 (s, 1H).

Example 79

Preparation of Compound #766

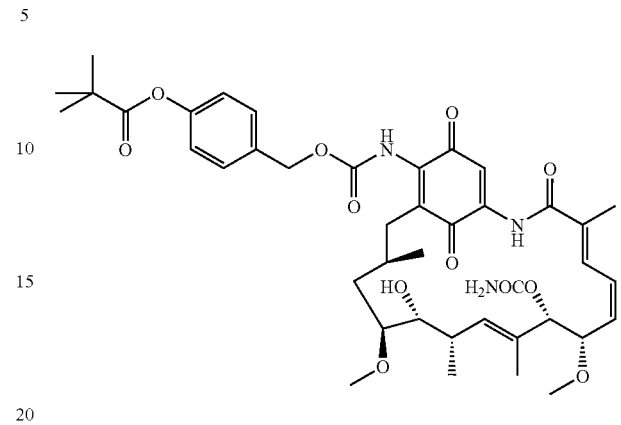

The compound #766 was prepared according to the procedure described for compound #656 using 4'-pivaloxy-benzyl chloroformate (freshly prepared from 4-piveloxy-benzyl alcohol) instead of ethylchloroformate. Rf=0.47 in 80:15:5 CH$_2$Cl$_2$: EtOAc: MeOH. $^1$H NMR CDCl$_3$ 0.92 (d, 3H), 0.95 (d, 3H), 1.36 (s, 9H), 1.64-1.74 (m, 3H), 1.78 (s, 3H), 2.03 (s, 3H), 2.56-2.58 (m, 2H), 2.74-2.79 (m, 1H), 3.32 (s, 3H), 3.34 (s, 3H), 3.32-3.34 (m, 1H), 3.42-3.45 (m, 1H), 4.32 (d, 1H), 5.16 (s, 1H), 5.18 (s, 2H), 5.74 (d, 1H), 5.91 (t, 1H), 6.56 (t, 1H), 6.91 (d, 1H), 7.08 (d, 2H), 7.33 (s, 1H), 7.41 (d, 2H), 7.44 (s, 1H), 8.72 (s, 1H).

Example 80

Preparation of Compound #822

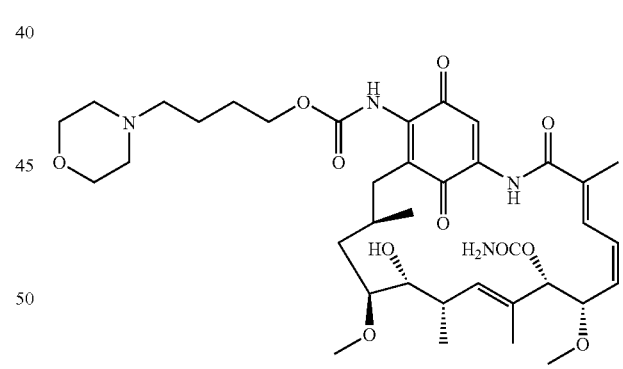

The compound #822 was prepared according to the procedure described for compound #656 using 4-N-morpholino-butyl chloroformate (freshly prepared from 4-(N-morpholino)-1-butanol-HCl) instead of ethylchloroformate. Rf=0.20 in 80:15:5 CH$_2$Cl$_2$: EtOAc: MeOH. $^1$H NMR CDCl$_3$ 0.93 (d, 6H), 1.57-1.64 (m, 2H), 1.68-1.75 (m, 5H), 1.77 (s, 3H), 2.01 (s, 3H), 2.39-2.42 (m, 2H), 2.48 (br s, 4H), 2.56 (d, 2H), 2.73-2.78 (m, 1H), 3.30-3.33 (m, 7H), 3.40-3.44 (m, 1), 3.74 (t, 4H), 4.18 (t, 2H), 4.31 (d, 1H), 5.14 (s, 1H), 5.73 (d, 1H), 5.90 (t, 1H), 6.54 (t, 1H), 6.91 (d, 1H), 7.28 (s, 1H), 7.42 (s, 1H), 8.72 (s, 1H).

Example 81

Preparation of Compound #495

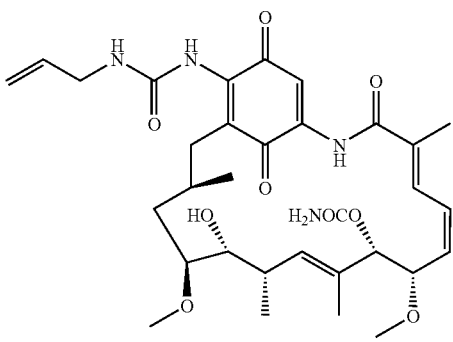

A solution of 17-aminogeldanamycin (20 mg, 0.036 mmol) in EtOAc (10 ml) was treated with Na$_2$S$_2$O$_4$ (10%, 0.5 ml) at rt. After 2 h, the aqueous layer was extracted twice with EtOAc and the combined organic layers were dried over 18,21-dihydro-17-aminogeldanamycin as a brown solid. This latter was dissolved in anhydrous THF (2 ml) under nitrogen atmosphere and to the resulting solution was added allylisocyanate (64 µl, 0.072 mmol) at rt. After 1 h, the solvent was removed under reduce pressure whereby the residue was dissolved in MeOH and stirred over night in presence of silica After filtration, the solvent was removed under reduce pressure and the residue was purified by flash chromatography to give 1-allyl-3-(17-geldanamycinyl)-urea as a brick colored solid (5 mg, 22%). Rf=0.38 in 80:15:5 CH$_2$Cl$_2$: EtOAc: MeOH. $^1$H NMR CDCl$_3$ δ 0.92 (d, 3H), 0.95 (d, 3H), 1.61-1.72 (m, 3H), 1.78 (d, 3H), 2.03 (s, 3H), 2.55 (br d, 2H), 2.74-2.78 (m, 1H), 3.31 (s, 3H), 3.34 (s, 3H), 3.31-3.34 (m, 1H), 3.90 (br s, 2H), 4.31 (d, 1H), 5.16 (s, 1H), 5.20-5.29 (m, 3H), 5.79 (d, 1H), 5.84-5.94 (m, 2H), 6.57 (t, 1H), 6.92 (d, 1H), 7.28 (s, 1H), 7.41 (s, 1H), 8.79 (s, 1H).

Example 82

Preparation of Compound #515

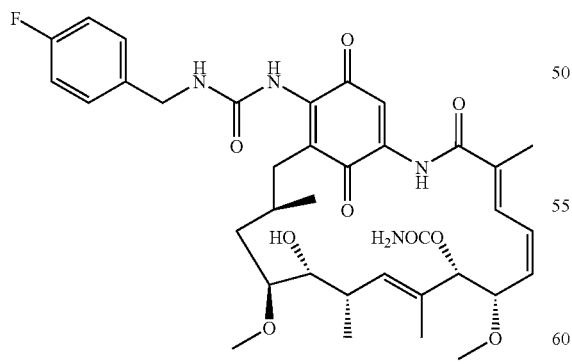

Compound #515 was prepared according to the procedure described for compound #495 using p-fluorobenzyl isocyanate instead of allylisocyanate. Rf=0.42 in 80:15:5 CH$_2$Cl$_2$: EtOAc: MeOH. Mp=175-177° C. $^1$H NMR CDCl$_3$ δ 0.93 (m, 6H), 1.68 (br s, 2H), 1.77 (br s, 4H), 2.02 (s, 3H), 2.50-2.55 (m, 2H), 2.74-2.78 (m, 1H), 3.31 (s, 3H), 3.33 (s, 3H), 3.29-3.32 (m, 1H), 3.40-3.43 (m, 1H), 4.30 (d, 1H), 4.41 (d, 2H), 5.14 (s, 1H), 5.75 (m, 2H), 5.89 (t, 1H), 6.56 (t, 1H), 6.91 (d, 1H), 7.01-7.05 (m, 2H), 7.28-7.31 (m, 2H), 7.37-7.39 (m, 2H), 8.78 (s, 1H).

11-Ester-geldanamycin

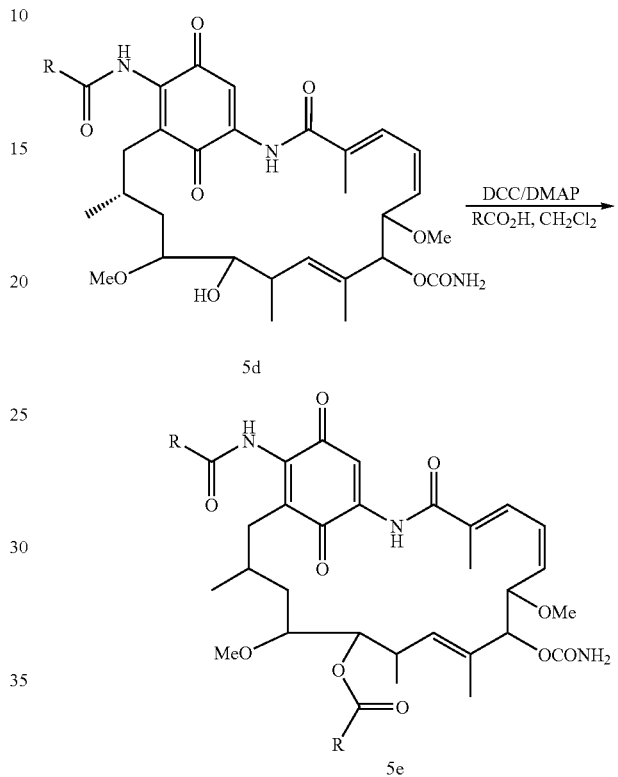

Example 83

Preparation of Compound #984

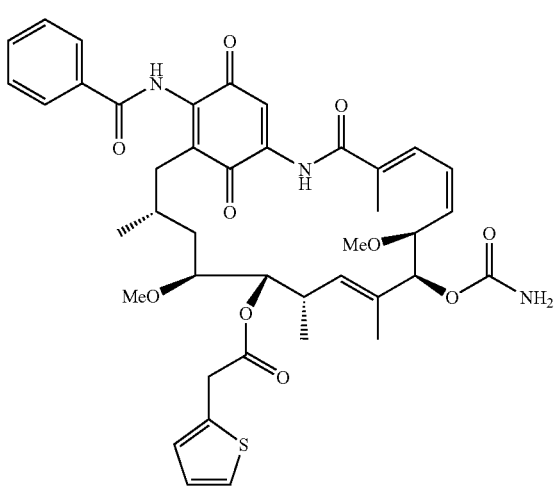

28.5 mg (0.04 mmol, 1 eq.) of compound #563 was combined in a flask with 15.9 mg (0.11 mmol, 2.8 eq) thiopheneacetic acid, 22.5 mg (0.11 mmol, 2.8 eq) DCC, 2.1 mg (0.02 mmol, 0.43 eq) DMAP and 1.5 mL of anhydrous $CH_2Cl_2$. After stirring at room temperature for 16 hours, the reaction mixture was diluted with $CH_2Cl_2$, filtered, and concentrated under vacuum. The residue was chromatographed using 40% Acetone/60% Hexanes to afford 9.5 mg (28% yield) of the ester as a yellow powder. Compound #984 was purified by preparative TLC 40% Acetone/60% Hexanes (Rf=0.32) $^1$H NMR (CDCl$_3$, 400 MHz) δ 0.89 (d, 3H), 1.02 (d, 3H), 1.18 (m, 1H), 1.52 (m, 1H), 1.75 (s, 3H), 1.83 (m, 1H), 2.03 (s, 3H), 2.44 (dd, 1H), 2.52 (m, 1H), 2.90 (m, 1H), 3.32 (s, 3H), 3.36 (s, 3H), 3.42 (m, 1H), 3.73 (s, 2H), 4.31 (d, 1H), 4.79 (br, 2H), 4.91 (m, 1H), 5.02 (d, 1H), 5.06 (s, 1H), 5.83 (t, 1H), 6.57 (t, 1H), 6.81 (d, 1H), 6.89 (dd, 1H), 7.15 (dd, 1H), 7.29 (m, 1H), 7.36 (s, 1H), 7.53 (m, 2H), 7.62 (m, 1H), 7.92 (m, 2H), 8.35 (s, 1H), 8.78 (s, 1H).

Example 84

Preparation of Compound #960

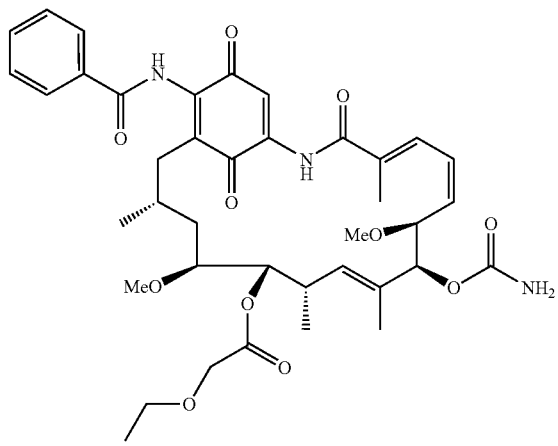

Compound #960 was prepared according to the procedure described for compound #984 using 2-ethoxyacetic acid instead of thiopheneacetic acid. Compound #960 was purified by preparative TLC 60% $CH_2Cl_2$/35% EtOAc/5% MeOH(Rf=0.35). $^1$H NMR (CDCl$_3$, 400 MHz) δ 0.96 (m, 6H), 1.18 (t, 3H), 1.25 (m, 1H), 1.61 (m, 1H), 1.71 (m, 1H), 1.76 (s, 3H), 2.05 (m, 3H), 2.37 (dd, 1H), 2.68 (m, 1H), 2.90 (m, 1H), 3.33 (s, 3H), 3.36 (s, 3H), 3.48 (m, 3H), 3.95 (d, 1H), 4.12 (d, 1H), 4.43 (d, 1H), 4.79 (br, 2H), 5.01 (m, 1H), 5.18 (m, 2H), 5.84 (t, 1H), 6.58 (t, 1H), 7.37 (s, 1H), 7.39 (m, 1H), 7.52 (m, 2H), 7.60 (m, 1H), 7.91 (m, 2H), 8.40 (s, 1H), 8.99 (s, 1H).

Example 85

Preparation of Compound #981

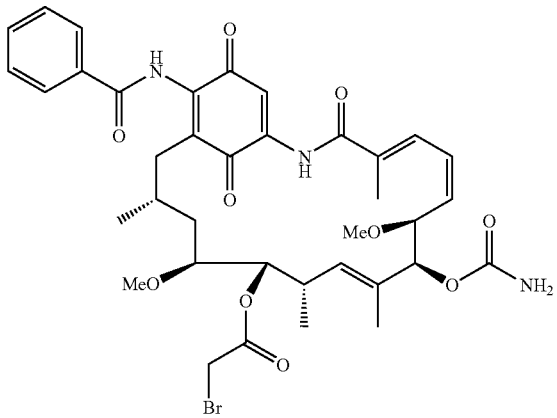

Compound #981 was prepared according to the procedure described for compound #984 using 2-bromoacetic acid instead of thiopheneacetic acid. Compound #981 was purified by preparative TLC 80% $CH_2Cl_2$/15% EtOAc/5% MeOH(Rf=0.32). $^1$H NMR (CDCl$_3$, 400 MHz) δ 0.88 (d, 3H), 0.97 (d, 3H), 1.25, (m, 2H), 1.77 (s, 3H), 1.86 (m, 1H), 2.05 (s, 3H), 2.45 (m, 1H), 2.61 (m, 1H), 2.96 (m, 1H), 3.33 (s, 3H), 3.39 (s, 3H), 3.48 (m, 1H), 3.68 (d, 1H), 3.76 (d, 1H), 4.39 (d, 1H), 4.60 (br, 2H), 4.97 (m, 1H), 5.19 (s, 1H), 5.24 (d, 1H), 5.86 (t, 1H), 6.59 (t, 1H), 7.29 (m, 1H), 7.40 (s, 1H), 7.52 (m, 2H), 7.62 (m, 1H), 7.91 (m, 2H), 8.40 (s, 1H), 8.85 (s, 1H).

Example 86

Preparation of Compound #982

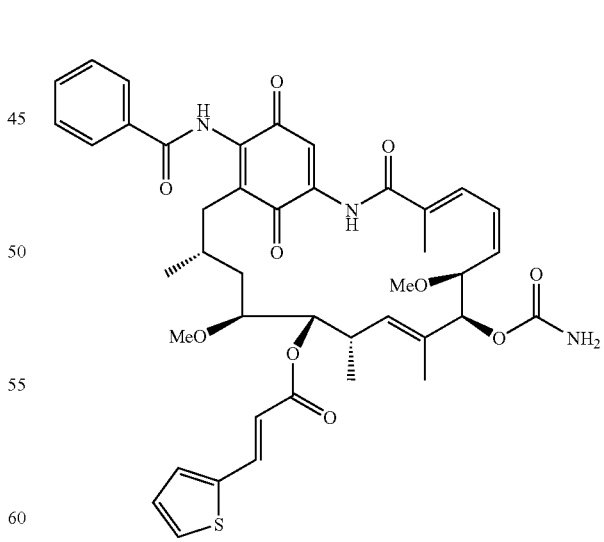

Compound #982 was prepared according to the procedure described for compound #984 using trans-3-(2-thienyl) acrylic acid instead of thiopheneacetic acid. Compound #982 was purified by preparative TLC 60% $CH_2Cl_2$/35% EtOAc/S% MeOH(Rf=0.36).

¹H NMR (CDCl₃, 400 MHz) δ 0.95 (m, 3H), 1.10-1.15 (m, 4H), 1.49 (m, 1H), 1.82 (d, 3H), 2.08 (m, 1H), 2.11 (s, 3H), 2.32 (m, 1H), 2.58 (dd, 1H), 3.04 (m, 1H), 3.34 (s, 3H), 3.40 (m, 1H), 3.45 (s, 3H), 4.43 (d, 1H), 4.75 (br, 2H), 4.96 (dd, 1H), 4.99 (s, 1H), 5.14 (d, 1H), 5.85 (t, 1H), 5.97 (d, 1H), 6.63 (t, 1H), 7.07 (dd, 1H), 7.30 (m, 2H), 7.40 (m, 2H), 7.50 (m, 2H), 7.60 (m, 2H), 7.89 (m, 2H), 8.30 (s, 1H), 8.87 (s, 1H).

Example 87

Preparation of Compound #983

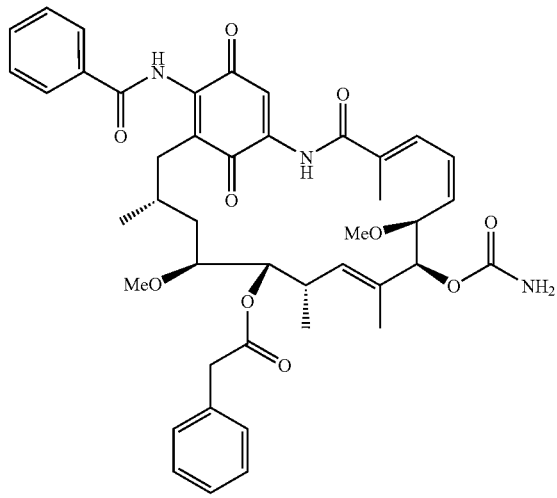

Compound #983 was prepared according to the procedure described for compound #984 using phenylacetic acid instead of thiopheneacetic acid. Compound #983 was purified by preparative TLC 40% Acetone/60% Hexanes (Rf=0.3). ¹H NMR (CDCl₃, 400 MHz) δ 0.83 (d, 3H), 1.01 (d, 3H), 1.16 (m, 1H), 1.50 (m, 1H), 1.71 (d, 3H), 1.89 (m, 1H), 2.03 (s, 3H), 2.46 (m, 2H), 2.85 (m, 1H), 3.30 (s, 3H), 3.34 (s, 3H), 3.40 (m, 1H), 3.50 (q, 2H), 4.25 (d, 1H), 4.87 (m, 4H), 5.80 (t, 1 μl), 6.55 (t, 1H), 7.12 (m, 2H), 7.32-7.22 (m, 5H), 7.36 (s, 1H), 7.53 (m 2H), 7.63 (m, 1H), 7.93 (m, 2H), 8.38 (s, 1H), 8.74 (s, 1H).

Example 88

Preparation of Compound #985

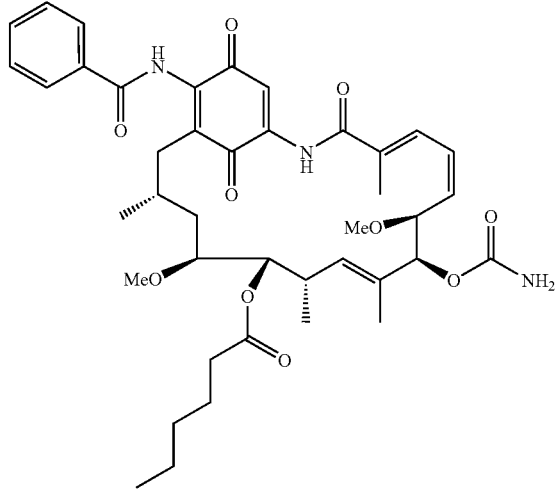

Compound #985 was prepared according to the procedure described for compound #984 using hexanoic acid instead of thiopheneacetic acid. Compound #985 was purified by preparative TLC 35% Acetone/65% Hexanes (Rf=0.3). ¹H NMR (CDCl₃, 400 MHz) δ 0.86 (t, 3H), 0.93 (d, 3H), 1.06 (d, 3H), 1.25-1.07 (m, 5H), 1.45 (m, 3H), 1.78 (s, 3H), 1.92 (m, 1H), 2.05 (s, 3H), 2.15 (m, 2H), 2.49 (d, 2H), 2.92 (m, 1H), 3.32 (s, 3H), 3.39 (m, 1H), 3.41 (s, 3H), 4.39 (d, 1H), 4.77 (br, 2H), 4.93 (m, 1H), 5.16 (s, 1H), 5.29 (d, 1H), 5.86 (t, 1H), 6.62 (t, 1H), 7.36 (s, 1H), 7.38 (d, 1H), 7.52 (m, 2H), 7.62 (m, 1H), 7.92 (m, 2H), 8.38 (s, 1H), 8.84 (s, 1H).

11-oxime-geldanamycin

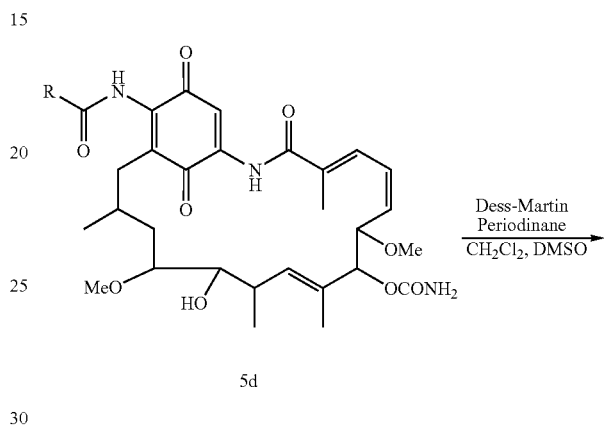

5d

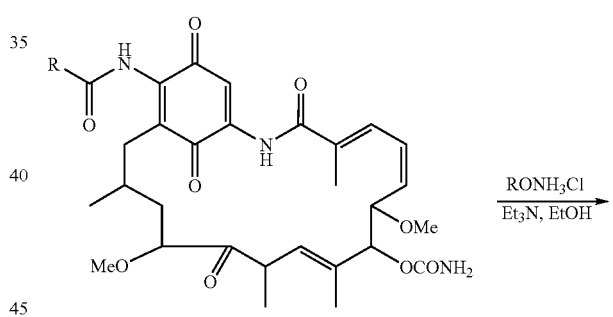

5f

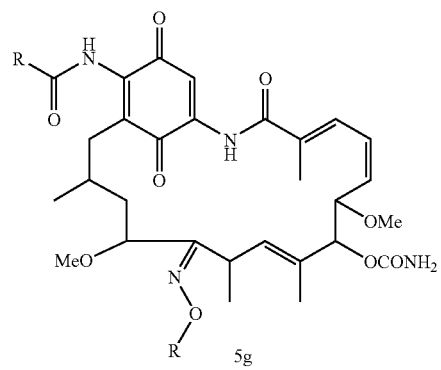

5g

Example 89

Preparation of Compound #1011

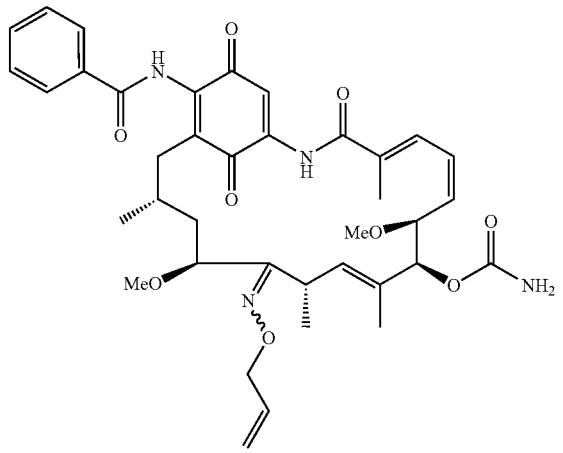

Allylhydroxylamine hydrochloride (0.032g, 0.29 mmol, 8.35 eq) was added to a flask containing 0.021 g (0.032 mmol, 8.35 eq) of #868 and 38 μL (0.29 mmol, 8.35 eq) triethylamine in 1 mL of ethanol. The reaction was stirred for 24 hours at room temperature and then concentrated under vacuum. Compound #1011 was obtained (18 mg, 78% yield) as a yellow solid after Preparative TLC (40% Acetone/60% Hexanes, Rf=0.3). $^1$H NMR (CDCl$_3$, 400 MHz) δ 0.86 (d, 3H), 1.24 (m, 3H), 1.52 (m, 1H), 1.70 (m, 1H), 1.77 (m, 1H), 1.83 (d, 3H), 2.03 (m, 3H), 2.48 (dd, 1H), 2.88 (dd, 1H), 3.27 (s, 3H), 3.28 (s, 3H), 3.93 (m, 1H), 4.03 (t, 1H), 4.27 (d, 1H), 4.54 (d, 2H), 4.81 (br, 2H), 5.10-5.24 (m, 3H), 5.76 (d, 1H), 5.83-5.89 (m, 1H), 5.89-5.98 (m, 1H), 6.53 (t, 1H), 7.01 (br, 1H), 7.43 (s, 1H), 7.53 (m, 2H), 7.62 (m, 1H), 7.92 (m, 2H), 8.52 (s, 1H), 8.92 (s, 1H).

Example 90

Preparation of Compound #1012

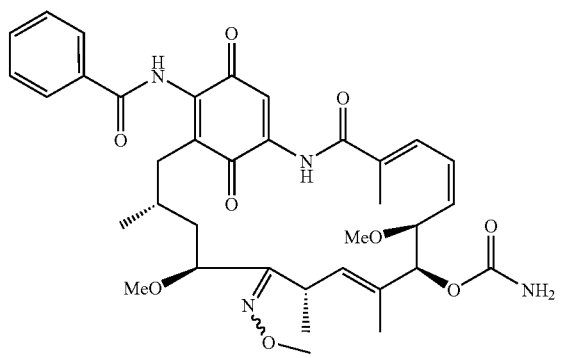

Compound #1012 was obtained in the same fashion as #1011 using O-methyl hydroxylamine hydrochloride instead of allylhydroxylamine hydrochloride. Preparative TLC (40% Acetone/60% Hexanes, Rf=0.28) afforded #1012 (22 mg, 68% yield) as a yellow solid. $^1$H NMR (CDCl$_3$, 400 MHz) δ 0.87 (d, 3H), 1.22 (d, 3H), 1.55 (m, 1H), 1.66 (m, 1H), 1.77 (s, 1H), 1.82 (s, 3H), 2.03 (s, 3H), 2.49 (dd, 1H), 2.89 (dd, 1H), 3.28 (s, 3H), 3.30 (s, 3H), 3.82 (s, 3H), 3.86 (m, 1H), 4.0 (t, 1H), 4.24 (d, 1H), 4.86 (br, 2H), 5.17 (s, 1H), 5.75 (d, 1H), 5.85 (t, 1H), 6.54 (t, 1H), 7.01 (br, 1H), 7.42 (s, 1H), 7.53 (t, 2H), 7.62 (t, 1H), 7.93 (d, 2H), 8.53 (s, 1H), 8.92 (s, 1H).

Example 91

Preparation of Compound #1013

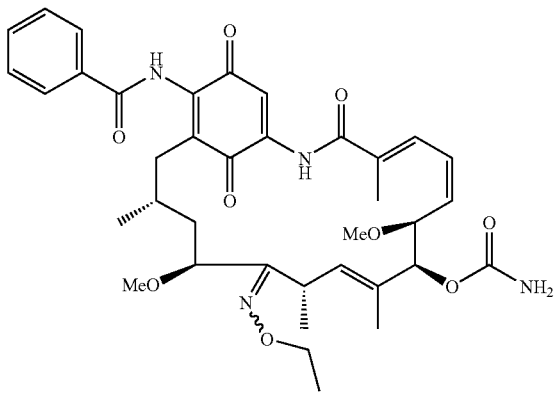

Compound #1013 was obtained in the same fashion as #1011 using O-ethyl hydroxylamine hydrochloride instead of allylhydroxylamine hydrochloride. Preparative TLC (40% Acetone/60% Hexanes, Rf=0.29) afforded #1013 (27 mg, 75% yield) as a yellow solid. $^1$H NMR (CDCl$_3$, 400 MHz) δ 0.87 (d, 3H), 1.22 (m, 6H), 1.52 (m, 1H), 1.68 (m, 1H), 1.75 (s, 1H), 1.80 (s, 3H), 2.03 (s, 3H), 2.49 (dd, 1H), 2.89 (dd, 1H), 3.27 (s, 3H), 3.29 (s, 3H), 3.90 (m, 1H), 4.07 (m, 3H), 4.26 (d, 1H), 4.83 (br, 2H), 5.18 (s, 1H), 5.72 (m, 1H), 5.86 (m, 1H), 6.54 (m, 1H), 7.01 (br, 1H), 7.42 (s, 1H), 7.53 (m, 2H), 7.62 (m, 1H), 7.92 (d, 2H), 8.52 (s, 1H), 8.92 (s, 1H).

17-Aryl-geldanamycin

Example 92

Preparation of Compound #133

Step 1: Preparation of 17-OTf-geldanamycin.

To a purple solution of 17-hydroxy-geldanamycin (0.68 g, 1.24 mmol) and (i-Pr)$_2$NEt (0.43 ml) in CH$_2$Cl$_2$ at 0° C. was added dropwise the triflic anhydride (0.28 ml, 1.62 mmol). After 30 min, the reaction mixture was concentrated under reduce pressure. The crude material was then purified by flash chromatography to give 17-OTf-geldanamycin as a yellow-solid (0.62 g, 74%). Rf=0.28 in 80:15:5 CH$_2$Cl$_2$: EtOAc: MeOH. $^1$H NMR (CDCl$_3$, 500 MHz) δ 0.89 (d, 3H), 1.09 (d, 3H), 1.53-1.62 (m, 2H), 1.68-1.74 (m, 1H), 1.77 (s, 3H), 2.03 (s, 3H), 2.49 (dd, 1H), 2.58 (dd, 1H), 2.78-2.83 (m, 1H), 3.25-3.27 (m, 1H), 3.30-3.32 (m, 1H), 3.35 (s, 3H), 3.38 (s, 3H), 4.32 (d, 1H), 5.10 (s, 1H), 5.59 (d, 1H), 5.96 (dd, 1H), 6.55 (t, 1H), 6.92 (d, 1H), 7.58 (s, 1H), 8.60 (s, 1H).

Step 2: A solution of 17-OTf-geldanamycin (0.20 g, 0.30 mmol), cesium bromide (128 mg, 0.60 mmol), cesium fluoride (91 mg, 0.60 mmol), Pd(dba)$_2$ (43 mg, 0.075 mmol) and phenyl boronic acid (73 mg, 0.60 mmol) in dioxane was heated at 40° C. for 12 hours whereupon it was cooled down to rt and concentrated under reduce pressure to give the crude product. This latter was dissolved in EtOAc and washed with sat. NaHCO$_3$, dried over Na$_2$SO$_4$ and concentrated under reduce pressure. The crude material was purified by flash chromatography to give 17-phenyl-geldanamycin as a yellow solid (90 mg, 50%). Rf=0.49 in 80:15:5 CH$_2$Cl$_2$: EtOAc: MeOH. $^1$H NMR (CDCl$_3$) δ 0.71 (d, 3H), 0.98 (d, 3H), 1.53-1.63 (m, 3H), 1.79 (s, 3H), 2.04 (s, 3H), 2.35 (dd, 1H), 2.54-2.60 (m, 1H), 2.73-2.77 (m, 1H), 3.31 (s, 3H), 3.34 (s, 3H), 3.35-3.37 (m, 1H), 3.47-3.52 (m, 1 µl), 4.36 (d, 1H), 5.24 (s, 1H), 5.75 (d, 1H), 5.90 (t, 1H), 6.58 (t, 1H), 6.96 (d, 1H), 7.12-7.14 (m, 2H), 7.40-7.43 (m, 3H), 7.56 (s, 1H), 8.68 (s, 1H).

Example 93

Preparation of Compound #212

Compound #212 was prepared according to the procedure described for 17-phenyl-geldanamycin except that 2-methoxy-phenyl boronic acid was used instead of phenyl boronic acid. Rf=0.36 in 80:15:5 CH$_2$Cl$_2$: EtOAc: MeOH. $^1$H NMR (CDCl$_3$) δ 0.98 (d, 3H), 1.04 (d, 3H), 1.53-1.63 (m, 3H), 1.80 (s, 3H), 2.03 (s, 3H), 2.52-2.62 (m, 2H), 2.78-2.83 (m, 1H), 2.85(d, 1H), 3.32 (s, 3H), 3.36 (s, 3H), 3;37-3.39 (m, 1), 3.54-3.56 (m, 1H), 3.76 (s, 3H), 4.34 (d, 1H), 5.19 (s, 1H), 5.83 (d, 1H), 5.90 (t, 1H), 6.58 (t, 1H), 6.89-6.92 (m, 2H), 6.96 (br d, 2H), 7.06 (br t, 1H), 7.29 (s, 1H), 8.74 (s, 1H).

Example 94

Synthesis of Compound #232

Compound #232 was prepared according to the procedure described for 17-phenyl-geldanamycin except that 2-thiophene boronic acid was used instead of phenyl boronic acid. Rf=0.50 in 80:15:5 CH$_2$Cl$_2$: EtOAc: MeOH. $^1$H NMR (CDCl$_3$) δ 0.82 (d, 3H), 0.97 (d, 3H), 1.50-1.603 (m, 3H), 1.78 (s, 3H), 2.05 (s, 3H), 2.42-2.50 (m, 2H), 2.76-2.81 (m, 1H), 3.33 (s, 3H), 3.34 (s, 3H), 3.33-3.36 (m, 1H), 3.48-3.50 (m, 1H), 4.35 (d, 1H), 5.21 (s, 1H), 5.72 (d, 1H), 5.91 (t, 1H), 6.57 (t, 1H), 6.92 (d, 1H), 7.12-7.14 (m, 1H), 7.55 (s, 1H), 7.55-7.58 (m, 2H), 8.68 (s, 1H).

8-hydroxymethyl GM Analogs

The following general synthetic scheme is applicable to Examples 95:

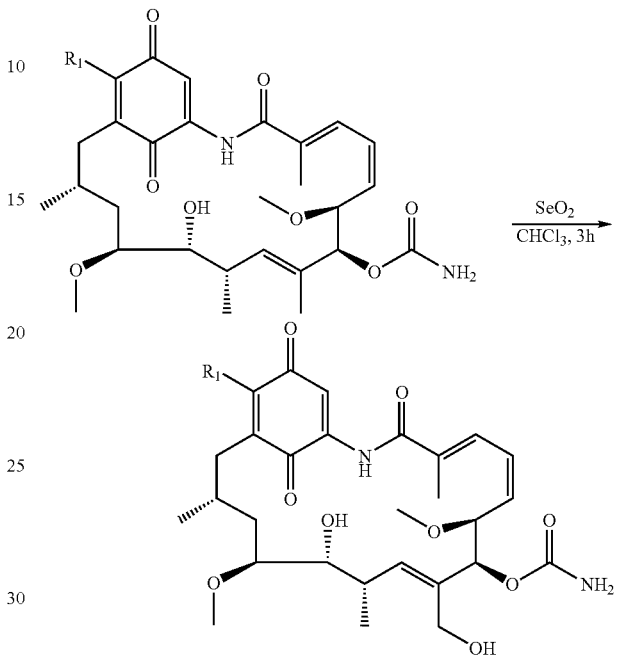

Example 95

Preparation of Compound #914

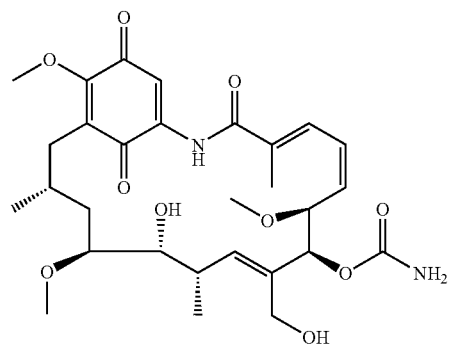

To Geldanamycin (500 mg, 0.89 mmol) in 10 mL of dioxane was added selenium(IV) dioxide (198 mg, 1.78 mmol) at room temperature. The reaction mixture was heated to 100° C. and stirred for 3 hours. After cooled down to room temperature, the solution was diluted with ethyl acetate, washed with water and brine, dried over magnesium sulfate, filtered and evaporated in vacuo. The final pure yellow product was obtained after column chromatography (silica gel); yield: 75%; $^1$H NMR (CDCl$_3$) δ 0.97(d, J=7.0 Hz, 3H, CH$_3$), 1.01(d, J=7.0 Hz, 3H, CH$_3$), 1.75(m, 3H, CH$_2$+CH), 2.04(s, 3H, CH$_3$), 2.41(d, J=9.9 Hz, 1H, CH$_2$), 2.53(t, J=9.9 Hz, 1H, CH$_2$), 2.95(m, 1H, CH), 3.30(m, 2H, CH+OH), 3.34(s, 6H, 2CH$_3$), 3.55(m, 1H, CH), 4.09(m, 1H, CH$_2$), 4.15(s, 3H, CH$_3$), 4.25(m, 1H, CH$_2$), 4.41(d, J=9.8 Hz, 1H, CH), 4.80(bs, 2H, CONH$_2$), 5.32(s, 1H, CH), 5.88(t, J=10.4 Hz, 1H, CH=), 6.04(d, J=9.7 Hz, 1H, CH=), 6.65(t, J=11.5 Hz, 1H, CH=), 6.95(d, J=11.5 Hz, 1H, CH=), 7.32(s, 1H, CH—Ar), 8.69(s, 1H, NH); MS (m/z)575.6 (M−1);

Example 96

Preparation of Compound #915

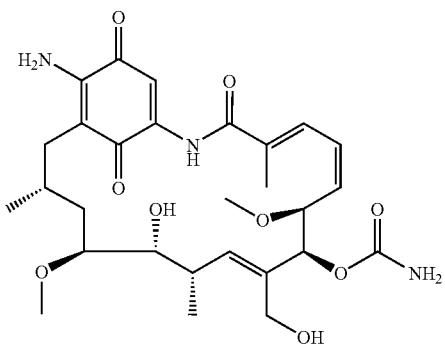

Compound #915 was prepared by the same method described for compound #914 except that 17-Amino-Geldanamycin was used instead of Geldanamycin. The final pure purple product was obtained after column chromatography (silica gel); yield: 65%; mp 288~290° C.; $^1$H NMR (CDCl$_3$) δ0.96(d, J=7.0 Hz, 3H, CH$_3$), 1.01(d, J=7.0 Hz, 3H, CH$_3$), 1.75(m, 3H, CH$_2$+CH), 1.95(t, J=10.4 Hz, 1H, CH$_2$), 2.05(s, 3H, CH$_3$), 2.65(d, J=10.4 Hz, 1H, CH$_2$), 2.93(m, 1H, CH), 3.32(s, 3H, CH$_3$), 3.34(s, 3H, CH$_3$), 3.45(m, 2H, CH+OH), 3.62(t, J=7.8 Hz, 1H, CH), 4.13(dd, J=12.4 Hz, 1H, CH$_2$), 4.26(m, 1H, CH$_2$), 4.36(d, J=6.4 Hz, OH), 4.40(d, J=10.0 Hz, 1H, CH), 4.80(bs, 2H, CONH$_2$), 5.30(s, 1H, CH), 5.48(bs, 2H, NH2), 5.87(t, J=10.0 Hz, 1H, CH=), 6.09(d, J=10.0 Hz, 1H, CH=), 6.66(t, J=11.4 Hz, 1H, CH=), 6.97(d, J=11.4 Hz, 1H, CH=), 7.27(s, 1H, CH), 9.09(s, 1H, NH); MS(m/z)584.7(M+Na);

Example 97

Preparation of Compound #760

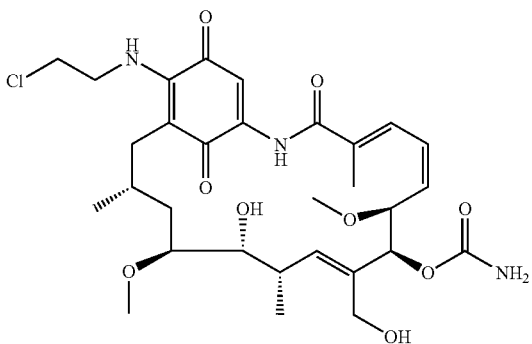

Compound #760 was prepared by the same method described for compound #914 except that 17-(2'-chloroethylamino)-Geldanamycin was used instead of Geldanamycin. The final pure purple product was obtained after column chromatography (silica gel); yield: 79%; mp 130.2° C.~132.0° C.; $^1$H NMR (CDCl$_3$) δ 0.98 (d, J=6.5 Hz, 3H, CH$_3$), 1.03 (d, J=6.9 Hz, 3H, CH$_3$), 1.79 (m, 1H, CH), 1.83 (m, 2H, CH$_2$), 2.04 (s, 3H, CH$_3$), 2.26 (m, 1H, CH$_2$), 2.70 (d, J=13.5 Hz, 1H, CH$_2$), 2.90(m, 1H, CH), 3.32 (s, 3H, CH$_3$), 3.34 (s, 3H, CH$_3$), 3.46 (m, 1H, CH), 3.46 (m, 1H, OH), 3.58 (t, J=6.8 Hz, 1H, CH), 3,72 (t, J=5.5 Hz, 2H, CH$_2$), 3.90 (m, 2H, CH$_2$), 4.10 (m, 1H, OH), 4.27 (m, 2H, CH$_2$), 4.41 (d, J=10.0 Hz, 1H, CH), 4.78 (s, 2H, NH$_2$), 5.35 (s, 1H, CH), 5.87(t, J=10.5 Hz, 1H, CH), 6.09 (d, J=9.8 Hz, 1H, CH), 6.43 (t, J=5.4 Hz, 1H, NH), 6.66 (t, J=11.1 Hz, 1H, CH), 6.98 (d, J=12.4 Hz, 1H, CH), 7.30 (s, 1H, CH), 9.09 (s, 1H, NH); MS(m/z) 623.26 (M−1);

Example 98

Preparation of Compound #842

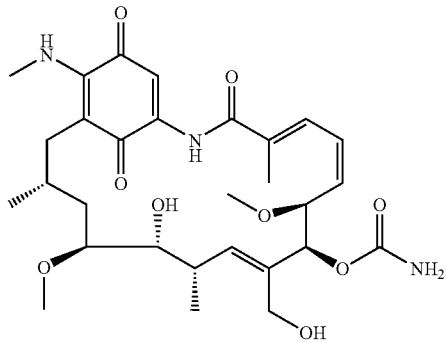

Compound #842 was prepared by the same method described for compound #914 except that 17-methylamino-Geldanamycin was used instead of Geldanamycin and the reaction mixture was heated to 70° C. for 24 h. The final pure purple product was obtained after column chromatography (silica gel); yield: 79%; mp ° C.; $^1$H NMR (CDCl$_3$) δ 0.99 (d, J=8 Hz, 3H, CH$_3$), 1.04 (d, J=8 Hz, 3H, CH$_3$), 1.77 (m, 1H, CH), 1.80 (m, 2H, CH$_2$), 2.06 (s, 3H, CH$_3$), 2.26 (m, 1H, CH$_2$), 2.67 (d, 1H, CH$_2$), 2.90(m, 1H, CH), 3.2 (d, J=6 Hz, 3H, NCH$_3$), 3.34 (s, 3H, CH$_3$), 3.36 (s, 3H, CH$_3$), 3.48 (m, 2H, OH+CH), 3.60 (t, J=6.8 Hz, 1H, CH), 4.11 (dd, J=12.44 Hz, J=4.5 Hz, 1H, CH$_2$), 4.30 (dd, J=12 Hz, J=4.5 Hz, 1H, CH$_2$), 4.45 (d, J=10.0 Hz, 1H, CH), 4.52 (bs, 1H, OH), 4.78 (bs, 2H, NH2), 5.37 (s, 1H, CH), 5.89(t, J=10.5 Hz, 1H, CH=), 6.10 (d, J=10 Hz, 1H, CH=), 6.55 (m, 1H, NH), 6.66 (t, J=12 Hz, 1H, CH=), 7.00 (d, J=12 Hz, 1H, CH=), 7.30 (s, 1H, CH=), 9.20 (s, 1H, CONH); MS(m/z) 574 (M−1);

8-substituted GM Analogs

The following general synthetic scheme is applicable to Examples 99-100:

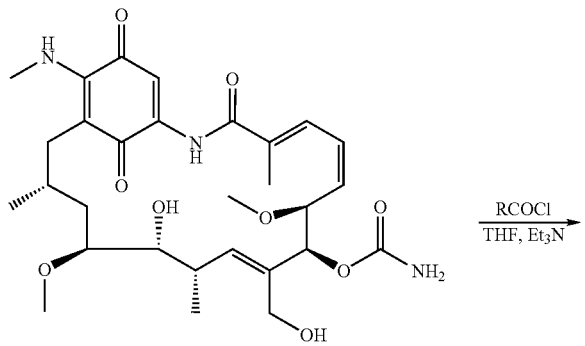

Example 99

Preparation of Compound #863

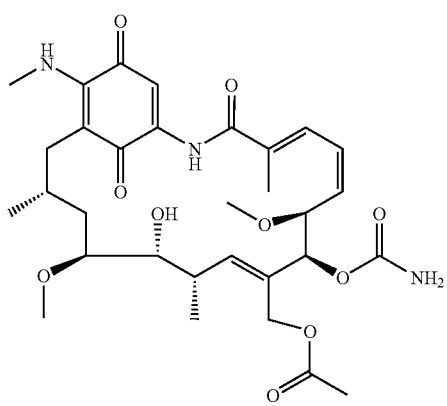

To compound #842 (30 mg, 0.052 mmol) in 1 mL of TBF was added Acetyl chloride (4.1 μl, 0.0574 mmol) and triethylamine (7.27 μl, 0.052 mmol). The reaction mixture was stirred at room temperature for 24 hours. The solvent was removed by rotary evaporation. The pure purple product was obtained after column chromatography (silica gel); yield: 70%; $^1$H NMR (CDCl$_3$) δ 0.98 (d, J=6.8 Hz, 3H, CH$_3$), 1.06 (d, J=6.8 Hz, 3H, CH$_3$), 1.78 (m, 1H, CH), 1.81 (m, 2H, CH$_2$), 2.06 (s, 6H, 2CH$_3$), 2.60 (m, 1H, CH$_2$), 2.63 (d, 1H, CH$_2$), 2.85(m, 1H, CH), 3.25 (d, J=6 Hz, 3H, NCH$_3$), 3.26 (s, 3H, CH$_3$), 3.36 (s, 3H, CH$_3$), 3.46 (m, 1H, CH), 3.57 (t, J=6.8 Hz, 1H, CH), 4.32 (d, J=10.0 Hz, 1H, CH), 4.62 (bs, 1H, OH), 4.80 (d, J=12. Hz, 1H, CH$_2$), 4.90 (d, J=12 Hz, 1H, CH$_2$), 5.27 (s, 1H, CH), 5.90(t, J=10.5 Hz, 1H, CH=), 6.30 (d, J=10 Hz, 1H, CH=), 6.54 (m, 1H, NH), 6.66 (t, J=12 Hz, 1H, CH=), 7.01 (d, J=12 Hz, 1H, CH=), 7.31 (s, 1H, CH=), 9.21 (s, 1H, CONH); MS(m/z) 616 (M−1);

Example 100

Preparation of Compound #964

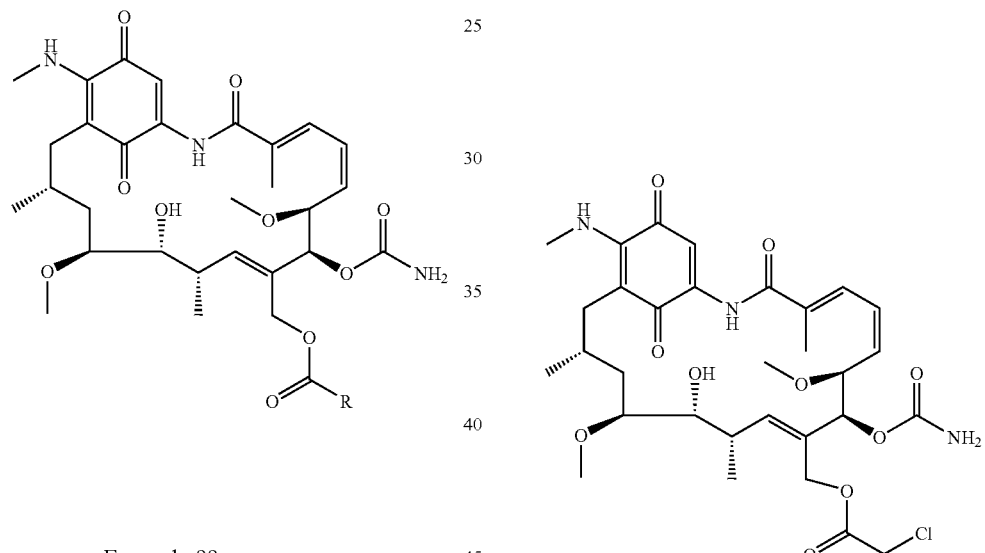

Compound #964 was prepared by the same method described for compound #863 except that chloroacetyl chloride was used instead of acetyl chloride. The final pure purple product was obtained after column chromatography (silica gel); yield: 55%; $^1$H NMR (CDCl$_3$) δ 1.00 (d, J=6.8 Hz, 3H, CH$_3$), 1.06 (d, J=6.8 Hz, 3H, CH$_3$), 1.78 (m, 1H, CH), 1.81 (m, 2H, CH$_2$), 2.06 (s, 6H, 2CH$_3$), 2.63 (m, 2H, CH$_2$), 2.85(m, 1H, CH), 3.25 (d, J=6 Hz, 3H, NCH$_3$), 3.26 (s, 3H, CH$_3$), 3.36 (s, 3H, CH$_3$), 3.46 (m, 1H, CH), 3.57 (t, J=6.8 Hz, 1H, CH), 4.08 (dd, 2H, CH$_2$), 4.34 (d, J=10.0 Hz, 1H, CH), 4.62 (bs, 1H, OH), 4.90 (d, J=12. Hz, 1H, CH$_2$), 5.07 (d, J=12 Hz, 1H, CH$_2$), 5.25 (s, 1H, CH), 5.89(t, J=10.5 Hz, 1H, CH=), 6.35 (d, J=10 Hz, 1H, CH=), 6.44 (m, 1H, NH), 6.56 (t, J=12 Hz, 1H, CH=), 7.01 (d, J=12 Hz, 1H, CH=), 7.31 (s, 1H, CH=), 9.21 (s, 1H, CONH); MS(m/z) 651 (M−1);

8-hydroxymethyl GM Dimer Analogs

The following general synthetic scheme is applicable to Examples 101-102:

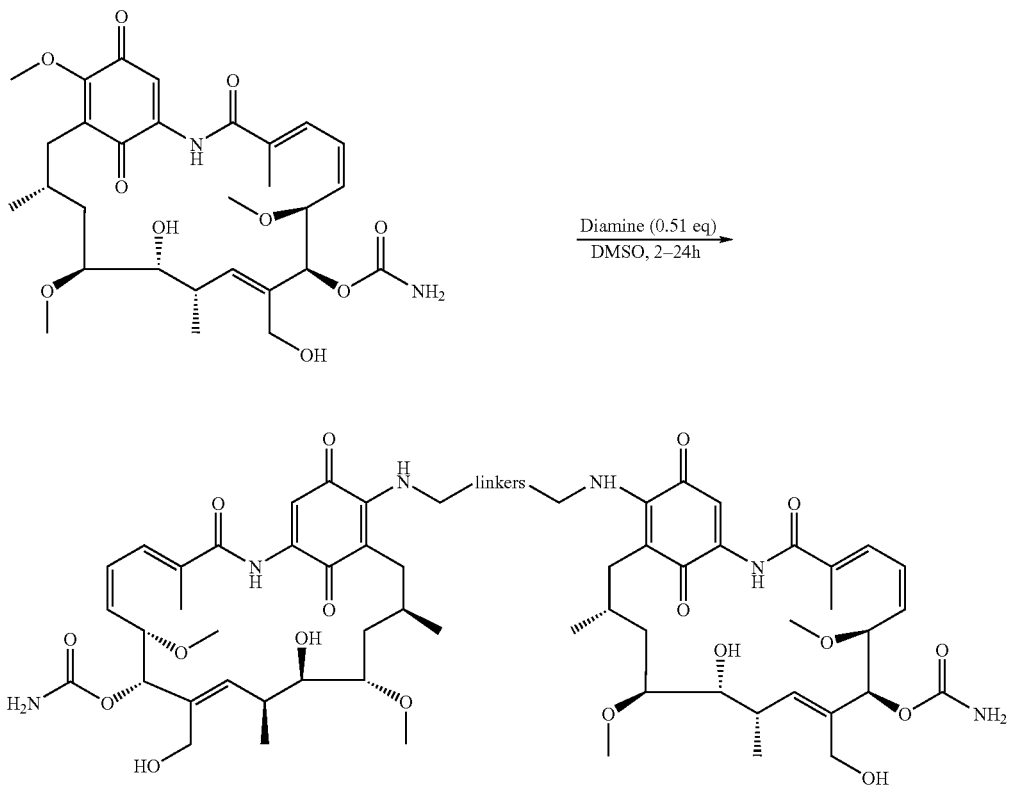

Example 101

Preparation of Compound #970

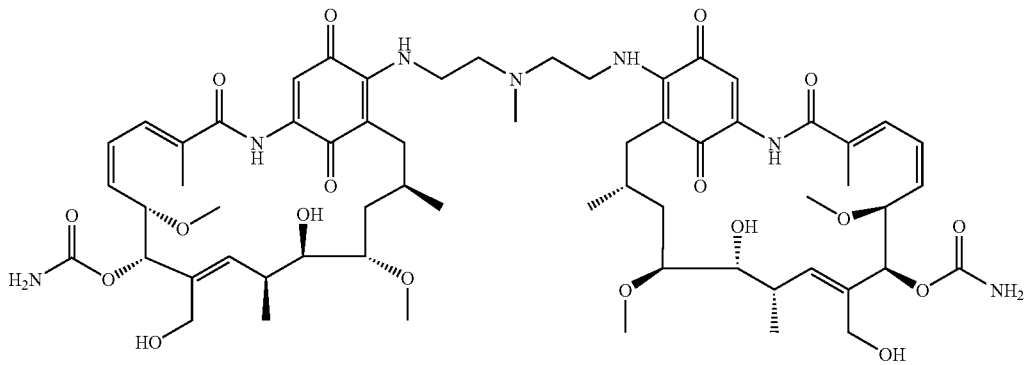

Compound #970 was prepared by the same method described for compound #483 except that compound #914 was used instead of Geldanamycin. The pure purple product was obtained after column chromatography (silica gel); yield: 89%; $^1$H NMR (CDCl$_3$) ☐ 0.98(d, J=7.0 Hz, 6H, 2CH$_3$), 1.02(d, J=7.0 Hz, 6H, 2CH$_3$), 1.76(m, 6H, 2CH$_2$+2CH), 2.03 (s, 6H, 2CH$_3$), 2.33(s, 3H, N—CH$_3$), 2.40(t, J=10.7 Hz, 2H, 2CH$_2$), 2.66(d, J=14 Hz, 2H, 2CH$_2$), 2.74(t, J=5.6 Hz, 4H, 2CH$_2$), 2.89(m, 2H, 2CH), 3.32(s, 6H, 2CH$_3$), 3.33(s, 6H, 2CH$_3$), 3.45(m, 4H, 2CH+2OH), 3.56(m, 4H, 2CH$_2$), 3.74 (m, 2H, 2CH), 4.12(m, 2H, 2CH$_2$), 4.30(m, 2H, 2CH$_2$), 4.42 (d, J=10 Hz, 2H, 2CH), 4.45(s, 2H, 2OH), 4.82(bs, 4H, 2CONH$_2$), 5.34(s, 2H, 2CH), 5.89(t, J=11.3 Hz, 2H, 2CH=), 6.08(d, J=9.7 Hz, 2H, 2CH=), 6.68(t, J=11.0 Hz, 2H, 2CH=), 6.80(t, J=4.5 Hz, 2H, 2NH), 6.97(d, J=11.0 Hz, 2H, 2CH=), 7.31(s, 2H, 2CH—Ar), 9.15(s, 2H, 2NH).

Example 102

Preparation of Compound #950

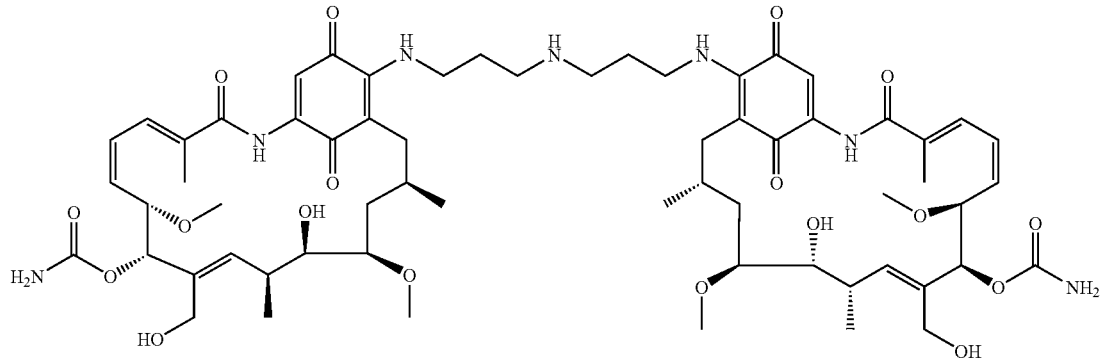

Compound #950 was prepared by the same method described for compound #237 except that #914 was used instead of Geldanamycin. The pure purple product was obtained after column chromatography (silica gel); yield: 89%; $^1$H NMR (CDCl$_3$) δ 0.98(d, J=7.0 Hz, 6H, 2CH$_3$), 1.02(d, J=7.0 Hz, 6H, 2CH$_3$), 1.76(m, 6H, 4CH$_2$+2CH), 1.88 (m, 4H, 2CH$_2$), 2.04(s, 6H, 2CH$_3$), 2.43(t, J=10.7 Hz, 2H, 2CH$_2$), 2.66(d, J=10.7 Hz, 2H, 2CH$_2$), 2.79(t, J=5.6 Hz, 4H, 2CH$_2$), 2.87(m, 2H, 2CH), 3.32(s, 6H, 2CH$_3$), 3.34(s, 6H, 2CH$_3$), 3.45(m, 4H, 2CH+2OH), 3.60(m, 4H, 2CH$_2$), 3.74 (m, 2H, 2CH), 4.12(d, J=10.0 Hz, 2H, 2CH$_2$), 4.30(d, J=10.0 Hz, 2H, 2CH$_2$), 4.42(d, J=10 Hz, 2H, 2CH), 4.51(s, 2H, 2OH), 4.82(bs, 4H, 2CONH$_2$), 5.34(s, 2H, 2CH), 5.89(t, J=11.3 Hz, 2H, 2CH=), 6.08(d, J=9.7 Hz, 2H, 2CH=), 6.66(t, J=11.0 Hz, 2H, 2CH=), 6.99(d, J=11.0 Hz, 2H, 2CH=), 7.25(s, 2H, 2CH—Ar), 9.15(s, 2H, 2NH); MS 1221.1(M$^+$H);

8-hydroxylmethyl-17 Substituted-amino GM Analogs

The following general synthetic scheme is applicable to Examples 103-107:

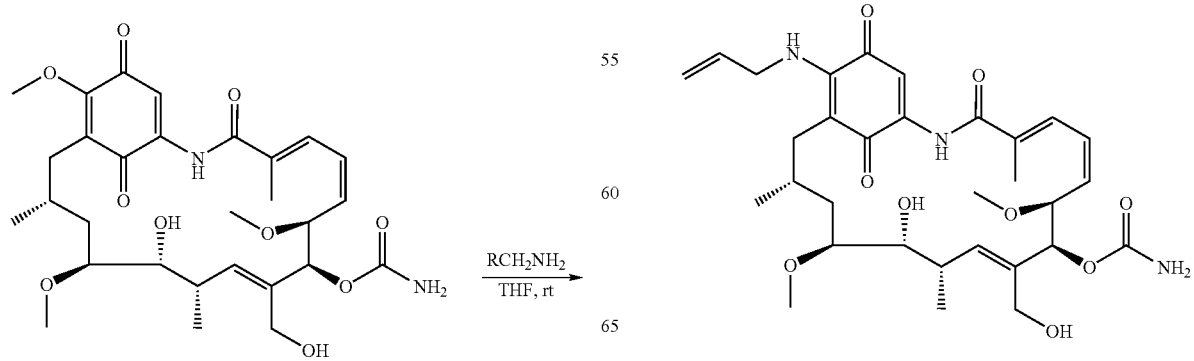

-continued

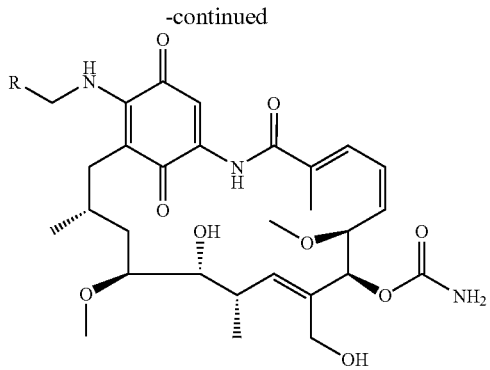

Example 103

Preparation of Compound #967

To compound #914 (50 mg, 0.05 mmol) in 3 mL of THF was added allylamine (3.5 mg, 0.06 mmol). The reaction mixture was stirred at room temperature for 24 hours. The solvent was removed by rotary evaporation. The pure purple product was obtained after column chromatography (silica gel); yield: 90%; $^1$H NMR (CDCl$_3$) δ 0.89(d, J=6.6 Hz, 3H, CH$_3$), 1.03 (d, J=6.9 Hz, 3H, CH$_3$), 1.78(m, 1H, CH), 1.82(m, 2H, CH$_2$), 2.04 (s, 3H, CH$_3$), 2.37(dd, J=13.7 Hz, 1H, CH$_2$), 2.65(d, J=13.7 Hz, 1H, CH$_2$), 2.90(m, 1H, CH), 3.33(s, 3H, CH$_3$), 3.34(s, 3H, CH$_3$), 3.45(m, 2H, CH+OH), 3.58(m, 1H, CH), 4.14(m, 3H, CH$_2$+CH$_2$), 4.16(m, 1H, CH$_2$), 4.42(s, 1H, OH), 4.43(d, J=10 Hz, 1H, CH), 4.75(bs, 2H, CONH$_2$), 5.33 (m, 2H, CH$_2$=), 5.35(s, 1H, CH), 5.91(m, 2H, CH=+ CH=), 6.09(d, J=9.9 Hz, 1H, CH=), 6.46(t, J=5.8 Hz, 1H, NH), 6.66(t, J=11.6 Hz, 1H, CH=), 6.97(d, J=11.6 Hz, 1H, CH=), 7.30(s, 1H, CH), 9.15(s, 1H, NH);

Example 104

Preparation of Compound #1126

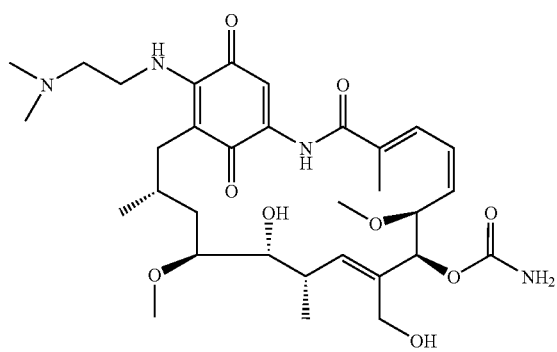

Compound #1126 was prepared by the same method described in #967 except that N,N-Dimethylethylenediamine was used instead of allylamine. The pure purple product was obtained after column chromatography (silica gel); yield: 80%; $^1$H NMR (CDCl$_3$) δ 0.96(d, J=7.0 Hz, 3H, CH$_3$), 1.02(d, J=7.0 Hz, H, CH$_3$), 1.75(m, 3H, CH$_2$+CH), 2.04(s, 3H, CH$_3$), 2.29(s, 6H, 2CH$_3$), 2.42(m, 1H, CH$_2$), 2.47(t, J=6.0 Hz, 2H, CH$_2$), 2.64(d, J=14 Hz, 1H, CH$_2$), 2.90(m, 1H, CH), 3.33(s, 3H, CH$_3$), 3.34(s, 3H, CH$_3$), 3.46(m, 2H, CH+OH), 3.62(m, 2H, C H$_2$), 3.75(m, 1H, C H), 4.10(d, J=12 Hz, 1H, CH$_2$), 4.28(dd, J=12 Hz, 1H, CH$_2$), 4.42(d, J=10 Hz, 1H, CH), 4.70(s, 2H, NH$_2$), 5.35(s, 1H, CH), 5.87(t, J=10.6 Hz, 1H, CH), 6.10(d, J=10.0 Hz, 1H, CH), 6.67(t, J=10.6 Hz, 1H, CH), 7.0(d, J=10.6 Hz, 1H, CH), 7.22(s, 1H, CH), 7.91(s, 1H, NH), 9.21(s, 1H, NH).

A variation of the above is compound #952, having structure:

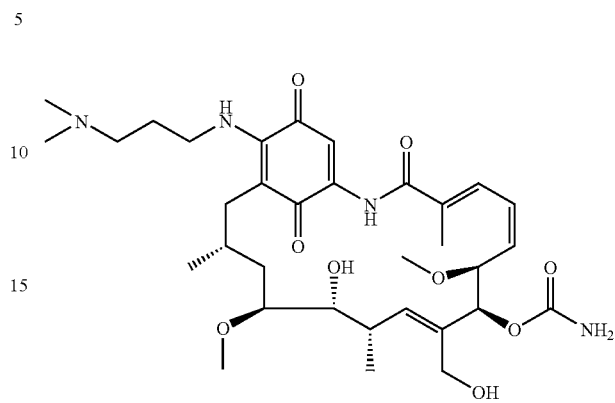

Compound #952 was prepared by the same method described for compound #967 except that N,N-Dimethyl-1,3-propanediamine was used instead of allylamine. The pure purple product was obtained after column chromatography (silica gel); yield: 85%; mp 114.2~115.6° C.; $^1$H NMR (CDCl$_3$) δ 0.96(d, J=7.0 Hz, 3H, CH3), 1.02(d, J=7.0 Hz, H, CH3), 1.75(m, 5H, CH2+CH2+CH), 2.04(s, 3H, CH3), 2.29 (s, 6H, 2CH3), 2.42(m, 1H, CH2), 2.47(t, J=6.0 Hz, 2H, CH2), 2.64(d, J=14 Hz, 1H, CH2), 2.90(m, 1H, CH), 3.33(s, 3H, CH3), 3.34(s, 3H, CH3), 3.46(m, 2H, CH+OH), 3.62(m, 2H, CH$_2$), 3.75(m, 1H, CH), 4.10(d, J=12 Hz, 1H, CH$_2$), 4.28(dd, J=12 Hz, 1H, CH$_2$), 4.42(d, J=10 Hz, 1H, CH), 4.70(s, 2H, NH2), 5.35(s, 1H, CH), 5.87(t, J=10.6 Hz, 1H, CH), 6.10(d, J=10.0 Hz, 1H, CH), 6.67(t, J=10.6 Hz, 1H, CH), 7.0(d, J=10.6 Hz, 1H, CH), 7.22(s, 1H, CH), 7.91(s, 1H, NH), 9.21(s, 1H, NH);

Example 105

Preparation of Compound #956

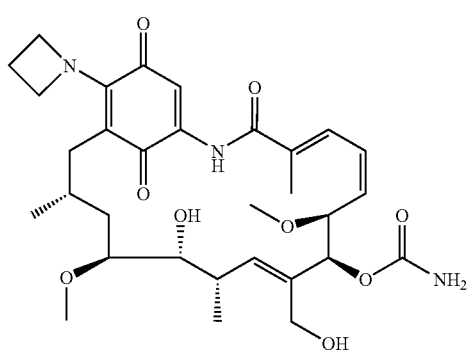

Compound #956 was prepared by the same method described for compound #967 except that Azetidine was used instead of allylamine. The final pure purple product was obtained after column chromatography (silica gel); yield: 89%; mp ° C.; $^1$H NMR (CDCl$_3$) δ 0.99 (d, J=6.8 Hz, 3H, CH$_3$), 1.04 (d, J=6.8 Hz, 3H, CH$_3$), 1.77 (m, 1H, CH), 1.80 (m, 2H, CH$_2$), 2.06 (s, 3H, CH$_3$), 2.26 (m, 1H, CH$_2$), 2.50(m, 2H, CH$_2$), 2.67 (d, 1H, CH$_2$), 2.90(m, 1H, CH), 3.34 (s, 3H, CH$_3$), 3.36 (s, 3H, CH$_3$), 3.48 (m, 2H, OH+CH), 3.60 (t, J=6.8 Hz, 1H, CH), 4.11 (dd, J=12 Hz, J=4.5 Hz, 1H, CH$_2$), 4.30 (dd, J=12 Hz, J=4.5 Hz, 1H, CH$_2$), 4.45 (d, J=10.0 Hz, 1H, CH), 4.72 (m, 5H, 2CH$_2$+OH), 4.78 (bs, 2H, NH2), 5.37 (s, 1H, CH), 5.89(t, J=10.5 Hz, 1H, CH=), 6.10 (d, J=10 Hz, 1H, CH=), 6.66 (t, J=12 Hz, 1H, CH=), 7.00 (d, J=12 Hz, 1H, CH=), 7.17 (s, 1H, CH=), 9.20 (s, 1H, CONH; MS(m/z) 602 (M+1);

Example 106

Preparation of Compound #965

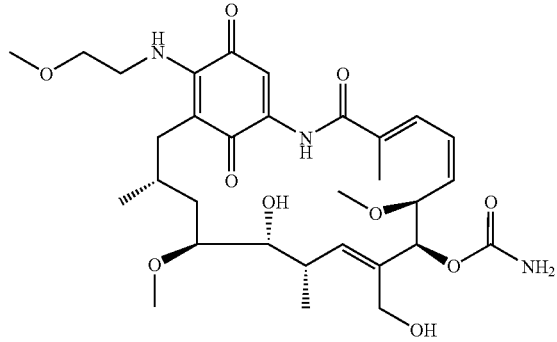

Compound #965 was prepared by the same method described for #967 except that 2-methoxyethylamine was used instead of allylamine. The final pure purple product was obtained after column chromatography (silica gel); yield: 90%; mp ° C.; $^1$H NMR (CDCl$_3$) δ 0.99 (d, J=8 Hz, 3H, CH$_3$), 1.04 (d, J=8 Hz, 3H, CH$_3$), 1.77 (m, 1H, CH), 1.80 (m, 2H, CH$_2$), 2.06 (s, 3H, CH$_3$), 2.26 (m, 1H, CH$_2$), 2.67 (d, 1H, CH$_2$), 2.90(m, 1H, CH), 3.34 (s, 3H, OCH$_3$), 3.36 (s, 3H, OCH$_3$), 3.44 (s, 3H, OCH$_3$), 3.52 (m, 2H, OH+CH), 3.63(m, 4H, 2CH$_2$), 3.80 (m, 1H, CH), 4.11 (dd, J=12.44 Hz, J=4.5 Hz, 1H, CH$_2$), 4.30 (dd, J=12 Hz, J=4.5 Hz, 1H, CH$_2$), 4.45 (d, J=10.0 Hz, 1H, CH), 4.52 (bs, 1H, OH), 4.78 (bs, 2H, NH2), 5.37 (s, 1H, CH), 5.89(t, J=10.5 Hz, 1H, CH=), 6.10 (d, J=10 Hz, 1H, CH=), 6.55 (m, 1H, NH), 6.66 (t, J=12 Hz, 1H, CH=), 7.30 (d, J=12 Hz, 1H, CH=), 7.30 (s, 1H, CH=), 9.17 (s, 1H, CONH); MS(m/z) 618 (M−1);

Example 107

Preparation of Compound #979

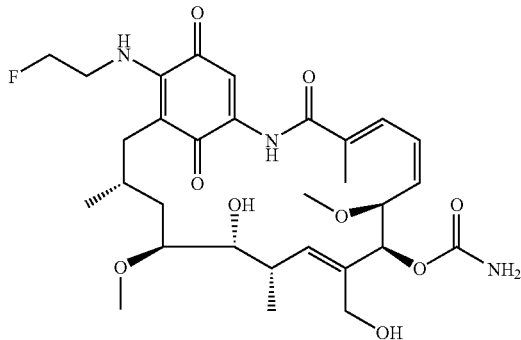

Compound #979 was prepared by the same method described for compound #967 except that 2-fluoroethylamine was used instead of allylamine. The final pure purple product was obtained after column chromatography (silica gel); yield: 90%; mp ° C.; $^1$H NMR (CDCl$_3$) δ 0.99 (d, J=6.8 Hz, 3H, CH$_3$), 1.04 (d, J=6.8 Hz, 3H, CH$_3$), 1.77 (m, 1H, CH), 1.80 (m, 2H, CH$_2$), 2.06 (s, 3H, CH$_3$), 2.26 (m, 1H, CH$_2$), 2.67 (d, 1H, CH$_2$), 2.90(m, 1H, CH), 3.34 (s, 3H, CH$_3$), 3.36 (s, 3H, CH$_3$), 3.48 (m, 2H, OH+CH), 3.60 (t, J=6.8 Hz, 1H, CH), 4.11 (dd, J=12.44 Hz, J=4.5 Hz, 1H, CH$_2$), 4.30 (dd, J=12 Hz, J=4.5 Hz, 1H, CH$_2$), 4.42 (bs, 1H, OH), 4.45 (d, J=10.0 Hz, 1H, CH), 4.61(t, 2H, CH$_2$), 4.75(t, 2H, CH$_2$), 5.37 (s, 1H, CH), 5.89(t, J=10.5 Hz, 1H, CH=), 6.10 (d, J=10 Hz, 1H, CH=), 6.55 (m, 1H, NH), 6.66 (t, J=12 Hz, 1H, CH=), 7.00 (d, J=12 Hz, 1H, CH=), 7.30 (s, 1H, CH=), 9.20 (s, 1H, CONH); MS(m/z) 607 (M−1);

8-hydroxylmethyl-17 Amide GM Analogs

Example 108

Preparation of Compound #951

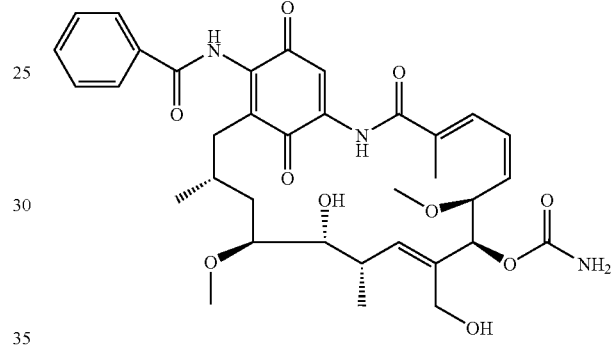

Compound #951 was prepared by the same method described for compound #563 except that compound #915 was used instead of 17-aminogeldanamycin. The final pure yellow product was obtained after column chromatography (silica gel); yield: 80%; $^1$H NMR (CDCl$_3$) δ0.92(d, J=7.0 Hz, 3H, CH$_3$), 0.97(d, J=7.0 Hz, 3H, CH$_3$), 1.78(m, 3H, CH+CH$_2$), 2.05(s, 3H, CH$_3$), 2.60(m, 2H, CH$_2$), 2.92(m, 2H, CH$_2$), 3.32(s, 3H, CH$_3$), 3.37(s, 3H, CH$_3$), 3.48(m, 2H, CH+OH), 4.14(dd, J=10.0 Hz, 1H, CH$_2$), 4.25(dd, J=10.0 Hz, 1H, CH$_2$), 4.42(d, J=9.5 Hz, 1H, CH$_2$), 4.85(bs, 2H, CONH$_2$), 5.30(s, 1H, CH), 5.92(t, J=10.2 Hz, 1H, CH=), 6.02(d, J=10.2 Hz, 1H, CH=), 6.67(t, J=11.5 Hz, 1H, CH=), 6.95(d, J=11.5 Hz, 1H, CH=), 7.45(s, 1H, CH—Ar), 7.52(t, J=7.8 Hz, 2CH—Ar), 7.62(t, J=7.8 Hz, 1H, CH—Ar), 7.93(d, J=7.8 Hz, 2H, 2CH—Ar), 8.48(s, 1H, NH), 8.87(s, 1H, NH); MS(m/z)688.7(M+Na);

8-hydroxylmethyl-17 Carbomate GM Analogs

Example 109

Preparation of Compound #996

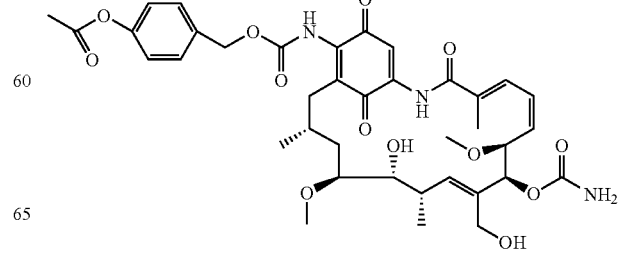

Compound #996 was prepared by the same method described for compound #709 except that compound #915 was used instead of 17-aminogeldanamycin. The final pure yellow product was obtained after column chromatography (silica gel); yield: 80%; mp 134.5~150 decomposed; $^1$H NMR (CDCl$_3$) δ0.92(d, J=7.0 Hz, 3H, CH$_3$), 0.97(d, J=7.0 Hz, 3H, CH$_3$), 1.78(m, 3H, CH+CH$_2$), 2.05(s, 3H, CH$_3$), 2.31 (s, 3H, CH$_3$), 2.60(dd, J=7.3 Hz, 1H, CH$_2$), 2.81(dd, J=7.3 Hz, 1H, CH$_2$), 2.93(m, 1H, CH), 3.32(s, 3H, CH$_3$), 3.33(m, 1H, CH), 3.36(s, 3H, CH$_3$), 3.44(m, 2H, CH+OH), 4.12(m, 2H, CH$_2$), 4.27(m, 1H, CH$_2$), 4.40(d, J=9.3 Hz, 1H, CH), 4.85(bs, 2H, CONH$_2$), 5.18(s, 2H, CH$_2$), 5.30(s, 1H, CH), 5.92(t, J=10.2 Hz, 1H, CH=), 5.96(d, J=10.2 Hz, 1H, CH=), 6.67(t, J=11.5 Hz, 1H, CH=), 6.95(d, J=11.5 Hz, 1H, CH=), 7.12(d, J=9.2 Hz, 2H, 2CH—Ar), 7.36(s, 1H, CH—Ar), 7.41 (s, 1H, NH), 7.45(d, J=9.2 Hz, 2H, 2CH—Ar), 8.71(s, 1H, NH); MS(m/z)776(M+Na);

11-Keto GM Dimer Analogs

The following general synthetic scheme is applicable to Examples 110-113:

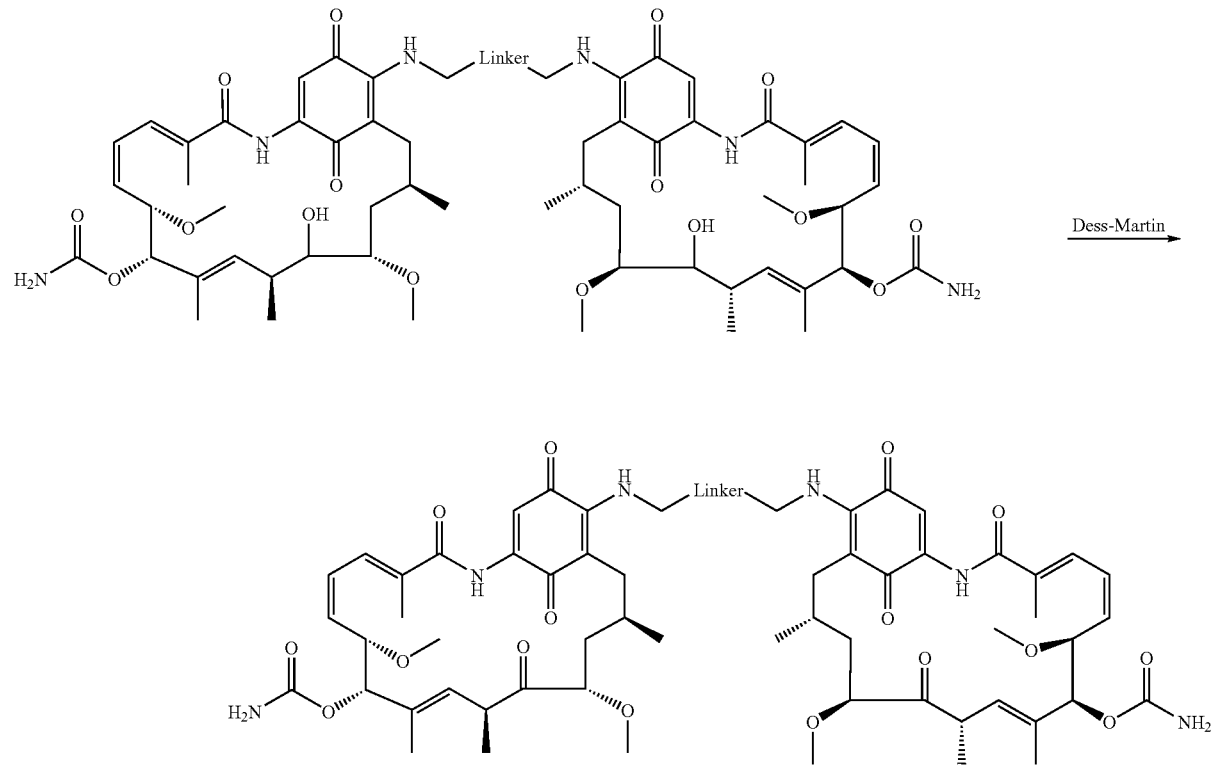

Example 110

Preparation of Compound #841

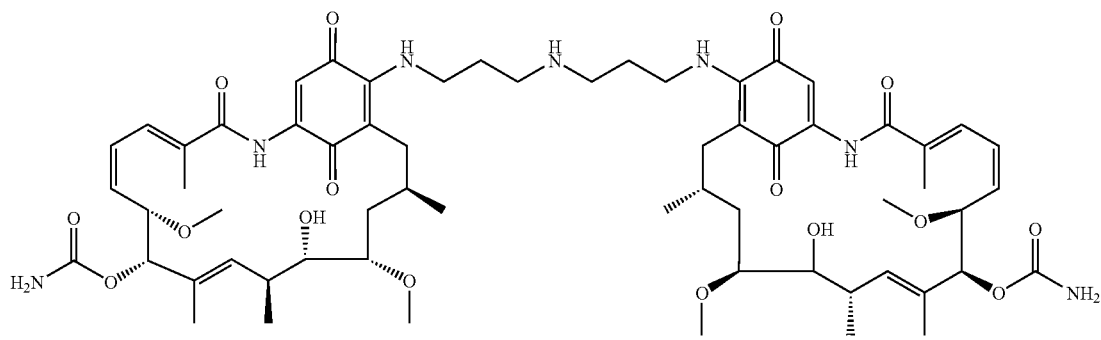

Compound #237 (100 mg, 0.084 mmol) was dissolved in CHCl$_3$ (5 ml) to which was added Dess-Martin reagent (107 mg, 0.253 mmol) at room temperature. After 24 h the reaction was complete and the mixture diluted with CHCl$_3$, washed with aqueous sodium thiosulfate and saturated aqueous sodium bicarbonate, and dried over sodium sulfate. The solvent was removed with a rotary evaporator. The pure purple product was obtained after column chromatography (silica gel); yield: 78%; mp 151.2-152.9° C.; $^1$H NMR (CDCl$_3$) δ 1.04(d, J=7.0 Hz, 6H, 2CH$_3$), 1.27(d, J=7.0 Hz, 6H, 2CH$_3$), 1.55(m, 4H, 2CH$_2$), 1.80 (m, 6H, 4CH$_2$+2CH), 1.84(s, 6H, 2CH$_3$), 2.0(s, 6H, 2CH$_3$), 2.40(dd, J=14 Hz, 2H, 2CH), 2.64 (dd J=14 Hz, 2H, 2CH), 2.83((m, 4H, 2CH$_2$), 3.33(s, 6H, 2CH$_3$), 3.34(s, 6H, 2CH$_3$), 3.67(m, 6H, 4CH$_2$+2CH), 4.15(m, 2H, 2CH), 4.33(d, J=8.2 Hz, 2H, 2CH), 4.80(bs, 4H, 2CONH2), 5.21(s, 2H, 2CH), 5.57(d, J=9.5 Hz, 2H, 2CH), 5.85(t, J=8.4 Hz, 2H, 2CH), 6.52(t, J=8.4 Hz, 2H, 2CH), 6.89(s, 2NH), 6.97(d, J=8.4 Hz, 2H, 2CH), 7.16(s, 2H, 2CH), 9.27(s, 2H, 2NH); MS (m/z)1207.5 (M+Na);

Example 111

Preparation of Compound #865

Compound #865 was prepared by the same method described for #841 except that compound #483 was used instead of compound #237. The pure purple product was obtained after column chromatography (silica gel); yield: 92%; mp 136.5~139° C.; $^1$H NMR (CDCl$_3$) δ1.06(d, J=7.0 Hz, 6H, 2CH$_3$), 1.27(d, J=7.0 Hz, 6H, 2CH$_3$), 1.70(m, 6H, 2CH$_2$+2CH), 1.84(s, 6H, 2CH$_3$), 2.05(s, 6H, 2CH$_3$), 2.33(s, 3H, N—CH$_3$), 2.40(m, 2H, 2CH$_2$), 2.62(s, 6H, 2CH$_3$), 2.67 (m, 2H, 2CH$_2$), 2.74(t, J=6.1 Hz, 4H, 2CH$_2$), 3.34(s, 6H, 2CH$_3$), 3.35(s, 6H, 2CH$_3$), 3.62(m, 4H, 2CH$_2$), 4.14(m, 2H, 2CH), 4.64(d, J=8.2 Hz, 2H, 2CH), 4.82(bs, 4H, 2CONH$_2$), 5.23(s, 2H, 2CH), 5.57(d, J=9.5 Hz, 2H, 2CH=), 5.85(t, J=9.5 Hz, 2H, 2CH=), 6.52(t, J=11.8 Hz, 2H, 2CH=), 6.62 (t, J=5.0 Hz, 2H, 2NH), 6.97(d, J=11.8 Hz, 2H, 2CH=), 7.19(s, 2H, 2CH), 9.26(s, 2H, 2NH).

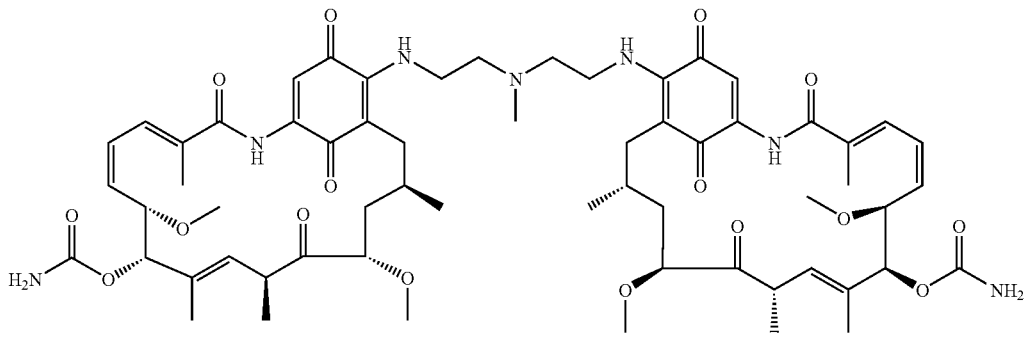

Example 112

Preparation of Compound #864

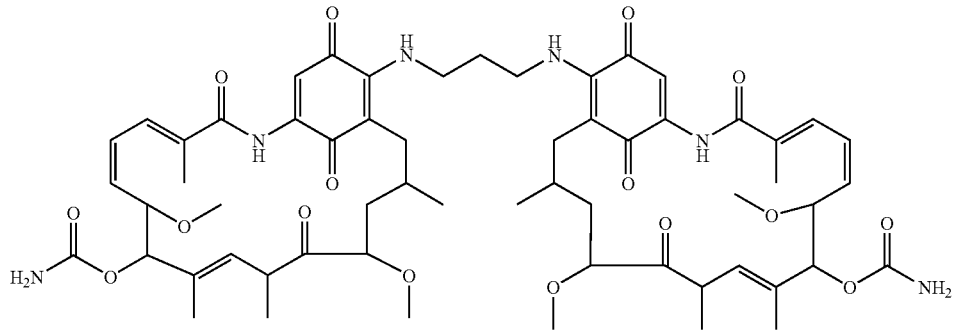

Compound #864 was prepared by the same method described for compound #841 except that compound #638 was used instead of compound #237. The pure purple product was obtained after column chromatography (silica gel); yield: 83%; mp 141.5-144.5° C.; $^1$H NMR (CDCl$_3$) δ 1.05(d, J=7.0 Hz, 6H, 2CH$_3$), 1.25(d, J=7.0 Hz, 6H, 2CH$_3$), 1.52(m, 2H, CH$_2$), 2.35(dd, J=14 Hz, 2H, 2CH$_2$), 2.63(dd, J=14 Hz, 2H, 2CH$_2$), 3.34(s, 12H, 6CH$_3$+6CH$_3$), 3.68(m, 6H, 4CH$_2$+ 2CH), 4.12(m, 2H, 2CH), 4.32(d, J=8.2 Hz, 2H, 2CH), 4.82

(bs, 4H, 2CONH$_2$), 5.20(s, 2H, 2CH=), 5.55(d, J=9.5 Hz, 2H, 2CH), 5.85(t, J=9.5 Hz, 2H, 2CH=), 6.12(t, J=5.8 Hz, 2H, 2NH), 6.52(t, J=11.5 Hz, 2H, 2CH=), 6.94(d, J=11.5 Hz, 2H, 2CH=), 7.19(s, 2H, 2CH—Ar), 9.21(s, 2H, 2NH);

Example 113

Preparation of Compound #867

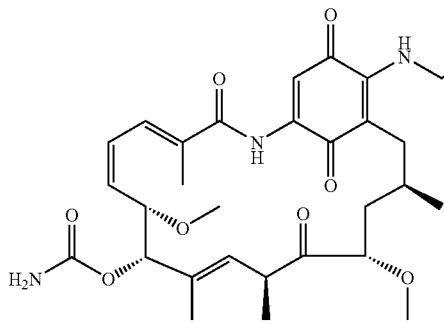

Compound #867 was prepared by the same method described for compound #841 except that compound #484 was used instead of compound #237. The pure purple product was obtained after column chromatography (silica gel); yield: 90%; mp 136.5~138° C.; $^1$H NMR (CDCl$_3$) δ 1.06(d, J=7.0 Hz, 6H, 2CH$_3$), 1.27(d, J=7.0 Hz, 6H, 2CH$_3$), 1.75(m, 6H, 2CH$_2$+2CH), 1.84(s, 6H, 2CH$_3$), 2.01(s, 6H, 2CH$_3$), 2.35(dd, J=14 Hz, 2H, 2CH$_2$), 2.63(dd, J=14 Hz, 2H, 2CH$_2$), 3.34(s, 12H, 6CH$_3$+6CH$_3$), 3.68(m, 6H, 4CH$_2$+2CH), 4.12(m, 2H, 2CH), 4.32(d, J=8.2 Hz, 2H, 2CH), 4.82(bs, 4H, 2CONH$_2$), 5.20(s, 2H, 2CH=), 5.55(d, J=9.5 Hz, 2H, 2CH), 5.85(t, J=9.5 Hz, 2H, 2CH=), 6.41(t, J=5.8 Hz, 2H, 2NH), 6.50(t, J=11.5 Hz, 2H, 2CH=), 6.94(d, J=11.5 Hz, 2H, 2CH=), 7.17(s, 2H, 2CH—Ar), 9.21(s, 2H, 2NH);

11-keto-17-amide GM Analogs

Example 114

Preparation of Compound #868

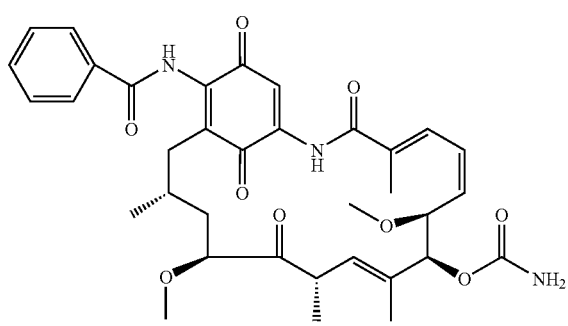

Compound #868 was prepared by the same method described for compound #841 except that compound #563 was used instead of compound #237. The final pure yellow product was obtained after column chromatography (silica gel); yield: 75%; mp 128~131.50C; $^1$H NMR (CDCl$_3$) δ1.02 (d, J=7.0 Hz, 3H, CH3), 1.16 (d, J=7.0 Hz, 3H, CH3), 1.45(m, 1H, CH), 1.68(m, 1H, CH), 1.79(s, 3H, CH3), 2.05(s, 3H, CH3), 2.39(dd, J=9.2 Hz, 1H, CH2), 2.64(dd, J=9.2 Hz, 1H, CH2), 3.40(s, 3H, CH3), 3.42(s, 3H, CH3), 3.85(m, 1H, CH), 3.93(t, J=4.3 Hz, 1H, CH), 4.38(d, J=8.2 Hz, 1H, CH), 4.77(s, 2H, NH2), 5.09(s, 1H, CH), 5.80(d, J=9.4 Hz, 1H, CH), 5.96(t, J=9.4 Hz, 1H, CH), 6.58(t, J=10.8 Hz, 1H, CH), 7.02 (d, J=10.8 Hz, 1H, CH), 7.55(m, 3H, 3CH), 7.62(t, J=7.2 Hz, 1H, CH), 7.93(d, J=7.2 Hz, 2H, 2CH), 8.55(s, 1H, NH), 8.98(s, 1H, NH); MS(m/z)670.7(M+Na);

Example 115

Preparation of Compound #840

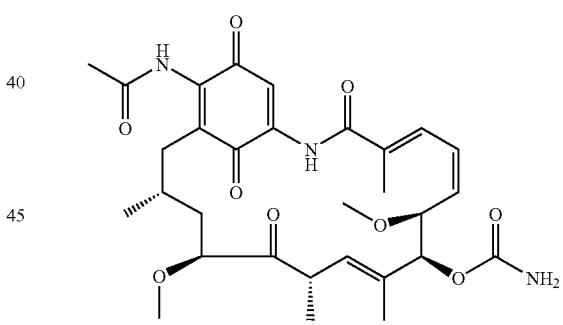

Compound #840 was prepared by the same method described for compound #841 except that compound #513 was used instead of compound #237. The final pure yellow product was obtained after column chromatography (silica gel); yield: 82%; $^1$H NMR (CDCl$_3$) δ0.96 (d, J=7.0 Hz, 3H, CH$_3$), 1.65(m, 3H, CH$_2$+CH), 1.79(s, 3H, CH$_3$), 2.05(s, 3H, CH3), 2.24(s, 3H, CH3), 2.39(dd, J=9.2 Hz, 1H, CH2), 2.54 (dd, J=9.2 Hz, 1H, CH2), 3.40(s, 3H, CH3), 3.42(s, 3H, CH3), 3.88(m, 2H, CH+CH), 4.38(d, J=8.2 Hz, 1H, CH), 4.77(bs, 2H, CONH2), 5.09(s, 1H, CH), 5.80(d, J=9.4 Hz, 1H, CH), 5.96(t, J=9.4 Hz, 1H, CH), 6.58(t, J=10.8 Hz, 1H, CH), 6.95 (d, J=10.8 Hz, 1H, CH), 7.49(s, 1H, CH), 7.75(s, 1H, NH), 8.82(s, 1H, N; MS 608.5(M+Na);

11-keto-17-carbomate GM Analogs

Example 116: Preparation of Compound #861

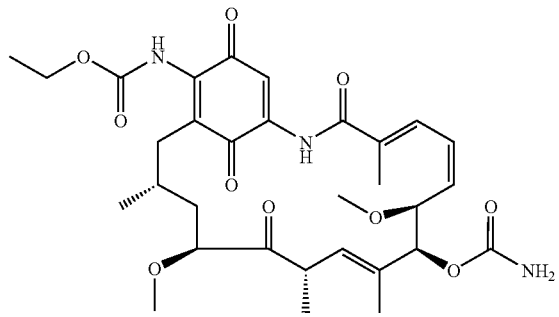

Compound #861 was prepared by the same method described for compound #841 except that compound #656 was used instead of compound #237. The final pure yellow product was obtained after column chromatography (silica gel); yield: 75%; $^1$H NMR (CDCl$_3$) δ1.03 (d, J=7.0 Hz, 3H, CH$_3$), 1.16 (d, J=7.0 Hz, 3H, CH$_3$), 1.34 (t, J=8 Hz, 3H, CH$_3$), 1.45(m, 1H, CH), 1.68(m, 1H, CH), 1.72(m, 1H, CH), 1.81(s, 3H, CH$_3$), 2.08(s, 3H, CH$_3$), 2.39(dd, J=9.2 Hz, 1H, CH$_2$), 2.64(dd, =9.21H, CH$_2$), 3.40(s, 3H, CH$_3$), 3.42(s, 3H, CH$_3$), 3.85(m, 1H, CH), 3.93(t, J=4.3 Hz, 1H, CH), 4.23 (m, 2H, CH$_2$), 4.38(d, J=8.2 Hz, 1H, CH), 4.77(s, 2H, NH2), 5.09(s, 1H, CH), 5.80(d, J=9.4 Hz, 1H, CH), 5.96(t, J=9.4 Hz, 1H, CH), 6.58(t, J=10.8 Hz, 1H, CH), 7.02(d, J=10.8 Hz, 1H, CH), 7.29 (s, 1H, CH=), 7.50(s, 1H, NH), 8.85(s, 1H, CONH); MS(m/z) 638 (M+Na).

J. Hemiacetal GM Analogs

Example 117: Preparation of Compound #1026

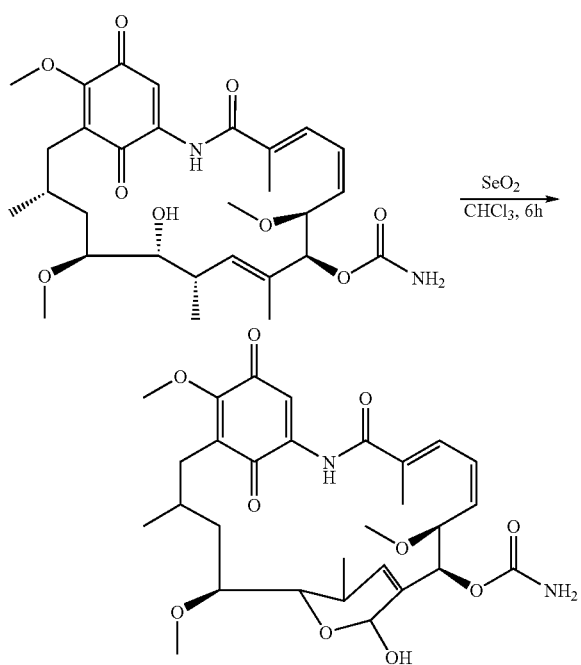

To Geldanamycin (500 mg, 0.89 mmol) in 10 mL of dioxane was added selenium(IV) dioxide (198 mg, 1.78 mmol) at room temperature. The reaction mixture was heated to 100° C. and stirred for 6 hours. After cooled down to room temperature, the solution was diluted with ethyl acetate, washed with water and brine, dried over magnesium sulfate, filtered and evaporated in vacuo. The final pure yellow product was obtained after column chromatography (silica gel); yield: 65%; $^1$H NMR (CDCl$_3$) δ 0.97(d, J=7.0 Hz, 3H, CH$_3$), 1.01(d, J=7.0 Hz, 3H, CH$_3$), 1.75 (m, 3H, CH$_2$+CH), 2.04(s, 3H, CH$_3$), 2.41(m, 3H, CH+CH$_2$), 3.28(s, 3H, CH$_3$), 3.38(s, 3H, CH$_3$), 3.43(m, 1H, CH), 3.87(m, 1H, CH), 3.94(s, 1H, OH), 4.15(s, 3H, CH$_3$), 4.54(d, J=9.8 Hz, 1H, CH), 4.76(bs, 2H, CONH$_2$), 4.79(s, 1H, CH), 5.48(s, 1H, CH), 5.92(t, J=10.4 Hz, 1H, CH=), 6.25(d, J=9.7 Hz, 1H, CH=), 6.55(t, J=11.5 Hz, 1H, CH=), 7.21(d, J=1.5 Hz, 1H, CH=), 7.32(s, 1H, CH—Ar), 8.69(s, 1H, NH); MS (m/z)597.6 (M+Na);

Example 118

Preparation of Compound #1048

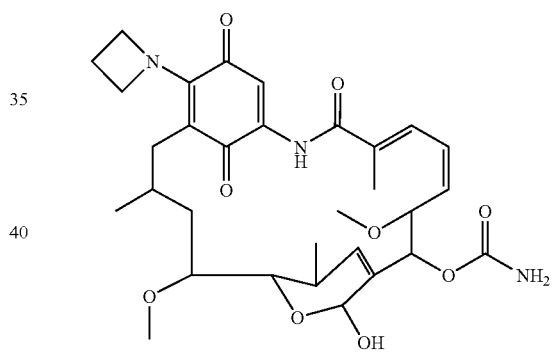

Compound #1048 was prepared by the same method described for compound #914 except that azetidine was used instead of allylamine and compound #1026 was used instead of compound #914. The final pure purple product was obtained after column chromatography (silica gel); yield: 89%; $^1$H NMR (CDCl$_3$) δ 0.99 (d, J=6.8 Hz, 3H, CH$_3$), 1.04 (d, J=6.8 Hz, 3H, CH$_3$), 1.80 (m, 3H, CH+2CH$_2$), 2.06 (s, 3H, CH$_3$), 2.26 (m, 1H, CH$_2$), 2.32(m, 1H, CH), 2.50(m, 2H, 2CH$_2$), 2.73(d, t=6.8 Hz, 1H, CH$_2$), 3.28 (s, 3H, CH$_3$), 3.36 (s, 3H, CH$_3$), 3.48 (m, 1H, CH), 4.02 (dd, J=12 Hz, J=4.5 Hz, 1H, CH=), 4.62(m, 3H, 2CH$_2$+CH), 4.78 (m, 2H, 2CH$_2$), 4.89(s, 1H, CH), 5.16(s, 1H, OH), 5.47 (s, 1H, CH), 5.89(t, J=10.5 Hz, 1H, CH=), 6.10 (d, J=10 Hz, 1H, CH=), 6.66 (t, J=12 Hz, 1H, CH=), 7.07 (d, J=12 Hz, 1H, CH=), 7.27 (s, 1H, CH—Ar), 8.77 (s, 1H, CONH);

Example 119

Preparation of Compound #1058

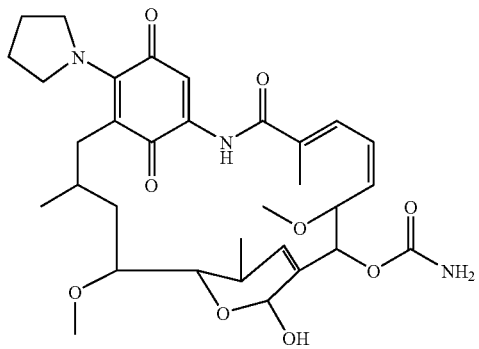

Compound #1058 was prepared by the same method described for compound #914 except that pyrrolidine was used instead of allylamine and compound #1026 was used instead of compound #914. The final pure purple product was obtained after column chromatography (silica gel); yield: 69%; $^1$H NMR (CDCl$_3$) δ 0.89 (d, J=6.8 Hz, 3H, CH$_3$), 0.93 (d, J=6.8 Hz, 3H, CH$_3$), 1.80 (m, 3H, CH+CH$_2$), 2.06 (s, 3H, CH$_3$), 2.26 (m, 3H, CH$_2$+CH), 2.32(m, 3H, CH+CH$_2$), 2.93 (d, t 6.8 Hz, 1H, CH$_2$), 3.27 (s, 3H, CH$_3$), 3.36 (s, 3H, CH$_3$), 3.48 (m, 1H, CH), 3.61(m, 2H, CH$_2$), 3.98 (m, 3H, CH+CH$_2$), 4.62(d, J=9.8 Hz, 1H, CH), 4.82 (bs, 2H, NH2), 4.89(s, 1H, CH), 5.04(s, 1H, OH), 5.47 (s, 1H, CH), 5.89(t, J=10.5 Hz, 1H, CH=), 6.15 (d, J=10 Hz, 1H, CH=), 6.53 (t, J=12 Hz, 1H, CH=), 7.09 (d, J=12 Hz, 1H, CH=), 7.30 (s, 1H, CH—Ar), 8.69 (s, 1H, CONH); MS (m/z)614.7 (M$^+$H);

Example 120

Preparation of Compound #1143

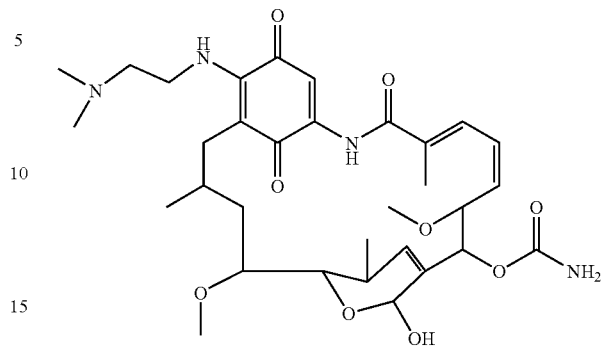

Compound #1143 was prepared by the same method described for compound #914 except that dimethylamino ethylamine was used instead of allylamine and compound #1026 was used instead of compound #914. The final pure purple product was obtained after column chromatography (silica gel); yield: 90%; $^1$H NMR (CDCl$_3$) δ 0.93 (d, J=6.8 Hz, 3H, CH$_3$), 0.99 (d, J=6.8 Hz, 3H, CH$_3$), 1.80 (m, 3H, CH+CH$_2$), 2.06 (s, 3H, CH$_3$), 2.26 (m, 2H, CH+CH$_2$), 2.28(s, 6H, 2CH$_3$), 2.56(t, J=5.6 Hz, 2H, CH$_2$), 2.93(d, t=6.8 Hz, 1H, CH$_2$), 3.27 (s, 3H, CH$_3$), 3.36 (s, 3H, CH$_3$), 3.48 (m, 3H, CH+CH$_2$), 3.98 (dd, J=9.9 Hz, 1H, CH), 4.62(d, J=9.8 Hz, 1H, CH), 4.82 (bs, 2H, NH2), 4.89(s, 1H, CH), 4.91(s, 1H, OH), 5.47 (s, 1H, CH), 5.89(t, J=10.5 Hz, 1H, CH=), 6.15 (d, J=10 Hz, 1H, CH=), 6.53 (t, J=12 Hz, 1H, CH=), 7.07(s, 1H, NH), 7.19 (d, J=12 Hz, 1H, CH=), 7.30 (s, 1H, CH—Ar), 8.76 (s, 1H, CONH); MS (m/z)631.94(M$^+$H);

New GM Dimer Analogs

Example 121

Preparation of Compound 635

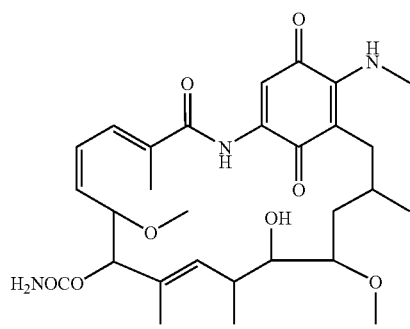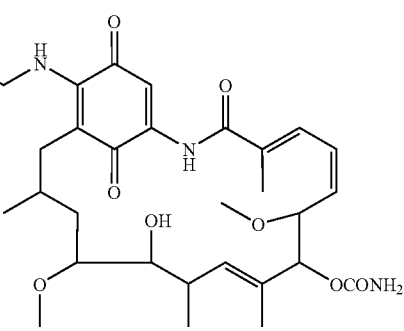

Compound #635 was prepared by the same method described for compound #594 except that diglycolyl chloride was used instead of terephthaloyl chloride. The pure purple product was obtained after column chromatography (silica gel); yield: 75%; $^1$H NMR (CDCl$_3$) δ 0.95 (d, J=7 Hz, 6H, 2CH$_3$), 1.0 (d, J=7 Hz, 6H, 2CH$_3$), 1.69 (m, 4H, 2 CH$_2$), 1.76 (s, 6H, 2 CH$_3$), 1.83 (m, 2H, 2CH), 2.0 (s, 6H, 2CH$_3$), 2.36 (dd, J=14 Hz, 2H, 2CH), 2.63 (d, 2H, 2CH), 2.75(m, 2H, 2CH), 3.25(s, 6H, 2OCH$_3$), 3.35(s, 6H, 2OCH$_3$), 3.4 (m, 2H, 2CH), 3.68(m, 2H, 2CH), 3.9 (m, 4H, 2CH$_2$), 4.3 (s, 4H, 2CH$_2$), 4.4(d, J=10 Hz, 2H, 2CH), 4.5(t, 4H, 2CH$_2$), 4.8(Bs, 4H, 2NH$_2$), 5.19(s, 2H, 2CH), 5.82(t, J=15 Hz, 2H, 2CH=), 5.89(d, J=10 Hz, 2H, 2CH=), 6.4 (t, 2H, 2NH), 6.59(t, J=15 Hz, 2H, 2CH=), 6.92 (d, J=10 Hz, 2H, 2CH=), 7.24(s, 2H, 2CH=), 9.21(s, 2H, 2NH); MS (m/z)1276 (M—H).

Example 122

Preparation of Compound #713

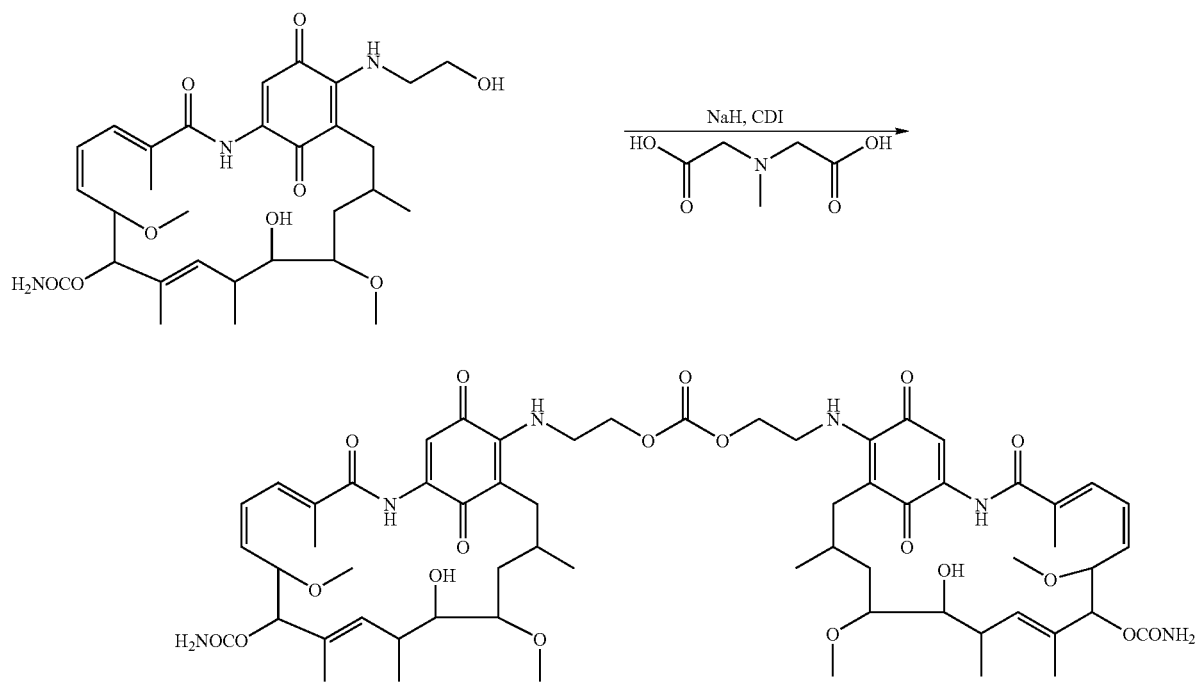

Sodium hydride (15.1 mg, 0.377 mmol) was added to a solution of compound A (reported in Kagen patent) (200 mg, 0.343 mmol) in THF (8 ml) in a flame dried flask under N$_2$ and stirred at room temperature (solution A). 1,1'-carbonyldiimidazole (61.1 mg, 0.377 mmol) was added to a solution of N-methyliminodiacetic acid (25.2 mg, 0.171 mmol) in THF (4 ml) and stirred for 20 mins (solution B). Then solution B was added to solution A at room temperature. The reaction mixture was diluted with water after 2 hours, and extracted with EtOAC, washed with water, brine and dried over MgSO$_4$. The crude was chromatographed (5% CH$_3$OH/ CH$_2$Cl$_2$) to afford the desired dimer as a purple solid (100 mg, 0.084 mmol). Yield: 50%; $^1$H NMR (CDCl$_3$) δ 0.95 (d, J=7 Hz, 6H, 2CH$_3$), 1.0 (d, J=7 Hz, 6H, 2CH$_3$), 1.69 (m, 4H, 2 CH$_2$), 1.76 (s, 6H, 2 CH$_3$), 1.83 (m, 2H, 2CH), 2.0 (s, 6H, 2CH$_3$), 2.36(dd, J=14 Hz, 2H, 2CH), 2.63 (d, 2H, 2CH), 2.75(m, 2H, 2CH), 3.25(s, 6H, 2OCH$_3$), 3.35(s, 6H, 2OCH$_3$), 3.4 (m, 2H, 2CH), 3.68(m, 2H, 2CH), 3.9 (m, 4H, 2CH$_2$), 4.4(d, J=10 Hz, 2H, 2CH), 4.5(t, 4H, 2CH$_2$), 4.8(Bs, 4H, 2NH$_2$), 5.19(s, 2H, 2CH), 5.82(t, J=15 Hz, 2H, 2CH=), 5.89(d, J=10 Hz, 2H, 2CH=), 6.4 (t, 2H, 2NH), 6.59(t, J=15 Hz, 2H, 2CH=), 6.92 (d, J=10 Hz, 2H, 2CH=), 7.24(s, 2H, 2CH=), 9.21(s, 2H, 2NH); MS (m/z)1204 (M–H);

Example 123

HSP90s Taken from Tumor Cell Lines More Avidly Bind Known HSP90 Modulators

Recently, Nicchitta et al., WO 01/72779 (PCT/US01/ 09512), demonstrated that HSP90 can assume a different conformation upon heat shock and/or binding by the fluorophore bis-ANS. Specifically, Nicchitta et al. demonstrated that this induced conformation exhibits a higher affinity for certain HSP90 ligands than for a different form of HSP90 that predominates in normal cells. Applicants build on Nicchitta's work by demonstrating that higher affinity HSP90 conformations predominate in tumors: Purified native HSP90 protein (Stressgen) or cell lysates prepared in lysis buffer (20 mM Hepes, pH 7.3, 1 mM EDTA, 5 mM MgCl$_2$, 100 mM KCl) were incubated in the absence or presence of 17-AAG or test compound for 15 min at 4° C. Biotin-geldanamycin (biotin-GM) was then added to the mixture as discussed previously, and the reaction was further incubated by rotating for 1 hr at 4° C. BioMag™ streptavidin magnetic beads were then added to the mixture, and the reaction was incubated by rotating for another 1 hr at 4° C. Tubes were placed on a magnetic rack, and the unbound supernatant removed. The magnetic beads were washed three times in the lysis buffer, and the washes discarded. SDS-PAGE sample buffer was added to the beads and boiled for 5 min at 95° C. Samples were analyzed on 10% SDS protein gels (Novex), and then Western blots using anti-HSP90 monoclonal antibody (Stressgen SPA-830). The bands in the Western Blots were quantitated using the Bio-rad Fluor-S Imager, and the % inhibition of binding of 17-AAG or test compound calculated. The IC50 reported is the concentration of the compound needed to cause half-maximal inhibition of binding. For experiments that utilized heat-shocked Hsp90, the purified HSP90 native protein was incubated for 15min at 50° C. For experiments that utilized bis-ANS treated HSP90, the purified HSP90 protein was incubated with bis-ANS (Molecular Probes) for 30 min at 37° C. The results are shown in Table 2.

TABLE 2

| Cmpd | Lysate (high affinity) IC50 nM | rHsp90 (low affinity) IC50 nM | ratio |
|---|---|---|---|
| 17AAG | 20 | 700 | 35 |
| 237 | 30 | 2000 | 67 |
| 529 | 15 | 1000 | 67 |
| 563 | 50 | 4500 | 90 |
| 661 | 10 | 1000 | 100 |
| 687 | 8 | 2000 | 250 |
| 709 | 9 | 1500 | 167 |
| 754 | 4 | 2000 | 500 |

Using various compounds of the invention as described in Table 3, Applicants repeated the studies described by Nicchitta et al., WO 01/72779 (PCT/US01/09512), to demonstrate that HSP90 bound by the fluorophore bis-ANS is selective for ansamycins selectivity for the related chaperonin, GRP94, is enhanced by 11-position of various ansamycins.

TABLE 3

| | BIS-ANS IC$_{50}$ µM | |
|---|---|---|
| Compound # | HSP90 | GRP94 |
| 17-AAG | 0.8 | 20.0 |
| 981 | 5.5 | 3.0 |
| 982 | 5.5 | 3.0 |
| 983 | 7.0 | 1.8 |
| 984 | 4.2 | 2.5 |
| 985 | 12.0 | 0.8 |
| 1011 | 5.0 | 0.3 |
| 1012 | 6.0 | 3.0 |
| 1013 | 5.2 | 2.0 |

Example 124

Her-2 Degradation in MCF7 Cancer Cells and Water Solubility

Various of the compounds described above were evaluated for their ability to degrade Her-2 and further evaluated for water solubility.

HER$_2$ Inhibition Assay

MCF7 cells are seeded in 24 well plates at a density of approximately 30,000 cells/well and allowed to grow for 16 hours in DMEM supplemented with 10% FBS. Drug is then added at a concentration range of 100 uM to 0.01 uM. Cells are incubated for an additional 24. Drug treated cells and untreated control cells are trypsinized, and incubated at room temperature for 15 minutes with anti Her-2 neu Ab conjugated with phycoerythrin (Becton Dickinson, San Jose Calif.; Cat no. 340552) at a concentration of 0.25 ug/ml, or non-specific control IgG1 conjugated with phycoerythrin (Becton Dickinson, San Jose Calif.; Cat no. 340761). Samples were analyzed using a FACS Calibur flow cytometer (Becton Dickinson) equipped with Argon-ion laser that which emits 15 mW of 488 nm light for excitation of the phycoerythrin fluorochrome. 10,000 events were collected per sample. A fluorescence histogram was generated and the mean fluorescence intensity (mfi) of each sample was determined using Cellquest software. The background was defined as the mfi generated from cells incubated with control IgG, and was subtracted from each sample stained with the HER-2/neu Ab. Percent degradation of Her-2 was calculated as follows:

% Her-2 degradation=(mfi HER-2 sample)/(mfi HER-2 untreated cells)×100

Water Solubility Studies

Various salts were prepared as described in the example section and dissolved in water at room temperature. Data for the HCl salts along with HER$_2$ degradation in MCF7 cells is shown in Table 4.

TABLE 4

| Compound | HER-2 degradation (IC$_{50}$ nM) | Solubility of the HCl salt in H$_2$O (mg/ml) |
|---|---|---|
| 17AAG | 5 | <0.01 |
| #207 | 12 | ≧13.0 |
| #208 | 11 | ≧20.0 |
| #237 | 20 | ≧13.0 |
| #238 | 20 | <0.01 |
| #133 | 25 | <0.01 |
| #212 | 10 | <0.01 |
| #232 | 80 | <0.01 |
| #530 | 100 | >2.0 |

Example 125

In Vitro Metabolism Evaluation

Compound #709 created per Example 72 was incubated with commercially available S9 fractions prepared from human livers (In-Vitro Technologies, Baltimore Md. 21227) to evaluate its metabolism in a human-derived system capable of both Phase I and Phase II metabolic reactions. The compound was incubated (in duplicate at a final concentration of 1.0 µM with human S9 containing an NADPH regenerating system and cofactors for phase II conjugation (sulfation and glucoronidation) at 37° C. with shaking for 1 hour. Duplicate control incubations were carried out using S9 inactivated by boiling for 5 minutes in a water bath. The enzymatic viability of the preparation was verified using coumarin (phase I activity) and 7-OH coumarin (phase II activity). The reactions were terminated by the addition of acetonitrile followed by isolation (by centrifugation) and evaporation of the aqeous/organic phase. The concentrations of Example 10 and 17-aminogeldanamycin (17-AG) were determined by reverse phase high performance liquid chromatography using UV detection (335 nm). The identity of 17-AG was confirmed by HPLC retention time and by its UV spectrum relative to an authentic standard.

Example 126

Antiviral Demonstration

O'Keeffe et al., Requirement for a Kinase-specific chaperone Pathway in the Production of a Cdk9/Cyclin T1 Heterodimer Responsible for P-TEFb-mediated Tat Stiumation of HIV-1 Transcription, Journal of Biological Chemistry, 2000, 275: 279-287 demonstrated that a subunit of P-TEFb called Cdk9 exists in a complex with HSP90, and that geldanamycin blocks the formation of an active P-TEFb which is needed for Tat-activation. Tat-activation of HIV-1 transcription is mediated by the trancription elongation factor, P-TEFb, which is known to phosphorylate and activate the Tat protein. Based on this, the inventors hypothesized that HSP90 inhibitors potentially can be used to thwart retroviral replication, particularly replication of those retroviruses that are dependent on Tat for replication, e.g., HIV. In this way, HSP90 inhibitors could be used as a treatment or prophylactic for individuals that are infected or stand to be infected. The results discussed herein validates this potential. All viruses that require Tat for their replication stand to be affected. Tat may vary in amino acid sequence between different serotypes and viruses.

Methods

Anti-HIV Efficacy of Conforma Compounds in Fresh Human PBMCs:

Five ansamycin compounds (17-AAG, Compound#208, Compound#483, Compound#749, Compound#1011) were tested at dilutions of 0.0009 μM, 0.003 μM, 0.01 μM, 0.032 μM, 0.1 μM, 0.32 μM, 1 μM, 3.16 μM, and 10 μM for anti-HIV activity against HIV-1$_{ROJO}$ in peripheral blood mononuclear cells (PBMC's). AZT was used as a positive control antiviral compound.

Anti-HIV PBMC assay: PBMCs were isolated from fresh human blood and the PBMC assay performed as described in Ojwang et al., 1995, Antimicrobial Agents and Chemotherapy, 39: 2426-2435. Briefly, the PBMC's were plated in 96 well plates at $5 \times 10^4$ cells/well. Test compounds were added to cells, and the cells pre-incubated for 2 hours. The HIV-1$_{ROJO}$ virus was then added to each well (final MOI≈0.1). Cells that did not get compounds were used as the virus control. Post-infection, the cultures were maintained for 7 days, and then the supernatant collected and assayed for reverse transcriptase activity as described in Buckheit et al., 1991, AIDS Research and Human Retroviruses, 7: 295-302.

MTS Assay to Measure Cytotoxicity of PBMC:

PBMC's in 96 well plates that were treated with compounds (without virus) were assayed for cell viability and compound toxicity using an MTS assay (CellTiter 96 Aqueous Non-Radioactivity Cell Proliferation Assay, Promega, Madison; Wis.).

Data Analysis

The results to the above assays are shown in FIG. 1. For each compound used, the raw data for antiviral activity and toxicity were graphed, and the IC$_{50}$ (50%, inhibition of virus replication), TC$_{50}$ (50% cytotoxicity) and a therapeutic index (T$_I$, TC$_{50}$/IC$_{50}$) are provided in Table 4. AZT was evaluated in parallel as a relevant positive control compound in the anti-HIV assay.

TABLE 5

Antiviral Efficacy of ansamycins against HIV-1$_{ROJO}$ in PBMCs

| Compound | IC$_{50}$ (μM) | TC$_{50}$ (μM) | TI |
|---|---|---|---|
| 17-AAG | 0.38 | 2.02 | 5.32 |
| Compound#208 | 0.007 | 0.27 | 38.6 |
| Compound#483 | 0.08 | 0.63 | 7.88 |
| Compound#749 | 0.02 | 1.12 | 56.0 |
| Compound#1011 | 0.2 | 2.9 | 14.5 |
| AZT Control | 0.0051 | >1.0 | >197.6 |

Example 127

Anti-Tumor Demonstration

FIGS. 3-6 show the tumor-inhibiting ability of various compounds of the invention.

Figure 3:
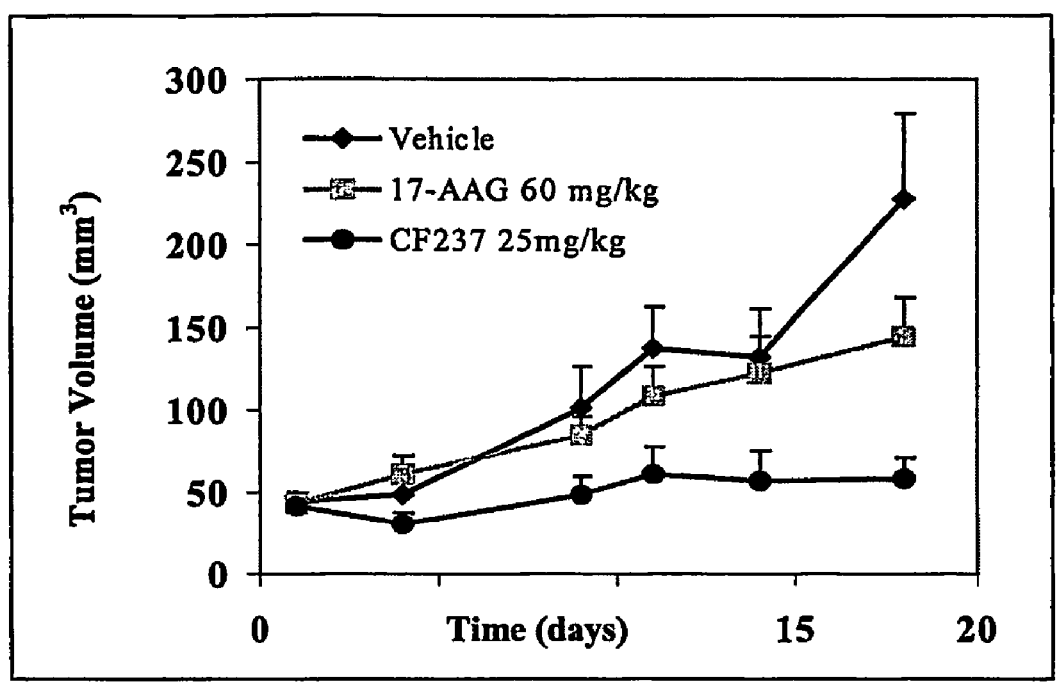
FIG. 3 shows that Compound #237 blocks the growth of A549 xenografts in vivo.

FIG. 3 shows that Compound#237 blocks the growth of A549 xenografts in vivo. Groups of five animals, each bearing two established subcutaneous A549 tumors, were given IP injections of 17-AAG or Compound#237 on three consecutive days each week for four weeks. Similar efficacy has been seen with five second-generation ansamycins, some of which are being developed as back-ups to Compound#237.

Figure 4:
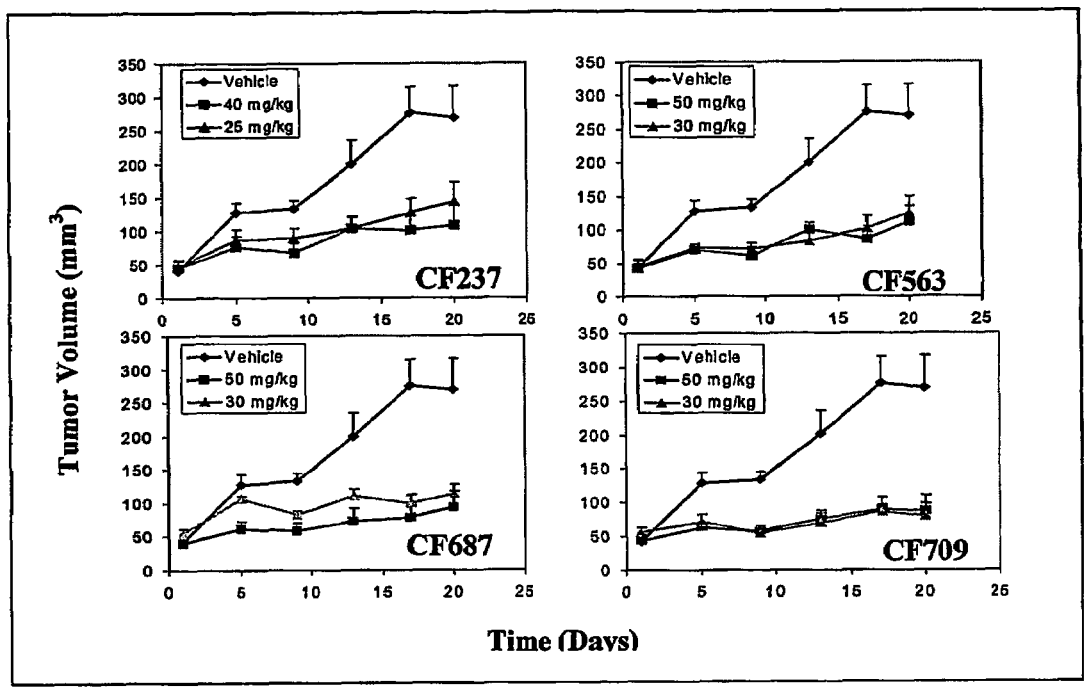
FIG. 4 shows the results of MDA435 tumor-bearing animals that received four courses of therapy with vehicle or compounds of the invention.
Figure 5:
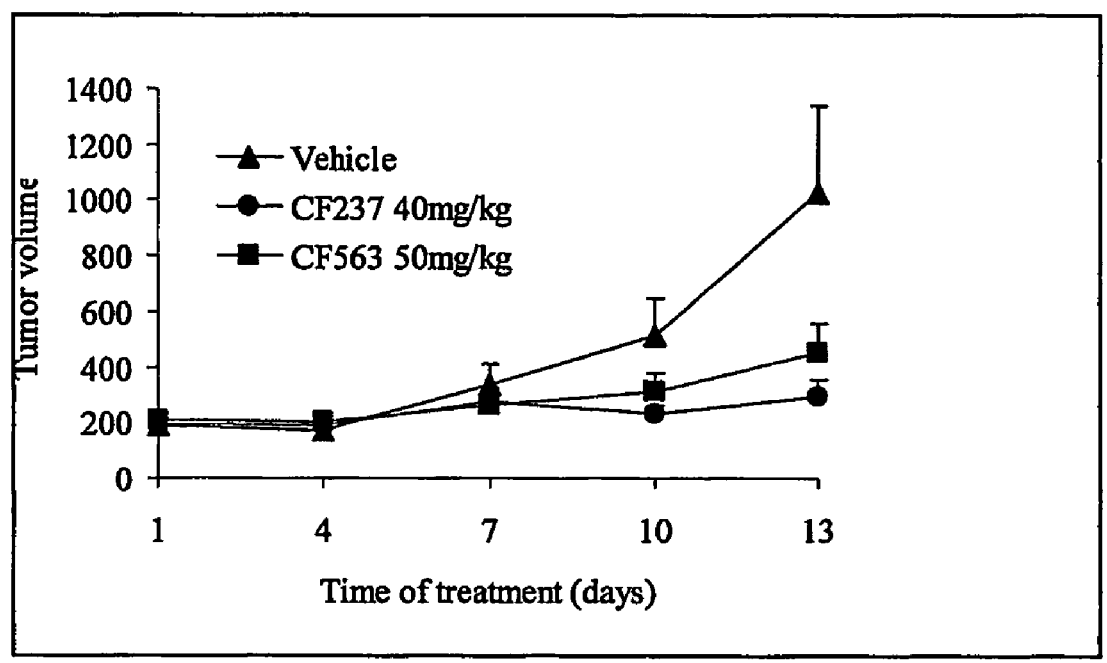
FIG. 5 shows the efficacy of Compound#237 and Compound#563 in a SKOV-3 ovarian xenograft model.

FIG. 4 shows the results of MDA435 tumor-bearing animals that received four courses of therapy with vehicle or compounds of the invention. The MDA435 breast tumor model is sensitive to ansamycins in vitro and grows rapidly in nude mice. FIG. 5 shows the data from four experiments in the MDA435 model. Animals were injected subcutaneously at two sites with 5×106 MDA435 breast tumor cells and the tumors were allowed to grow for 10 days. When the tumors were ~50 mm3 in size, the animals were randomized into groups of five (10 tumors/group). Therapy commenced under the schedule described for the A549 model. Animals were treated with vehicle (triangles) or one of two doses (25 or 30 mg/kg, squares; 40 or 50 mg/kg, circles) of drugs. In MDA435, 17-AAG failed to demonstrate any significant anti-tumor activity while Compound#237 and the other lead second-generation compounds caused a 70 to 100% inhibition of tumor growth.

Figure 6:
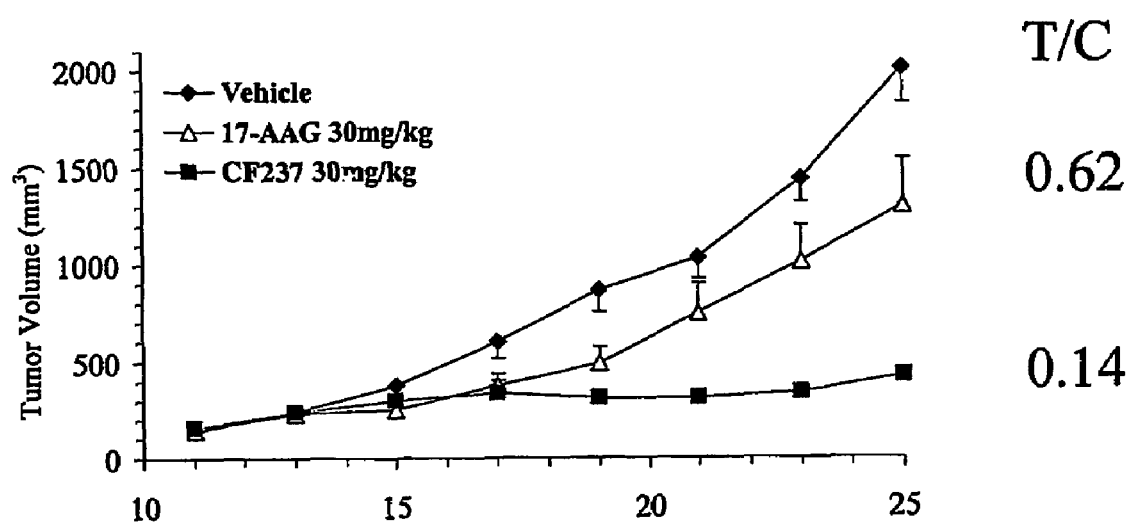
FIG. 6 shows the efficacy of Compound#237 and 17-AAG in a transplantable human breast cancer xenograft model.

FIG. 5 shows the efficacy of Compound#237 and Compound#563 in a SKOV-3 ovarian xenograft model. Compounds have also been tested in HER-2 over-expressing tumor models such as BT474 breast and SKOV-3 ovarian carcinoma A therapy experiment with SKOV-3 is shown in FIG. 6. The treatment, doses, and schedule were the same as used in the A549 and MDA435 experiments. In this case, the tumors were allowed to become established and grow to a relatively large size (200 mm3) before commencement of treatment. Both Compound#237 and Compound#563 suppressed tumor growth almost completely. These data confirm the sensitivity of HER-2 driven cancers and demonstrate that these compounds are effective against well-established solid tumor xenografts. Similar efficacy has been demonstrated with the BT474 xenograft model.

FIG. 6 shows the efficacy of Compound#237 and 17-AAG in a transplantable human breast cancer xenograft model. The activity of 17-AAG and Compound#237 was compared in a primary human breast tumor xenograft model. These tumors were generated from transplantation of primary human malignant material and have been maintained exclusively by serial passage in animals. The data are shown in FIG. 7. Both compounds were given at 30 mg/kg intraperitoneally. 17-AAG showed only marginal anti-tumor activity in this model. By contrast, those animals treated with Compound#237 displayed tumor growth inhibition of 86%.

The foregoing examples are not limiting and are merely representative of various aspects and embodiments of the present invention. All documents cited are indicative of the levels of skill in the art to which the invention pertains. The disclosure of each document is incorporated by reference herein to the same extent as if each had been incorporated by reference in its entirety individually, although none of the documents is admitted to be prior art. Reagents described are all commercially available or otherwise readily attainable by those of ordinary skill in the art, or produced without undue experimentation by such person of skill having the benefit of this application.

One skilled in the art will readily appreciate that the present invention is well adapted to carry out the objects and obtain the ends and advantages mentioned, as well as those inherent therein. The methods and compositions described illustrate preferred embodiments, are exemplary, and are not intended as limitations on the scope of the invention. Certain modifications and other uses will occur to those skilled in the art, and are encompassed within the spirit of the invention, as defined by the scope of the claims.

It will be readily apparent to one skilled in the art that varying substitutions and modifications may be made to the invention without departing from the scope and spirit of the invention. Thus, such additional embodiments are within the scope of the invention and the following claims.

The invention illustratively described herein suitably may be practiced in the absence of any element or elements, limitation or limitations which is not specifically disclosed herein. Thus, for example, while the terms "comprising", "consisting essentially of" and "consisting of," each carries a different meaning as a transition phrase, each such phrase may be used in lieu of the others to endow the claims with a different breadth. The terms and expressions which have been employed are used as terms of description and not of limitation, and there is no intention in the use of such terms and expressions of excluding any equivalents of the features shown and described, or portions thereof. It is recognized that various modifications are possible within the scope of the invention claimed.

In addition, where features or aspects of the invention are described in terms of Markush groups or other grouping of alternatives, those skilled in the art will recognize that the invention is also thereby described in terms of any individual member or subgroup of members of the Markush group or other group, and exclusions of individual members as appropriate, e.g., by proviso.

Other embodiments are within the following claims.

We claim:
1. A compound of formula (I)

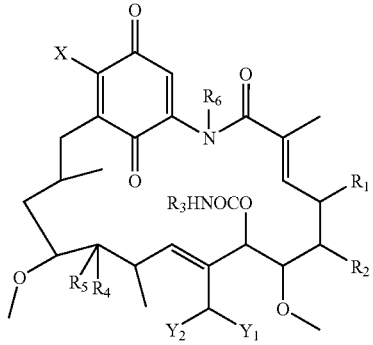

or pharmaceutically acceptable salt thereof, wherein
X is selected from optionally substituted (C1-C20)alkyl, optionally substituted heteroalkyl, optionally substituted (C2-C20)alkenyl, optionally substituted heteroalkenyl, optionally substituted (C2—C20)alkynyl, optionally substituted aryl, optionally substituted heteroaryl, optionally substituted arylalkyl, optionally substituted heteroarylalkyl, optionally substituted cycloalkyl, optionally substituted heterocycloalkyl, —N($R_9$)—C(O)$R_7$, —N($R_9$)—C(O)—O$R_7$, —N($R_9$)—C(O)—N($R_7$)($R_8$), —N($R_9$)—C(S)$R_7$, —N($R_9$) -C(S)—O$R_7$, —N($R_9$)—C(S)—N$R_7R_8$, —O$R_6$ and —N($R_{14}$)($R_{15}$);

$R_1$ and $R_2$ are both H or together form a bond;
$R_3$ is selected from H and optionally substituted C1-C3 alkyl;
$R_4$ and $R_5$ are independently selected from H, —OH, O-alkyl, O-acetyl, —O-aryl, OC(O)$R_{10}$, —$SO_2$—$R_{10}$, and —NH$R_{10}$, or together form oxo (=O), hydroxylimine (=N—OH), alkoxyimine, aryloxyimine, or thioketo, wherein $R_{10}$ is selected from H, optionally substituted (C1-C20)alkyl, optionally substituted heteroalkyl, optionally substituted aryl; and optionally substituted heteroaryl;
$R_6$ is selected from H, optionally substituted C1-C8alkyl, and optionally substituted C5-C8 aryl;
$R_7$ and $R_8$ each independently is selected from H, optionally substituted (C1- C20) alkyl, optionally substituted heteroalkyl, optionally substituted (C2-C20)alkenyl, optionally substituted heteroalkenyl, optionally substituted (C2-C20)alkynyl, optionally substituted aryl, optionally substituted heteroaryl, optionally substituted arylalkyl, optionally substituted heteroarylalkyl, optionally substituted cycloalkyl, and optionally substituted heterocycloalkyl; or $R_7$ and $R_8$ are taken together with the nitrogen to which they are bound to form an optionally substituted saturated or unsaturated 4-7 membered heterocyclic ring;
$R_9$ is selected from H, optionally substituted C1-C6 alkyl, optionally substituted aryl containing from 6 to 12 carbon atoms, and optionally substituted heteroaryl containing from 5 to 12 carbon atoms, or together with $R_7$ or $R_8$ forms an optionally substituted 4-7 membered heterocyclic ring;
$R_{14}$ and $R_{15}$ are independently selected from H, optionally substituted (C1- C20) alkyl, optionally substituted heteroalkyl, optionally substituted (C2-C20)alkenyl, optionally substituted heteroalkenyl, optionally substituted (C2-C20)alkynyl, optionally substituted aryl, optionally substituted heteroaryl, optionally substituted arylalkyl, optionally substituted heteroarylalkyl, optionally substituted cycloalkyl, and optionally substituted heterocycloalkyl; or $R_{14}$ and $R_{15}$ are taken together with the nitrogen to which they are bound to form an optionally substituted saturated or unsaturated 4-7 membered heterocyclic ring;

wherein $Y_1$ and $Y_2$ are independently selected from H, —OH, O-alkyl, O-acetyl, —O-aryl, OC(O) $R_{10}$, —SO$_2$—$R_{10}$, and —NHR$_{10}$, or together form oxo (=O), hydroxylimine (=N—OH), alkoxyimine, aryloxyimine, or thioketo, wherein $R_{10}$ is selected from H, optionally substituted (C1-C20)alkyl, optionally substituted heteroalkyl, optionally substituted aryl and optionally substituted heteroaryl;

or $Y_1$ or $Y_2$ taken with $R_4$ or $R_5$ form an optionally substituted 5-7 membered heterocyciic or carbocyclic ring;

provided that, if $Y_1$ and $Y_2$ are both H and X is N($R_{14}$)($R_{15}$) or —OR$_6$, then at least one of $R_4$, $R_5$, $R_6$, $R_{14}$, and $R_{15}$ comprises a phosphorous moiety selected from —OP(O)(OR$_{16}$)$_2$, —CH$_2$P(O)(OR$_{16}$)$_2$, and —NP(O)(OR$_{16}$)$_2$, wherein $R_{16}$ is seiected from H, alkyl, heteroalkyl, alkenyl, heteroalkenyl, alkynyl, heteroalkynyl, aryl and heteroaryl;

wherein said heteroalkyl and heteroalkenyl are corresponding alkyl and alkenyl groups in which one or more skeletal chain atoms are independently selected from oxygen, nitrogen, sulfur, and phosphorous;

wherein said heteroaryl are corresponding aromatic groups in which one or more skeletal ring atoms are independently selected from oxygen, nitrogen, sulfur, and phosphorous; and wherein said optionaiiy substituted groups are unsubstituted groups or groups substituted by one or more substituents independently selected from alkyl, alkenyl, alkynyl, heteroalkyl, haloalkyl, haloalkenyl, haloalkynyl, cycloalkyl, aryl, heteroaryl, arylalkyl, heteroarylalkyl, alkoxy, aryloxy, haloalkoxy, amino, alkylamino, dialkylamino, alkylthio, arylthio, heteroarylthio, oxo, —C(O)OR wherein R is selected from alkyl, aryl, and arylalkyl, —N(R')C(O)R wherein R' and R are independently selected from H, alkyl, aryl and aryalkyl, —OC(O)R wherein R is selected from H, alkyl, alkenyl, alkynyl, aryl, and arylalkyl, F, Cl, Br, I, CN, NO$_2$, N$_3$, SH, OH, CO$_2$, amido, sulfonato, sulfato, sulphonamido, carbamoyl, ureido, thioureido, thioamido, thioalkyls, —OP(O)(OR$_6$)$_2$, and —NP(O)(OR$_{16}$)$_2$; and wherein the alkyl substituent is itself optionally substituted by one or more substituents inderendentlv selected from alkyl, alkenyl, alkynyl, heteroalkyl, haloalkyl, haloalkenyl, haloalkynyl, cycloalkyl, aryl, heteroaryl, arylalkyl, heteroarylalkyl, alkoxy, aryloxy, haloalkoxy, amino, alkylamino, dialkylamino, alkylthio, arylthio, heteroarylthio, oxo, —C(O)OR wherein R is selected from alkyl, aryl, and arylalkyl, —N(R')C(O)R wherein R' and R are independently selected from H, alkyl, aryl and arylalkyl, —OC(O)R wherein R is selected from H, alkyl, alkenyl, alkynyl, aryl, and arylalkyl, F, Cl, Br, OH, —OP(O)(OR$_{16}$)$_2$, —CH$_2$P(O)(OR$_{16}$)$_2$, and —NP(O)(OR$_{16}$)$_2$.

2. The compound or pharmaceutically acceptable salt thereof of claim 1 wherein X is selected from —N(R$_9$)—C(O) R$_7$, —N(R$_9$)—C(O)—OR$_7$, —N(R$_9$)—C(O)—NR$_7$, —N(R$_9$)—C(S)R$_7$, —N(R$_9$)—C(S)—OR$_7$,—(R$_9$)—C(S)—NR$_7$, and —N(R$_{14}$)(R$_{15}$).

3. The compound or pharmaceutically acceptable salt thereof of claim 1 wherein X is selected from optionally substituted (C1-C20)alkyl, optionally substituted heteroalkyl, optionally substituted (C2-C20)alkenyl, optionally substituted heteroalkenyl, optionally substituted (C2-C20)alkynyl, optionally substituted aryl, optionally substituted heteroaryl, optionally substituted optionally substituted arylalkyl, optionally substituted heteroarylalkyl, optionally substituted cycloalkyl, and optionally substituted heterocycloalkyl.

4. The compound or pharmaceutically acceptable salt thereof of claim 2 wherein X is —N(R$_{14}$)(R$_{15}$).

5. The compound or pharmaceutically acceptable salt thereof of claim 2 wherein X is —N(R$_9$)—C(O) R$_7$.

6. The compound or pharmaceutically acceptable salt thereof of claim 1 wherein X is —N(R$_9$)—C(O)—OR$_7$.

7. The compound or pharmaceutically acceptable salt thereof of claim 1 wherein X is —OR$_6$.

8. A compound of formula (II)

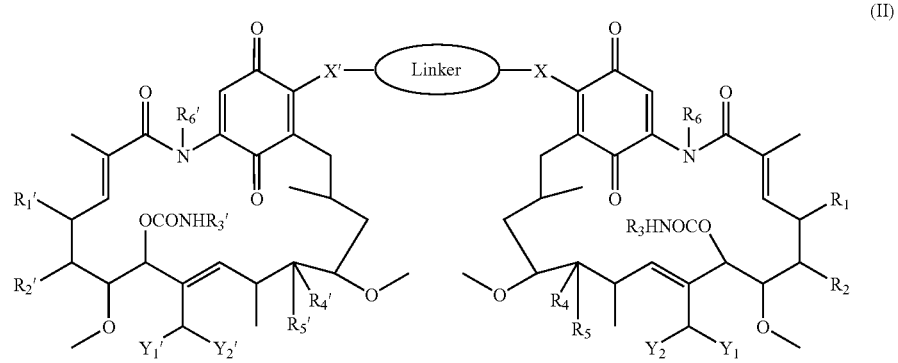

(II)

or a pharmaceutically acceptable salt thereof, wherein $R_1$ and $R_2$ are both H or together form a bond;

$R_1'$ and $R_2'$ are both H or together form a bond;

$R_3$ and $R_3'$ are independently selected from H and optionally substituted C1-C6 alkyl;

$R_4$ and $R_5$ are independently selected from H, —OH, O-alkyl, O-acetyl, —O-aryl, OC(O)R$_{10}$, —SO$_2$—R$_{10}$, and —NHR$_{10}$, or together form oxo (=O), hydroxylimine (=N—OH), alkoxyimine, aryloxyimine, or thioketo, wherein R$_{10}$ is selected from H, optionally substituted (C1-C20)alkyl, optionally substituted heteroalkyl, optionally substituted aryl; and optionally substituted heteroaryl;

R$_4$' and R$_5$' are independently selected from H, —OH, O-alkyl, O-acetyl, —O-aryl, OC(O) R$_{10}$, —SO$_2$—R$_{10}$, and —NHR$_{10}$, or together form oxo (=O), hydroxylimine (=N—OH), alkoxyimine, aryloxyimine, or thioketo, wherein R$_{10}$ is selected from H, optionally substituted (C1-C20)alkyl, optionally substituted heteroalkyl, optionally substituted aryl; and optionally substituted heteroaryl;

R$_6$ and R$_6$' are independently selected from H, optionally substituted (C1- C6) alkyl, optionally substituted (C5-C10)aryl, and optionally substituted (C1-C6)acyl;

X and X' are independently selected from NR$_{11}$R$_{12}$, —NHC(O)—, —N(R$_{13}$)—, —NC(O)—O, —NC(S)—, —NC(O)N—, —NC(CH$_2$)—, —NC(NH)—, optionally substituted alkyl, optionally substituted alkenyl, optionally substituted alkynyl, optionally substituted aryl, optionally substituted heteroaryl, —OR$_{11}$—, and —SR$_{11}$—; wherein R$_{11}$ and R$_{12}$ are independently selected from optionally substituted (C1-C20)alkyl, optionally substituted (C2-C20)alkenyl, optionally substituted (C2-C20)alkynyl, optionally substituted aryl, optionally substituted heteroaryl, optionally substituted arylalkyl, and optionally substituted cycloalkyl; and wherein R$_{13}$ is selected from H, optionally substituted (C1- C6) alkyl, and optionally substituted (C5--C10) aryl; and wherein Y$_1$ and Y$_2$ are independently selected from H, —OH, O-alkyl, O-acetyl, —O—aryl, OC(O)R$_{10}$, —SO$_2$—R$_{10}$, and —NHR$_{10}$, or together form oxo (=O), hydroxylimine (=N—OH), alkoxyimine, aryloxyimine, orthioketo, wherein R$_{10}$ is selected from H, optionally substituted (C1-C20)alkyl, optionally substituted heteroalkyl, optionally substituted aryl and optionally substituted heteroaryl;

or Y$_1$ or Y$_2$ taken with R$_4$ or R$_5$ form an optionally substituted 5-7 membered heterocyclic or carbocyclic ring; and the Linker is an optionally substituted 3-20 carbon atom chain having at least 1 heteroatom moiety in the chain, wherein said heteroatom moiety is selected from —NR$_6$, —O—, —S—, —P—, —SO$_3$ and —Y—C(O)-Q -C(O)—Y—, wherein Y is selected from O, S, and NH, and wherein Q is selected from optionally substituted alkylene, optionally substituted arylene, and optionally substituted heteroarylene;

wherein said heteroalkyl and heteroalkenyl are corresponding alkyl and alkenyl groups in which one or more skeletal chain atoms are independently selected from oxygen, nitrogen, sulfur, and phosphorous;

wherein said heteroaryl are corresponding aromatic groups in which one or more skeletal ring atoms are independently selected from oxygen, nitrogen, sulfur, and phosphorous; and wherein said optionally substituted groups are unsubstituted groups or groups substituted by one or more substituents independently selected from alkyl, alkenyl, allynyl, heteroalkyl, haloalkyl, haloalkenyl, haloalkynyl, cycloalkyl, aryl, heteroaryl, arylalkyl, heteroarylalkyl, alkoxy, aryloxy, haloalkoxy, amino, alkylamino, dialkylamino, alkylthio, arylthio, heteroarylthio, oxo, —C(O)OR wherein R is selected from alkyl, aryl, and arylalkyl, —N(R')C(O)R wherein R' and R are independently selected from H, alkyl, aryl and arylalkyl, —OC(O)R wherein R is selected from H, alkyl, alkenyl,alkynyl, aryl, and arylalkyl, F, Cl, Br, I, CN, NO$_2$, N$_3$, SH, OH, CO$_2$H, amido, sulfonato, sulfato, sulphonamido, carbamoyl, ureido, thioureido, thioamido, thioalkyls, —OP(O)(OR$_{16}$)$_2$, —CH$_2$P(O)(OR$_{16}$)$_2$, and —NP(O)(OR$_{16}$)$_2$; and wherein the alkyl substituent is itself optionally substituted by one or more substituents independently selected from alkyl, alkenyl, alkynyl, heteroalkyl, haloalkyl, haloalkenyl, haloalkynyl, cycloalkyl, aryl, heteroaryl, arylalkyl, heteroarylalkyl, alkoxy, aryloxy, haloalkoxy, amino, alkylamino, dialkylamino, alkylthio, arylthio, heteroarvlthio, oxo, —C(O)OR wherein R is selected from alkyl, aryl, and arylalkyl, —N(R')C(O)R wherein R' and R are independently selected from H, alkyl, aryl and a rvlalkyl, —OC(O)R wherein R is selected from H, alkyl, alkenyl,alkynyl, aryl, and arylalkyl, F, Cl, Br, OH, —OP(O)(OR$_{16}$)$_2$, —CH$_2$P(O)(OR$_{16}$)$_2$, and —NP(O)(OR$_{16}$)$_2$.

9. The compound or pharmaceutically acceptable salt thereof of ciaim 8 wherein said compound or pharmaceutically acceptable salt thereof is a homodimer.

10. The compound or pharmaceutically acceptable salt thereof of claim 8 wherein said compound or pharmaceutically acceptable salt thereof is a heterodimer.

11. The compound or pharmaceutically acceptable salt thereof of claim 8 represented by formula:

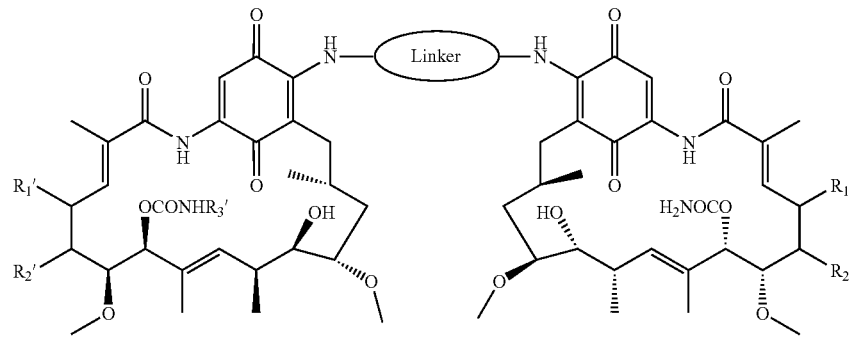

12. A pharmaceutical composition comprising a compound or pharmaceutically acceptable salt thereof according to claim 1 and further comprising one or more members selected from pharmaceutically acceptable excipients, carriers, bulking agents, salts, water, and alcohol.

13. The pharmaceutical composition of claim 12 formulated for intravenous administration, and optionally disposed in a container member selected from vials and syringes.

14. The pharmaceutical composition of claim 13 formulated for oral administration, and optionally disposed in a container member selected from gel capsules, tablets, bottles, vials, and inhalers.

15. The compound or pharmaceutically acceptable salt thereof of claim 1 selected from:

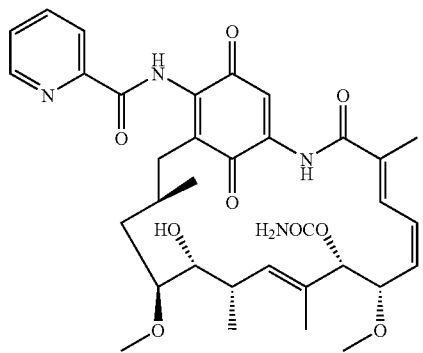

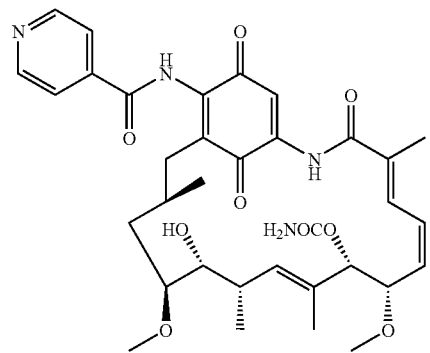

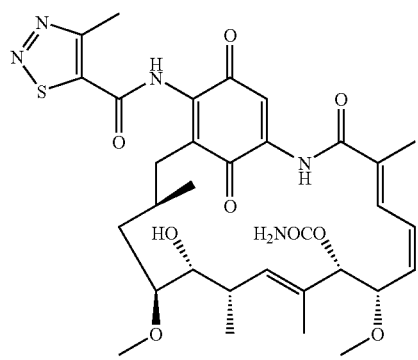

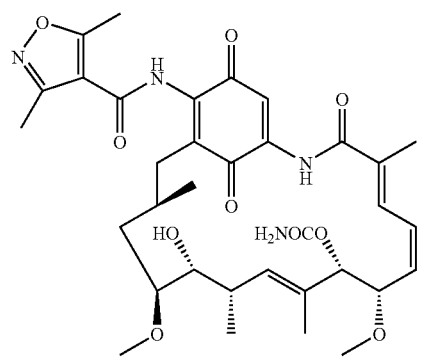

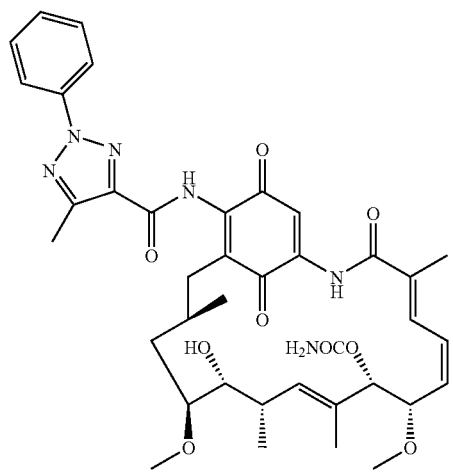

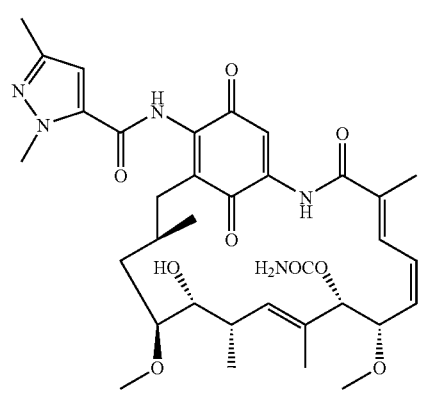

215
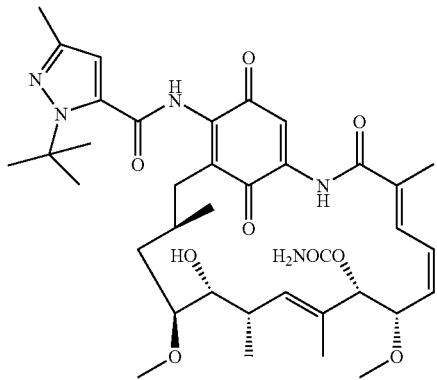
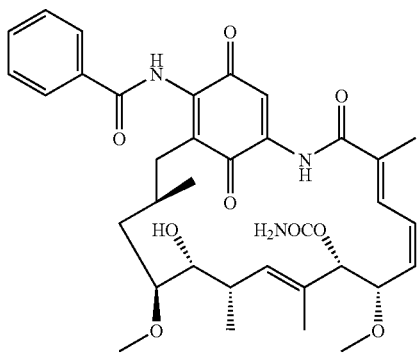
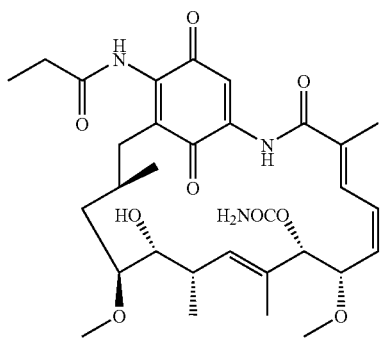
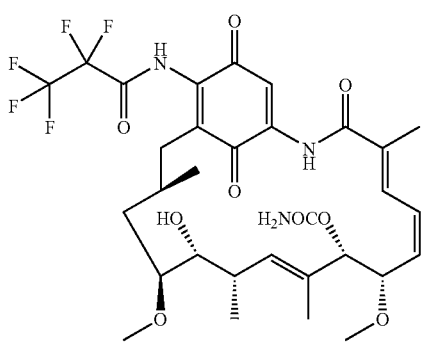
216
-continued
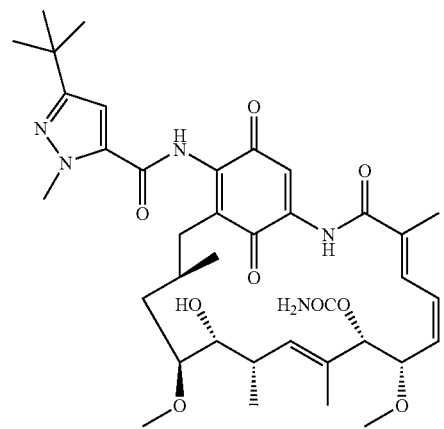
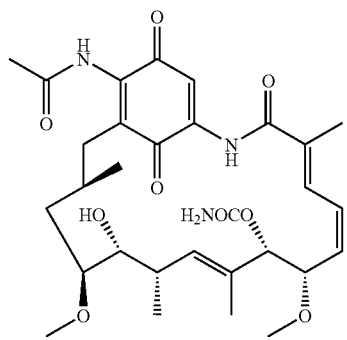
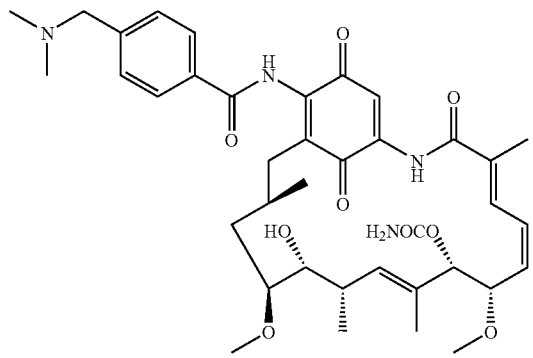
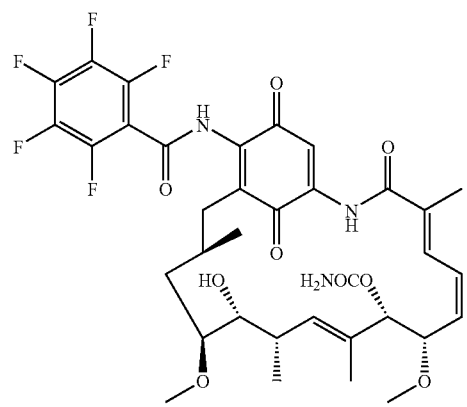

217     218
-continued
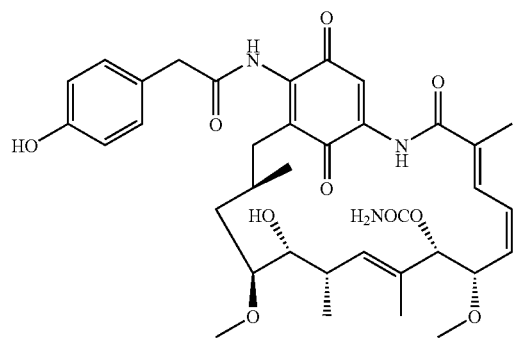 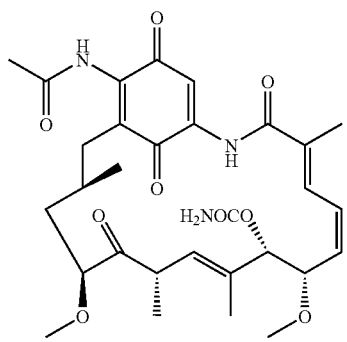
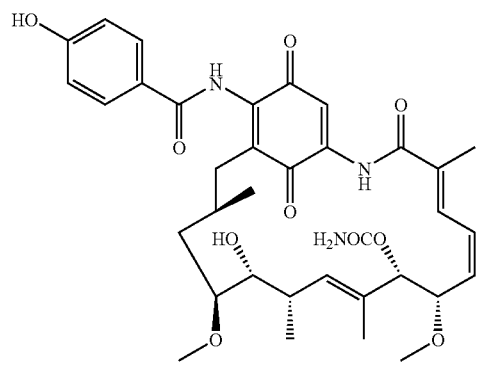 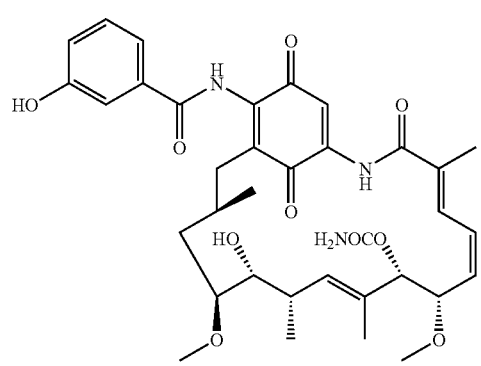
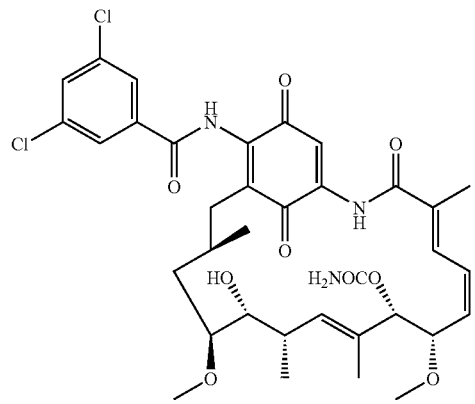 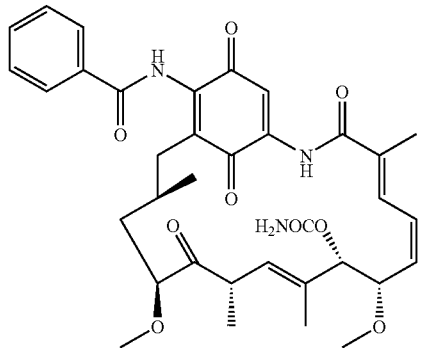
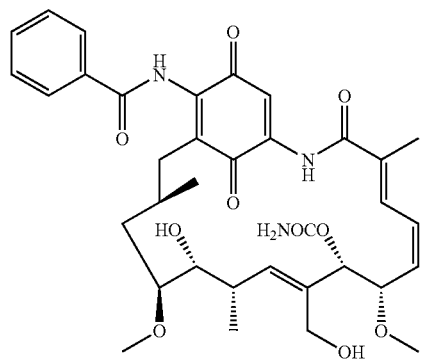 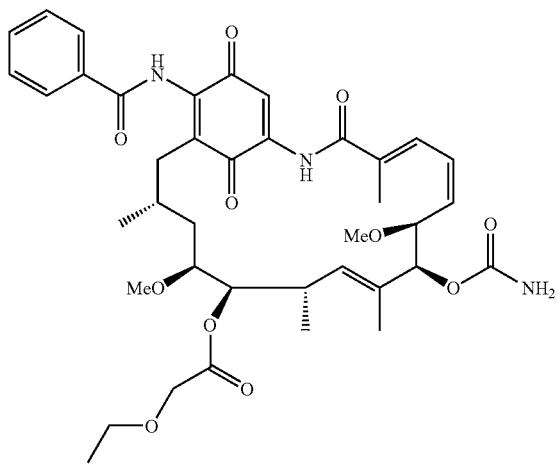

-continued
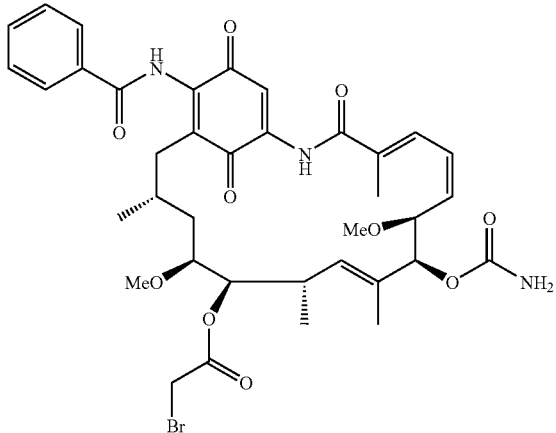
219
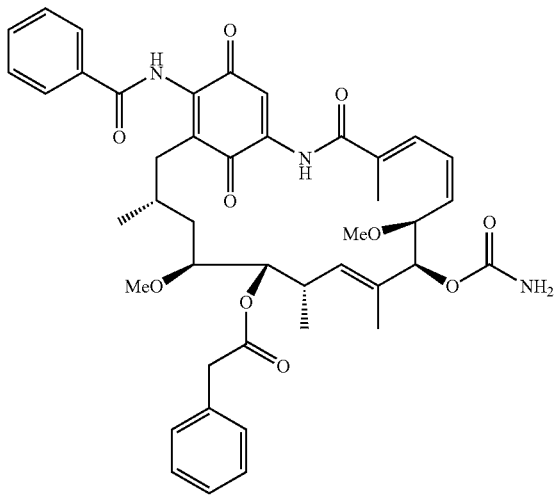
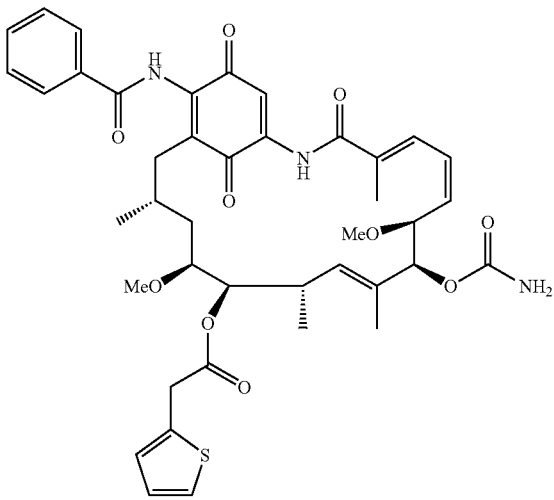
220
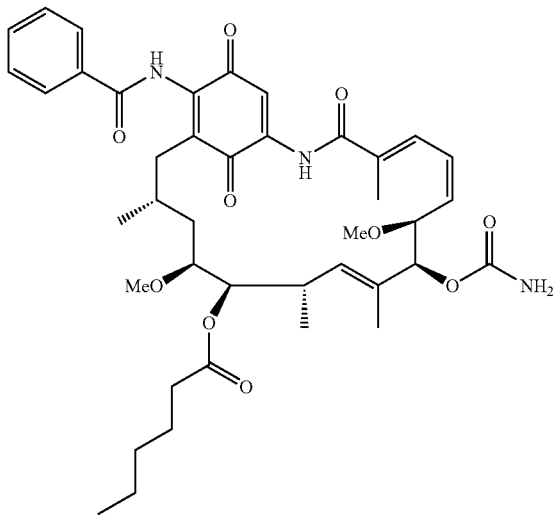

221 222
-continued
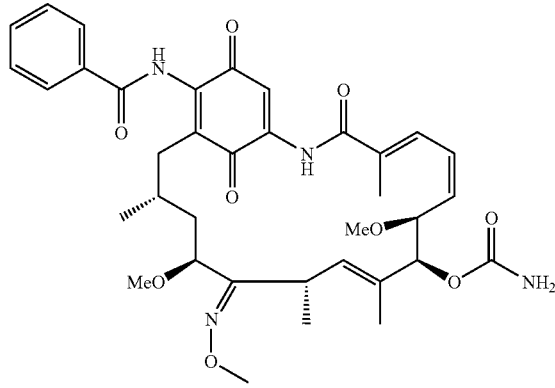
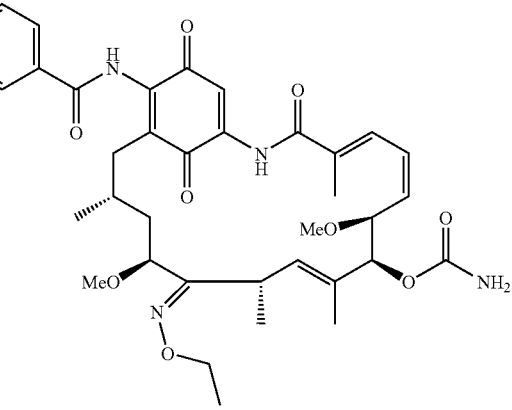
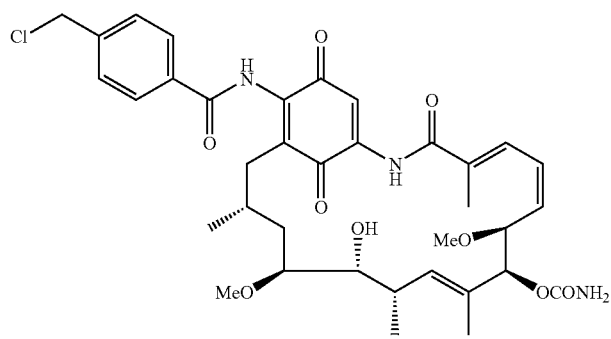
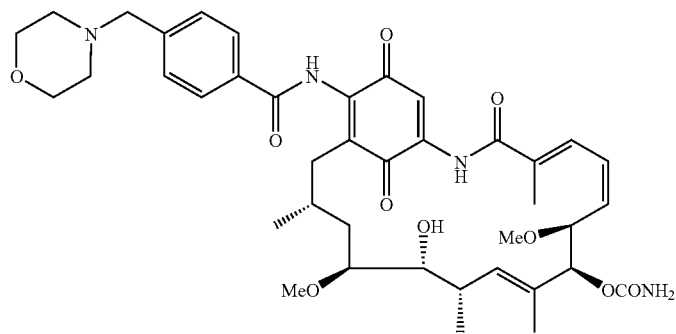
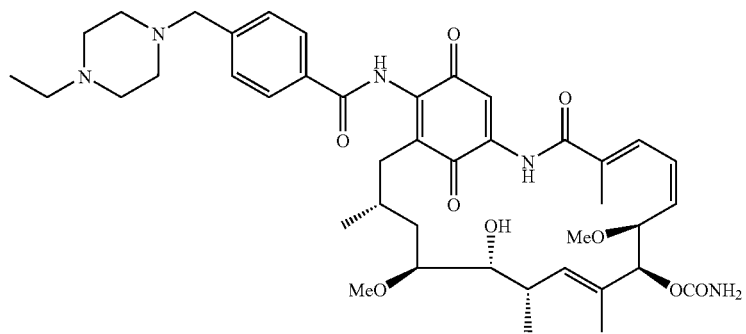

-continued
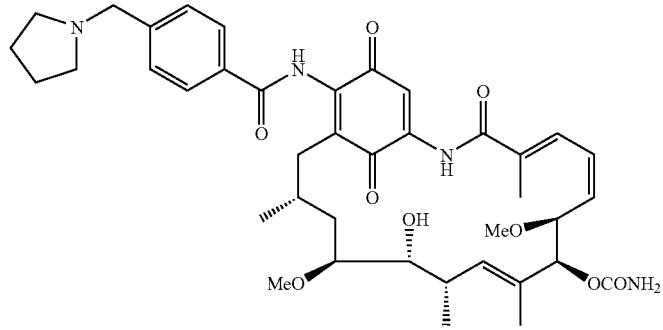
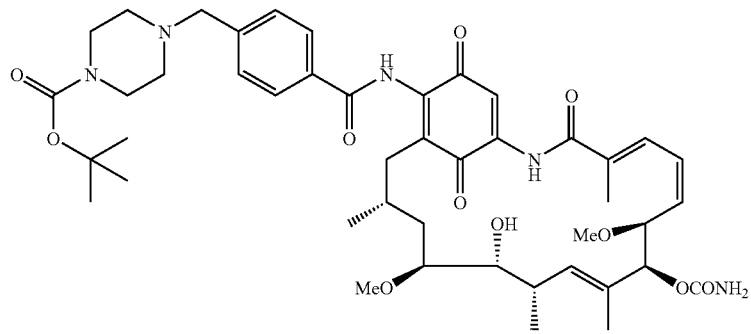
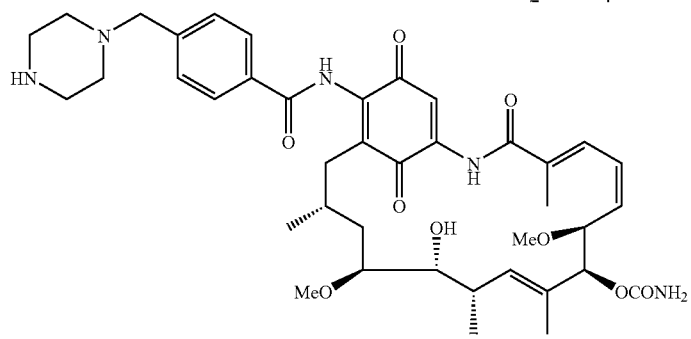
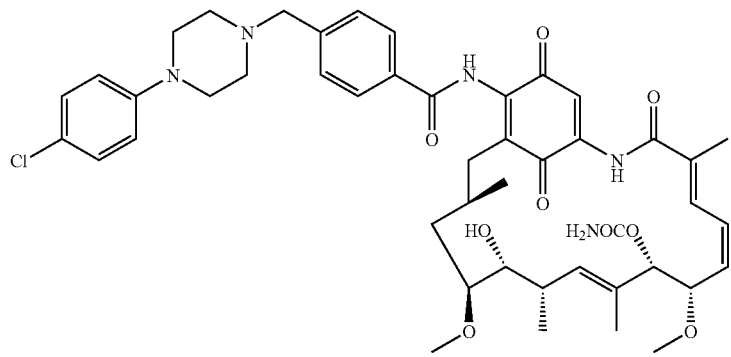
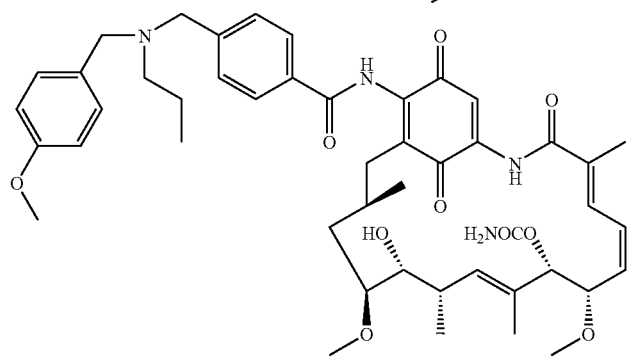

-continued
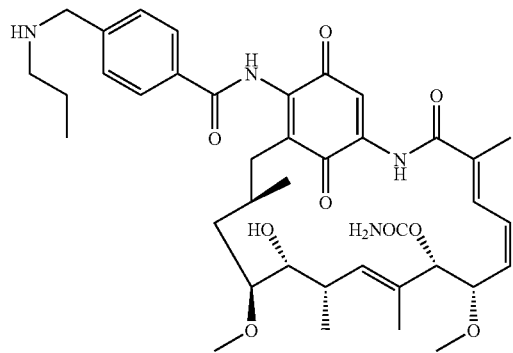
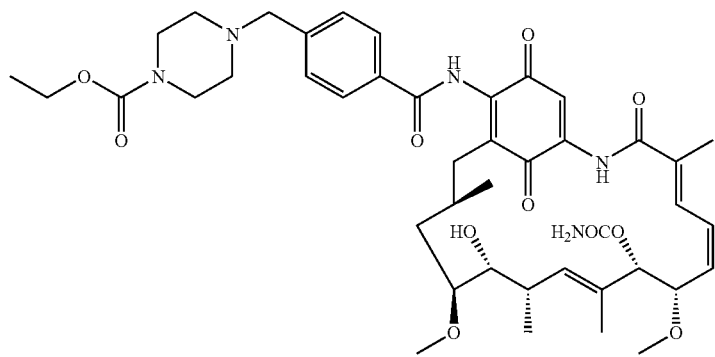
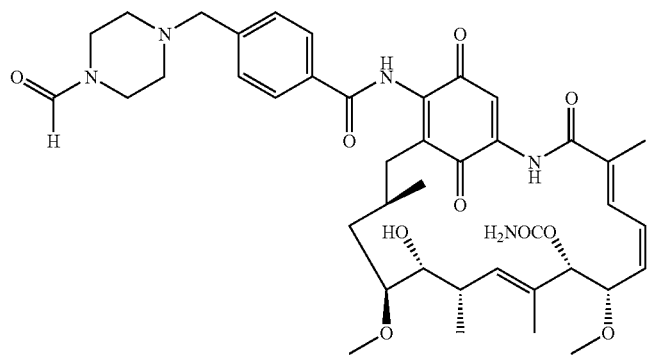
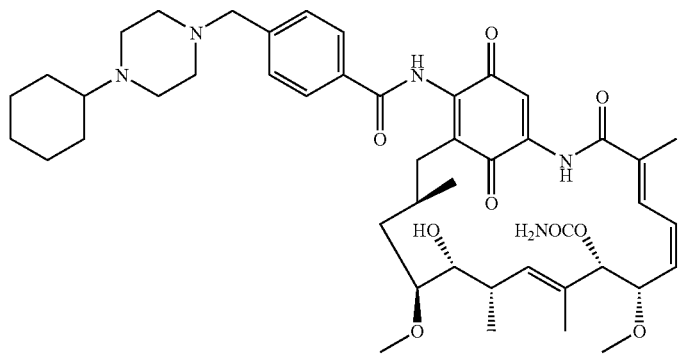

-continued
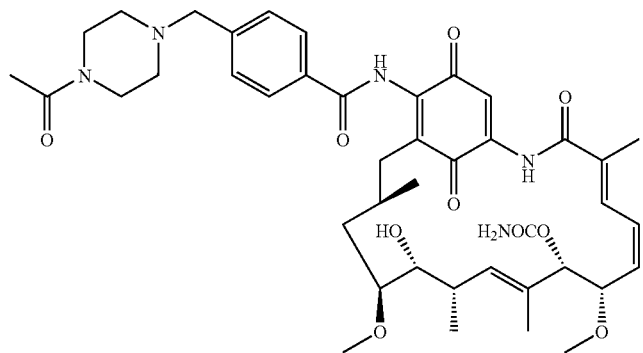
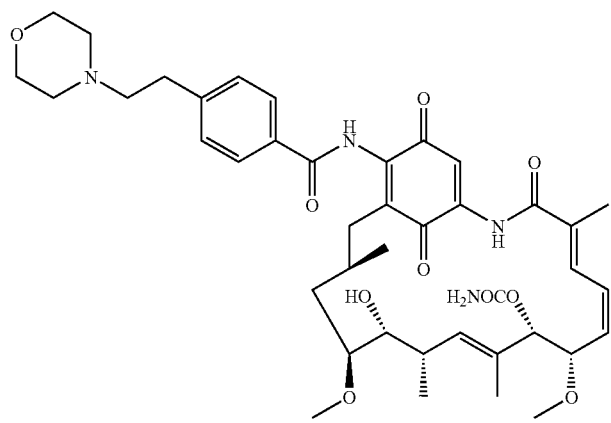
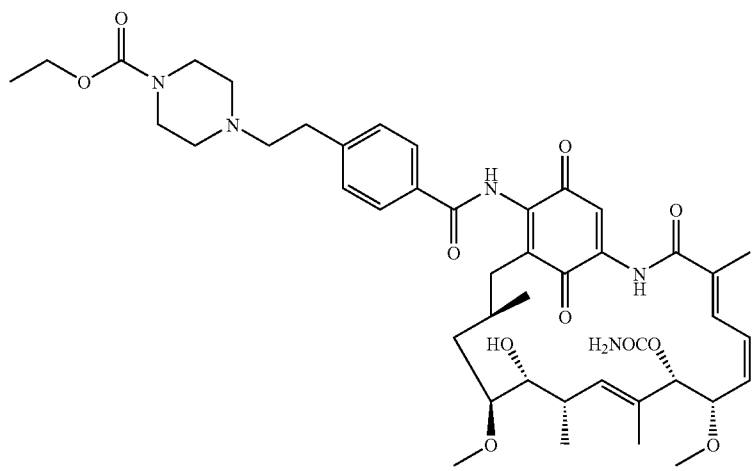
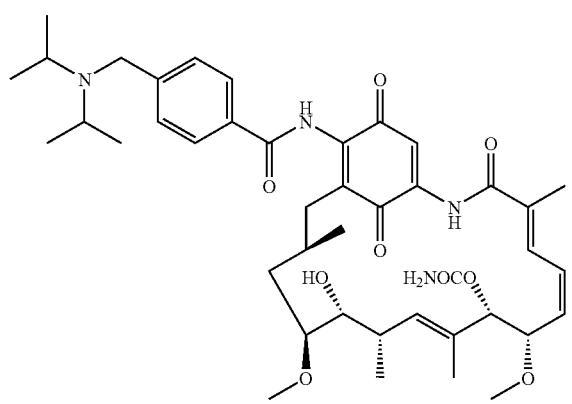

-continued
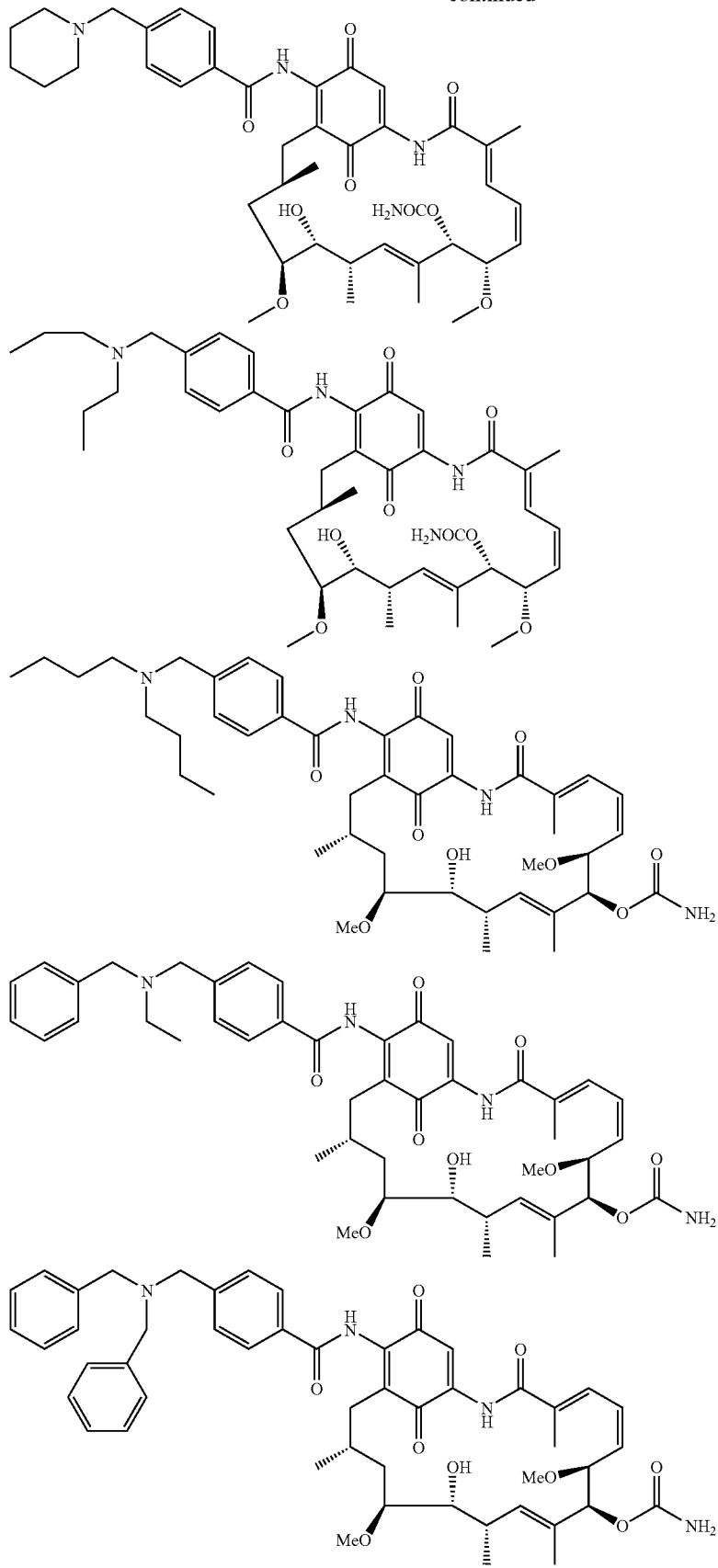

231 232
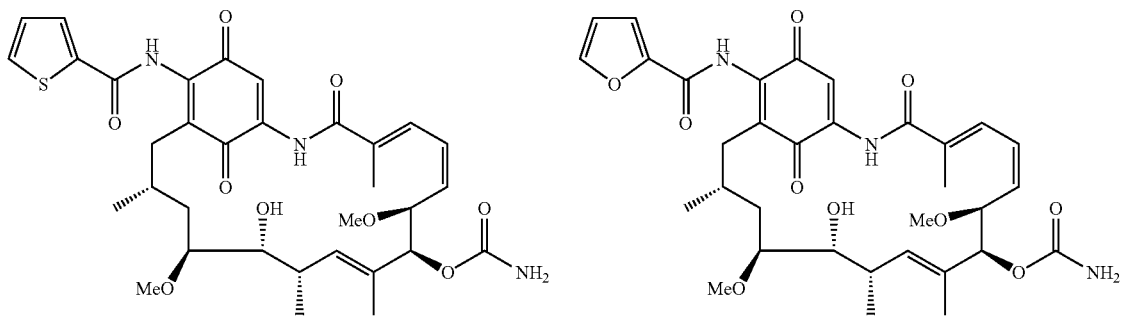
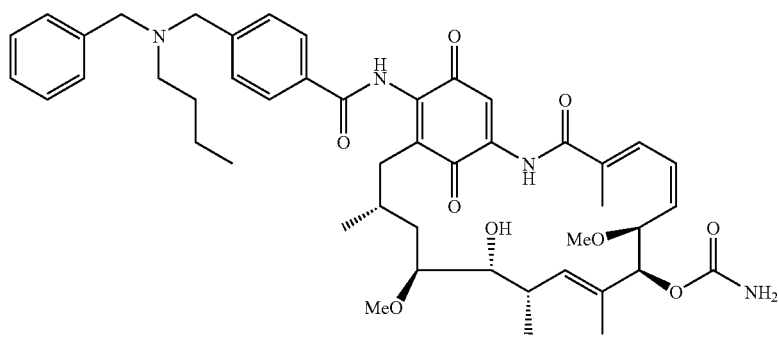
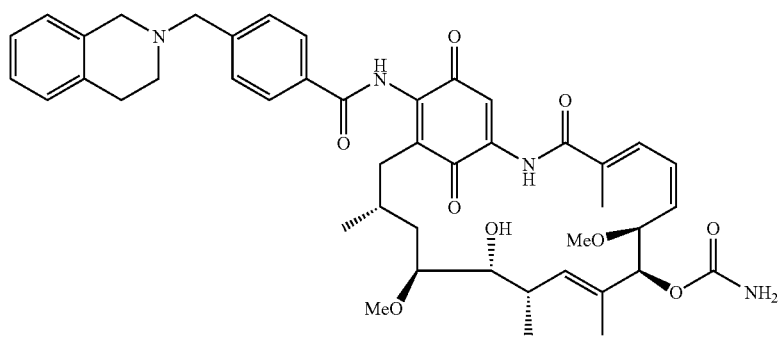
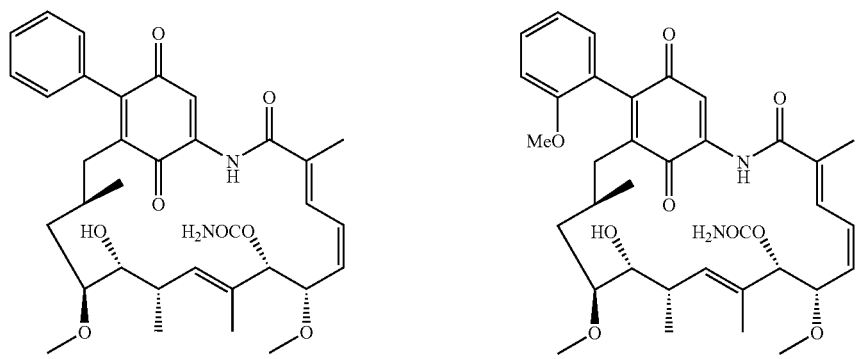

233
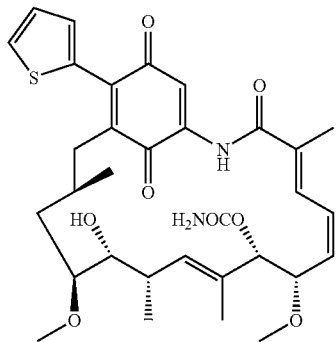
234
-continued
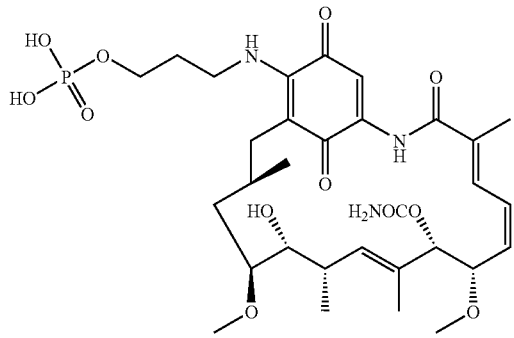
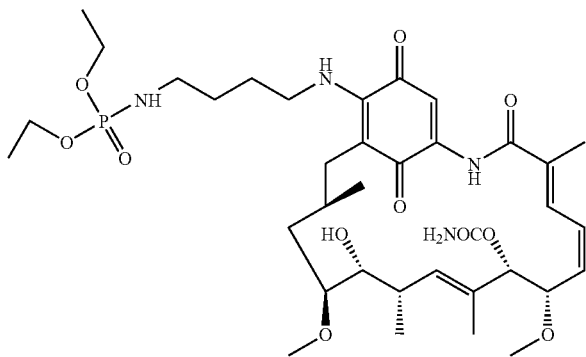
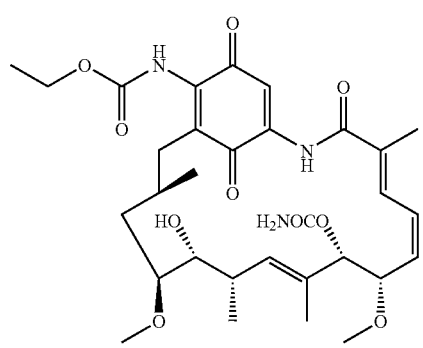
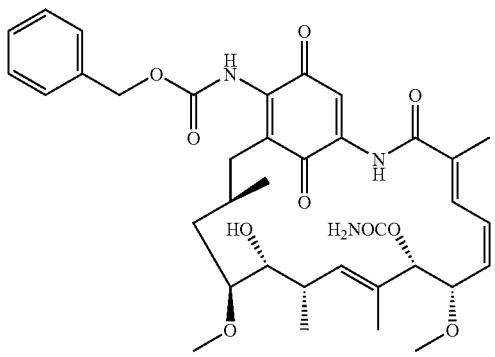
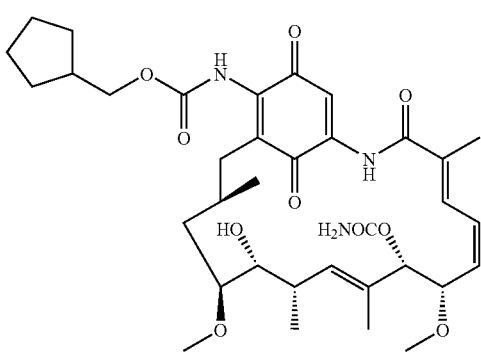
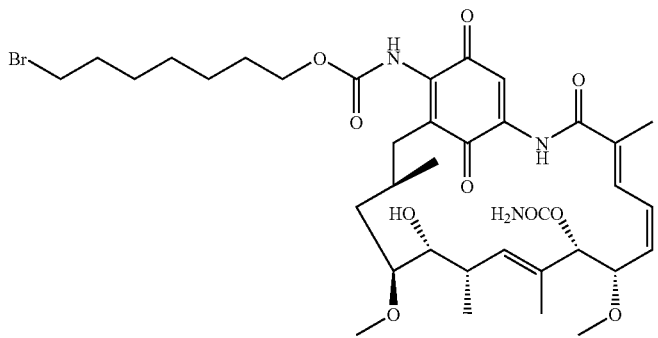

235
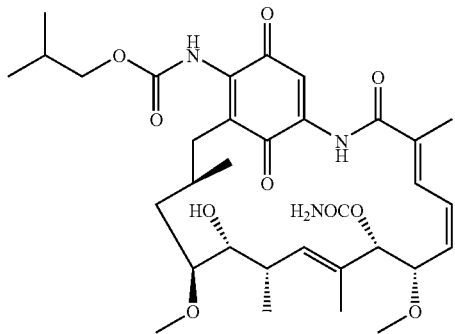
236
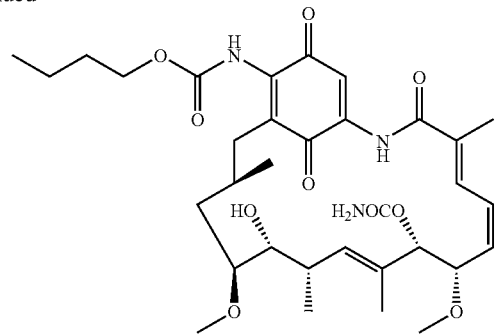
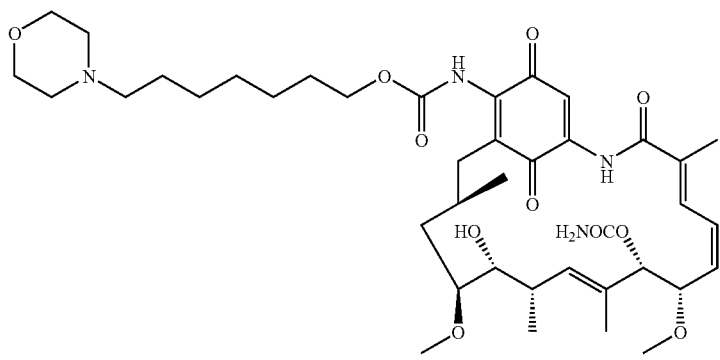
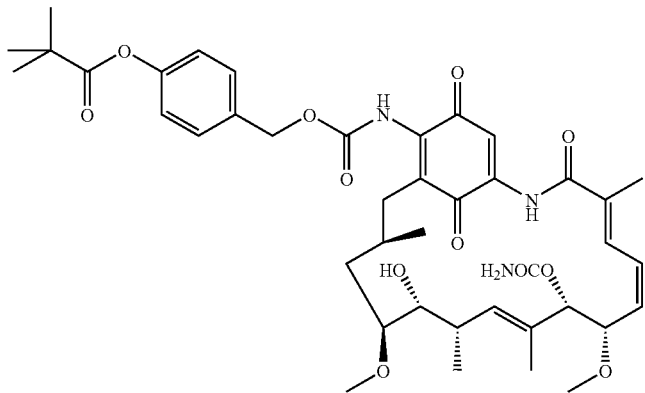
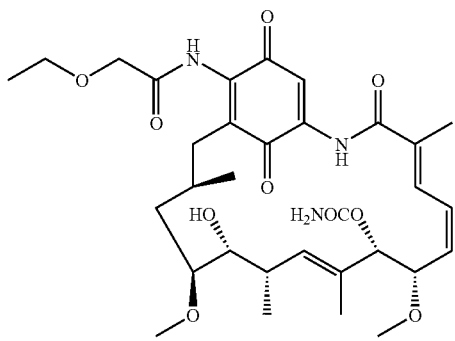
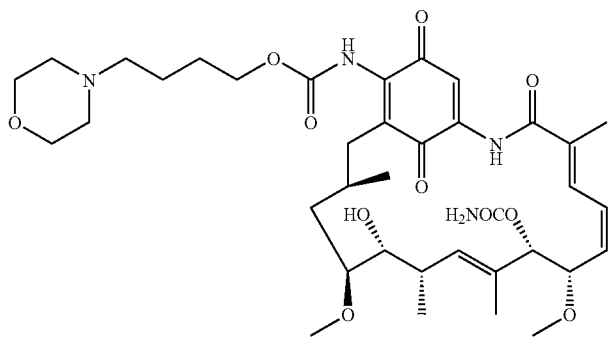

237
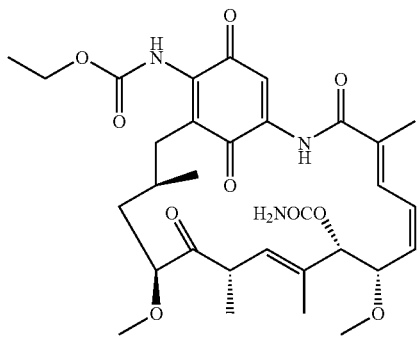
238
-continued
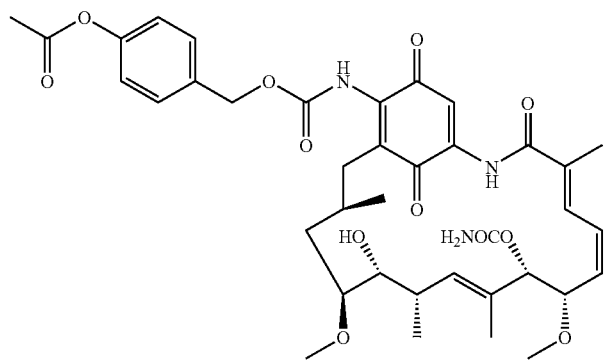
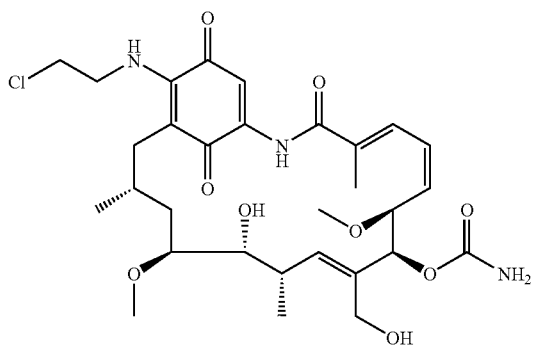
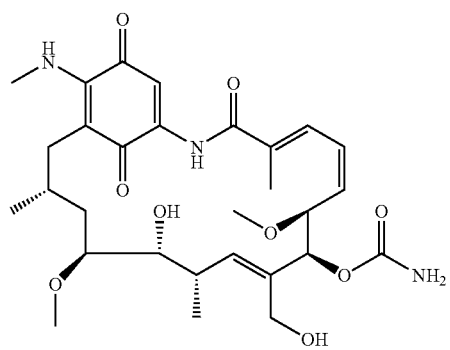
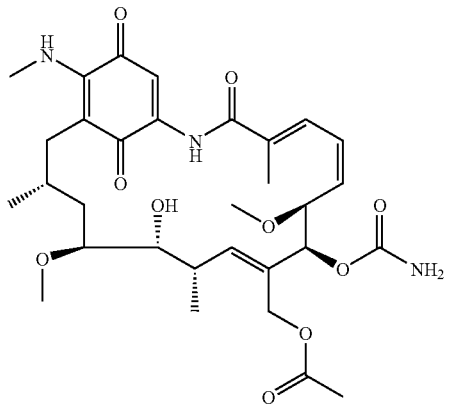
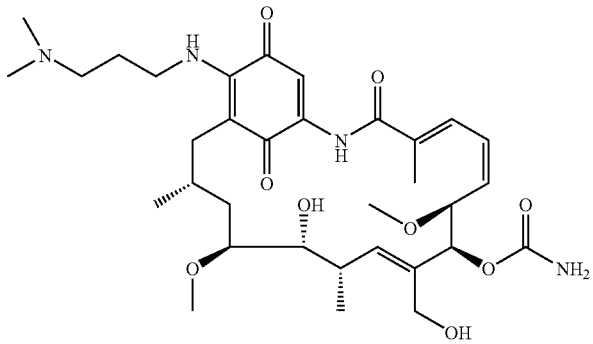
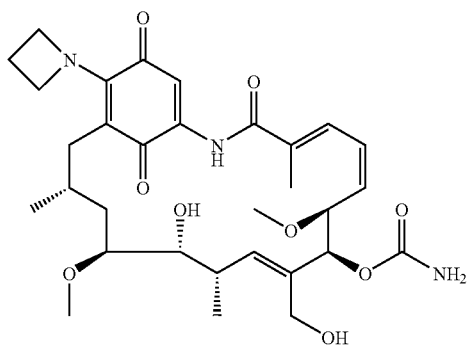
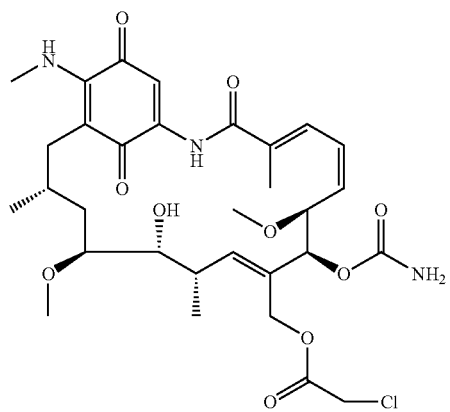

239 240
-continued
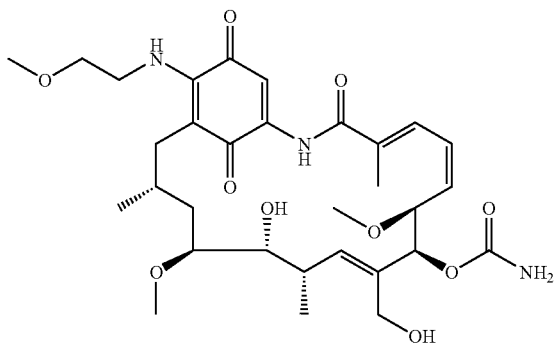
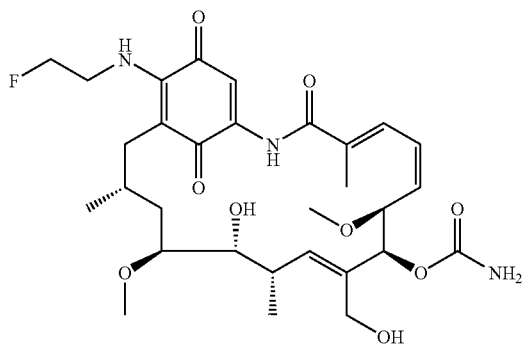
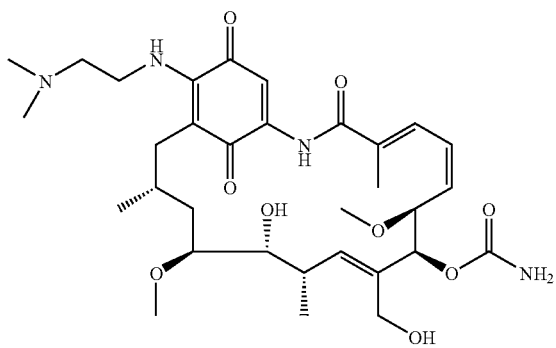
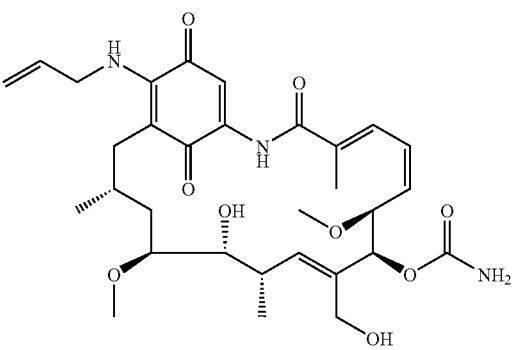
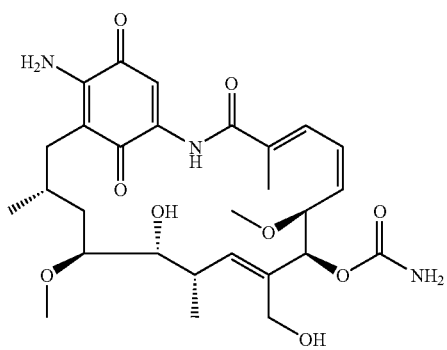
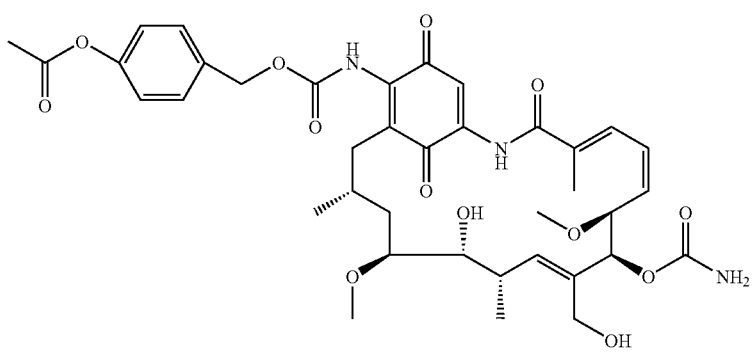

241 242
-continued
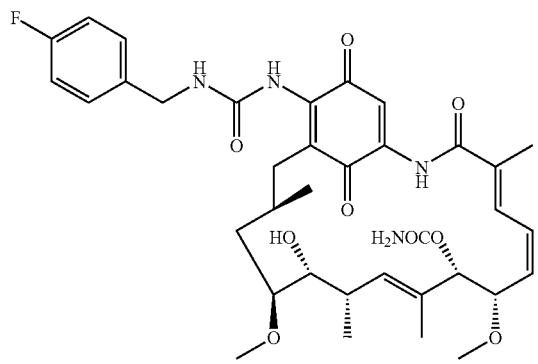
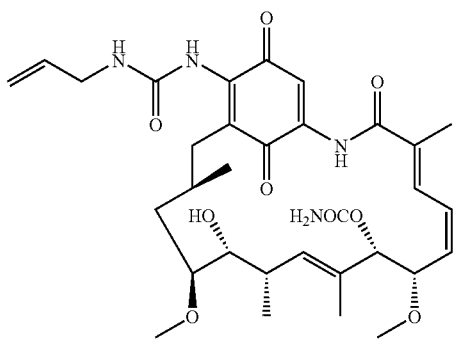
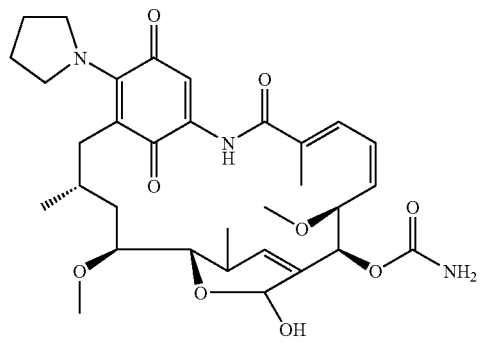
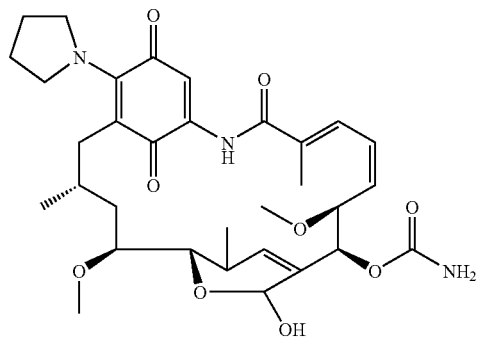
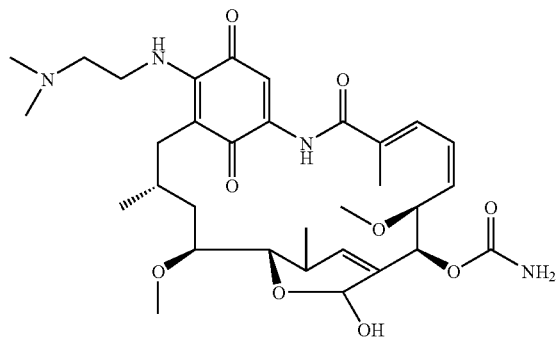
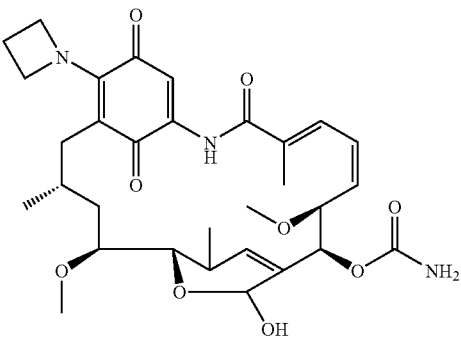
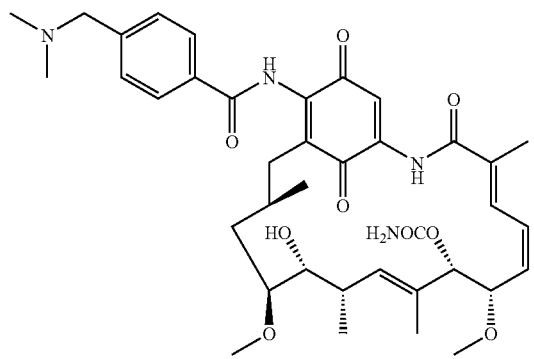

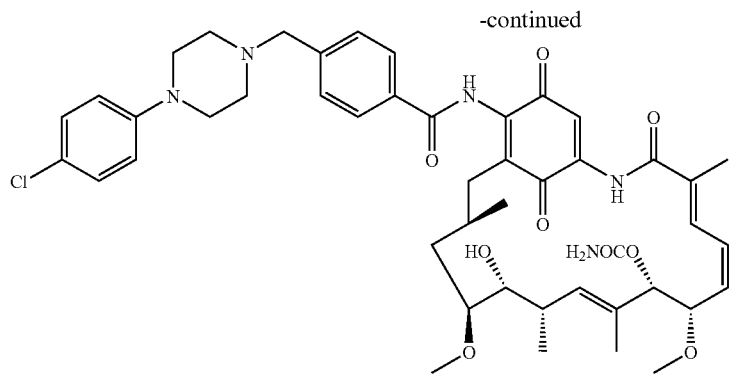
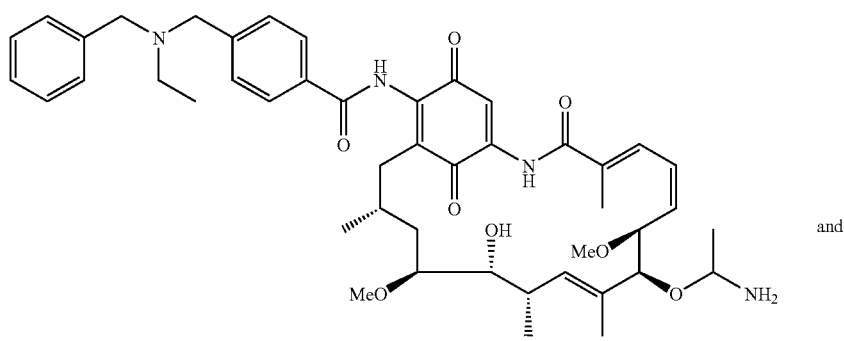
and
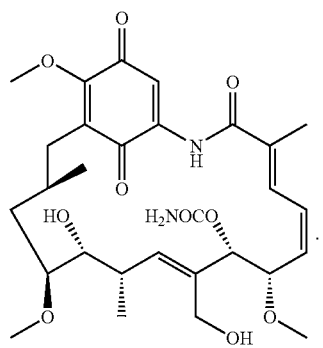
16. The compound or pharmaceutically acceptable salt thereof of claim 8 selected from:
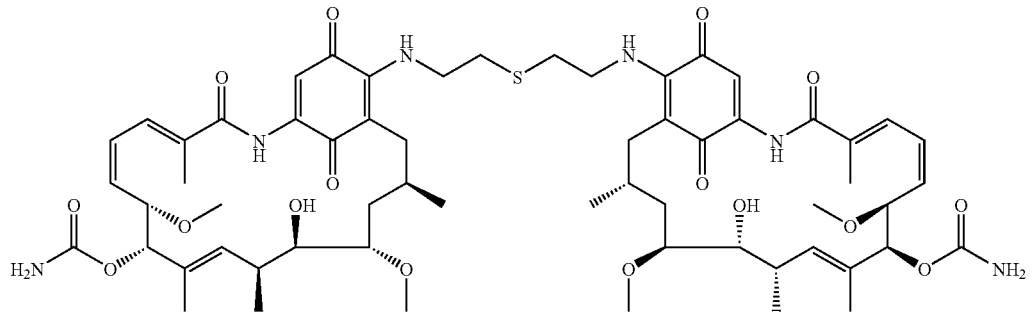

245 246
-continued
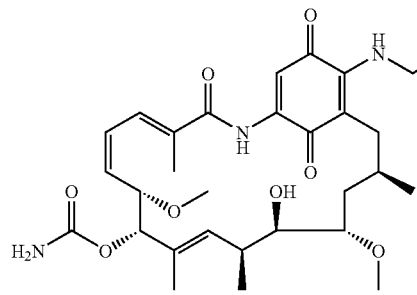 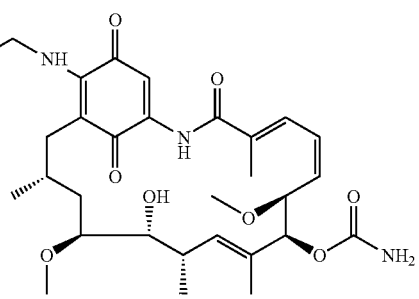
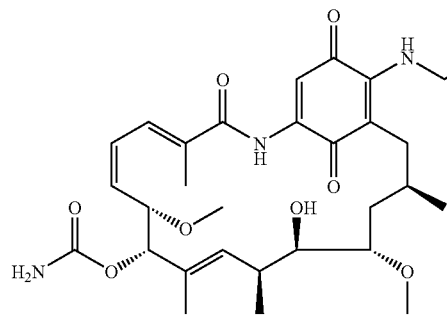 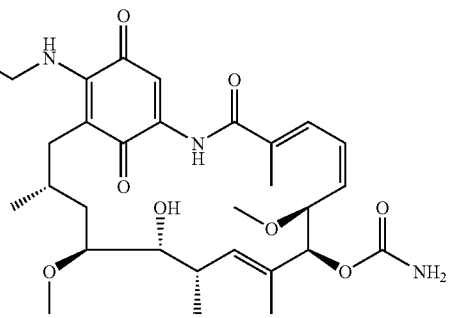
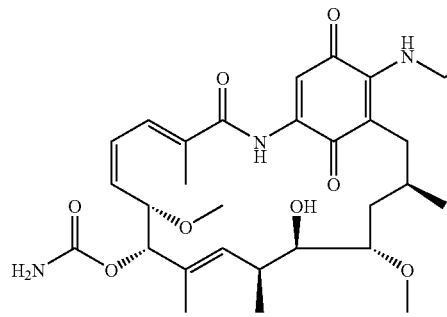 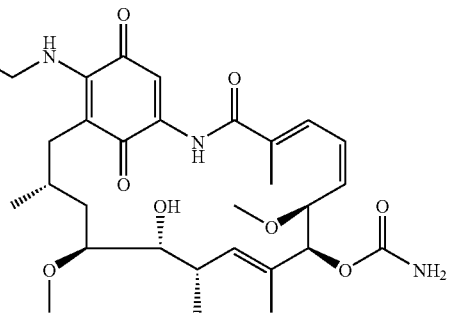
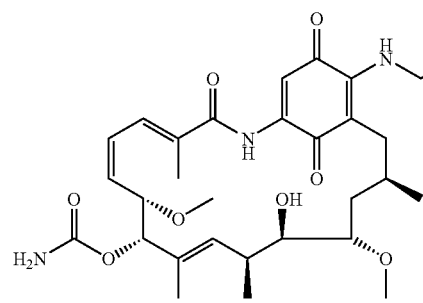 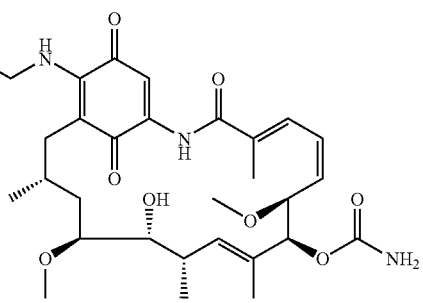

247 248
-continued
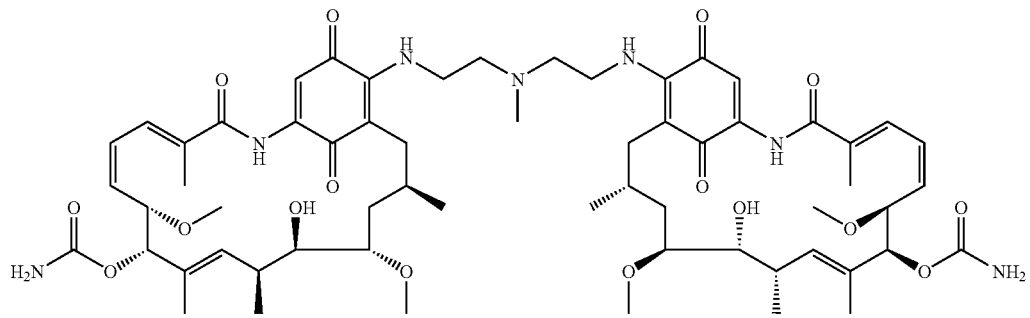
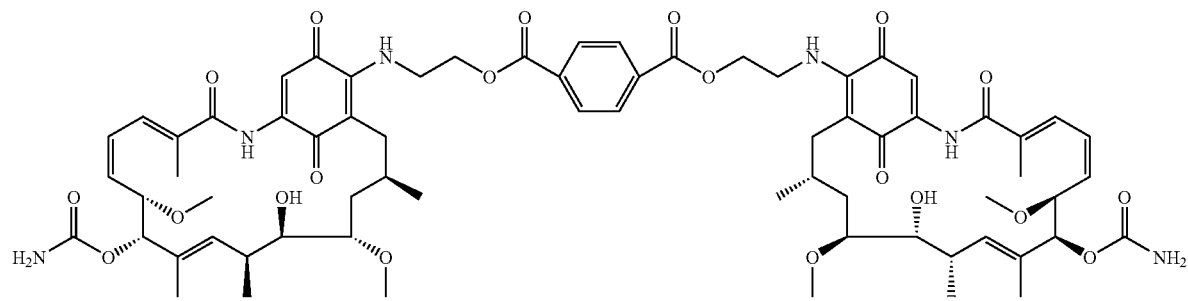
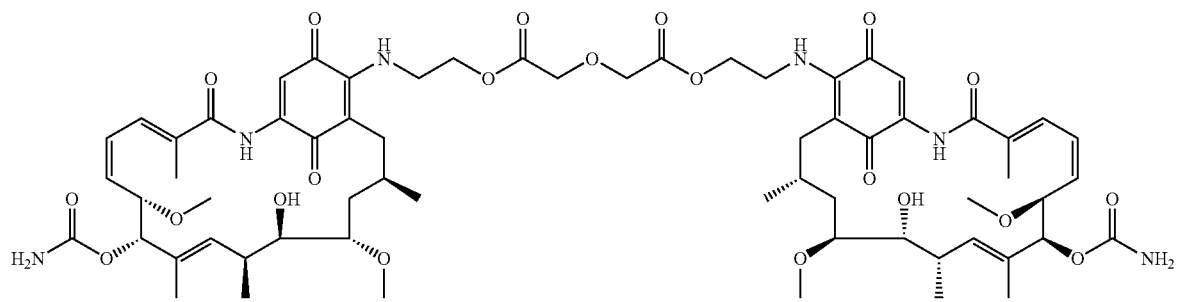
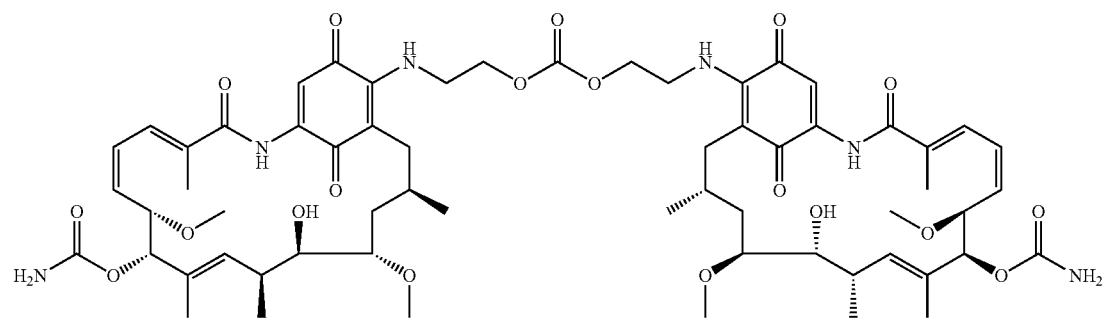

249 250
-continued
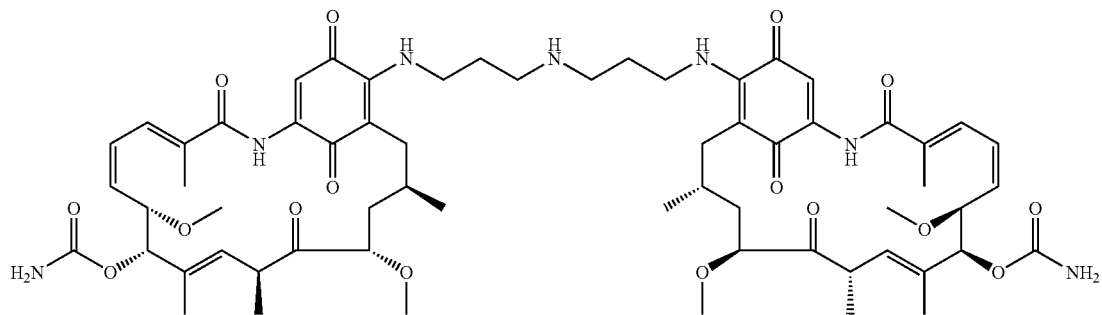
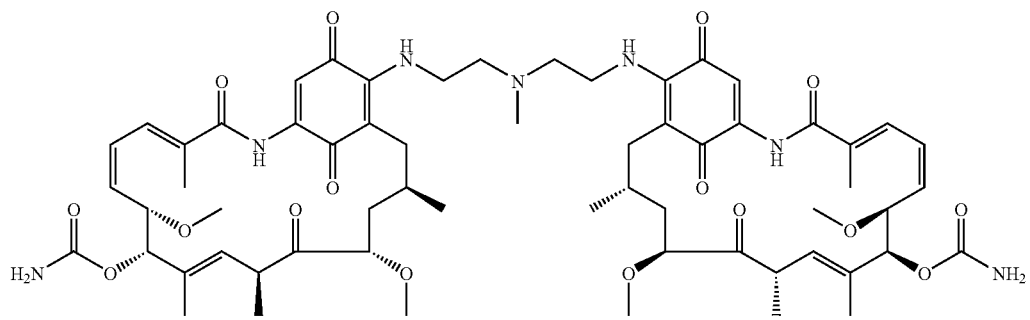
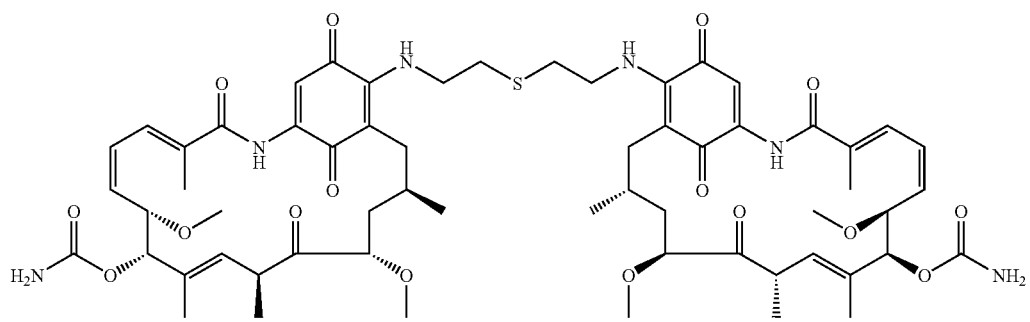
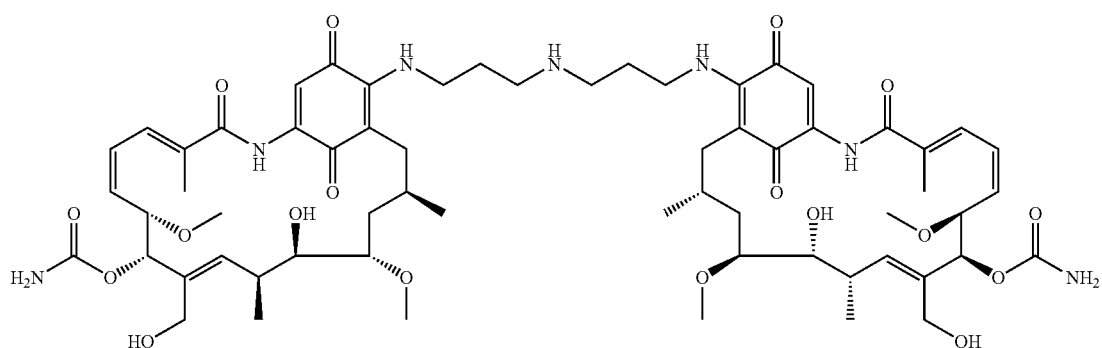

251 252
-continued
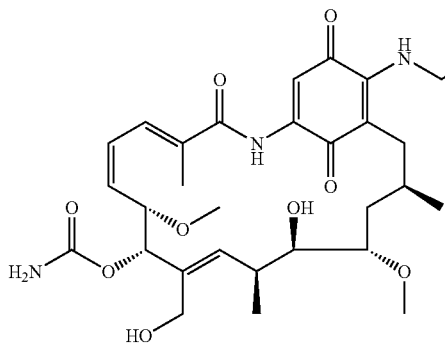 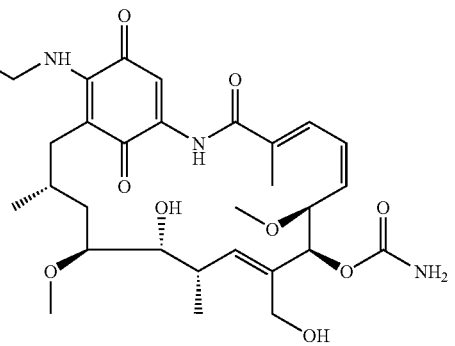
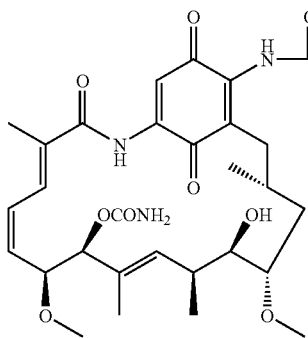 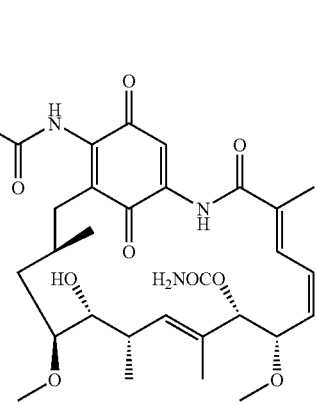
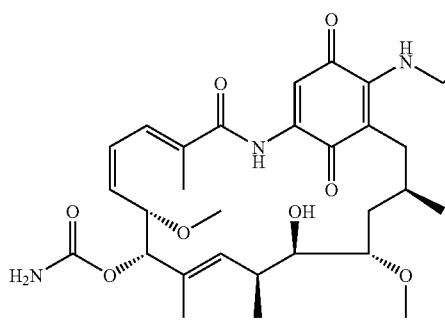 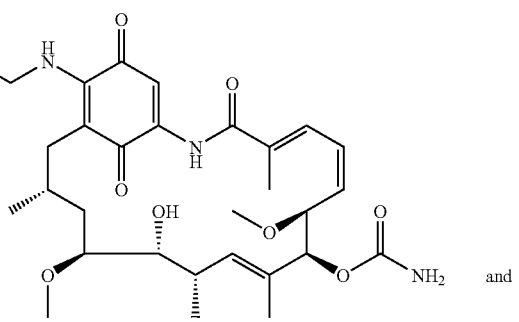 and
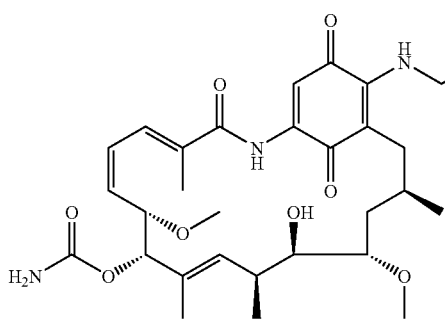 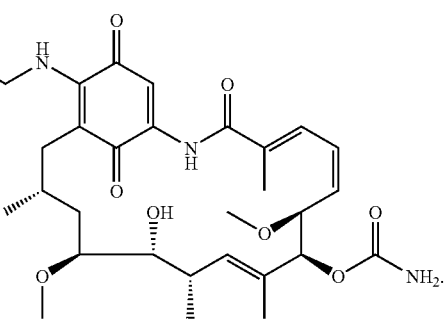.

17. A pharmaceutical composition comprising a compound or pharmaceutically acceptable salt thereof according to claim 8 and further comprising one or more members selected from pharmaceutically acceptable excipients, carriers, bulking agents, salts, water, and alcohol.

18. The pharmaceutical composition of claim 17 formulated for intravenous administration, and optionally disposed in a container member selected from vials and syringes.

19. The pharmaceutical composition of claim 18 formulated for oral administration, and optionally disposed in a container member selected from gel capsules, tablets, bottles, vials, and inhalers.

20. compound or pharmaceutically acceptable salt thereof according to a formula:

21. A compound or pharmaceutically acceptable salt thereof selected from:

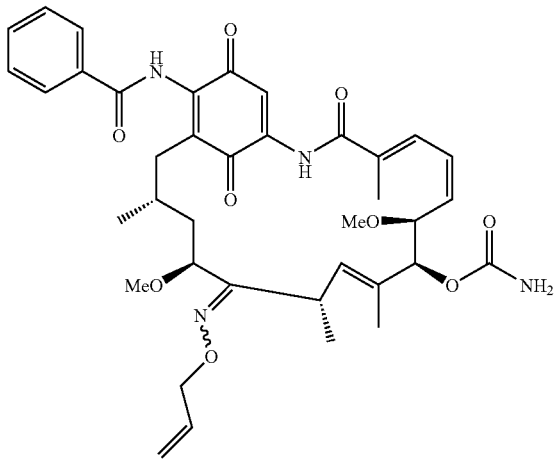

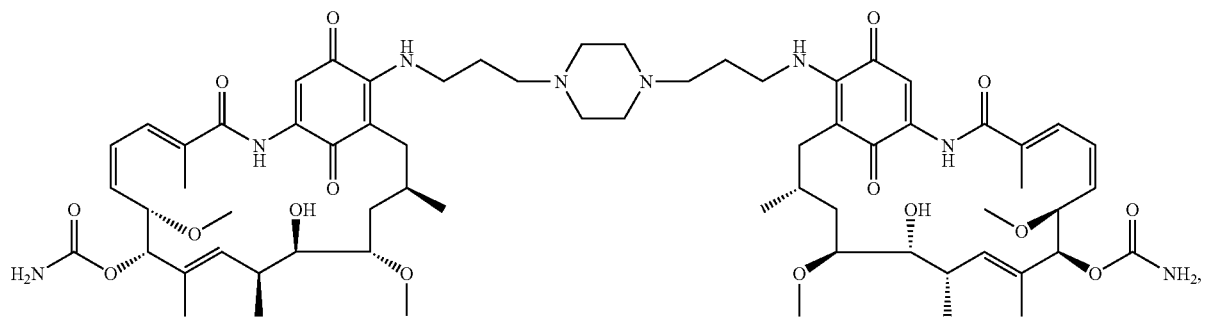

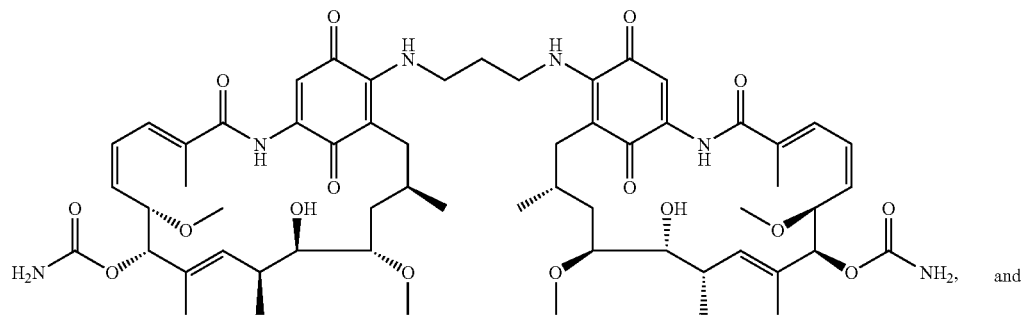

and

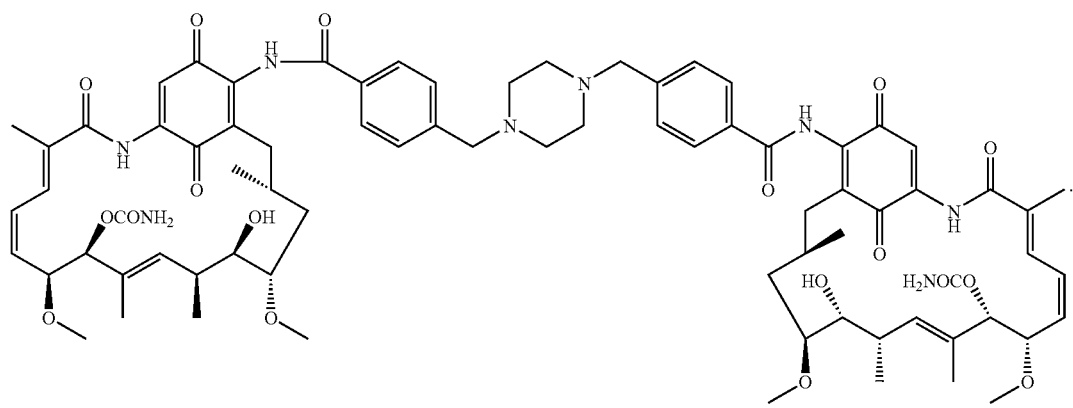

22. A method of synthesizing an amide-containing ansanamycin comprising:

(a) dissolving a compound or salt thereof according to formula 5a in EtOAc to form a solution of compound 5a

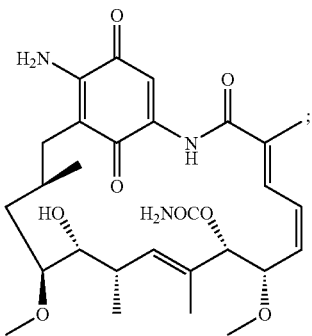

5a (b) treating the solution of compound 5a with $Na_2S_2O_4$ to form a compound or salt thereof according to formula 5b

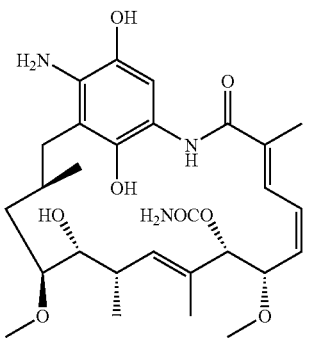

5b (c) dissolving the compound or salt thereof according to formula 5b in THF to form a solution of compound 5b;

(d) reacting the compound or salt thereof of formula 5b with an alkyl or aryl carboxyl halide or anhydride to form an amide compound or salt thereof according to formula 5c

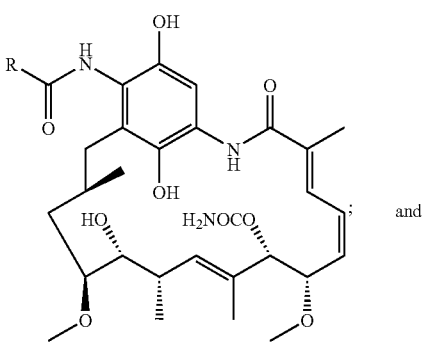

5c and (e) oxidizing the compound or salt thereof according to formula 5c to produce the compound or pharmaceutically acceptable salt thereof of formula 5d

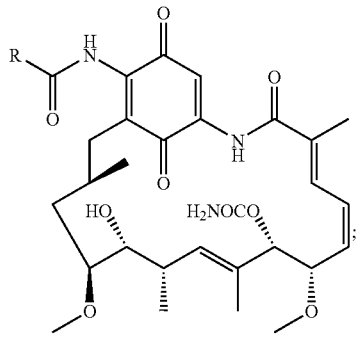

5d wherein R is $R_7$, $OR_7$, or $NR_7 R_8$;

wherein $R_7$ and $R_8$ each independently is selected from H, optionally substituted (C1-C20)alkyl, optionally substituted heteroalkyl, optionally substituted (C2-C20)alkenyl, optionally substituted heteroalkenyl, optionally substituted (C2-C20)alkynyl, optionally substituted aryl, optionally substituted heteroaryl, optionally substituted arylalkyl, optionally substituted heteroarylalkyl, optionally substituted cycloalkyl, and optionally substituted heterocycloalkyl; or $R_7$ and $R_8$ are taken together with the nitrogen to which they are bound to form an optionally substituted saturated or unsaturated 4-7 membered heterocyclic ring;

wherein said heteroalkyl and heteroalkenyl are corresponding alkyl and alkenyl groups in which one or more skeletal chain atoms are independently selected from oxygen, nitrogen, sulfur, and phosphorous;

wherein said heteroaryl is an aromatic group in which one or more skeletal ring atoms are independently selected from oxygen, nitrogen, sulfur, and phosphorous; and wherein said optionally substituted groups are unsubstituted groups or groups substituted by one or more substituents independently selected from alkyl, alkenyl, alkynyl, heteroalkyl, haloalkyl, haloalkenyl, haloalkynyl, cycloalkyl, aryl, heteroaryl, arylalkyl, heteroarylalkyl, alkoxy, aryloxy, haloalkoxy, amino, alkylamino, dialkylamino, alkylthio, arylthio, heteroarylthio, oxo, —C(O)OR wherein R is selected from alkyl, aryl, and arylalkyl, —N(R')C(O)R wherein R' and R are independently selected from H, alkyl, aryl and arylalkyl, —OC(O)R wherein R is selected from H, alkyl, alkenyl, alkynyl, aryl, and arylalkyl, F, Cl, Br, I, ON, $NO_2$, $N_3$, SH, OH, $CO_2H$, amido, sulfonato, sulfato, sulphonamido, carbamoyl, ureido, thioureido, thioamido, thioalkyls, —OP(O)(OR$_{16}$)$_2$, —CH$_2$P(O)(OR$_{16}$)$_2$, and —NP(O)(OR$_{16}$)$_2$; and wherein the alkyl substituent is itself optionally substituted by one or more substituents independently selected from alkyl, alkenyl, alkynyl, heteroalkyl, haloalkyl, haloalkenyl, haloalkynyl, cycloalkyl, aryl, heteroaryl, arylalkyl, heteroarylalkyl, alkoxy, aryloxy, haloalkoxy, amino, alkylamino, dialkylamino, alkylthio, arvlthio, heteroarylthio, oxo, —C(O)OR wherein R is selected from alkyl, aryl, and arylalkyl, —N(R')C(OR wherein R' and R are independently selected from H, alkyl, aryl and arylalkyl, —OC(O)R wherein R is selected from H, alkyl, alkenyl, alkynyl, aryl, and arylalkyl, F, Cl, Br, OH, —OP(O)(OR$_{16}$)$_2$, —CH$_2$P(O)(OR$_{16}$)$_2$, and —NP(O)(OR$_{16}$)$_2$.

23. A method of synthesizing an ansanamycin comprising:
(a) providing a compound or salt thereof according to formula I

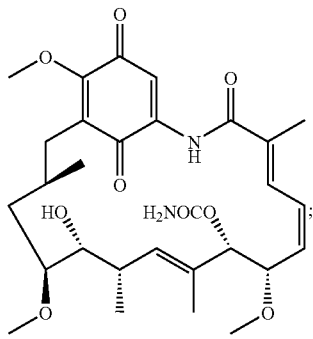

I (b) contacting the compound or salt thereof of formula I with Ba(OH)$_2$ hydrolyzing the compound or pharmaceutically acceptable salt of formula I to form a compound or pharmaceutically acceptable salt thereof according to formula II

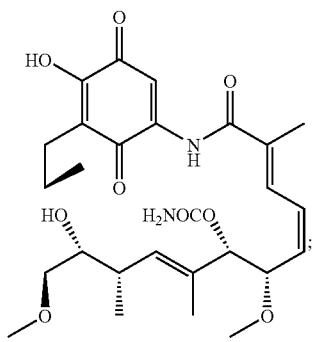

II (c) reacting the compound or salt thereof according to formula II with triflic anhydride to yield a triflate according to formula III

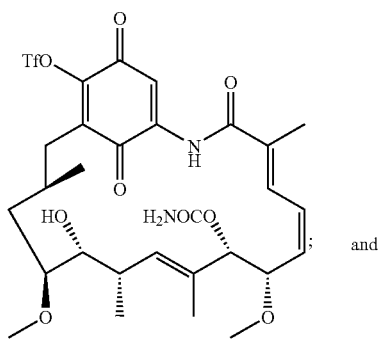

III and (d) reacting the compound or salt thereof according to formula III with RB(OH)$_2$ in a solution comprising cesium bromide, cesium fluoride, and dioxane to yield a compound or salt thereof according to formula IV

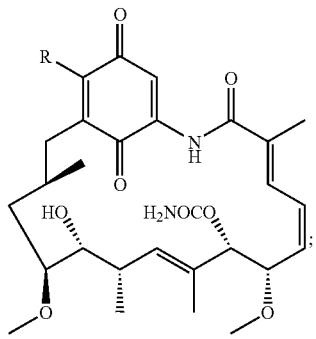

IV wherein R is selected from optionally substituted (C1-C20) alkyl, optionally substituted heteroalkyl, optionally substituted (C2-C20)alkenyl, optionally substituted heteroalkenyl, optionally substituted (C2-C20)alkynyl, optionally substituted aryl, optionally substituted heteroaryl, optionally substituted arylalkyl, optionally substituted heteroarylalkyl, optionally substituted cycloalkyl, and optionally substituted heterocycloalkyl;

wherein said heteroalkyl and heteroalkenyl are corresponding alkyl and alkenyl groups in which one or more skeletal chain atoms are independently selected from oxygen, nitrogen, sulfur, and phosphorous;

wherein said heteroaryl are corresponding aromatic groups in which one or more skeletal ring atoms are independently selected from oxygen, nitrogen, sulfur, and phosphorous; and wherein said optionally substituted groups are unsubstituted groups or groups substituted by one or more substituents independently selected from alkyl, alkenyl, alkynyl, heteroalkyl, haloalkyl, haloalkenyl, haloalkynyl, cycloalkyl, aryl, heteroaryl, arylalkyl, heteroarylalkyl, alkoxy, aryloxy, haloalkoxy, amino, alkylamino, dialkylamino, alkylthio, arylthio, heteroarylthio, oxo, —C(O)OR wherein R is selected from alkyl, aryl, and arylalkyl, —N(R')C(O)R wherein R' and R are independently selected from H, alkyl, aryl and arylalkyl, —OC(O)R wherein R is selected from H, alkyl, alkenyl, alkynyl, aryl, and arylalkyl, F, Cl, Br, I, CN, NO$_2$, N$_3$, SH, OH, CO$_2$H, amido, sulfonato, sulfato, sulphonamido, carbamoyl, ureido, thioureido, thioamido, thioalkyls, —OP(O)(OR$_{16}$)$_2$, —CH$_2$P(O)(OR$_{16}$)$_2$, and —NP(O)(OR$_{16}$)$_2$; and wherein the alkyl substituent is itself optionally substituted by one or more substituents independently selected from alkyl, alkenyl, alkynyl, heteroalkyl, haloalkyl, haloalkenyl, haloalkynyl, cycloalkyl, aryl, heteroaryl, arylalkyl, heteroarylalkyl, alkoxy, aryloxy, haloalkoxy, amino, alkylamino, dialkylamino, alkylthio, arylthio, heteroarylthio, oxo, —C(O)OR wherein R is selected from alkyl, aryl, and arylalkyl, —N(R')C(O)R wherein R' and R are independently selected from H, alkyl, aryl and arylalkyl, —OC(O)R wherein R is selected from H, alkyl, alkenyl, alkynyl, aryl, and arylalkyl, F, Cl, Br, OH, —OP(O)(OR$_{16}$)$_2$, —CH$_2$P(O)(OR$_{16}$)$_2$, and —NP(O)(OR$_{16}$)$_2$.

* * * * *